(12) United States Patent
Alcaraz et al.

(10) Patent No.: US 8,455,483 B2
(45) Date of Patent: Jun. 4, 2013

(54) COMPOUNDS—801

(75) Inventors: Lilian Alcaraz, Cheshire (GB); Andrew Bailey, Cheshire (GB); Nicholas Kindon, Cheshire (GB)

(73) Assignees: AstraZeneca AB, Sodertalje (SE); Pulmagen Therapeutics (Synergy) Limited, Essex (GB)

( * ) Notice: Subject to any disclaimer, the term of this patent is extended or adjusted under 35 U.S.C. 154(b) by 220 days.

(21) Appl. No.: 12/847,000

(22) Filed: Jul. 30, 2010

(65) Prior Publication Data

US 2011/0053909 A1 Mar. 3, 2011

(30) Foreign Application Priority Data

Jul. 31, 2009 (GB) .................................. 0913342.2

(51) Int. Cl.
*C07D 498/10* (2006.01)
*A61K 31/5386* (2006.01)

(52) U.S. Cl.
USPC ........................................ 514/230.5; 544/71

(58) Field of Classification Search
USPC ........................................ 544/71; 514/230.5
See application file for complete search history.

(56) References Cited

U.S. PATENT DOCUMENTS 2,707,186 A 4/1955 Duschinsky

FOREIGN PATENT DOCUMENTS

| EP | 1852434 | 11/2007 |
|---|---|---|
| WO | WO97/33202 | 9/1997 |
| WO | WO97/46577 | 12/1997 |
| WO | WO01/44170 | 6/2001 |
| WO | WO2005/085226 | 9/2005 |
| WO | WO2007/027134 | 3/2007 |
| WO | WO2007/069986 | 6/2007 |
| WO | WO2007/102771 | 9/2007 |
| WO | WO 2008/021375 | 2/2008 |
| WO | WO2008/075025 | 6/2008 |
| WO | WO2008/096127 | 8/2008 |
| WO | WO2008/096129 | 8/2008 |
| WO | WO2009/098448 | 8/2009 |

OTHER PUBLICATIONS

Bauerlein et al. "Synthesis of Long-chain 1-Alkylimidazole-2-thiols, 1-Alkylimidazoles, and Some Related Benzimidazole Compounds" Liebigs Ann. Chem. 1979 (11) 1818-1827.

Birch et al. "A New Modification of the Pomeranz-Fritsch Isoquinoline Synthesis" J. Chem. Soc. Perkin I 1974 (19) 2185-2190.
Deng et al. "A Practical Synthesis of Enantiopure 7-Alkoxy-4-aryl-tetrahydroisoquinoline, a Dual Serotonin Reuptake Inhibitor/Histamine $H_3$ Antagonist" Org. Proc. Res. Dev. 2007 (11) 1043-1050.
Gao et al. "Synthesis and Structure Revision of Nakiterpiosin" J. Am. Chem. Soc. 2009 (131) 1410-1412.
Giles et al. "Development of a Manufacturing Process for Sibenadet Hydrochloride, the Active Ingredient of Viozan" Org. Proc. Res. Dev. 2004 (8) 628-642.
Kaye et al. "Preparation of N-Substituted Aminoacetals" J. Am. Chem. Soc. 1949 (71) 2272-2273.
Lindner et al. "Macrocyclic Di- and Tetranuclear Osmacycloferrocenophanes" Organometallics 2002 (21) 4217-4225.
Main, B.G. "β-Adrenergic Receptors" in Comprehensive Medicinal Chemistry (Alderley Park, UK Pergamon Press, 1990) pp. 187-228.
Plaue et al. "A new preparation of 4-(boc-aminoacyloxymethyl)phenylacetic acids for solid-phase peptide synthesis" Tet. Lett. 1987 (28) 1401-1404.
Van Noord et al. "Comparison of tiotropium once daily, formoterol twice daily and both combined once daily in patients with COPD" Eur. Respir. J. 2005 (26) 214-222.

*Primary Examiner* — Kahsay T Habte
(74) *Attorney, Agent, or Firm* — Fish & Richardson P.C.

(57) ABSTRACT

Spirocyclic amide derivatives of formula I

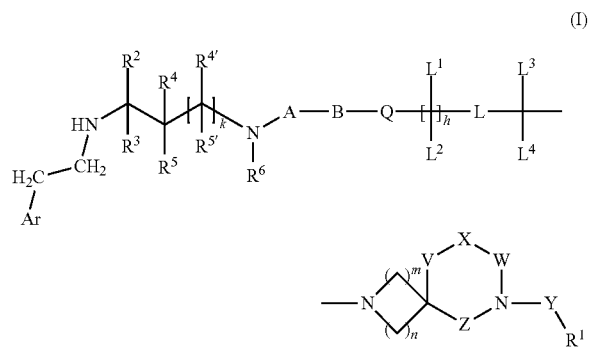

wherein
$ArCH_2CH_2NH$— represents a β-adrenoceptor binding group, processes for their preparation, pharmaceutical compositions containing them, a process for preparing such pharmaceutical compositions, their use in therapy, and intermediates for use in their preparation.

15 Claims, 10 Drawing Sheets

COMPOUNDS—801

This application claims the benefit under 35 U.S.C. §119 (a-d) of Application No. 09113342.2 filed 31 Jul. 2009, which is incorporated herein by reference in its entirety.

The present invention relates to spirocyclic amide derivatives, a process for their preparation, pharmaceutical compositions containing them, a process for preparing such pharmaceutical compositions, their use in therapy, and intermediates for use in their preparation.

First-line treatment for a variety of pulmonary disorders including chronic obstructive pulmonary disease (COPD) and asthma is through the use of bronchodilators. Muscarinic-receptor antagonists (anti-cholinergics) are bronchodilators that exert their efficacy by reducing vagal cholinergic tone, the main reversible component of airway constriction in COPD. β-adrenoceptor agonists are also bronchodilators due to their ability to functionally antagonise the bronchoconstrictor responses to a range of mediators, including acetylcholine.

In addition to improving lung function, these agents improve dyspnoea (breathlessness), quality of life, exercise tolerance and they reduce exacerbations. A number of clinical studies have demonstrated that combined administration of an anti-cholinergic and a $\beta_2$-receptor agonist is more efficacious than either of the individual components (van Noord, J. A., Aumann, J-L., Janssens, E., Smeets, J. J., Verhaert, J., Disse, B., Mueller, A. & Cornelissen, P. J. G., 2005. "Comparison of tiotropium once daily, formoterol twice daily and both combined once daily in patients with COPD", *Eur. Respir. J.*, vol 26, pp 214-222). A single molecule possessing activities at muscarinic and $\beta_2$-receptors (MABAs) may provide additional benefits to COPD patients in terms of efficacy and side-effect profile over either single agent. Moreover, a molecule possessing dual activity may also offer benefits in terms of ease-of-use and patient compliance over co-administration of the single therapies. A single agent may also be beneficial from the perspective of formulation compared to two separate compounds, also offering the potential, if combined with another therapeutic, for triple action therapies.

According to a first aspect of the invention we now provide a compound of formula I

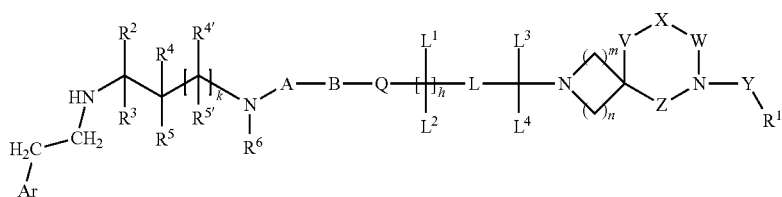

(I)

wherein $ArCH_2CH_2NH$— represents a β-adrenoceptor binding group;

each of $R^2$, $R^3$, $R^4$, $R^5$, $R^{4'}$ and $R^{5'}$ is independently hydrogen or $C_{1-6}$ alkyl;

k is 0 or 1

$R^6$ is a $C_{1-8}$ alkyl group optionally substituted by up to 3 substituents selected from halogen, $C_{1-6}$ alkyl (optionally substituted by up to 3 halogen atoms), $OR^{10}$, $C_{1-6}$ alkylS$(O)_{0-2}$, $NR^8R^9$, $OC(O)(C_{1-6}$ alkyl), $C_{3-8}$ cycloalkyl (wherein one or two of the carbon atoms can be replaced by O, S or N) optionally substituted by up to 3 substituents independently selected from halogen, $C_{1-6}$ alkyl (optionally substituted by up to 3 halogen atoms), $OR^{10}$, $C_{1-6}$ alkylS$(O)_{0-2}$, $NR^8R^9$, and $OC(O)(C_{1-6}$ alkyl);

or $R^6$ is a $C_{1-8}$ alkyl group substituted by an optionally substituted aryl or heteroaryl group;

or $R^6$ is a $C_{3-9}$ cycloalkyl group (wherein one or two of the ring carbon atoms can be replaced by O, S or N) and optionally substituted by up to 3 substituents independently selected from halogen, $C_{1-6}$ alkyl (optionally substituted by up to 3 halogen atoms and/or wherein two alkyl groups may form a ring of up to 9 ring atoms), $OR^{10}$, $C_{1-6}$ alkylS$(O)_{0-2}$, $NR^8R^9$, $OC(O)(C_{1-6}$ alkyl), and optionally substituted aryl or heteroaryl;

or $R^6$ is a $C_{7-9}$ bicycloalkyl group optionally substituted by up to 3 substituents independently selected from halogen, $C_{1-6}$ alkyl, $OR^{10}$ and $C_{1-6}$ alkylS$(O)_{0-2}$ or $R^6$ is a 5- or 6-membered aromatic or non-aromatic heterocyclic ring containing up to two heteroatoms independently selected from N, O and S;

$R^8$ and $R^9$ are independently hydrogen, $C_{1-6}$ alkyl, or $R^8$ and $R^9$ may be joined together to form a heterocyclic ring comprising up to 9 ring atoms (optionally containing a further heteroatom selected from O, N or S) wherein the ring may be optionally substituted by up to three substituents independently selected from halogen, hydroxyl, $C_{1-6}$ alkyl or $C_{3-6}$ cycloalkyl, and wherein alkyl and cycloalkyl may be optionally substituted by up to three substituents independently selected from halogen, hydroxyl and $C_{1-6}$ alkoxy;

$R^{10}$ represents hydrogen, $C_{1-6}$ alkyl or $C_{3-6}$ cycloalkyl, wherein alkyl and cycloalkyl may be optionally substituted by up to three substituents independently selected from halogen, hydroxyl and $C_{1-6}$ alkoxy;

A is $C(O)$ or $S(O)_2$;

B is $C_{1-4}$ alkylene optionally substituted by up to two $C_{1-3}$ alkyl groups Q is oxygen, sulphur or $NR^7$;

$R^7$ is hydrogen or $C_{1-6}$ alkyl;

L represents a straight or branched hydrocarbyl chain of up to 9 carbon atoms;

wherein up to three of the carbon atoms in the chain are optionally substituted once or twice by groups independently selected from halogen, $S(O)_{0-2}R^{10}$, $NR^8R^9$, $S(O)_2NR^8R^9$, $C(O)NR^8R^9$, $C(O)OR^{10}$, $NR^{10}S(O)_2R^{11}$, $NR^{10}C(O)R^{10}$, $NR^{10}C(O)OR^{11}$, $NR^{10}C(O)NR^8R^9$, $OR^{10}$, $C_{1-6}$ alkyl and $C_{3-6}$ cycloalkyl, and wherein alkyl and cycloalkyl may be optionally substituted by up to three substituents independently selected from halogen, hydroxyl and $C_{1-6}$ alkoxy;

wherein up to three carbon atoms of the chain may be replaced by groups independently selected from O, $NR^{10}$, S, $S(O)$, $S(O)_2$, $C(O)O$, $OC(O)$, $NR^{10}C(O)$, $C(O)NR^{10}$, $NR^{10}S(O)_2$, $S(O)_2NR^{10}$, $NR^{10}C(O)NR^{10}$, $NR^{10}S(O)_2NR^{10}$, $OC(O)$ $NR^{10}$, $NR^{10}C(O)O$, provided that any such groups in the chain are separated by at least two chain carbon atoms; and wherein up to six carbon atoms of the chain may form part of an aryl, heteroaryl, fused bicyclic, alicyclic, or heteroaliphatic ring having up to four heteroatoms independently selected from N, O or S, said ring comprising up to 10 ring atoms, and wherein the ring is optionally substituted by up to three substituents independently selected from halogen, $S(O)_{0-2}R^{10}$, $NR^8R^9$, $S(O)_2NR^8R^9$, $C(O)NR^8R^9$, $C(O)OR^{10}$, $NR^{10}S(O)_2R^{11}$, $NR^{10}C(O)R^{10}$, $NR^{10}C(O)OR^{11}$, $NR^{10}C(O)NR^8R^9$, $OR^{10}$, $C_{1-6}$ alkyl and $C_{3-6}$ cycloalkyl, and wherein alkyl and cycloalkyl may be optionally substituted by up to three substituents independently selected from halogen, hydroxyl and $C_{1-6}$ alkoxy;

and the chain may comprise up to two of such rings each selected independently;

$R^{11}$ represents $C_{1-6}$ alkyl or $C_{3-6}$ cycloalkyl, wherein the $C_{1-6}$ alkyl and $C_{3-6}$ cycloalkyl may be optionally substituted by up to three substituents independently selected from halogen, hydroxyl or $C_{1-6}$ alkoxy;
and wherein the chain may additionally comprise up to three carbon-carbon double bonds; and wherein the chain may additionally comprise up to three carbon-carbon triple bonds;

$L^1$ and $L^2$ independently represent hydrogen, $C_{1-6}$ alkyl or $C_{3-6}$ cycloalkyl;

h is 0 or 1

$L^3$ and $L^4$ independently represent hydrogen, $C_{1-6}$ alkyl or $C_{3-6}$ cycloalkyl;

$R^1$ is selected from the following;

(i) an optionally substituted 3-8 membered ring, said ring being aromatic or fully or partially saturated and wherein up to four of the ring atoms may be replaced by heteroatoms independently selected from N, O and S. Examples of such rings include phenyl, thiazolyl, thienyl, isoxazolyl, furyl, cyclohex-3-enyl, cyclohexyl, cycloheptyl (ii) an optionally substituted fused bicyclic ring system of up to 10 atoms, said rings being aromatic or fully or partially saturated, and wherein up to four of the ring atoms may be replaced by heteroatoms independently selected from N, O and S.
Examples of such rings include benzo[b]thienyl, benzofuranyl, benzo[d]imidazolyl, quinoxalinyl, pyrazolo[1,5-a]pyrimidinyl, pyrazolo[1,5-a]pyridinyl, dihydrobenzo[b][1,4]dioxinyl, 4,5,6,7-tetrahydro-2H-indazolyl, benzo[d][1,3]dioxolyl (iii) an optionally substituted $C_{1-6}$ alkyl group wherein one or two of the carbon atoms can be replaced by O, S or N and wherein said alkyl group may be substituted once or twice by a ring system independently selected from (i) and (ii) above, and wherein the $C_{1-6}$ alkyl chain may be substituted by up to five substituents selected from halogen, cyano, $S(O)_{0-2}R^{10}$, $NR^8R^9$, $S(O)_2NR^8R^9$, $C(O)NR^8R^9$, $C(O)OR^{10}$, $NR^{10}S(O)_2R^{11}$, $NR^{10}C(O)R^{10}$, $NR^{10}C(O)OR^{11}$, $NR^{10}C(O)NR^8R^9$, $OR^{10}$, $C_{1-6}$ alkyl and $C_{3-6}$ cycloalkyl (wherein two $C_{1-3}$ alkyl chains may be joined to form an optionally substituted cycloalkyl ring of up to eight ring atoms), and wherein for any ring in (i), (ii) and (iii) above "optionally substituted" means optionally substituted by up to four substituents independently selected from halogen, cyano, nitro, SH, $S(O)_{0-2}R^{10}$, $NR^8R^9$, $S(O)_2NR^8R^9$, $C(O)NR^8R^9$, $C(O)OR^{10}$, $NR^{10}S(O)_2R^{11}$, $NR^{10}C(O)R^{10}$, $NR^{10}C(O)OR^{11}$, $NR^{10}C(O)NR^8R^9$, $OR^{10}$, $C_{1-6}$ alkyl or $C_{3-6}$ cycloalkyl (wherein a carbon atom of alkyl or cycloalkyl may be optionally replaced by N, O or S, and alkyl or cycloalkyl may be optionally substituted by up to five substituents selected from $C_{1-6}$ alkyl, halogen, cyano, SH, $S(O)_{0-2}R^{10}$, $NR^8R^9$, $S(O)_2NR^8R^9$, $C(O)NR^8R^9$, $C(O)OR^{10}$, $NR^{10}S(O)_2R^{11}$, $NR^{10}C(O)R^{10}$, $NR^{10}C(O)OR^{11}$, $NR^{10}C(O)NR^8R^9$, and)$OR^{10}$, and wherein the saturated ring systems in (i) and (iii) may also be substituted by up to three $C_{1-6}$ alkyl groups that can be joined to form bridged ring structures, optionally substituted by halogen or $OR^{10}$. Examples of these ring systems include adamantyl and bicyclo[2.2.1]heptanyl;

X represents O, $S(O)_{0-2}$ or $CR^{12}R^{13}$;

m=0, 1, 2 or 3;

n=1, 2, 3 or 4; provided that m+n is greater than or equal to 2;

W represents $CR^{12}R^{13}$—$CR^{12}R^{13}$ or $CR^{12}R^{13}$—$CR^{12}R^{13}$—$CR^{12}R^{13}$;

V and Z independently represent a bond, $CR^{12}R^{13}$ or $CR^{12}R^{13}$—$CR^{12}R^{13}$, provided that when X represents either O or $S(O)_{0-2}$ then m, V and Z are such that all the heteroatoms in the rings are separated by at least two carbon atoms;

Y represents $C(O)$, $C(O)NR^{10}$, $SO_2$ or $SO_2NR^{10}$;

$R^{12}$ and $R^{13}$ are each independently represent hydrogen, fluorine, $C_{1-6}$ alkyl or $C_{3-6}$ cycloalkyl; or $R^{12}$ and $R^{13}$ when attached to the same carbon atom, together with the carbon atom to which they are both attached, may additionally form a 3 to 6 membered aliphatic ring;

and pharmaceutically acceptable salts thereof.

By "β-adrenoceptor binding group" we mean a group capable of binding a β-adrenergic receptor; such as for example as outlined in the review article "β-adrenergic receptors in Comprehensive Medicinal Chemistry, 1990, B. E. Main, p 187 (Pergamon Press). Such groups are also known from, for example in WO/2005092841, US/20050215542, WO/2005070872, WO/2006023460, WO/2006051373, WO/2006087315, WO/2006032627. See also WO2007018461, WO2008075025, WO2008075026, and WO2008096119

Examples of convenient Ar groups within the β-adrenoceptor binding groups include

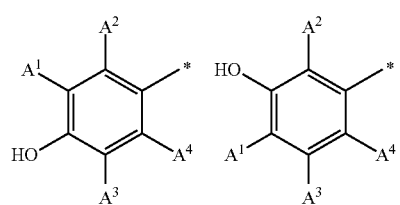

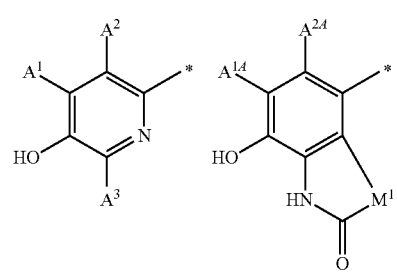

-continued

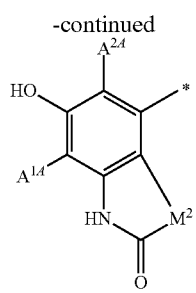

$M^1$ is S, C(O), $NA^5$, $CA^6A^7$, $CH_2CH_2$, CH=CH, $CH_2O$ or $OCH_2$;

$M^2$ is S, C(O), $NA^5$, $CA^6A^7$, $CH_2CH_2$, CH=CH, $CH_2O$ or $OCH_2$;

$A^1$, $A^2$, $A^3$ and $A^4$ are independently hydrogen, halogen, trifluoromethyl, cyano, carboxy, hydroxy, nitro, $S(O)_2A^8$, $NA^9S(O)_2A^{10}$, $C(O)NA^{11}A^{12}$, $NA^{13}C(O)A^{14}$, $C_{1-6}$ alkyl, $C_{1-6}$ alkoxy, $C(O)(C_{1-6}$ alkyl) or $C(O)OC_{1-6}$ alkyl;

$A^3$ can also be $CH_2OH$, NHCHO, $NHC(O)OC_{1-6}$ alkyl, $NHS(O)_2NA^{15}A^{16}$ or $NHSO_2A^{17}$;

$A^{1A}$ and $A^{2A}$ are independently hydrogen, halogen, trifluoromethyl, cyano, carboxy, hydroxy, nitro, $S(O)_2A^8$, $NA^9S(O)_2A^{10}$, $C(O)NA^{11}A^{12}$, $NA^{13}C(O)A^{14}$, $C_{1-6}$ alkyl, $C_{1-6}$ alkoxy, $C(O)(C_{1-6}$ alkyl) or $C(O)OC_{1-6}$ alkyl;

$A^5$, $A^6$, $A^7$, $A^9$, $A^{11}$, $A^{12}$, $A^{13}$, and $A^{14}$ are independently hydrogen or $C_{1-6}$ alkyl;

$A^{15}$ and $A^{16}$ are independently hydrogen, $C_{1-6}$ alkyl or $C_{3-6}$ cycloalkyl;

$A^8$, $A^{10}$ and $A^{17}$ are independently $C_{1-6}$ alkyl or $C_{3-6}$ cycloalkyl;

and * defines the attachment point of Ar to the rest of the molecule

Conveniently the Ar group is selected from:

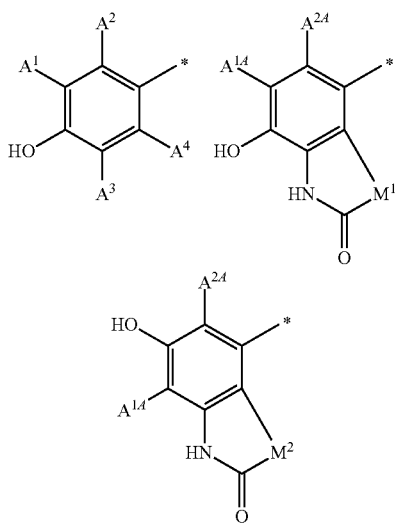

wherein $M^1$ is S, CH=CH, $CH_2O$ or $OCH_2$;
$M^2$ is S, CH=CH, $CH_2O$ or $OCH_2$;
$A^1$, $A^2$, and $A^4$ are independently hydrogen, halogen, $C_{1-6}$ alkyl, or $C_{1-6}$ alkoxy;
$A^3$ can be $CH_2OH$, NHCHO, $NHS(O)_2NA^{15}A^{16}$ or $NHS(O)_2A^{17}$;
$A^{1A}$ and $A^{2A}$ are independently, hydrogen, halogen, trifluoromethyl, cyano, carboxy, hydroxy, nitro, $S(O)_2A^8$, $NA^9S(O)_2A^{10}$, $C(O)NA^{11}A^{12}$, $NA^{13}C(O)A^{14}$, $C_{1-6}$ alkyl, $C_{1-6}$ alkoxy, $C(O)(C_{1-6}$ alkyl) or $C(O)OC_{1-6}$ alkyl;
$A^{15}$ and $A^{16}$ are independently selected from hydrogen, $C_{1-6}$ alkyl or $C_{3-6}$ cycloalkyl;
$A^{17}$ is $C_{1-6}$ alkyl or $C_{3-6}$ cycloalkyl;

Examples of $C_{1-6}$ alkyl include $C_{1-4}$ alkyl and $C_{1-2}$ alkyl. Examples of $C_{3-6}$ cycloalkyl include $C_{3-5}$ cycloalkyl and $C_{3-4}$ cycloalkyl. Examples of $C_{1-6}$ alkoxy include $C_{1-4}$ alkoxy and $C_{1-2}$ alkoxy.

Conveniently the Ar group is selected from:

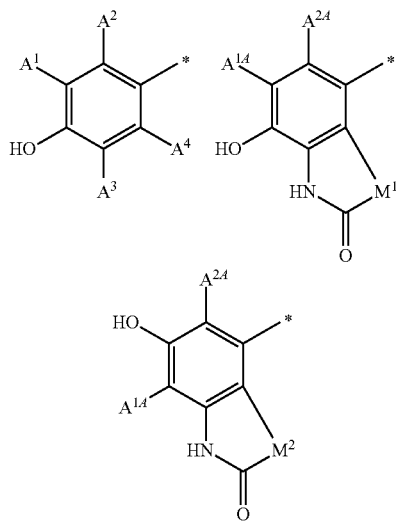

wherein $A^1$, $A^2$, $A^4$ are all hydrogen, $A^3$ is $CH_2OH$ or NHCHO, $A^{1A}$ and $A^{2A}$ are, is hydrogen $M^1$ is S, CH=CH, or $OCH_2$; $M^2$ is S, CH=CH, or $OCH_2$.

Conveniently the Ar group is selected from:

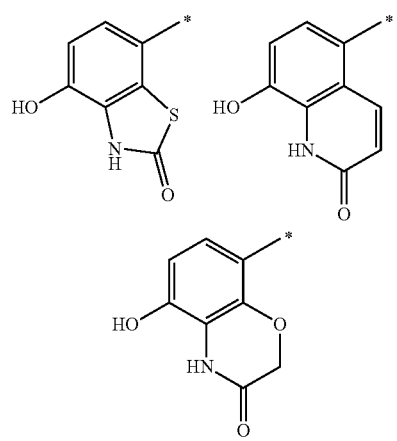

each of $R^2$, $R^3$, $R^4$, $R^5$, $R^{4'}$ and $R^{5'}$ is, independently, hydrogen or $C_{1-6}$ alkyl;
conveniently each of $R^2$, $R^3$, $R^4$, $R^5$, $R^{4'}$ and $R^{5'}$ is hydrogen or methyl;
more conveniently each of $R^2$, $R^3$, $R^4$, $R^5$, $R^{4'}$ and $R^{5'}$ is hydrogen.

The Group $R^6$

Conveniently $R^6$ is a $C_{1-8}$ alkyl group optionally substituted by a $C_{1-8}$ cycloalkyl group, optionally substituted by up to 3 substituents selected from halogen, hydroxy, $C_{1-6}$ alkyl or $C_{1-6}$ alkoxy; more conveniently $R^6$ is a $C_{1-8}$ alkyl group optionally substituted by up to two $C_{1-6}$ alkyl groups;

Conveniently $R^6$ is a $C_{3-9}$ cycloalkyl group; more conveniently $R^6$ is a cyclopentyl or cyclohexyl or cycloheptyl group;

The Groups Q and A

A is C(O) or S(O)$_2$; Conveniently A is C(O);

B is $C_{1-4}$ alkylene optionally substituted by up to two $C_{1-3}$ alkyl groups Conveniently B is ethylene Q is oxygen, sulphur or NR$^7$; Conveniently Q is oxygen The Integers h & k h is an integer from 0 to 1; Conveniently h is 1;

k is 0 or 1; conveniently k is 0;

The Group:

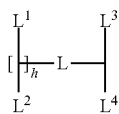

Conveniently $L^1$ and $L^2$ independently represent hydrogen,
Conveniently $L^3$ and $L^4$ independently represent hydrogen,
Conveniently the species -L- is represented by the group of Formula (II)

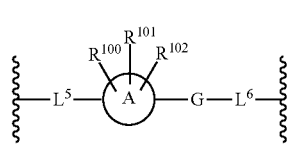
(II)

wherein $L^5$ is connected to $C(L^1)(L^2)$ and $L^6$ is connected to $C(L^3)(L^4)$ and;

wherein ring D represents a phenyl, thiophene, furan or thiazole ring;

$R^{100}$, $R^{101}$ and $R^{102}$ are each independently selected from hydrogen, halogen (e.g. fluorine or chlorine), $C_{1-4}$ alkyl, $C_{1-4}$ alkoxy and CF$_3$;

$L^5$ represents a $C_{1-4}$ alkylene group optionally substituted by up to 2 methyl groups; or $L^5$ represents —(CH$_2$)$_q$Q$^1$(CH$_2$)$_t$— where Q$^1$ is oxygen or sulphur and t is 0, 1 or 2 and q is 1 or 2

G represents a bond, oxygen, CR$^{10}$R$^{10}$ or S;

when G represents oxygen or S then $L^6$ is a $C_{1-2}$ alkylene group optionally substituted by up to two methyl groups;

when G represents a bond or CR$^{10}$R$^{10}$ then $L^6$ is a bond or a $C_{1-2}$ alkylene group optionally substituted by up to two methyl groups;

$L^5$ and G can be separated by 3, 4 or 5 bonds

Conveniently $L^5$ and G can be separated by 4 or 5 bonds

Conveniently the species -L- is selected from
—CH$_2$(phen-1,4-ylene)-;
—CH$_2$(phen-1,3-ylene)-;
—CH$_2$(phen-1,4-ylene)CH$_2$—;
—CH$_2$(phen-1,3-ylene)CH$_2$—;
—CH$_2$(phen-1,3-ylene)OCH$_2$—;
—CH$_2$(phen-1,4-ylene)OCH$_2$—;
—CH$_2$(phen-1,3-ylene)OCH$_2$CH$_2$—;
—CH$_2$(phen-1,4-ylene)OCH$_2$CH$_2$—;
—CH$_2$CH$_2$(phen-1,3-ylene)-;
—CH$_2$CH$_2$(phen-1,4-ylene)-;
—CH$_2$CH$_2$CH$_2$(phen-1,3-ylene)-;
—CH$_2$CH$_2$CH$_2$(phen-1,4-ylene)-;
—CH$_2$OCH$_2$(phen-1,3-ylene)-;
—CH$_2$OCH$_2$(phen-1,4-ylene)-;
—CH$_2$CH$_2$O(phen-1,3-ylene)-;
—CH$_2$CH$_2$O(phen-1,4-ylene)-;
—CH$_2$O(phen-1,3-ylene)-;
—CH$_2$O(phen-1,4-ylene)-;
—CH$_2$CH$_2$S(phen-1,3-ylene)-;
—CH$_2$CH$_2$S(phen-1,4-ylene)-;
—CH$_2$S(phen-1,3-ylene)-;
—CH$_2$S(phen-1,4-ylene)-;
—CH$_2$(thien-3,5-ylene)-;
—CH$_2$(thien-2,4-ylene)-;
—CH$_2$(thien-2,5-ylene)-;
—CH$_2$(thien-3,5-ylene)CH$_2$—;
—CH$_2$(thien-2,5-ylene)CH$_2$—;
—CH$_2$(thien-2,4-ylene)CH$_2$—;

wherein in each case phenylene is optionally substituted by 3, 2, or 1 of Cl, F, $C_{1-3}$ alkyl or $C_{1-3}$ alkoxy (selected independently)

Conveniently -L- is selected from
—CH$_2$(phen-1,3-ylene)-,
—CH$_2$(phen-1,4-ylene)CH$_2$—;
—CH$_2$(phen-1,3-ylene)CH$_2$—;
—CH$_2$(thien-3,5-ylene)CH$_2$—;
—CH$_2$(thien-2,5-ylene)CH$_2$—;
—CH$_2$(thien-2,4-ylene)CH$_2$—;

wherein in each case phenylene is optionally substituted by 3, 2, or 1 of Cl, F, $C_{1-3}$ alkyl or $C_{1-3}$ alkoxy (selected independently)

The Group $R^1$

Conveniently $R^1$ represents (i) a phenyl ring or a 5- or 6-membered heteroaryl ring;

(ii) a fused bicyclic ring;

(iii) $R^1$ may also conveniently represent an optionally substituted $C_{1-6}$ alkyl group wherein one or two of the carbon atoms can be replaced by O, S or N and wherein said alkyl group may be substituted by the ring systems described in (i) and (ii), and a convenient $C_{1-6}$alkyl group is methylene or ethylene or propylene;

wherein each ring in (i), (ii) and (iii) is optionally substituted by up to three substituents independently selected from halogen, cyano, OR$^{10}$, $C_{1-6}$ alkyl or $C_{3-8}$ cycloalkyl (wherein each alkyl and cycloalkyl is optionally substituted by up to three halogen atoms), a phenyl ring optionally substituted by up to three substituents independently selected from halogen, cyano, OR$^{10}$, $C_{1-6}$ alkyl or $C_{3-6}$ cycloalkyl (wherein alkyl and cycloalkyl may be optionally substituted by up to three substituents independently selected from halogen, hydroxyl, $C_{1-6}$ alkoxy, cyano, and NH$_2$).

Conveniently $R^1$ is selected from thiophene or thiazole or benzofuran or pyrazolo[1,5-a]pyridine each optionally substituted by one or two substituents. One of the optional substituents is conveniently selected from H, Cl, F and $C_{1-3}$alkyl. The other optional substituent is selected from methyl, ethyl, propyl, n-butyl, CF$_3$, CH$_2$CF$_3$, CH(CH$_3$)$_2$, CH(CH$_2$CH$_3$)$_2$, CH(CH$_3$)CH$_2$, CH$_3$, CH$_2$CH(CH$_3$)$_2$, C(CH$_3$)$_3$, cyclopropyl, cyclobutyl and cyclopentyl;

Conveniently R¹ is selected from

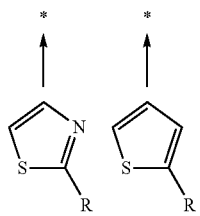

wherein the arrow marks the attachment point to the group Y and R is selected from methyl, ethyl, propyl, n-butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl;

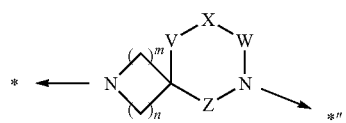

The Group Y and the Group
Conveniently Y represents C(O);
Conveniently
  X represents O or S.
  m=1 or 2;
  n=1 or 2;
  W represents $CR^{12}R^{13}CR^{12}R^{13}$ or $CR^{12}R^{13}CR^{12}R^{13}CR^{12}R^{13}$;
  V and Z independently represent a bond or $CR^{12}R^{13}$
V and Z are such that all the heteroatoms in the rings are separated by at least two carbon atoms (e.g. When V is a bond then Z is $CR^{12}R^{13}$).
  Y represents C(O), C(O)NR¹⁰, SO₂ or SO₂NR¹⁰;
  Conveniently
  (i) m and n=2, V=bond, Z=CH₂, X=O and W=CH₂CH₂
  (ii) m and n=2, V=bond, Z=CH₂, X=O and W=CF₂CH₂
  (iii) m and n=1, V=bond, Z=CH₂, X=O and W=CH₂CH₂
  (iv) m and n=2, V=bond, Z=CH₂CH₂, X=O and W=CH₂CH₂
  Conveniently the spirocycle is selected from (i), (ii) or (iii) above.
  Conveniently the spirocycle is (i)
  Each exemplified compound of the invention or any convenient combination thereof represents a particular and independent aspect of the invention.
  It will be understood that certain compounds of the present invention may exist in solvated, for example hydrated, as well as unsolvated forms. It is to be understood that the present invention encompasses all such solvated forms. Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.
  It is also to be understood that the present invention encompasses the replacement of any quaternary carbon, more specifically the quaternary carbon present in the spirocyclic system, by a silicon atom for example as disclosed in "Silicon switches of Marketed Drugs Mini-reviews in Med. Chem.", 2006, 6, 1169-1177.

DEFINITIONS

Unless otherwise specified:
The term 'heteroaryl' means an aromatic ring system of up to 7 atoms, conveniently 5 or 6 atoms, having up to three heteroatoms selected from N, O and S. Examples of such heteroaryl rings include thiazolyl, thienyl, isoxazolyl, furyl, isoxazolyl, isothiazolyl, oxazolyl, oxadiazolyl, pyrazinyl, pyridazinyl, pyrazolyl, pyridyl, pyrimidinyl, pyrrolyl, tetrazolyl, 1,3,4-thiadiazolyl, thiazolyl, thienyl, triazolyl and the like. The heteroaryl group may be attached by any available carbon or nitrogen atom.

The term 'fused bicyclic ring' means a ring system of up to 12 atoms wherein 2 rings are fused together. The system may optionally contain up to 4 heteroatoms selected from N, S and O. The rings may independently be aromatic, partially saturated or fully saturated. Examples of such fused bicyclic ring systems include benzo[b]thienyl, benzofuranyl, benzo[d]imidazolyl, quinoxalinyl, pyrazolo[1,5-a]pyrimidinyl, pyrazolo[1,5-a]pyridinyl, dihydrobenzo[b][1,4]dioxinyl, 4,5,6,7-tetrahydro-2H-indazolyl, benzo[d][1,3]dioxolyl, benzoxazolyl, benzothiazolyl, benzofuranyl, benzothienyl, naphthyl, indanyl, 1,2,3,4-tetrahydronaphthyl, 1,2,3,4-tetraydroquinolinyl, 5,6,7,8-tetrahydroquinolinyl and the like. The ring system may be joined to the rest of the molecule by any convenient nitrogen or carbon atom.

The term 'aryl' means an aromatic carbocyclic ring. Examples are phenyl, naphthyl and the like.

The term 'alicyclic' means a group having a carbocyclic ring structure which may be saturated or unsaturated, but may not be a benzenoid or other aromatic system.

The term 'aliphatic' means a non-aromatic group.

The term 'heteroaliphatic ring' means a heterocyclic ring that is wholly or partially saturated, but not aromatic. The ring has up to 10 atoms with up to 4 heteroatoms selected from N, O or S. Examples are piperidine, morpholine, tetrahydrofuran, pyrrolidine and the like.

The groups 'aryl', 'heteroaryl', 'fused bicyclic', 'alicyclic' and 'heteroaliphatic' ring may be substituted by one or more substituent groups selected from $C_{1-6}$ alkyl, $C_{3-6}$ cycloalkyl, halogen, cyano, nitro, SH, $S(O)_{0-2}R^{10}$, $NR^8R^9$, $S(O)_2NR^8R^9$, $C(O)NR^8R^9$, $C(O)OR^{10}$, $NR^{10}S(O)_2R^{11}$, $NR^{10}C(O)R^{10}$, $NR^{10}C(O)OR^{11}$, $NR^{10}C(O)NR^8N^9$, $OR^{10}$ Unless otherwise stated, in the context of the present specification alkyl groups and moieties may be straight or branched chain and include, for example, methyl, ethyl, n-propyl, iso-propyl, n-butyl, iso-butyl or tert-butyl. Cycloalkyl groups are monocyclic, for example cyclopentyl or cyclohexyl. Halogen is for example, fluoride, chloride or bromide.

In the context of the present specification, where it is stated that a group may be optionally substituted with up to three substituents, the group may be unsubstituted or substituted; when substituted the group will generally be substituted with one, two or three substituents. In general, a hydroxyl moiety will not be attached to a carbon atom which is adjacent to a nitrogen atom, another oxygen atom or a sulfur atom.

The invention further provides a process for the preparation of a compound of formula (I) or a pharmaceutically acceptable salt thereof as defined above which comprises:
  (i) when R³ is hydrogen, by reacting a compound of formula (III), or a suitable salt thereof, wherein R², R⁴, R⁵, R⁴', R⁵', R⁶, A, B, k, h, Q, L, L¹, L², L³, L⁴, R¹, m, n, V, W, X, Y and Z are as defined in formula (I), with a compound of formula (T) or a suitable salt thereof, wherein Ar is as defined in formula (I), in the presence of a suitable reducing agent (e.g. sodium cyanoborohydride, sodium triacetoxyborohydride, or hydrogen in the presence of a suitable palladium on carbon or platinum oxide catalyst) in a suitable solvent such as methanol or NMP.

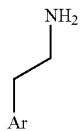

(T)

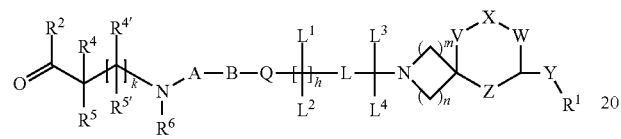

(III)

When $R^3$ is hydrogen, a compound of formula (III) can be prepared from a compound of formula (IV), wherein $R^{200}$ is an alkyl group and $R^2$, $R^4$, $R^5$, $R^{4'}$, $R^{5'}$, $R^6$, A, B, k, Q, h, L, $L^1$, $L^2$, $L^3$, $L^4$, $R^1$, m, n, V, W, X, Y and Z are as defined in formula (I), under suitable reaction conditions such as tosic acid in a suitable solvent such as tetrahydrofuran or dichloromethane.

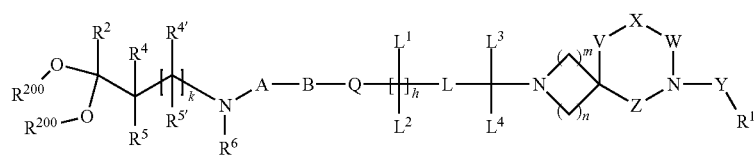

(IV)

also where $R^3$ is hydrogen, a compound of formula (III) can be prepared from a compound of formula (V), wherein $R^2$, $R^4$, $R^5$, $R^{4'}$, $R^{5'}$, $R^6$, A, B, k, h, Q, L, $L^1$, $L^2$, $L^3$, $L^4$, $R^1$, m, n, V, W, X, Y and Z are as defined in formula (I), using a suitable oxidising reagent (e.g. Dess-Martin periodinane, Swern reagent or pyridinium chlorochromate) in a suitable solvent (e.g. dichloromethane).

(V)

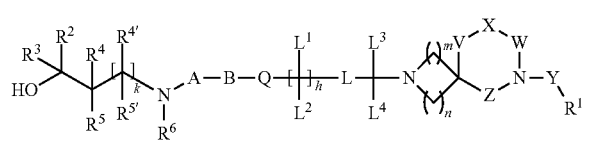

Where $R^2$ and $R^3$ are both hydrogen, a compound of formula (V) can be prepared from a compound of formula (VI), wherein $R^{201}$ is a hydrogen, an alkyl group or benzyl and $R^4$, $R^5$, $R^{4'}$, $R^{5'}$, $R^6$, A, B, k, h, Q, L, $L^1$, $L^2$, $L^3$, $L^4$, $R^1$, m, n, V, W, X, Y and Z are as defined in formula (I), using a suitable reducing reagent (e.g. borane or borane dimethylsulphide complex) in a suitable solvent such as tetrahydrofuran at a suitable temperature from e.g. −5° C. to 70° C.

(VI)

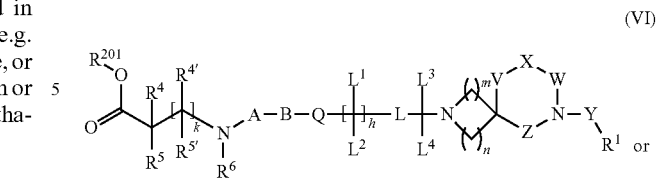

(ii) by reacting a compound of formula (VII) wherein $LG^1$ is a suitable leaving group such as halogen, tosylate or mesylate, $R^2$ is hydrogen and $R^3$, $R^4$, $R^5$, $R^{4'}$, $R^{5'}$, $R^6$, A, B, k, h, Q, L, $L^1$, $L^2$, $L^3$, $L^4$, $R^1$, m, n, V, W, X, Y and Z are as defined in formula (I), with a compound of formula (T) in a suitable solvent such as MeCN or NMP at a temperature of rt to 90° C. in the presence of a suitable base (e.g. triethylamine, Hunig's base, cesium carbonate or potassium carbonate).

(VII)

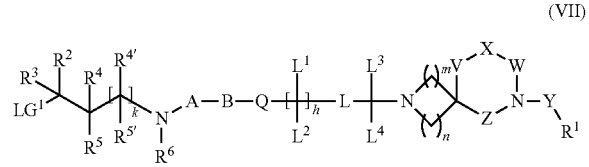

A compound of formula (VII) can be made from compound (V) using suitable reaction conditions (e.g. where $LG^1$ is OTs or OMs: TsCl or MsCl, a suitable base (e.g. triethylamine, Hunig's base, cesium carbonate or potassium carbonate), in a suitable solvent such as dichloromethane or NMP; where $LG^1$ is bromide: $CBr_4$ and $PPh_3$ in a suitable solvent such as dichloromethane).

or (iii) by reacting a compound of formula (IX) wherein $R^2$, $R^3$, $R^4$, $R^5$, $R^{4'}$, $R^{5'}$, $R^6$, A, B, k, h, Q, L, $L^1$, $L^2$, $L^3$, $L^4$, $R^1$, m, n, V, W, X, Y and Z are as defined in formula (I), with a compound of formula (VIII), wherein Ar is as defined in formula (I), in the presence of a suitable reducing agent (e.g. sodium cyanoborohydride, sodium triacetoxyborohydride, or hydrogen in the presence of a suitable palladium on carbon or platinum oxide catalyst) in a suitable solvent such as methanol or NMP.

(VIII)

(IX)

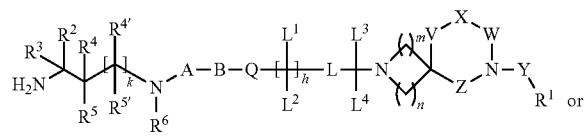

(iv) by reacting a compound of formula (X) wherein $LG^2$ is a suitable leaving group such as halogen, tosylate or mesylate with a compound of formula (IX) wherein $R^2$, $R^3$, $R^4$, $R^5$, $R^{4'}$, $R^{5'}$, $R^6$, A, B, k, h, Q, L, $L^1$, $L^2$, $L^3$, $L^4$, $R^1$, m, n, V, W, X, Y and Z are as defined in formula (I), in the presence of a suitable base (such as triethylamine, Hunig's base, cesium carbonate or potassium carbonate) in a suitable solvent such as MeCN or NMP at a temperature of rt to 90° C.

(x)

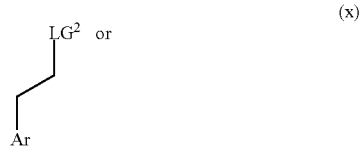

(v) where A is C(O), from a compound of formula (XI) (where $PG^1$ is a suitable nitrogen protecting group (e.g. tert-butylcarbamate or 3-nitrophenylsulfonyl) and Ar, $R^2$, $R^3$, $R^4$, $R^5$, $R^{4'}$, $R^{5'}$, $R^6$, and k are as defined in formula (I)) and a compound of formula (XII), wherein $LG^{10}$ represents hydroxyl or a leaving group (e.g. chlorine) and B, h, Q, L, $L^1$, $L^2$, $L^3$, $L^4$, $R^1$, m, n, V, W, X, Y and Z are as defined in formula (I); followed by removal of the protective group (e.g. treatment with hydrochloric or trifluoroacetic acid, thiophenol, thioacetic acid).

When $LG^{10}$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in the presence of a base (e.g. triethylamine), at a temperature, for example in the range from 0 to 60° C. When $LG^{10}$ represents chlorine, the reaction is conveniently carried out in the presence of a base, (e.g. triethylamine or diisopropylethylamine) in an organic solvent, (e.g. dichloromethane or tetrahydrofuran) at a temperature, for example, in the range from 0 to 25° C.

(XI)

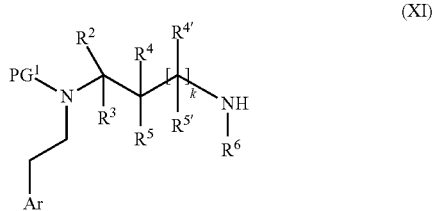

(XII)

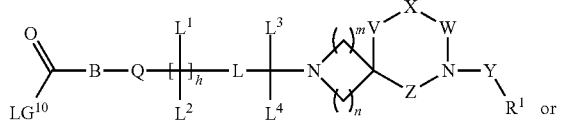

(vi) where A is C(O) and B is $CH_2CH_2$ from a compound of formula (XIII) (wherein $PG^1$ is a suitable nitrogen protecting group and Ar, $R^2$, $R^3$, $R^4$, $R^5$, $R^{4'}$, $R^{5'}$, $R^6$, and k are as defined in formula (I)) and a compound of formula (XIV) (wherein Q, h, L, $L^1$, $L^2$, $L^3$, $L^4$, $R^1$, m, n, V, W, X, Y and Z are as defined in formula (I)) under suitable reaction conditions such as with benzyltrimethylammonium hydroxide in a suitable solvent or mixture of solvents such as toluene or acetonitrile; followed by removal of the protective group.

(XIII)

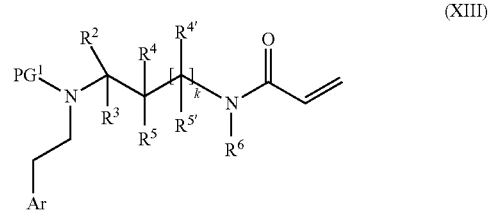

(XIV)

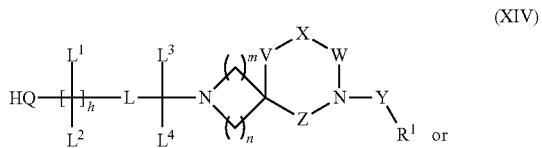

(vii) when $L^4$ represents hydrogen, by reacting a compound of formula (XV) wherein $PG^2$ is a suitable nitrogen protecting group (e.g. tert-butylcarbamate or 3-nitrophenylsulfonyl) and Ar, $R^2$, $R^3$, $R^4$, $R^5$, $R^{4'}$, $R^{5'}$, $R^6$, A, B, k, h, Q, L, $L^1$, $L^2$, $L^3$ are as defined in formula (I) with a compound of formula (XVI) where $R^1$, m, n, V, W, X, Y and Z are as defined in formula (I), in the presence of a suitable reducing agent (e.g. sodium cyanoborohydride, sodium triacetoxyborohydride, or hydrogen in the presence of a palladium on carbon or platinum oxide catalyst), followed by removal of the protective group (e.g. treatment with hydrochloric or trifluoroacetic acid, thiophenol, thioacetic acid).

(XV)

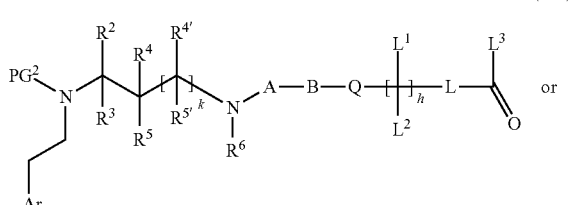

(XVI)

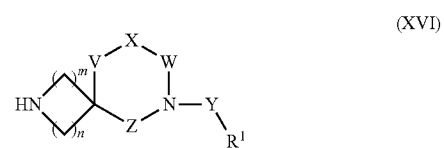

(viii) by reacting a compound of formula (XVII) wherein $PG^2$ is a suitable nitrogen protecting group (e.g. tert-butylcarbamate or 3-nitrophenylsulfonyl) and Ar, $R^2$, $R^3$, $R^4$, $R^5$, $R^{4'}$, $R^{5'}$, $R^6$, A, k, h, Q, L, $L^1$, $L^2$, $L^3$, $L^4$, are as defined in formula (I) and $LG^3$ is a suitable leaving group such as halogen, tosylate or mesylate with a compound of formula (XVI) wherein $R^1$, m, n, V, W, X, Y and Z are as defined in formula (I)) in the presence of a suitable base (such as triethylamine, Hunig's base, cesium carbonate or potassium carbonate) in a suitable solvent (such as MeCN or NMP) at a temperature of rt to 80° C., followed by removal of the protective group (e.g. treatment with hydrochloric or trifluoroacetic acid, thiophenol, thioacetic acid).

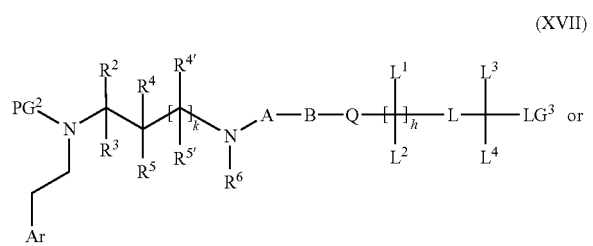

(XVII)

(ix) by reacting a compound of formula (XVIII), wherein $PG^3$ is a suitable nitrogen protecting group (e.g. tert-butylcarbamate or 3-nitrophenylsulfonyl) and Ar, $R^2$, $R^3$, $R^4$, $R^5$, $R^{4'}$, $R^{5'}$, $R^6$, A, B, k, h, Q, L, $L^1$, $L^2$, $L^3$, $L^4$ are as defined in formula (I), with a compound of formula (XIX) wherein $R^1$ and Y are as defined in formula (I) and $LG^4$ represent hydroxyl or a leaving group (e.g. a halide such as chloride), or a suitable salt thereof, followed by removal of the protective group (e.g. using hydrochloric acid or trifluoroacetic acid).

When $LG^4$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in the presence of a base (e.g. triethylamine), at a temperature, for example in the range from 0 to 60° C.

When $LG^4$ represents a halide (e.g. chloride), the reaction is conveniently carried out in the presence of a base, for example, triethylamine, diisopropylethylamine or pyridine in an organic solvent, for example, dichloromethane or tetrahydrofuran at a temperature, for example, in the range from 0 to 25° C.

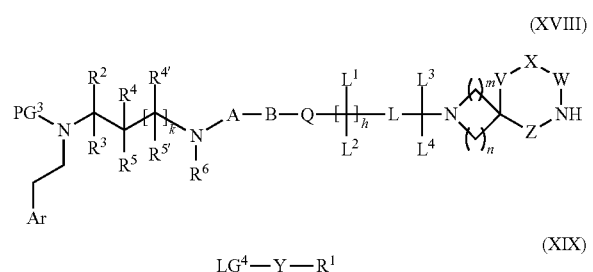

(XVIII)

(XIX)

A compound of formula (IV) where A is C(O) can be made from a compound of formula (XX), wherein $R^{200}$ is an alkyl group and $R^2$, $R^3$, $R^4$, $R^5$, $R^{4'}$, $R^{5'}$, $R^6$ and k are as is defined in formula (I), and a compound of formula (XII) where $LG^{10}$ represents hydroxyl or a leaving group (e.g. chlorine);

When $LG^{10}$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in the presence of a base (e.g. triethylamine), at a temperature, for example in the range from 0 to 60° C., when $LG^{10}$ represents chlorine, the reaction is conveniently carried out in the presence of a base, (e.g. triethylamine or diisopropylethylamine) in an organic solvent, (e.g. dichloromethane or tetrahydrofuran) at a temperature, for example, in the range from 0 to 25° C.

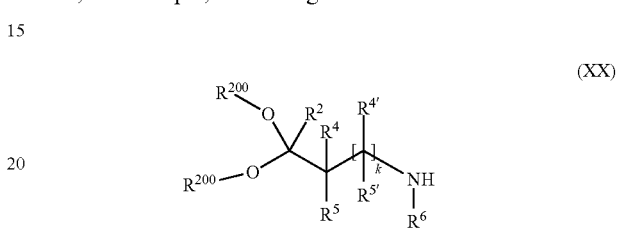

(XX)

A compound of formula (V) where A is C(O) can be made from a compound of formula (XXI), wherein $R^2$, $R^3$, $R^4$, $R^5$, $R^{4'}$, $R^{5'}$, $R^6$ and k are as defined in formula (I), and a compound of formula (XII) where $LG^{10}$ represents hydroxyl or a leaving group (e.g. chlorine);

When $LG^{10}$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in the presence of a base (e.g. triethylamine), at a temperature, for example in the range from 0 to 60° C., when $LG^{10}$ represents chlorine, the reaction is conveniently carried out in the presence of a base, (e.g. triethylamine or diisopropylethylamine) in an organic solvent, (e.g. dichloromethane or tetrahydrofuran) at a temperature, for example, in the range from 0 to 25° C.

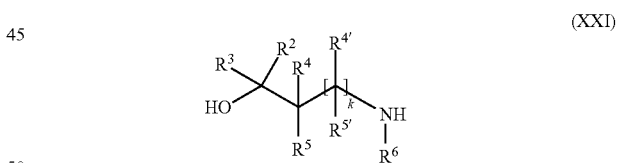

(XXI)

A compound of formula (VI) where A is C(O) can be made from a compound of formula (XXII), wherein $R^{201}$ is an alkyl group and $R^4$, $R^5$, $R^{4'}$, $R^{5'}$, $R^6$ and k are as defined in formula (I), and a compound of formula (XII) where $LG^{10}$ is represent hydroxyl or a leaving group (e.g. chlorine).

When $LG^{10}$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in the presence of a base (e.g. triethylamine), at a temperature, for example in the range from 0 to 60° C.

When $LG^{10}$ represents chlorine, the reaction is conveniently carried out in the presence of a base, (e.g. triethylamine or diisopropylethylamine) in an organic solvent, (e.g. dichloromethane or tetrahydrofuran) at a temperature, for example, in the range from 0 to 25° C.

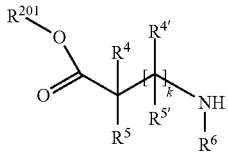
(XXII)

A compound of formula (XII), or a suitable salt thereof, wherein $LG^{10}$ is hydroxyl and where A is C(O) and B, h, Q, L, $L^1$, $L^2$, $L^3$, $L^4$, $R^1$, m, n, V, W, X, Y and Z are as defined in formula (I), can be made from a compound of formula (XXIII), wherein $R^{202}$ is an alkyl group such as tert-butyl under suitable reaction conditions such as acidic conditions (e.g. trifluoroacetic acid in dichloromethane).

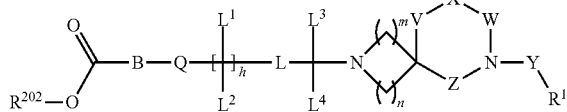
(XXIII)

A compound of formula (XII), or a suitable salt thereof, wherein $LG^{10}$ is chloride and where A is C(O) and h, Q, L, $L^1$, $L^2$, $L^3$, $L^4$, $R^1$, m, n, V, W, X, Y and Z are as defined in formula (I), can be prepared from a compound of formula (XII) where $LG^{10}$ is hydroxyl under suitable reaction conditions (e.g. oxalyl chloride or thionyl chloride) in a suitable solvent such as dichloromethane.

A compound of formula (XXIII), or a suitable salt thereof, where A is C(O) and B is $CH_2CH_2$ and Q, h, L, $L^1$, $L^2$, $L^3$, $L^4$, $R^1$, m, n, V, W, X, Y and Z are as defined in formula (I), can be made from a compound of formula (XIV) and a compound of formula (XXIV) (where $R^{202}$ is alkyl e.g. tert-butyl) under suitable reaction conditions such as with benzyltrimethylammonium hydroxide in a suitable solvent or mixture of solvents such as toluene or acetonitrile.

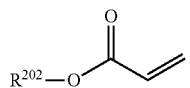
(XXIV)

When $L^4$ is hydrogen, a compound of formula (XIV) can be prepared by reacting a compound of formula (XXV), wherein Q is oxygen or sulphur and h, L, $L^1$, $L^2$, $L^3$, are as defined in formula (I), with a compound of formula (XVI) or a suitable salt thereof wherein $R^1$, m, n, V, W, X, Y and Z are as defined in formula (I), in the presence of a suitable reducing agent (e.g. sodium cyanoborohydride, sodium triacetoxyborohydride, or hydrogen in the presence of a suitable palladium on carbon or platinum oxide catalyst) in a suitable solvent such as methanol or NMP.

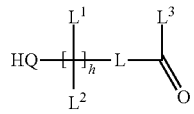
(XXV)

A compound of formula (XIV) wherein Q is oxygen, $L^4$ is hydrogen and L, $L^1$, $L^2$, $L^3$, are as defined in formula (I) can be prepared by reacting a compound of formula (XXVI), wherein Q is oxygen, $L^4$ is hydrogen and h, L, $L^1$, $L^2$, $L^3$, are as defined in formula (I), and $LG^4$ is a suitable leaving group such as halogen, tosylate or mesylate with a compound of formula (XVI) wherein $R^1$, m, n, V, W, X, Y and Z are as defined in (I), in the presence of a suitable base (such as triethylamine, Hunig's base, cesium carbonate or potassium carbonate) in a suitable solvent (such as MeCN or NMP) at a temperature of rt to 80° C.

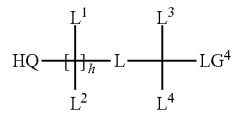
(XXVI)

A compound of formula (XIV) can be prepared by reacting a compound of formula (XXVII), wherein Q is oxygen, h, L, $L^1$, $L^2$, $L^3$, $L^4$, m, n, V, W, X and Z are as defined in formula (I), with a compound of formula (XIX) wherein $R^1$ and Y are as defined in formula (I) and $LG^4$ represent hydroxyl or a leaving group (e.g. halide such as chloride), or a suitable salt thereof.

When $LG^4$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in the presence of a base (e.g. triethylamine), at a temperature, for example in the range from 0 to 60° C.

When $LG^4$ represents a halide (e.g. chloride), the reaction is conveniently carried out in the presence of a base, for example, triethylamine, diisopropylethylamine or pyridine in an organic solvent, for example, dichloromethane or tetrahydrofuran at a temperature, for example, in the range from 0 to 25° C.

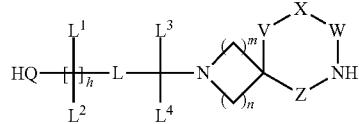
(XXVII)

A compound of formula (IX) where A is C(O) can be made from a compound of formula (XXVIII) (where $PG^4$ is a suitable nitrogen protecting group (e.g. tert-butylcarbamate or 3-nitrophenylsulfonyl) and $R^2$, $R^3$, $R^4$, $R^5$, $R^{4'}$, $R^{5'}$, $R^6$ and k are as defined in formula (I)) and a compound of formula (XII) where $LG^{10}$ represents hydroxyl or a leaving group (e.g. chlorine) and h, Q, L, $L^1$, $L^2$, $L^3$, $L^4$, $R^1$, m, n, V, W, X, Y and Z are as defined in formula (I); followed by removal of the protective group (e.g. treatment with hydrochloric or trifluoroacetic acid, thiophenol, thioacetic acid).

When $LG^{10}$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N, N',N'-tetramethyluroniumhexafluorophosphate (HATU), in an organic solvent, for example, N,N-dimethylformamide or dichloromethane, optionally in the presence of a base (e.g. triethylamine), at a temperature, for example in the range from 0 to 60° C., when $LG^{10}$ represents chlorine, the reaction is conveniently carried out in the presence of a base, (e.g. triethylamine or diisopropylethylamine) in an organic solvent, (e.g. dichloromethane or tetrahydrofuran) at a temperature, for example, in the range from 0 to 25° C.

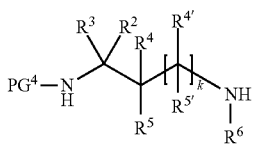

(XXVIII)

A compound of formula (XI) can be prepared by reacting a compound of formula (XXIX) wherein $PG^5$ is a suitable protecting group and $R^2$, $R^3$, $R^4$, $R^5$, $R^{4'}$, $R^{5'}$, $R^6$ and k are as defined in formula (I), with a compound of formula (VIII) in the presence of a suitable reducing agent (e.g. sodium cyanoborohydride, sodium triacetoxyborohydride, or hydrogen in the presence of a suitable palladium on carbon or platinum oxide catalyst) in a suitable solvent such as methanol or NMP; followed by addition of $PG^1$ and removal of $PG^5$.

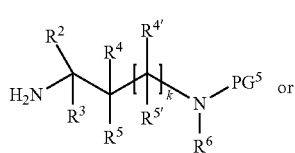

(XXIX)

a compound of formula (XI) wherein $PG^1$ is a suitable protecting group, can be prepared by reacting a compound of formula (XXIX) wherein $PG^5$ is a suitable protecting group $R^2$, $R^3$, $R^4$, $R^5$, $R^{4'}$, $R^{5'}$, $R^6$ and k are as defined in formula (I), with a compound of formula (X) wherein $LG^2$ is a suitable leaving group such as halogen, tosylate or mesylate in the presence of a suitable base (such as triethylamine, Hunig's base, cesium carbonate or potassium carbonate) in a suitable solvent such as MeCN or NMP at a temperature of rt to 80° C.

or

A compound of formula (XI) wherein $PG^1$ is a suitable protecting group, can be prepared by reacting a compound of formula (XXX) wherein $PG^5$ is a suitable nitrogen protecting group, $R^3$ is hydrogen and $R^2$, $R^4$, $R^5$, $R^{4'}$, $R^{5'}$, $R^6$ and k are as defined in formula (I), with a compound of formula (T) in the presence of a suitable reducing agent (e.g. sodium cyanoborohydride, sodium triacetoxyborohydride, or hydrogen in the presence of a suitable palladium on carbon or platinum oxide catalyst) in a suitable solvent such as methanol or NMP; followed by addition of $PG^1$ and removal of $PG^5$.

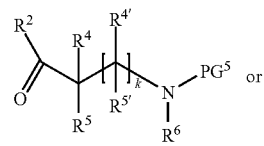

(XXX)

A compound of formula (XI), wherein $PG^1$ is a suitable protecting group and $R^2$, $R^3$, $R^4$, $R^5$, $R^{4'}$, $R^{5'}$, $R^6$ and k are as defined in (I), can be prepared by reacting a compound of formula (XXXI) wherein $PG^6$ is a suitable nitrogen protecting group, $R^2$, $R^3$, $R^4$, $R^5$, $R^{4'}$, $R^{5'}$, $R^6$ and k are as defined in formula (I), and $LG^5$ is a suitable leaving group such as halogen, tosylate or mesylate with a compound of formula (T) in the presence of a suitable base (such as triethylamine, Hunig's base, cesium carbonate or potassium carbonate) in a suitable solvent such as MeCN or NMP at a temperature of rt to 80° C.; followed by addition of $PG^1$ and removal of $PG^6$.

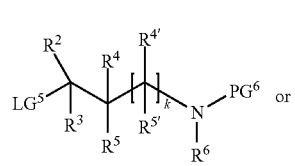

(XXXI)

A compound of formula (XVIII), wherein A is C(O), $PG^3$ is a suitable protecting group and Ar, $R^2$, $R^3$, $R^4$, $R^5$, $R^{4'}$, $R^{5'}$, $R^6$, B, k, h, Q, L, $L^1$, $L^2$, $L^3$, $L^4$ are as defined in formula (I), can be prepared by reacting a compound of formula (XI), wherein $PG^1$=$PG^3$ and Ar, $R^2$, $R^3$, $R^4$, $R^5$, $R^{4'}$, $R^{5'}$, $R^6$, k are as defined in formula (I), with a compound of formula (XXXII) wherein $PG^7$ is suitable nitrogen protecting group and $LG^{11}$ represent hydroxyl or a leaving group (e.g. halide, chloride), or a suitable salt thereof, B, h, Q, L, $L^1$, $L^2$, $L^3$, $L^4$, m, n, V, W, X and Z are as defined in formula (I).

When $LG^{11}$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N, N',N'-tetramethyluroniumhexafluorophosphate (HATU), in an organic solvent, for example, N,N-dimethylformamide or dichloromethane, optionally in the presence of a base (e.g. triethylamine), at a temperature, for example in the range from 0 to 60° C.

When $LG^{11}$ represents a halide (e.g. chloride), the reaction is conveniently carried out in the presence of a base, for example, triethylamine, diisopropylethylamine or pyridine in an organic solvent, for example, dichloromethane or tetrahydrofuran at a temperature, for example, in the range from 0 to 25° C.;

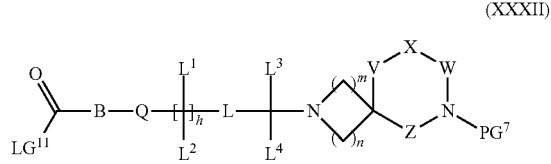

(XXXII)

A compound of formula (XXXII), or a suitable salt thereof (wherein $LG^{11}$ is hydroxy, A is C(O), B is $CH_2CH_2$, h, Q, L, $L^1$, $L^2$, $L^3$, $L^4$, m, n, V, W, X and Z are as defined in formula (I), $PG^7$ is suitable nitrogen protecting group) can be made from a compound of formula (XXXIII) (wherein $PG^7$ is suitable nitrogen protecting group and Q, h, L, $L^1$, $L^2$, $L^3$, $L^4$, m, n, V, W, X and Z are as defined in formula (I)) and a compound of formula (XXIV) (where $R^{202}$ is alkyl e.g. tert-butyl) under suitable reaction conditions such as with benzyltrimethylammonium hydroxide in a suitable solvent or mixture of solvents such as toluene or acetonitrile; followed by conversion to the carboxylic acid ($LG^{11}$ is hydroxyl) under suitable conditions (e.g. when $R^{202}$ is tert-butyl: treatment with TFA in dichloromethane).

A compound of formula (XXXII), or a suitable salt thereof, wherein $LG^{11}$ is chloride can be prepared from a compound of formula (XXXII) where $LG^{11}$ is hydroxyl under suitable reaction conditions (e.g. oxalyl chloride or thionyl chloride) in a suitable solvent such as dichloromethane.

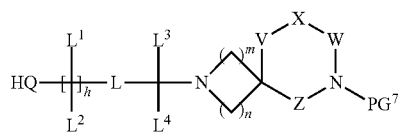

(XXXIII)

When $L^4$ is hydrogen, a compound of formula (XXXIII) can be prepared by reacting a compound of formula (XXV), wherein Q is oxygen or sulphur and h, L, $L^1$, $L^2$, $L^3$, are as defined in formula (I), with a compound of formula (XXXIV) or a suitable salt thereof (wherein $PG^7$ is a suitable nitrogen protecting group and m, n, V, W, X and Z are as defined in formula (I)) in the presence of a suitable reducing agent (e.g. sodium cyanoborohydride, sodium triacetoxyborohydride, or hydrogen in the presence of a suitable palladium on carbon or platinum oxide catalyst) in a suitable solvent such as methanol or NMP.

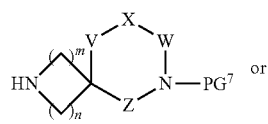

(XXXIV)

A compound of formula (XXXIII), wherein $L^4$ is hydrogen, can be prepared by reacting a compound of formula (XXVI), wherein Q is oxygen, $L^4$ is hydrogen and h, L, $L^1$, $L^2$, $L^3$, are as defined in formula (I), and $LG^4$ is a suitable leaving group such as halogen, tosylate or mesylate with a compound of formula (XXXIV) (wherein $PG^7$ is a suitable nitrogen protecting group and m, n, V, W, X and Z are as defined in formula (I)) in the presence of a suitable base (such as triethylamine, Hunig's base, cesium carbonate or potassium carbonate) in a suitable solvent (such as MeCN or NMP) at a temperature of rt to 80° C.

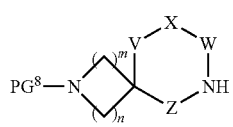

(XXXV)

A compound of formula (XXXV), wherein V represents a bond, X represents O, W represents $CH_2CH_2$, Z represents $CH_2$, m and n are as defined in formula (I) and $PG^8$ represents an appropriate nitrogen protecting group such tert-butoxycarbonyl, can be prepared from a compound of formula (XXXVI), wherein m and n are as defined in compound of formula (XXXV), by treatment with a suitable reducing agent such as borane-THF complex in a suitable solvent such as tetrahydrofuran at 30-70° C. with the resulting boron complex decomposed with a suitable amine such as N1, N2-dimethylethane-1,2-diamine in methanol at 60-90° C.

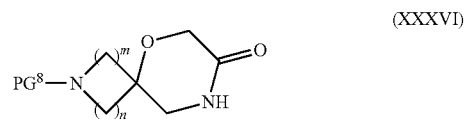

(XXXVI)

A compound of formula (XXXVI) can be prepared from a compound of formula (XXXVII), wherein $LG^{12}$ is a suitable leaving group such as halogen or tosylate and $PG^8$, m and n are as defined in compound of formula (XXXV), by treatment with a suitable base such as potassium tert-butoxide in a suitable solvent such as tetrahydrofuran at 50-90° C.

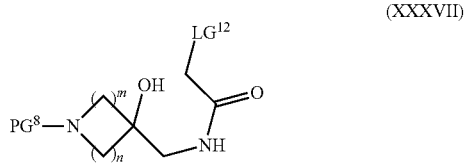

(XXXVII)

A compound of formula (XXXVII) can be prepared by reacting a compound of formula (XXXVIII) with a compound of formula (XXXIX) wherein $LG^{13}$ represents a hydroxyl or halogen group such as chloride and $PG^8$, m, n and $LG^{12}$ are as defined in compound of formula (XXXVII);

For the case where $LG^{13}$ represents hydroxyl, the reaction is conveniently carried out in the presence of an activating reagent, for example, carbonyldiimidazole, 1-propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in a presence of a suitable base (e.g. triethylamine), at a temperature, for example in the range from 0 to 60° C.

For the case where $LG^{13}$ represents chloride, the reaction is conveniently carried out in the presence of a base, for example, triethylamine or diisopropylethylamine in an organic solvent, for example, dichloromethane or tetrahydrofuran at a temperature, for example, in the range from 0 to 25° C.

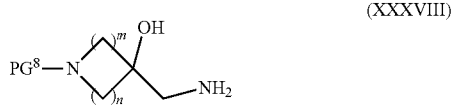

(XXXVIII)

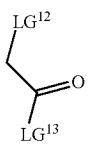
(XXXIX)

A compound of formula (XXXVIII) can be prepared by reacting a compound of formula (XL), wherein $PG^8$, m and n are as defined in compound of formula (XXXV), with ammonia in a suitable solvent such as methanol at a temperature in the range from 20-60° C.

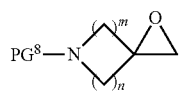
(XL)

A compound of formula (XL) can be prepared by reacting a compound of formula (XLI), wherein $PG^8$, m and n are as defined in compound of formula (XXXV), with trimethyl sulfoxonium iodide in the presence of a suitable base such as sodium hydride or potassium tert-butoxide in a suitable solvent such as dimethylsufoxide at a temperature in the range from 0-20° C.

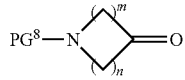
(XLI)

A compound of general formula (XXXV), wherein m and n are as defined in formula (I), V represents a bond, X represents O, W represents $CH_2CH_2$, Z represents $CH_2$, and $PG^8$ represents an appropriate nitrogen protecting group can be prepared from a compound of formula (XLII) under suitable reaction conditions such as in strong acid

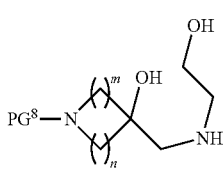
(XLII)

A compound of general formula (XLII), wherein $PG^8$ is a suitable protecting group, can be made by reacting a compound of formula (XL) with ethanolamine.

A compound of general formula (XXXV), wherein m and n are as defined in formula (I), V represents a bond, X represents O, W represents $CH_2CH_2$, Z represents $CH_2$, and $PG^8$ represents an appropriate nitrogen protecting group can be prepared from a compound of formula (XLIII) where $LG^{14}$ is a suitable leaving group such as halogen, OMs or OTs under suitable reaction conditions.

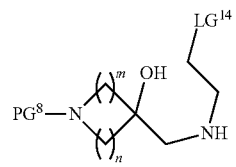
(XLIII)

A compound of general formula (XLIII), wherein $PG^8$, m and n are as defined in formula (XXXV), can be formed from a compound of formula (XLII) under appropriate conditions.

Convenient compounds of formula (III) include those where $R^2$, $R^4$ and $R^5$ are hydrogen, k is 0, A is C(O), B is $CH_2CH_2$, h is 1, Q is oxygen, $L^1$, $L^2$, $L^3$, $L^4$ are each hydrogen, m and n=2, V=bond, Z=$CH_2$, X=O and W=$CH_2CH_2$, Y=CO, $R^1$ is 4-thiazole optionally substituted in the 2-position of the thiazole by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl; or $R^1$ is 3-thiophene optionally substituted in the 5-position of the thiophene by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl.
4-thiazole and 3-thiophene are as represented in formula (XLIV)

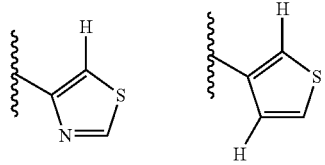
(XLIV)

Convenient compounds of formula (IV) include those where $R^2$, $R^4$ and $R^5$ are hydrogen, k is 0, A is C(O), B is $CH_2CH_2$, h is 1, Q is oxygen, $L^1$, $L^2$, $L^3$, $L^4$ are each hydrogen, m and n=2, V=bond, Z=$CH_2$, X=O and W=$CH_2CH_2$, Y=CO, $R^1$ is 4-thiazole optionally substituted in the 2-position of the thiazole by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl; or $R^1$ is 3-thiophene optionally substituted in the 5-position of the thiophene by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl.
$R^1$=4-thiazole and 3-thiophene are as represented in formula (XLIV).

Convenient compounds of formula (XII) include those where h is 1, Q is oxygen, $L^1$, $L^2$, $L^3$, $L^4$ are each hydrogen, m and n=2, V=bond, Z=$CH_2$, X=O and W=$CH_2CH_2$, Y=CO, $R^1$ is 4-thiazole optionally substituted in the 2-position of the thiazole by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl; or $R^1$ is 3-thiophene optionally substituted in the 5-position of the thiophene by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl;
$R^1$=4-thiazole and 3-thiophene are as represented in formula (XLIV)

Convenient compounds of formula (XIV) include those where Q is oxygen, $L^1$, $L^2$, $L^3$, $L^4$ are each hydrogen, m and n=2, V=bond, Z=$CH_2$, X=O and W=$CH_2CH_2$, Y=CO, $R^1$ is 4-thiazole optionally substituted in the 2-position of the thiazole by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl; or $R^1$ is 3-thiophene optionally substituted in the 5-position of the thiophene by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl; $R^1$=4-thiazole and 3-thiophene are as represented in formula (XLIV).

Convenient compounds of formula (XVI) include those where m and n=2, V=bond, Z=$CH_2$, X=O and W=$CH_2CH_2$, Y=CO, $R^1$ is 4-thiazole optionally substituted in the 2-position of the thiazole by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl; or $R^1$ is 3-thiophene optionally substituted in the 5-position of the thiophene by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl;
$R^1$=4-thiazole and 3-thiophene are as represented in formula (XLIV)

Convenient compounds of formula (XXIII) include those where $R^{202}$ is tert-butyl, B $CH_2CH_2$, h is 1, $L^1$, $L^2$, $L^3$, $L^4$ are each hydrogen, Q is oxygen, m and n=2, V=bond, Z=$CH_2$, X=O and W=$CH_2CH_2$, Y=CO, $R^1$ is 4-thiazole optionally substituted in the 2-position of the thiazole by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl; or $R^1$ is 3-thiophene optionally substituted in the 5-position of the thiophene by methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl;
$R^1$=4-thiazole and 3-thiophene are as represented in formula (XLIV).

Compounds of formula (T), (VIII), (X), (XXIV), (XIX), (XXXIX), (XLI)) are either commercially available, known in the literature, or can be readily prepare by those skilled in the art using one of the process described above or using known techniques.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the addition or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

Compounds of formula (I) can be converted into further compounds of formula (I) using standard procedures.

The compounds of formula I have activity as pharmaceuticals, in particular as dual adrenergic β receptor agonists and anticholinergic agents including muscarinic receptor (M1, M2, and M3) antagonists, in particular M3 antagonists. Diseases and conditions which may be treated with the compounds of formula (I) and their pharmaceutically acceptable salts include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinophilic gastro-enteritis, mastocytosis, Crohn's disease, ulcerative colitis, microscopic colitis, indeterminate colitis, irritable bowel disorder, irritable bowel syndrome, non-inflammatory diarrhea, food-related allergies which have effects remote from the gut, e.g., migraine, rhinitis and eczema.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating, or reducing the risk of, an inflammatory disease or condition (including a reversible obstructive airways disease or condition) which comprises administering to a patient in need thereof a therapeutically effective amount of a compound of formula (I) or a pharmaceutically acceptable salt thereof as hereinbefore defined.

In particular, the compounds of this invention may be used in the treatment of adult respiratory distress syndrome (ARDS), pulmonary emphysema, bronchitis, bronchiectasis, chronic obstructive pulmonary disease (COPD), asthma and rhinitis.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, Hydrofluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the abovementioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

In particular, the compounds of the present invention and salts thereof may be used in the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The compounds of the invention may also be administered in conjunction with other compounds used for the treatment of the above conditions.

The invention therefore further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed above.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxifylline.

In addition the invention relates to a combination of a compound of the invention, or a pharmaceutically acceptable salt thereof, with a monoclonal antibody targeting B-Lymphocytes (such as CD20 (rituximab), MRA-aIL16R) or T-Lymphocytes (CTLA4-Ig, HuMax I1-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4 selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$- or $B_2$-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$. or $NK_3$. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; (xxvii) inhibitor of transcription factor activation such as NFkB, API or STATS; or (xxviii) a glucocorticoid receptor (GR-receptor) agonist.

In a further aspect the present invention provides a combination (for example for the treatment of COPD, asthma or allergic rhinitis) of a compound of formula (I) and one or more agents selected from the list comprising:
- a non-steroidal glucocorticoid receptor (GR-receptor) agonist;
- a PDE4 inhibitor including an inhibitor of the isoform PDE4D;
- a modulator of chemokine receptor function (such as a CCR1 receptor antagonist);
- a steroid (such as budesonide); and
- an inhibitor of p38 kinase function.

A compound of the invention, or a pharmaceutically acceptable salt thereof, can also be used in combination with an existing therapeutic agent for the treatment of cancer, for example suitable agents include:
(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);
(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;
(iii) an agent which inhibits cancer cell invasion (for example a metalloproteinase inhibitor like marimastat or an inhibitor of urokinase plasminogen activator receptor function);
(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;
(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);
(vi) a vascular damaging agent such as combretastatin A4, or a compound disclosed in WO 99/02166, WO 00/40529, WO 00/41669, WO 01/92224, WO 02/04434 or WO 02/08213;
(vii) an agent used in antisense therapy, for example one directed to one of the targets listed above, such as ISIS 2503, an anti-ras antisense;
(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

The compounds of formula (I) above may be converted to a pharmaceutically acceptable salt thereof, for example an acid addition salt such as a hydrochloride (for example a dihydrochloride), hydrobromide (for example a dihydrobromide), trifluoroacetate (for example a di-trifluoroacetate), sulphate, phosphate, acetate, fumarate, maleate, tartrate, lactate, citrate, pyruvate, succinate, oxalate, methanesulphonate or p-toluenesulphonate.

The invention will now be illustrated but not limited by reference to the following Examples wherein the following General Methods were used:

General Methods

Unless stated otherwise, starting materials were commercially available. All solvents and commercial reagents were of laboratory grade and were used as received. All operations were carried out at ambient temperature, i.e. in the range 17 to 28° C. and, where appropriate, under an atmosphere of an inert gas such as nitrogen. 'Microwave' heating refers to heating to constant temperature, using variable power microwave irradiation in a CEM Discover® microwave reactor. Hydrogenation reactions were carried out using a Büchi Peteric® system or a ThalesNano H-Cube® system, as detailed. Concentration of all solutions was carried out by evaporation under reduced pressure (in vacuo), e.g. using a Büchi Rotavapor® rotary evaporator.

Thin Layer Chromatography (TLC) was carried out using aluminium- or glass-backed plates coated with silica (particle size<63 µm; porosity 60 Å; surface area ~500 m²/g), with a fluorescent ($UV_{254}$) indicator. Following elution, the plates were visualized by either $UV_{254}$ irradiation, or development with a suitable indicator, such as iodine (pre-absorbed onto silica), an aqueous solution of potassium permanganate, or an aqueous solution of cerium (IV) ammonium nitrate. Examples of indicator preparations can be found in 'Experimental Organic Chemistry: Preparative and Microscale' $2^{nd}$ Ed. (Harwood, L., Moody, C. and Percy, J.), WileyBlackwell, 1998.

Analytical HPLC was carried out using either a Waters XBridge™ C8 3.5 µm column eluting with a gradient of acetonitrile in either 0.1% aqueous trifluoroacetic acid, 0.1% aqueous formic acid, 0.1% aqueous ammonium acetate or 0.1% aqueous ammonia; a Waters XBridge™ C18 3.5 µm column with a gradient of acetonitrile in 0.1% aqueous ammonia; a Waters Symmetry™ C18 3.5 µm column with a gradient of acetonitrile in 0.1% aqueous trifluoroacetic acid; a Waters Sunfire™ C8 3.5 µm column with a gradient of acetonitrile in 0.1% aqueous trifluoroacetic acid; or a Phenomenex Gemini™ C18 3 µm column with a gradient of acetonitrile in 0.1% aqueous trifluoroacetic acid. UV spectra of the eluted peaks were measured using a diode array on an Agilant 1100® system, or equivalent.

Medium pressure liquid chromatography (MPLC) on silica (particle size<63 µm; porosity 60 Å; surface area ~500 m²/g) was carried out using pre-packed Biotage FLASH™ columns or equivalent, e.g. Thomson SINGLE StEP™, Biotage Isolute™, Teledyne Isco RediSep™, or Silicycle UltraPure silica columns at recommended solvent flow rates and sample loadings. Fraction purity was determined by either TLC or analytical HPLC.

Preparative HPLC was carried out using a gradient of acetonitrile or methanol in 0.1% or 0.2% aqueous TFA, aqueous formic acid or aqueous ammonia solution, using a Phenomenex Gemini™ NX C18 (30×100 mm, 5 µm) column, a Waters Sunfire™ Prep C8 (30×100 mm, 10 µm) column, a Waters Sunfire™ Prep C18 (30×100 mm, 5 µm) column or a Waters XBridge™ C8 (30×100 mm, 5 µm) column as stationary phase at a flow rate of 30-35 mL/min, as detailed. Fractions were collected following detection by UV spectroscopy at a wavelength such as 220 or 254 nm. Fraction purity was determined by either TLC or analytical HPLC.

$^1$H NMR spectra were recorded on Bruker Avance 600 (600 MHz), a Bruker DRX 500 (500 MHz) or a Varian UnityInova 500 MHz, 400 MHz or 300 MHz instrument. Either the central peaks of chloroform-d ($CDCl_3$; $\delta_H$ 7.27 ppm), dimethylsulfoxide-$d_6$ ($d_6$-DMSO; $\delta_H$ 2.50 ppm) or methanol-$d_4$ ($CD_3OD$; $\delta_H$ 3.31 ppm), or an internal standard of tetramethylsilane (TMS; $\delta_H$ 0.00 ppm) were used as references. Mass spectra were recorded on an Agilent MSD (+ve and −ve APCI and/or electrospray (e.g. in multimode)) following analytical HPLC.

All other processes were carried out using standard laboratory techniques, e.g. as detailed in 'Experimental Organic Chemistry: Preparative and Microscale' $2^{nd}$ Ed. (Harwood, L., Moody, C. and Percy, J.), WileyBlackwell, 1998.

The abbreviations or terms used in the examples have the following meanings g grammes h hour(s)

min minute(s)

mL milliliters

AIBN azobisisobutyronitrile

CDI 1,1'-carbonyldiimidazole

DCM dichloromethane

DMF N,N-dimethylformamide

DMSO dimethylsulphoxide

HATU O-(7-azabenzotriazol-1-yl)-N,N,N',N'-tetramethyluronium hexafluorophosphate HCl hydrogen chloride/hydrochloric acid HPLC high performance liquid chromatography Hunig's base N,N-diisopropylethylamine IPA isopropanol MeOH methanol MTBE methyl tert-butyl ether NBS N-bromosuccinimide NCS N-chlorosuccinimide NMP 1-methylpyrrolidin-2-one RT room temperature T3P 2-propanephosphonic acid anhydride TBAF tetrabutylammonium fluoride TFA trifluoroacetic acid THF tetrahydrofuran Tosic-65 macroporous polymer bound ion exchange resin supplied by Biotage AB.

Triton-B benzyltrimethylammonium hydroxide

PREPARATION OF SYNTHETIC INTERMEDIATES

A) Preparation of Aromatic Linker Portions

Aromatic Intermediate 1

4-Chloro-3-(2-hydroxyethyl)benzaldehyde

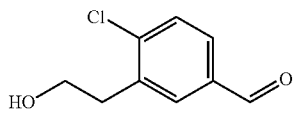

a) 3-(Carboxymethyl)-4-chlorobenzoic acid

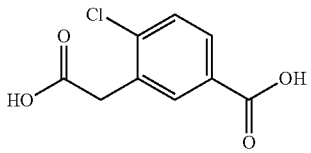

Potassium hydroxide (1.55 g) in water (15 mL) was added to a suspension of 4-chloro-3-(cyanomethyl)benzoic acid [WO 2006040568] (2.07 g) in ethanol (15 mL) and the resulting solution was heated at reflux for 4 hours, then allowed to cool. The mixture was concentrated under reduced pressure to remove the ethanol and then diluted with water and washed twice with ethyl acetate. The organic phases were discarded, whilst the aqueous phase was acidified to pH 1 with concentrated hydrochloric acid and extracted twice with ethyl acetate. The combined extracts were washed with brine, dried over anhydrous magnesium sulphate and concentrated under reduced pressure to afford the subtitled compound as a pale brown solid. Yield 2.06 g.

m/z 214 (M+) (EI).

b) 2-(2-Chloro-5-(hydroxymethyl)phenyl)ethanol

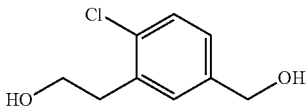

A solution of borane dimethyl sulfide complex (2M in THF, 12.0 mL) was added portionwise over 3 minutes to a suspension of 3-(carboxymethyl)-4-chlorobenzoic acid [Aromatic Intermediate 1, step a] (2.06 g) in dry THF (30 mL) at room temperature. The resulting effervescing dense suspension was stirred at room temperature for 1 hour, then heated to reflux for 1 hour. The cooled mixture was quenched by the portionwise addition of methanol (10 mL) over 2 minutes. The solution was stirred at room temperature for 30 minutes and then concentrated onto silica and purified by flash chromatography on silica eluted with 5% methanol in dichloromethane to afford the subtitled compound as a white solid. Yield 0.983 g.

$^1$H NMR (400 MHz, CDCl$_3$) δ 7.35 (d, J=8.2 Hz, 1H), 7.28 (d, J=2.1 Hz, 1H), 7.18 (dd, J=8.2, 2.1 Hz, 1H), 4.65 (s, 2H), 3.89 (t, J=6.7 Hz, 2H), 3.02 (t, J=6.5 Hz, 2H). Two exchangeable protons not observed.

c) 4-Chloro-3-(2-hydroxyethyl)benzaldehyde

Manganese (IV) dioxide (1.00 g) was added to a solution of 2-(2-chloro-5-(hydroxymethyl)phenyl)ethanol [Aromatic Intermediate 1, step b] (0.205 g) in DCM (10 mL), and the resulting suspension was stirred at room temperature overnight. The mixture was then filtered through Celite, washing the filter pad well with DCM. The filtrate and washings were concentrated under reduced pressure to afford the titled compound as a colourless oil. Yield 0.159 g.

$^1$H NMR (400 MHz, CDCl$_3$) δ 9.97 (s, 1H), 7.81 (d, J=2.0, 1H), 7.70 (dd, J=2.0, 8.2, 1H), 7.53 (t, J=6.7, 1H), 3.94 (dd, J=6.4, 11.6, 2H), 3.10 (t, J=6.6, 2H), 1.46 (t, J=5.2, 1H).

Aromatic Intermediate 2

2-(5-(Bromomethyl)-2-fluorophenyl)ethanol

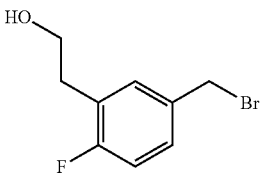

Dibenzoyl peroxide (1 g) was added to a solution of NBS (10.6 g) and 2-(2-fluoro-5-s methylphenyl)acetic acid (10 g) in DCM (250 mL) and the resulting mixture was heated under reflux for 12 h. The solvent was evaporated and the white solid partitioned between ethyl acetate (250 mL) and 10% sodium chloride solution (500 mL). The layers were separated and the organic phase washed with 10% sodium chloride solution (500 mL), dried over magnesium sulphate, filtered and evaporated. The white solid obtained was redissolved in tetrahydrofuran (150 mL) and cooled in an ice bath. A solution of borane dimethyl sulfide complex (2M in THF, 89 mL) was added cautiously and the mixture was then allowed to warm to RT and stirred overnight. The reaction was cooled in an ice bath and cautiously quenched with methanol. Once bubbling had ceased the solvent was evaporated and the residue was triturated with a 4:1 mixture of isohexane:ether.

Purification was by silica gel chromatography eluting with 9:1 to 4:1 ethyl acetate:isohexane gradient to give the titled compound as a clear oil. Yield 6.5 g.

¹H NMR (300 MHz, CDCl₃) δ 7.32-7.21 (m, 2H), 7.04-6.97 (m, 1H), 4.46 (s, 2H), 3.87 (t, J=6.5 Hz, 2H), 2.93-2.87 (m, 2H). One exchangeable proton not observed.

Aromatic Intermediate 3

(5-(2-(tert-Butyldimethylsilyloxy)ethyl)-2-fluorophenyl)methanol

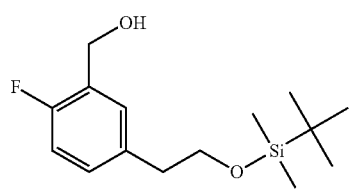

a) tert-Butyl(4-fluorophenethoxy)dimethylsilane

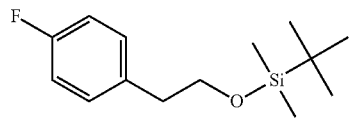

tert-Butyldimethylsilyl chloride (9.03 g) was added portionwise to a stirred solution of 2-(4-fluorophenyl)ethanol (7 g) and imidazole (4.08 g) in DMF (100 mL) at 20° C. The reaction mixture was stirred for 3 hours at room temperature and then partitioned between ethyl acetate and brine. The organic layer was washed twice with brine, dried, filtered and the solvent concentrated under reduced pressure. The crude product was purified by flash silica chromatography eluting with 2% ethyl acetate in isohexane. Fractions containing the product were evaporated to dryness to afford the subtitled compound. Yield 11.60 g.

¹H NMR (400 MHz, CDCl₃) δ 7.18-7.13 (m, 2H), 6.98-6.93 (m, 2H), 3.77 (t, J=6.9 Hz, 2H), 2.78 (t, J=6.8 Hz, 2H), 0.86 (s, 9H), −0.03 (s, 6H).

b) 5-(2-(tert-Butyldimethylsilyloxy)ethyl)-2-fluorobenzaldehyde

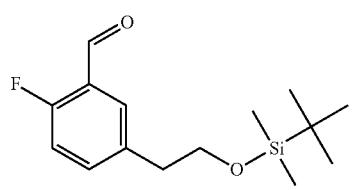

To a solution of 2,2,6,6-tetramethylpiperidine (10.77 g) in THF (200 mL) at 0° C. was added over 25 minutes butyllithium (1.6M in hexanes, 48 mL). The mixture was cooled to −78° C. and a solution of tert-butyl(4-fluorophenethoxy)dimethylsilane [Aromatic Intermediate 3, step a] (9.7 g) in THF (50 mL) was added dropwise over 25 minutes. The reaction mixture was stirred at −78° C. for 90 minutes. DMF (9.3 mL) was then added dropwise over 10 minutes. The reaction mixture was stirred at 0° C. for 1 hour and then poured into ice-cold aqueous HCl (0.5 M, 500 mL). The mixture was extracted with ethyl acetate and the organic layer washed twice with water, dried, filtered and the solvent concentrated under reduced pressure to give the subtitled compound. Yield 10.00 g.

¹H NMR (400 MHz, CDCl₃) δ 10.36 (s, 1H), 7.72-7.69 (m, 1H), 7.48-7.43 (m, 1H), 7.11-7.06 (m, 1H), 3.80 (t, J=6.5 Hz, 2H), 2.83 (t, J=6.4 Hz, 2H), 0.85 (s, 9H), 0.04 (s, 6H).

c) (5-(2-(tert-Butyldimethylsilyloxy)ethyl)-2-fluorophenyl)methanol

Sodium borohydride (1.33 g) was added portionwise over 30 minutes to a solution at 0° C. of 5-(2-(tert-butyldimethylsilyloxy)ethyl)-2-fluorobenzaldehyde [Aromatic Intermediate 3, step b] (9.9 g) in ethanol (120 mL). The reaction mixture was then stirred at room temperature for 30 minutes before being reduced to half the initial volume by concentration under reduced pressure. The residue was partitioned between ethyl acetate and brine, the organic layer was washed with brine, dried, filtered and the solvent concentrated under reduced pressure. The crude product was purified by flash silica chromatography using 12% ethyl acetate in isohexane as solvent. Fractions containing the product were concentrated to dryness to afford the titled compound. Yield 7.30 g.

¹H NMR (400 MHz, CDCl₃) δ 7.26-7.23 (m, 1H), 7.13-7.08 (m, 1H), 6.98-6.93 (m, 1H), 4.73 (d, J=6.2 Hz, 2H), 3.78 (t, J=6.9 Hz, 2H), 2.79 (t, J=6.9 Hz, 2H), 1.71 (t, J=6.5 Hz, 1H), 0.87 (s, 9H), −0.02 (s, 6H).

Aromatic Intermediate 4

2-(3-(Bromomethyl)-5-fluorophenyl)ethanol

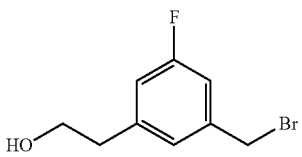

a) 2-(3-(Bromomethyl)-5-fluorophenyl)acetic acid

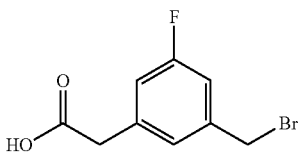

Dibenzoyl peroxide (0.5 g) was added to a stirred mixture of 2-(3-fluoro-5-methylphenyl)acetic acid (5.95 g) and NBS (6.93 g) in dichloromethane (120 mL). The resultant mixture was heated at reflux for 5 hours. The reaction mixture was cooled to room temperature and then washed twice with water. The organic layer was dried, filtered and the solvent concentrated under reduced pressure. The crude product was purified by flash silica chromatography using 1% acetic acid and 17% ethyl acetate in isohexane as solvent. Fractions containing the product were concentrated to dryness to afford the subtitled compound. Yield 6.50 g.

¹H NMR (400 MHz, D₆-DMSO) δ 7.22-7.17 (m, 2H), 7.09-7.05 (m, 1H), 4.68 (s, 2H), 3.61 (s, 2H). One exchangeable proton not observed.

b) 2-(3-(Bromomethyl)-5-fluorophenyl)ethanol

Borane dimethyl sulfide complex (2M in THF, 26.3 mL) was added dropwise over 10 minutes to a solution of 2-(3-(bromomethyl)-5-fluorophenyl)acetic acid [Aromatic Intermediate 4, step a] (6.5 g) in THF (120 mL) at 0° C. The mixture was stirred at 0° C. for 10 minutes and then at 20° C. for 1 hour. The reaction mixture was quenched by dropwise addition of methanol and the solvents were removed under reduced pressure. The crude product was purified by flash silica chromatography using 30% ethyl acetate in isohexane. Fractions containing the product were concentrated to dryness to afford the titled compound. Yield 4.70 g.

¹H NMR (400 MHz, CDCl₃) δ 7.04 (s, 1H), 6.98 (d, J=9.3 Hz, 1H), 6.89 (d, J=9.2 Hz, 1H), 4.43 (s, 2H), 3.88 (t, J=6.4 Hz, 2H), 2.86 (t, J=6.5 Hz, 2H), 1.43 (s, 1H).

Aromatic Intermediate 5

3-(2-(tert-Butyldimethylsilyloxy)ethyl)-2-fluorobenzaldehyde

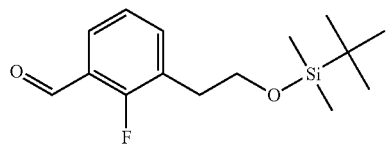

a) tert-Butyl(2-fluorophenethoxy)dimethylsilane

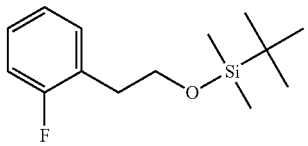

A solution of 2-(2-fluorophenyl)ethanol (5.5 g) and imidazole (8.0 g) in DMF (50 mL) was cooled in ice-water, treated with tert-butyldimethylchlorosilane (6.52 g), then removed from the cooling bath and stirred at room temperature for 3.5 hours. The solution was poured into water and extracted three times with diethyl ether. The combined organic extracts were washed three times with water, once with brine, then dried over anhydrous magnesium sulphate and concentrated under reduced pressure to afford the subtitled compound as a colourless oil. Yield 9.9 g.

¹H NMR (400 MHz, CDCl₃) δ 7.25-7.14 (m, 2H), 7.07-6.97 (m, 2H), 3.81 (t, J=7.0 Hz, 2H), 2.87 (t, J=6.9 Hz, 2H), 0.86 (s, 9H), −0.03 (s, 6H).

b) 3-(2-(tert-Butyldimethylsilyloxy)ethyl)-2-fluorobenzaldehyde

A solution of 2,2,6,6-tetramethylpiperidine (11.0 g) in anhydrous THF (200 mL) was cooled to −78° and treated with butyllithium (37.5 mL), added steadily over 5 minutes via a syringe. The solution was stirred at −78° for 15 minutes and then treated with a solution of tert-butyl(2-fluorophenethoxy)dimethylsilane [Aromatic Intermediate 5, step a] (9.9 g) in THF (25 mL), added dropwise over 15 minutes. The solution that was stirred at −78° for 2 hours, then treated with a solution of DMF (9.0 mL) in THF (25 mL), added dropwise over 10 minutes. The solution was stirred at −78° for 1 hour, then the cooling bath was removed and the solution was allowed to warm to room temperature overnight. The reaction mixture was poured into aqueous HCl (0.5 M) and extracted three times with ethyl acetate. The combined organic phases were washed three times with water, once with brine, then dried over magnesium sulphate, filtered and concentrated under reduced pressure to afford the titled compound. Yield 10.1 g.

¹H NMR (400 MHz, CDCl₃) δ 10.41 (s, 1H), 7.79-7.74 (m, 1H), 7.55 (td, J=7.4, 1.6 Hz, 1H), 7.22 (t, J=7.6 Hz, 1H), 3.88 (t, J=6.5 Hz, 2H), 2.96 (t, J=6.6 Hz, 2H), 0.88 (s, 9H), 0.00 (s, 6H).

Aromatic Intermediate 6

Mixture of 4-(2-(tert-butyldimethylsilyloxy)ethyl)thiophene-2-carbaldehyde with 3-(2-(tert-butyldimethylsilyloxy)ethyl)thiophene-2-carbaldehyde

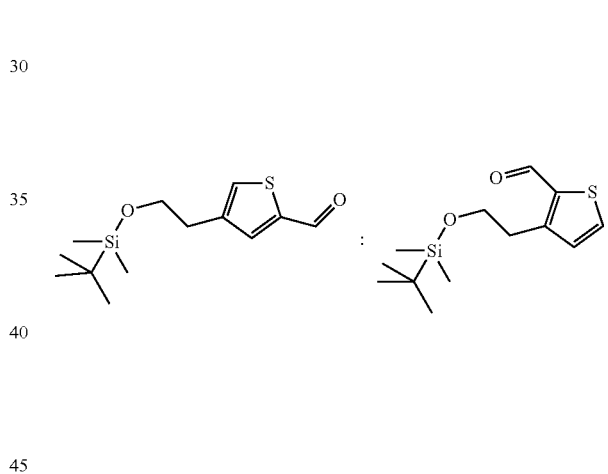

Butyllithium (36.1 mL) was added dropwise to stirred solution of tert-butyldimethyl(2-(thiophen-3-yl)ethoxy)silane [J. Med. Chem. 2000, 43(8), 1508] (10.0 g) in THF (200 mL) cooled to −78° C. After the addition the reaction mixture was stirred in an ice bath for 1 h and then cooled to −78° C. DMF (31.9 mL) was added dropwise over 5 min, and after a further 10 min the cooling bath was removed. After 1 h, the reaction mixture was partitioned between water and ethyl acetate and the ethyl acetate solution was washed twice with water and brine, dried over sodium sulphate, filtered and evaporated under reduced pressure. Purification by silica gel chromatography eluting with ethyl acetate:isohexane, 1:20, gave a 5:1 mixture of 4-(2-(tert-butyldimethylsilyloxy)ethyl)thiophene-2-carbaldehyde and 3-(2-(tert-butyldimethylsilyloxy)ethyl)thiophene-2-carbaldehyde by ¹H NMR as an oil. Yield 8.1 g. 4-(2-(tert-butyldimethylsilyloxy)ethyl)thiophene-2-carbaldehyde:

¹H NMR (400 MHz, CDCl₃) δ 9.93 (d, J=1.2 Hz, 1H), 7.71 (d, J=1.5 Hz, 1H), 7.52 (s, 1H), 3.92-3.84 (m, 2H), 2.91 (t, J=6.5 Hz, 2H), 0.92 (s, 9H), 0.04 (s, 6H). 3-(2-(tert-butyldimethylsilyloxy)ethyl)thiophene-2-carbaldehyde:

¹H NMR (400 MHz, CDCl₃) δ 10.08 (s, 1H), 7.69 (d, J=5.0 Hz, 1H), 7.09 (d, J=5.0 Hz, 1H), 3.92-3.84 (m, 2H), 3.22 (t, J=6.5 Hz, 2H), 0.89 (s, 9H), −0.01 (s, 6H).

Aromatic Intermediate 7

2-Chloro-5-(2-hydroxyethyl)benzaldehyde

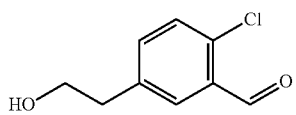

a) 2-Chloro-5-(cyanomethyl)benzoic acid

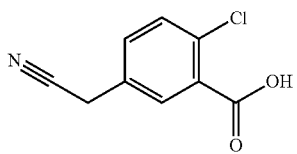

A solution of 5-(bromomethyl)-2-chlorobenzoic acid [WO 2001044170] (1.75 g) in DMF (20 mL) was treated with a solution of potassium cyanide (0.91 g) in water (7 mL) and the resulting solution was stirred at room temperature over 3 days. The mixture was diluted with water and extracted twice with ethyl acetate. The organic phases were discarded, whilst the aqueous phase was carefully acidified with concentrated hydrochloric acid (5 mL), venting any liberated HCN through bleach solution via a stream of nitrogen. After being stirred for 20 minutes, the aqueous phase was extracted twice more with ethyl acetate. The combined organic phases were washed three times with water, once with brine, then dried over anhydrous magnesium sulphate and concentrated in vacuo to afford the crude subtitled compound as a brown solid. Yield 1.25 g.
m/z 195 M⁺ (EI).

b) 5-(Carboxymethyl)-2-chlorobenzoic acid

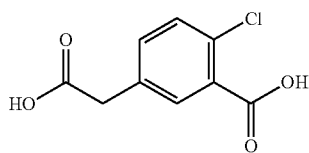

Potassium hydroxide (0.969 g) in water (10 mL) was added to a solution of 2-chloro-5-(cyanomethyl)benzoic acid [Aromatic Intermediate 7, step a] (1.25 g) in ethanol (10 mL) and the resulting mixture was heated at reflux for 2.25 hours, then allowed to cool. The mixture was concentrated in vacuo to remove the ethanol and then diluted with water and washed twice with ethyl acetate. The organic phases were discarded, whilst the aqueous phase was acidified to pH 1 with concentrated hydrochloric acid and extracted twice with ethyl acetate. The combined extracts were dried over anhydrous magnesium sulphate and concentrated in vacuo to afford the subtitled compound as a brown gum. Yield 1.38 g.

¹H NMR (400 MHz, D₆-DMSO) δ 12.93 (br s, 2H), 7.69 (d, J=2.1 Hz, 1H), 7.48 (d, J=8.3 Hz, 1H), 7.42 (dd, J=8.3, 2.2 Hz, 1H), 3.66 (s, 2H).

c) 2-(4-Chloro-3-(hydroxymethyl)phenyl)ethanol

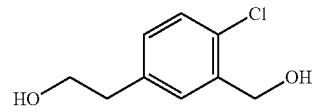

A solution of borane dimethyl sulfide complex (2M in THF, 6.50 mL) was added portionwise over 5 minutes to a solution of 5-(carboxymethyl)-2-chlorobenzoic acid [Aromatic Intermediate 7, step b] (1.37 g) in dry THF (20 mL) at room temperature. The resulting effervescing solution was stirred at room temperature for 1.5 hours, then heated to reflux for 1 hour. The cooled mixture was quenched by the portionwise addition of methanol (5 mL) over 5 minutes. The solution was stirred at room temperature for 2 hours and then purified by flash chromatography on silica eluted with 5% methanol in dichloromethane to afford the subtitled compound as a colourless oil. Yield 0.933 g.

¹H NMR (400 MHz, CDCl₃) δ 7.36 (d, J=2.1 Hz, 1H), 7.30 (d, J=7.9 Hz, 1H), 7.11 (dd, J=8.1, 2.2 Hz, 1H), 4.77 (s, 2H), 3.87 (t, J=6.5 Hz, 2H), 2.86 (t, J=6.5 Hz, 2H). Two exchangeable protons not observed.

d) 2-Chloro-5-(2-hydroxyethyl)benzaldehyde

Manganese (IV) dioxide (1.00 g) was added to a solution of 2-(4-chloro-3-(hydroxymethyl)phenyl)ethanol [Aromatic Intermediate 7, step c] (0.200 g) in DCM (5 mL), and the resulting suspension was stirred at room temperature overnight. The mixture was then filtered through Celite, washing the residue well with DCM. The filtrate and washings were concentrated in vacuo to afford the subtitled compound as a colourless oil. Yield 0.197 g.

¹H NMR (400 MHz, CDCl₃) δ 10.47 (s, 1H), 7.80 (d, J=2.1 Hz, 1H), 7.42 (d, J=2.1 Hz, 1H), 7.41 (s, 1H), 3.89 (br t, J=5.9 Hz, 2H), 2.90 (t, J=6.4 Hz, 2H), 1.42 (br s, 1H).

Aromatic Intermediate 8

2-(3-(Bromomethyl)-5-chlorophenyl)ethanol

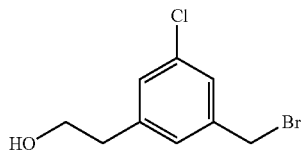

a) 2-(3-(Bromomethyl)-5-chlorophenyl)acetic acid

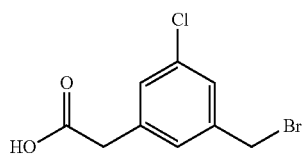

Benzoyl peroxide (0.112 g) was added to a suspension of 2-(3-chloro-5-methylphenyl)acetic acid [WO 9746577] (0.752 g) and N-bromosuccinimide (0.801 g) in DCM (15 mL), and the resulting mixture was heated at 50° C. under nitrogen overnight. The mixture was concentrated in vacuo to remove the dichloromethane and the residue was dissolved in ethyl acetate (10 mL). The solution was heated at 85° C. under nitrogen for 4 hours, then cooled. The solution was washed three times with water and once with brine, then dried over anhydrous magnesium sulphate and purified by flash chromatography on silica eluted with 1:20:79 acetic acid:ethyl acetate:isohexane to afford the crude subtitled compound as a pale yellow solid. Yield 0.735 g.

$^1$H NMR (400 MHz, CDCl$_3$) δ 7.33-7.31 (m, 1H), 7.24-7.22 (m, 1H), 7.21-7.18 (m, 1H), 4.41 (s, 2H), 3.64 (s, 2H). One exchangeable proton not observed.

b) 2-(3-(Bromomethyl)-5-chlorophenyl)ethanol

A solution of borane dimethyl sulfide complex (2M in THF, 2.8 mL) was added portionwise over 5 minutes to a solution of 2-(3-(bromomethyl)-5-chlorophenyl)acetic acid [Aromatic Intermediate 8, step a] (0.73 g) in dry THF (10 mL) at room temperature. The resulting effervescing solution was stirred for 1 hour, then cooled in ice-water and quenched by the portionwise addition of methanol (3 mL) over 5 minutes. The solution was stirred at room temperature for a further 20 minutes and then concentrated in vacuo. The residue was purified by flash chromatography on silica eluted with 25% ethyl acetate in isohexane to afford the crude subtitled compound as a white solid. Yield 0.46 g.

$^1$H NMR (400 MHz, CDCl$_3$) δ 7.29-7.24 (m, 1H), 7.19-7.13 (m, 2H), 4.41 (s, 2H), 3.87 (t, J=6.5 Hz, 2H), 2.84 (t, J=6.4 Hz, 2H). One exchangeable proton not observed.

Aromatic Intermediate 9

3-(2-Hydroxyethyl)phenethyl methanesulfonate

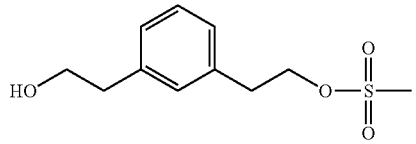

Methanesulfonyl chloride (0.67 mL) in DCM (2 mL) was added dropwise to a stirred solution at 0° C. of 2,2'-(1,3-phenylene)diethanol (1.30 g) and triethylamine (1.36 mL) in DCM (30 mL). The reaction mixture was stirred for 1 hour at 0° C. and then washed with water. The aqueous layer was re-extracted with DCM and the combined organic phases were dried, filtered and the solvent evaporated under reduced pressure. The crude product was purified by flash silica chromatography using 3% methanol in dichloromethane as solvent. Fractions containing the product were evaporated to dryness to afford the titled compound. Yield 0.52 g.

$^1$H NMR (400 MHz, D$_6$-DMSO) δ 7.22 (t, J=7.6 Hz, 1H), 7.15-7.07 (m, 3H), 4.61 (t, J=5.2 Hz, 1H), 4.40 (t, J=6.8 Hz, 2H), 3.62-3.56 (m, 2H), 3.09 (s, 3H), 2.96 (t, J=6.9 Hz, 2H), 2.70 (t, J=7.2 Hz, 2H).

Aromatic Intermediate 10

4-(2-Hydroxyethyl)phenethyl methanesulfonate

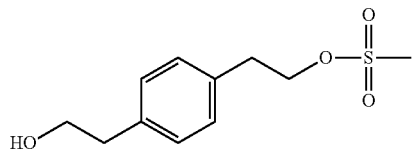

Prepared by the method of Aromatic Intermediate 9, using 2,2'-(1,4-phenylene)diethanol (1.30 g) in place of 2,2'-(1,3-phenylene)diethanol. Yield 0.56 g.

$^1$H NMR (400 MHz, D$_6$-DMSO) δ 7.21-7.14 (m, 4H), 4.60 (t, J=5.3 Hz, 1H), 4.38 (t, J=6.8 Hz, 2H), 3.60-3.55 (m, 2H), 3.10 (s, 3H), 2.95 (t, J=6.8 Hz, 2H), 2.69 (t, J=7.2 Hz, 2H).

Aromatic Intermediate 11

2-Chloro-3-(2-hydroxyethyl)benzaldehyde

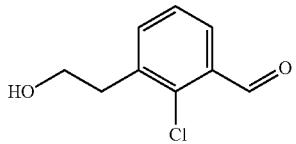

a) 3-(Bromomethyl)-2-chlorobenzoic acid

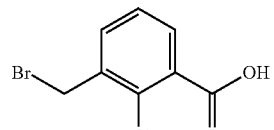

Benzoyl peroxide (1.33 g) was added to a suspension of 2-chloro-3-methylbenzoic acid (25 g) and N-bromosuccinimide (28.7 g) in chlorobenzene (250 mL) and the resulting mixture was heated to 85° C. for 4 h. The mixture was diluted with ethyl acetate (100 mL) and washed with 10% aqueous brine (3×100 mL). The organic layer was dried over magnesium sulphate, filtered and evaporated. The beige solid was recrystallised from ethyl acetate (~75 mL)/isohexane (~250 mL) to give the subtitled compound as a white solid. Yield 25.3 g.

¹H NMR (400 MHz, CDCl₃) δ 7.93 (d, J=7.7 Hz, 1H), 7.66 (d, J=7.4 Hz, 1H), 7.36 (t, J=7.7 Hz, 1H), 4.67 (s, 2H). One exchangeable proton not observed.

b) 2-Chloro-3-(cyanomethyl)benzoic acid

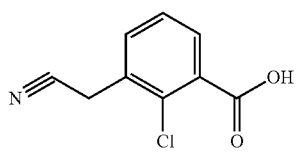

A solution of 3-(bromomethyl)-2-chlorobenzoic acid [Aromatic Intermediate 11, step a] (13.2 g) in DMF (150 mL) was treated with a solution of potassium cyanide (7.23 g) in water (50 mL) and the resulting solution was stirred at room temperature overnight. The mixture was diluted with water (200 mL) and carefully acidified with concentrated hydrochloric acid (25 mL), venting any liberated HCN through bleach solution via a stream of nitrogen. After being stirred for 2 hours, the aqueous phase was extracted with ethyl acetate (3×250 mL). The combined organic phases were washed with water (3×250 mL) and brine (250 mL), dried over magnesium sulphate, filtered and evaporated to give the subtitled compound as a white solid. Yield 10.3 g.

¹H NMR (300 MHz, D₆-DMSO) δ 13.54 (s, 1H), 7.75-7.67 (m, 2H), 7.48 (t, J=7.7 Hz, 1H), 4.16 (s, 2H).

c) 3-(Carboxymethyl)-2-chlorobenzoic acid

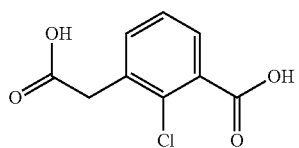

Concentrated sulfuric acid (60 mL) was added dropwise to ice-cold water (75 mL) and the resulting solution was added to 2-chloro-3-(cyanomethyl)benzoic acid [Aromatic Intermediate 11, step b] (14 g). The resulting suspension was heated to reflux (165° C.) for 30 min during which the starting material dissolved and a new precipitate was observed. The reaction was allowed to cool and was diluted with water (250 mL) and extracted with ethyl acetate (3×500 mL). The combined organic phases were washed with water (250 mL) and brine (250 mL), then dried over magnesium sulphate and evaporated to give the subtitled compound as a white solid. Yield 13.7 g.

¹H NMR (400 MHz, D₆-DMSO) δ 7.62 (dd, J=7.7, 1.8 Hz, 1H), 7.54 (dd, J=7.7, 1.8 Hz, 1H), 7.37 (t, J=7.7 Hz, 1H), 3.78 (s, 2H). Two exchangeable protons not observed.

d) 2-(2-Chloro-3-(hydroxymethyl)phenyl)ethanol

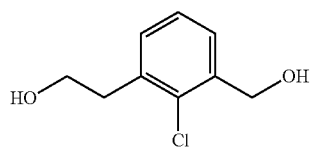

A solution of borane dimethyl sulfide complex (2M in THF, 220 mL) was added portionwise over 5 minutes to a suspension of 3-(carboxymethyl)-2-chlorobenzoic acid [Aromatic Intermediate 11, step c] (18.9 g) in dry THF (800 mL) at room temperature. The resulting effervescing suspension was stirred at room temperature for 30 minutes, then heated to reflux for 60 minutes, and allowed to cool to room temperature overnight. The mixture was quenched by the portionwise addition of methanol (100 mL) over 15 minutes and stirred until bubbling ceased. Concentrated aqueous HCl (25 mL) was added, the mixture was stirred for 30 min and concentrated under reduced pressure. The gummy residue was partitioned between ethyl acetate (500 mL) and aqueous HCl (2M, 200 mL). The phases were separated and the aqueous phase extracted with ethyl acetate (2×300 mL). The combined organic phases were washed with brine (300 mL), dried over magnesium sulphate, filtered and evaporated to give the subtitled compound as a yellow oil. Yield 17.8 g.

¹H NMR (400 MHz, D₆-DMSO) δ 7.40 (dd, J=7.0, 2.2 Hz, 1H), 7.29-7.21 (m, 2H), 5.34 (t, J=5.5 Hz, 1H), 4.71 (t, J=4.9 Hz, 1H), 4.55 (d, J=5.1 Hz, 2H), 3.63-3.56 (m, 2H), 2.87 (t, J=7.2 Hz, 2H).

e) 2-Chloro-3-(2-hydroxyethyl)benzaldehyde

Manganese (IV) dioxide (43.1 g) was added to a slight suspension of 2-(2-chloro-3-(hydroxymethyl)phenyl)ethanol [Aromatic Intermediate 11, step d] (18.5 g) in chloroform (500 mL), and the resulting suspension was heated at reflux for 2 h. The reaction mixture was cooled, filtered through Celite and the filter pad washed with DCM (3×300 mL). The combined washings and filtrate were evaporated and the residue purified by flash silica chromatography eluting with 3:1 to 1:1 isohexane:ethyl acetate gradient. The fractions containing product were combined and evaporated to give the titled compound as a white solid. Yield 12.00 g.

$^1$H NMR (400 MHz, CDCl$_3$) δ 10.55 (s, 1H), 10.54 (t, J=5.6 Hz, 1H), 7.83 (dd, J=7.7, 1.8 Hz, 1H), 7.55 (dd, J=7.4, 1.8 Hz, 1H), 7.35 (t, J=7.6 Hz, 1H), 3.94 (q, J=6.4 Hz, 2H), 3.11 (t, J=6.5 Hz, 2H).

Aromatic Intermediate 12

2-(4-(2-Hydroxyethyl)phenoxy)acetaldehyde

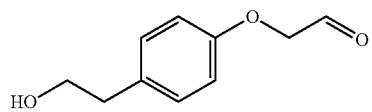

a) 2-(4-(2,2-Diethoxyethoxy)phenyl)ethanol

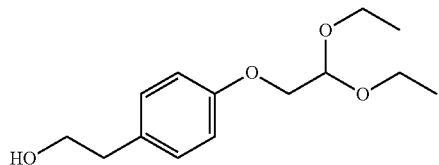

Cesium carbonate (28.3 g) was added to a solution of 4-(2-hydroxyethyl)phenol (10 g) and 2-bromo-1,1-diethoxyethane (11.8 mL) in DMF (150 mL). The resulting suspension was heated at 90° C. for 16 h. The reaction was poured into water (500 mL). The aqueous phase was extracted with ethyl acetate (3×200 mL). The combined organic solutions were washed with water (200 mL) and brine (200 mL), then dried over magnesium sulfate, filtered and evaporated in vacuo. Purification was by silica gel chromatography eluting with isohexane to 1:1 ethyl acetate:isohexane gradient to give the subtitled compound as a yellow oil. Yield 10 g.

$^1$H NMR (300 MHz, CDCl$_3$) δ 7.14 (d, J=6.9 Hz, 2H), 6.88 (d, J=6.9 Hz, 2H), 4.83 (t, J=5.0 Hz, 1H), 4.00 (d, J=5.0 Hz, 2H), 3.87-3.70 (m, 4H), 3.70-3.56 (m, 2H), 2.81 (t, J=6.4 Hz, 2H), 1.25 (t, J=6.9 Hz, 6H). One exchangeable proton not observed.

b) 2-(4-(2-Hydroxyethyl)phenoxy)acetaldehyde

Concentrated hydrochloric acid (5 mL) was added to a solution of 2-(4-(2,2-diethoxyethoxy)phenyl)ethanol [Aromatic Intermediate 12, step a] (0.76 g) in 1,4-dioxane (10 mL) and the resulting mixture was stirred for 1 h. The reaction was diluted with water (50 mL) and extracted with ethyl acetate (3×50 mL). The combined organic solutions were washed with water (50 mL) and brine (50 mL), then dried over sodium sulphate, filtered and evaporated in vacuo to give the subtitled compound, which was used directly. Yield 0.35 g.

Aromatic Intermediate 13

2-(5-(2-(tert-Butyldimethylsilyloxy)ethyl)thiophen-2-yl)ethanol

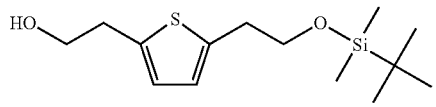

tert-Butyldimethylsilyl chloride (6.63 g) was added portionwise to a solution of imidazole (2.99 g) and 2-(5-(2-hydroxyethyl)thiophen-2-yl)acetic acid [WO 2008096129] (3.9 g) in DMF (50 mL) over 20 minutes. The resulting solution was stirred for 1 h. THF (50 mL) was then added and the reaction cooled in an ice bath. A solution of potassium carbonate (4.05 g) in water (50 mL) was then added and the mixture stirred for 20 min. The reaction was partitioned between ethyl acetate and brine. The organic layer was separated and washed twice with brine, dried over sodium sulphate, filtered and the solvent evaporated in vacuo. The residue was dissolved in THF (80 mL) and borane tetrahydrofuran complex (1M solution in THF, 62.8 mL) was added dropwise. The resulting solution was stirred for 2 h and quenched by dropwise addition of methanol (30 mL). The solvents were then evaporated in vacuo. Purification was by silica gel chromatography, eluting with 83:17 isohexane:ethyl acetate to give the subtitled compound as a yellow liquid. Yield 4.6 g.

$^1$H NMR (300 MHz, CDCl$_3$) δ 6.69-6.63 (m, 2H), 3.87-3.75 (m, 4H), 3.05-2.91 (m, 4H), 0.89 (s, 9H), 0.03 (s, 6H). One exchangeable proton not observed.

Aromatic Intermediate 14

2-(3-(2-Hydroxyethyl)phenoxy)acetaldehyde

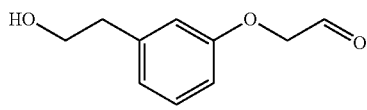

Prepared by the method of Aromatic Intermediate 12 using 3-(2-hydroxyethyl)phenol in place of 4-(2-hydroxyethyl)phenol.

$^1$H NMR (400 MHz, CDCl$_3$) δ 9.86 (s, 1H), 7.28-7.13 (m, 1H), 6.92-6.66 (m, 3H), 4.57 (s, 2H), 3.87 (t, J=6.5 Hz, 2H), 2.86 (t, J=6.5 Hz, 2H). One exchangeable proton not observed.

Aromatic Intermediate 15

3-(3-Hydroxypropylthio)benzaldehyde

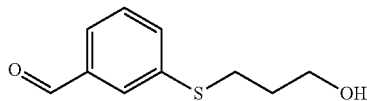

a) 3-(3-Ethoxy-3-oxopropylthio)benzoic acid

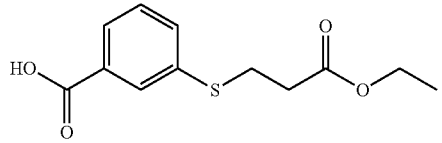

A solution of 3-mercaptobenzoic acid (3.4 g) in DMF (50 mL) was treated with potassium carbonate (3.18 g) and stirred for 5 minutes. A solution of ethyl 3-bromopropionate (2.8 mL) in DMF (10 mL) was added dropwise over 30 minutes and the resulting mixture was stirred for a further 30 minutes. The mixture was partitioned between ethyl acetate and water, and the phases separated. The aqueous phase was acidified with aqueous HCl and extracted further with ethyl acetate. The organic phases were washed with water, dried, filtered and concentrated under reduced pressure to afford the subtitled compound. Yield 5.3 g.

$^1$H NMR (400 MHz, D$_6$-DMSO) δ 13.11 (s, 1H), 7.84 (t, J=1.7 Hz, 1H), 7.77 (dt, J=7.8, 1.4 Hz, 1H), 7.60 (ddd, J=7.7, 2.1, 1.8 Hz, 1H), 7.47 (t, J=7.7 Hz, 1H), 4.06 (q, J=7.1 Hz, 2H), 3.22 (t, J=7.0 Hz, 2H), 2.62 (t, J=6.9 Hz, 2H), 1.17 (t, J=7.2 Hz, 3H).

b) 3-(3-(Hydroxymethyl)phenylthio)propan-1-ol

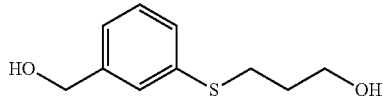

A solution of lithium aluminum hydride (2M in THF, 2.2 mL) was added portionwise over 5 minutes to a solution of 3-(3-ethoxy-3-oxopropylthio)benzoic acid [Aromatic Intermediate 15, step a] (1.0 g) in THF (20 mL), pre-cooled in ice-water. After ~½ the addition the mixture formed a thick precipitate and was diluted with more THF (15 mL) to maintain stirring. The mixture was removed from the cooling bath and stirred at room temperature for 3.5 hours. The mixture was cooled back down in ice-water and treated with more lithium aluminum hydride (2M in THF, 2.2 mL). The mixture was removed from the cooling bath and stirred at room temperature overnight. The cloudy solution was cooled in ice water and then quenched by the careful addition of methanol (5 mL), added portionwise over 30 minutes. After ~½ of the addition, the mixture was removed from the cooling bath and allowed to warm to room temperature for 45 minutes. The mixture was poured into aqueous HCl (2M) and extracted three times with ethyl acetate. The combined organic extracts were washed with brine, dried over anhydrous magnesium sulphate, filtered and concentrated under reduced pressure to give the subtitled compound as a pale yellow oil. Yield 0.55 g.

$^1$H NMR (400 MHz, CDCl$_3$) δ 7.38-7.35 (s, 1H), 7.31-7.24 (m, 2H), 7.20-7.12 (m, 1H), 4.67 (s, 2H), 3.77 (t, J=6.0 Hz, 2H), 3.06 (t, J=7.0 Hz, 2H), 1.90 (ddd, J=13.1, 7.1, 6.1 Hz, 2H). Two exchangeable protons not observed.

c) 3-(3-Hydroxypropylthio)benzaldehyde

Manganese dioxide (1.76 g) was added to a solution of 3-(3-(hydroxymethyl)phenylthio)propan-1-ol [Aromatic Intermediate 15, step b] (0.40 g) in DCM (10 mL). The resulting mixture was stirred at room temperature for three days. The suspension was then filtered over Celite, washing the residue well with DCM. The combined filtrate and washings were concentrated under reduced pressure to afford the titled compound as a yellow gum. Yield 0.33 g.

$^1$H NMR (400 MHz, CDCl$_3$) δ 9.98 (s, 1H), 7.82 (t, J=1.8 Hz, 1H), 7.66 (dt, J=7.5, 1.3 Hz, 1H), 7.58 (ddt, J=0.1, 7.7, 1.3 Hz, 1H), 7.45 (t, J=7.6 Hz, 1H), 3.80 (q, J=5.7 Hz, 2H), 3.12 (t, J=7.2 Hz, 2H), 1.97-1.89 (m, 2H), 1.48 (t, J=5.3 Hz, 1H).

Aromatic Intermediate 16

3-(2-Hydroxyethylthio)benzaldehyde

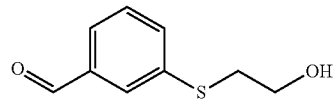

a) 3-(2-(tert-Butyldimethylsilyloxy)ethylthio)benzoic acid

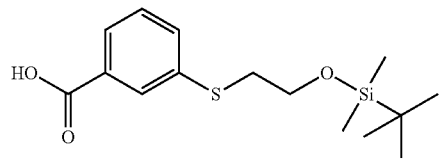

(2-Bromoethoxy)(tert-butyl)dimethylsilane (1.48 mL) was added dropwise to a suspension of 3-mercaptobenzoic acid (1.07 g) and potassium carbonate (1.91 g) in DMF (15 mL). The resulting suspension was stirred for 2 h. The reaction was carefully acidified by dropwise addition of aqueous HCl (2M, 10 mL) and poured into water (100 mL). The resulting aqueous was extracted with ethyl acetate (3×100 mL). The combined organics were washed with brine (50 mL), dried over sodium sulphate, filtered and evaporated to give the subtitled compound as a clear oil. Yield 2.8 g.

$^1$H NMR (400 MHz, D$_6$-DMSO) δ 13.11 (s, 1H), 7.89 (t, J=1.7 Hz, 1H), 7.79-7.74 (m, 1H), 7.66-7.61 (m, 1H), 7.47 (t, J=7.7 Hz, 1H), 3.82 (t, J=6.4 Hz, 2H), 3.19 (t, J=6.4 Hz, 2H), 0.87 (s, 9H), 0.05 (s, 6H).

b) 2-(3-(Hydroxymethyl)phenylthio)ethanol

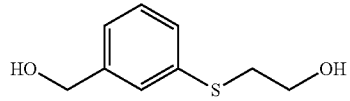

Borane dimethyl sulfide complex (2M in THF, 17.3 mL) was added dropwise to an ice cold solution of 3-(2-(tert-butyldimethylsilyloxy)ethylthio)benzoic acid [Aromatic Intermediate 16, step a] (2.16 g) in THF (50 mL). The reaction was allowed to warm to RT, then heated at reflux for 2 h. The reaction was cooled in an ice bath and aqueous HCl solution (2M, 50 mL) was added dropwise. The resulting mixture was stirred overnight. The reaction was concentrated to half its original volume and the resulting aqueous extracted with DCM (3×100 mL). The combined organics were washed with brine (100 mL), dried over sodium sulphate, filtered and evaporated. The residue was purified by silica gel chromatography eluting with 4:1 isohexane:ethyl acetate to 100% ethyl acetate gradient. The fractions containing product were combined and evaporated to give the subtitled compound as a clear oil. Yield 0.77 g.

$^1$H NMR (400 MHz, D$_6$-DMSO) δ 7.29-7.23 (m, 2H), 7.21-7.17 (m, 1H), 7.13-7.09 (m, 1H), 5.20 (t, J=5.8 Hz, 1H), 4.92 (t, J=5.6 Hz, 1H), 4.47 (d, J=5.9 Hz, 2H), 3.59-3.53 (m, 2H), 3.02 (t, J=6.9 Hz, 2H).

c) 3-(2-Hydroxyethylthio)benzaldehyde

Manganese dioxide (1.36 g) was added to a solution of 2-(3-(hydroxymethyl)phenylthio)ethanol [Aromatic Intermediate 16, step b] (0.29 g) in DCM (10 mL). The resulting mixture was heated at reflux for 4 h, cooled and filtered through Celite. The filter pad was washed with DCM (3×20 mL). The filtrate and washing were combined and evaporated to give the subtitled compound as a yellow gum. Yield 0.2 g.

$^1$H NMR (400 MHz, D$_6$-DMSO) δ 9.99 (s, 1H), 7.84 (s, 1H), 7.71-7.64 (m, 2H), 7.54 (t, J=7.7 Hz, 1H), 4.99 (t, J=5.6 Hz, 1H), 3.64-3.57 (m, 2H), 3.13 (t, J=6.7 Hz, 2H).

Aromatic Intermediate 17

5-(2-(tert-Butyldimethylsilyloxy)ethyl)thiophene-3-carbaldehyde

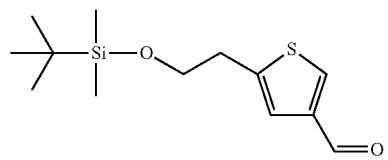

a) tert-Butyl(2-(5-chlorothiophen-2-yl)ethoxy)dimethylsilane

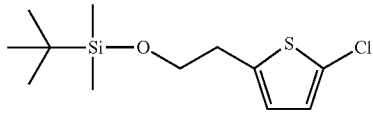

NCS (0.826 g) was added portionwise to a solution of tert-butyldimethyl(2-(thiophen-2-yl)ethoxy)silane [WO 2008096129] (1.5 g) in chloroform (50 mL) and the resulting mixture was heated at reflux for 3 days. The mixture was diluted with DCM (100 mL) and washed with saturated aqueous sodium bicarbonate (2×100 mL) and brine (100 mL), then dried over sodium sulphate, filtered and evaporated. The residue was purified by silica gel chromatography eluting with isohexane to give the subtitled compound as a clear oil. Yield 1.00 g.

$^1$H NMR (300 MHz, CDCl$_3$) δ 6.69 (d, J=3.5 Hz, 1H), 6.57-6.54 (m, 1H), 3.75 (t, J=6.5 Hz, 2H), 2.89 (t, J=6.4 Hz, 2H), 0.87 (2, J=3.1 Hz, 9H), 0.01 (s, 6H).

b) 5-(2-(tert-Butyldimethylsilyloxy)ethyl)-2-chlorothiophene-3-carbaldehyde

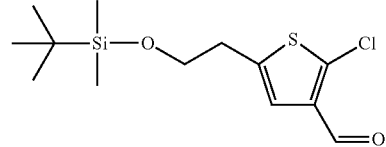

tert-Butyl(2-(5-chlorothiophen-2-yl)ethoxy)dimethylsilane [Aromatic Intermediate 17, step a] (0.8 g) was added dropwise over 5 min to a stirred solution of butyllithium (2.5M in hexanes, 1.73 mL) and 2,2,6,6-tetramethylpiperidine (0.73 mL) in THF (25 mL) at −78° C. The resulting mixture was stirred for 2 h then DMF (0.67 mL) was added. The mixture was stirred for a further 1 h and allowed to warm to RT. The reaction mixture was cautiously poured into aqueous HCl (0.5M, 200 mL) and extracted with ethyl acetate (3×100 mL). The combined organic phases were washed with water (2×100 mL) and brine (100 mL), then dried over sodium sulphate, filtered and evaporated. The resulting oil was purified by silica gel chromatography eluting with isohexane to 5% ether in isohexane gradient. The fractions containing product were combined and evaporated to give the subtitled compound as a clear oil. Yield 0.80 g.

$^1$H NMR (300 MHz, CDCl$_3$) δ 9.96 (s, 1H), 7.05 (s, 1H), 3.79 (t, J=6.0 Hz, 2H), 2.92 (t, J=6.0 Hz, 2H), 0.91 (s, 9H), 0.05 (s, 6H).

c) 5-(2-(tert-Butyldimethylsilyloxy)ethyl)thiophene-3-carbaldehyde

A slurry of palladium on carbon (10%, 0.28 g) in water (0.5 mL) was added cautiously to a solution of 5-(2-(tert-butyldimethylsilyloxy)ethyl)-2-chlorothiophene-3-carbaldehyde [Aromatic Intermediate 17, step b] (0.80 g) and triethylamine (0.91 mL) in ethanol (50 mL) and the resulting mixture stirred overnight under 4 bar pressure of hydrogen. The mixture was filtered through Celite and the filter pad washed with ethanol (10 mL). The combined filtrate and washings were evaporated and azeotroped with toluene (20 mL) to give a yellow oil. The residue was dissolved in DCM (100 mL), manganese dioxide (2.28 g) was added and the resulting suspension heated at reflux overnight. The mixture was filtered through Celite and the filter pad washed with DCM (50 mL). The combined filtrate and washings were evaporated to give the titled compound as a yellow oil. Yield 0.60 g.

$^1$H NMR (300 MHz, CDCl$_3$) δ 9.80 (s, 1H), 7.93-7.90 (m, 1H), 3.80 (t, J=6.2 Hz, 2H), 2.99 (t, J=5.9 Hz, 2H), 0.88 (s, 9H), 0.01 (s, 6H). One proton obscured by CDCl$_3$ peak.

Aromatic Intermediate 18

3-(3-Hydroxypropyl)benzaldehyde

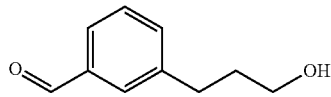

a) 3-(3-(Hydroxymethyl)phenyl)prop-2-yn-1-ol

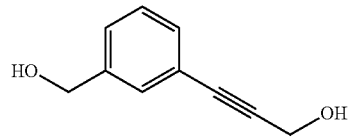

Copper (I) iodide (0.037 g) and tetrakis(triphenylphosphine)palladium (0) (0.075 g) were added to a solution of (3-iodophenyl)methanol (2.27 g), tert-butyldimethyl(prop-2-ynyloxy)silane (1.1 g) and triethylamine (2.7 mL) in NMP (20 mL) and the mixture stirred at ambient temperature under nitrogen for 18 hours. The mixture was diluted with water and extracted into ethyl acetate (×3). The combined extracts were washed successively with 10% brine, 30% brine and saturated brine, dried over magnesium sulfate, filtered and the solvent removed. The crude product was purified by flash silica chromatography, elution gradient 10, 15 and 20% ethyl acetate in isohexane. Appropriate fractions were evaporated to dryness to give a mixture of product and starting material. The mixture was purified by preparative HPLC (XBridge™, Gradient: 65-99% acetonitrile in 0.2% aqueous TFA) to afford the subtitled compound as a pale yellow oil. Yield 0.44 g.

$^1$H NMR (400 MHz, CDCl$_3$) δ 7.46-7.28 (m, 4H), 4.68 (s, 2H), 4.49 (s, 2H). Two exchangeable protons not observed. Note: The silyl protecting group was cleaved during the HPLC purification process.

b) 3-(3-(Hydroxymethyl)phenyl)propan-1-ol

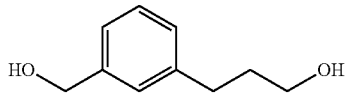

A solution of 3-(3-(hydroxymethyl)phenyl)prop-2-yn-1-ol [Aromatic Intermediate 18, step a] (0.44 g) in ethanol (20 mL) was hydrogenated using an H-Cube™ Hydrogenation Reactor (ThalesNano Nanotechnology Inc) with 10% Pd/C catalyst at 50° C. and 40 bar. The solution was passed through the H-cube three times, and concentrated in vacuo to afford the subtitled compound as a pale yellow oil. Yield (0.40 g).

$^1$H NMR (400 MHz, CDCl$_3$) δ 7.31-7.12 (m, 4H), 4.68 (s, 2H), 3.68 (q, J=6.6 Hz, 2H), 2.72 (t, J=7.7 Hz, 2H), 1.94-1.86 (m, 2H). Two exchangeable protons not observed.

c) 3-(3-Hydroxypropyl)benzaldehyde

Manganese dioxide (2.07 g) was added to a solution of 3-(3-(hydroxymethyl)phenyl)propan-1-ol [Aromatic Intermediate 18, step b] (0.40 g) in dichloromethane (20 mL) and the mixture stirred at ambient temperature for 18 hours. The mixture was filtered through Celite and concentrated in vacuo. The crude product was purified by flash silica chromatography, elution gradient 40%, 50% and 60% ethyl acetate in isohexane. Fractions containing the product were evaporated to dryness to afford the titled compound as a colourless oil. Yield 0.21 g.

$^1$H NMR (400 MHz, CDCl$_3$) δ 10.00 (s, 1H), 7.74-7.69 (m, 2H), 7.51-7.43 (m, 2H), 3.73-3.66 (m, 2H), 2.81 (t, J=7.8 Hz, 2H), 1.97-1.88 (m, 2H), 1.34 (t, J=5.0 Hz, 1H).

Aromatic Intermediate 19

3-(4-(tert-Butyldimethylsilyloxy)butyl)benzaldehyde

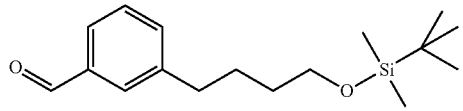

a) (3-(4-(tert-Butyldimethylsilyloxy)but-1-ynyl)phenyl)methanol

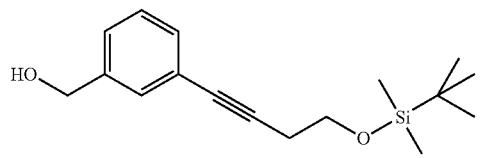

Prepared by the method of Aromatic Intermediate 18, step a using tert-butyldimethyl(but-3-ynyloxy)silane (0.92 g) in place of tert-butyldimethyl(prop-2-ynyloxy)silane. The preparative HPLC conditions were changed to XBridge™, Gradient: 75-99% methanol in 0.2% aqueous ammonia to avoid cleavage of the silyl protecting group. Yield 0.79 g.

¹H NMR (400 MHz, CDCl₃) δ 7.40 (s, 1H), 7.34-7.26 (m, 3H), 4.66 (d, J=5.9 Hz, 2H), 3.82 (t, J=7.2 Hz, 2H), 2.62 (t, J=7.0 Hz, 2H), 1.63 (t, J=6.0 Hz, 1H), 0.92 (s, 9H), 0.10 (s, 6H).

b) (3-(4-(tert-Butyldimethylsilyloxy)butyl)phenyl)methanol

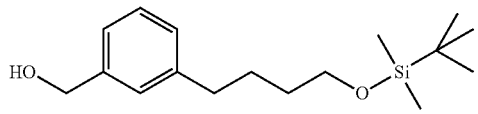

Prepared by the method of Aromatic Intermediate 18, step b using (3-(4-(tert-butyldimethylsilyloxy)but-1-ynyl)phenyl)methanol [Aromatic Intermediate 19, step a] (0.79 g) in place of 3-(3-(hydroxymethyl)phenyl)prop-2-yn-1-ol. Yield 0.72 g.
¹H NMR (400 MHz, CDCl₃) δ 7.30-7.10 (m, 4H), 4.66 (t, J=5.8 Hz, 2H), 3.63 (t, J=6.3 Hz, 2H), 2.63 (t, J=7.7 Hz, 2H), 1.72-1.51 (m, 4H), 0.89 (s, 9H), 0.04 (s, 6H).

c) 3-(4-(tert-Butyldimethylsilyloxy)butyl)benzaldehyde

Prepared by the method of Aromatic Intermediate 18, step c using (3-(4-(tert-butyldimethylsilyloxy)butyl)phenyl)methanol [Aromatic Intermediate 19, step b] (0.72 g) in place of 3-(3-(hydroxymethyl)phenyl)propan-1-ol. Yield 0.64 g.
¹H NMR (400 MHz, CDCl₃) δ 10.00 (s, 1H), 7.72-7.68 (m, 2H), 7.46-7.43 (m, 2H), 3.63 (t, J=6.4 Hz, 2H), 2.72 (t, J=7.7 Hz, 2H), 1.76-1.67 (m, 2H), 1.60-1.52 (m, 2H), 0.89 (s, 9H), 0.04 (s, 6H).

Aromatic Intermediate 20

2-(4-(2-(tert-Butyldimethylsilyloxy)ethyl)thiophen-2-yl)ethanol

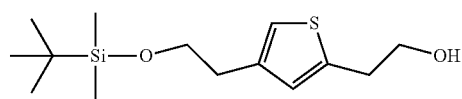

a) (4-(2-(tert-Butyldimethylsilyloxy)ethyl)thiophen-2-yl)methanol

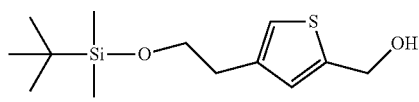

Sodium borohydride (1.40 g) was added portionwise to a stirred solution at 0° C. of 4-(2-(tert-butyldimethylsilyloxy)ethyl)thiophene-2-carbaldehyde [Aromatic Intermediate 6] (10 g) in ethanol (70 mL). The reaction mixture was stirred for 1 hour at 0° C. and then partitioned between ethyl acetate and aqueous brine and separated. The organic layer was dried, filtered and the solvent was evaporated under reduced pressure. The crude product was purified by flash silica chromatography using 12% ethyl acetate in isohexane as solvent. Fractions containing the product were evaporated to dryness to afford the subtitled compound. Yield 6.00 g.
¹H NMR (400 MHz, D₆-DMSO) δ 7.04 (s, 1H), 6.82 (s, 1H), 5.35 (t, J=5.6 Hz, 1H), 4.55 (d, J=5.6 Hz, 2H), 3.73 (t, J=7.0 Hz, 2H), 2.69 (t, J=6.9 Hz, 2H), 0.85 (s, 9H), 0.00 (s, 6H).

b) 2-(4-(2-(tert-Butyldimethylsilyloxy)ethyl)thiophen-2-yl)acetonitrile

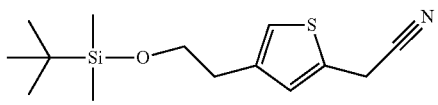

Triphenylphosphine (7.16 g) followed by carbon tetrabromide (8.62 g) were added in one portion to (4-(2-(tert-butyldimethylsilyloxy)ethyl)thiophen-2-yl)methanol [Aromatic Intermediate 20, step a] (6.00 g) in DCM (50 mL) at 0° C. under nitrogen. The resulting solution was stirred at room temperature for 1 hour. The reaction mixture was cooled to 0° C. and treated with tetraethylammonium cyanide (4.92 g), added in one portion. The mixture was diluted further with dichloromethane (20 mL) and stirred at room temperature for 40 minutes. The reaction mixture was partitioned between dichloromethane and aqueous brine, the organic layer was separated, dried over sodium sulphate and the solvent removed under reduced pressure. The crude product was purified by flash silica chromatography, elution gradient 2 to 6% ethyl acetate in isohexane. Fractions containing the product were evaporated to dryness to afford the subtitled compound. Yield 4.20 g.
¹H NMR (400 MHz, CDCl₃) δ 6.93 (s, 1H), 6.92 (s, 1H), 3.86 (s, 2H), 3.78 (t, J=6.7 Hz, 2H), 2.78 (t, J=6.7 Hz, 2H), 0.88 (s, 9H), 0.00 (s, 6H).

c) 2-(4-(2-Hydroxyethyl)thiophen-2-yl)acetic acid

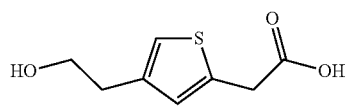

A solution of 2-(4-(2-(tert-butyldimethylsilyloxy)ethyl)thiophen-2-yl)acetonitrile [Aromatic Intermediate 20, step b] (4.20 g) dissolved in ethanol (30 mL) was added to a stirred solution of potassium hydroxide (1.67 g) in water (30 mL). The resulting mixture was stirred at 100° C. for 3 hours. The mixture was partitioned between aqueous brine and ethyl acetate, and the phases separated. The aqueous layer was cooled with ice and acidified by dropwise addition of concentrated hydrochloric acid. The aqueous layer was then extracted with ethyl acetate (×2), the combined organic phases were washed with aqueous brine, dried over sodium sulphate and the solvent evaporated under reduced pressure to give a yellow solid which was triturated with ether (20 mL) to give the subtitled compound. Yield 2.33 g.
¹H NMR (400 MHz, D₆-DMSO) δ 12.46 (s, 1H), 7.00 (s, 1H), 6.81 (s, 1H), 4.61 (t, J=4.9 Hz, 1H), 3.73 (s, 2H), 3.60-3.54 (m, 2H), 2.66 (t, J=7.0 Hz, 2H).

d) 2-(4-(2-(tert-Butyldimethylsilyloxy)ethyl)thiophen-2-yl)ethanol tert-Butyldimethylsilyl chloride (2.21 g) was added portionwise to a mixture of imidazole (1.00 g) and 2-(4-(2-hydroxyethyl)thiophen-2-yl)acetic acid [Aromatic Intermediate 20, step c] (1.3 g) in DMF (15 mL) at 20° C. over a period of 20 minutes. The resulting solution was stirred at 20° C. for 1 hour. The reaction mixture was diluted with THF (15 mL), cooled in ice-water, and treated with a solution of potassium carbonate (1.35 g) in water (15 mL). This mixture was stirred at 0° C. for 20 minutes. The mixture was partitioned between ethyl acetate and aqueous brine, and the phases separated. The organic layer was washed twice with aqueous brine, dried, filtered and the solvent removed under reduced pressure. The residue was dissolved in THF (40 mL), cooled in an ice bath and treated with borane tetrahydrofuran complex (1M in THF, 21 mL), added dropwise. The resultant solution was stirred at 20° C. for 2 hours. The reaction mixture was quenched by dropwise addition of methanol (10 mL) and the solvents were removed under reduced pressure. The crude product was purified by flash silica chromatography using 17% ethyl acetate in isohexane as solvent. Fractions containing the product were evaporated to dryness to afford the titled compound. Yield 1.25 g.

$^1$H NMR (400 MHz, D$_6$-DMSO) δ 6.94 (s, 1H), 6.75 (s, 1H), 4.75 (t, J=5.3 Hz, 1H), 3.74 (t, J=6.9 Hz, 2H), 3.62-3.56 (m, 2H), 2.86 (t, J=6.9 Hz, 2H), 2.69 (t, J=6.8 Hz, 2H), 0.85 (s, 9H), 0.00 (s, 6H).

Aromatic Intermediate 21

2-(4-(2-(Methylsulfonyloxy)ethyl)thiophen-2-yl)ethyl acetate

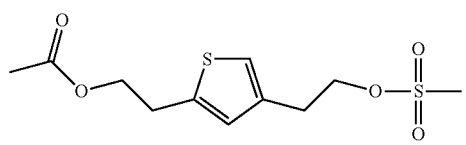

a) 2-(4-(2-(tert-Butyldimethylsilyloxy)ethyl)thiophen-2-yl)ethyl acetate

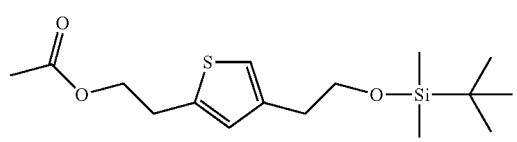

A solution of acetyl chloride (0.36 mL) in dry THF (3 mL) was added dropwise over 10 minutes to a stirred solution at 20° C. of 2-(4-(2-(tert-butyldimethylsilyloxy)ethyl)thiophen-2-yl)ethanol [Aromatic Intermediate 20] (1.10 g) and triethylamine (1.18 mL) in dry THF (30 mL). The mixture was stirred at 20° C. for 20 minutes and then partitioned between ethyl acetate and brine. The organic layer was dried, filtered and the solvent evaporated under reduced pressure to give the subtitled compound. Yield 1.20 g.

$^1$H NMR (400 MHz, CDCl$_3$) δ 6.81 (s, 1H), 6.72 (s, 1H), 4.27 (t, J=6.9 Hz, 2H), 3.78 (t, J=6.9 Hz, 2H), 3.09 (t, J=6.8 Hz, 2H), 2.77 (t, J=6.9 Hz, 2H), 2.06 (s, 3H), 0.88 (s, 9H), 0.00 (s, 6H).

b) 2-(4-(2-Hydroxyethyl)thiophen-2-yl)ethyl acetate

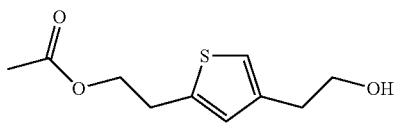

TBAF (1M in THF, 3.65 mL) was added dropwise to a solution of 2-(4-(2-(tert-butyldimethylsilyloxy)ethyl)thiophen-2-yl)ethyl acetate [Aromatic Intermediate 21, step a] (1.2 g) in dry THF (30 mL). This solution was allowed to stand at 20° C. for 1 hour, then the solvents were evaporated under reduced pressure and the residue was purified by flash silica chromatography, using 40% ethyl acetate in isohexane as solvent. Fractions containing the product were evaporated to dryness to afford the subtitled compound. Yield 0.63 g.

$^1$H NMR (400 MHz, D$_6$-DMSO) δ 6.97 (s, 1H), 6.80 (s, 1H), 4.60 (t, J=5.3 Hz, 1H), 4.17 (t, J=6.7 Hz, 2H), 3.60-3.54 (m, 2H), 3.04 (t, J=6.5 Hz, 2H), 2.65 (t, J=7.0 Hz, 2H), 2.01 (s, 3H).

c) 2-(4-(2-(Methylsulfonyloxy)ethyl)thiophen-2-yl)ethyl acetate

A solution of 2-(4-(2-hydroxyethyl)thiophen-2-yl)ethyl acetate [Aromatic Intermediate 21, step b] (0.6 g) and triethylamine (0.47 mL) in DCM (30 mL) at 0° C. was treated dropwise over 20 minutes with a solution of methanesulphonyl chloride (0.24 mL) in DCM (3 mL). The mixture was stirred at 20° C. for 1 hour and then washed with water. The organic layer was dried, filtered and the solvent evaporated under reduced pressure to afford the titled compound. Yield 0.80 g.

$^1$H NMR (500 MHz, CDCl$_3$) δ 6.91 (s, 1H), 6.74 (s, 1H), 4.40 (t, J=6.7 Hz, 2H), 4.27 (t, J=6.7 Hz, 2H), 3.11 (t, J=6.5 Hz, 2H), 3.02 (t, J=6.8 Hz, 2H), 2.91 (s, 3H), 2.07 (s, 3H).

Aromatic Intermediate 22

3-(2-(tert-Butyldimethylsilyloxy)ethyl)-2-methylbenzaldehyde

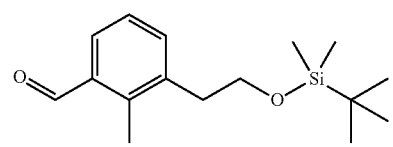

a) 1-Bromo-3-(2-methoxyvinyl)-2-methylbenzene (E/Z mixture)

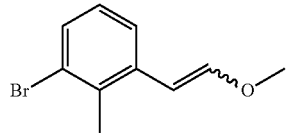

Potassium tert-butoxide (2.64 g) was added portionwise, over 20 minutes, to a stirred suspension of (methoxymethyl)triphenylphosphonium chloride (8.66 g) in THF (20 mL), pre-cooled in ice-water. A deep red colour developed. The cooling bath was removed and the mixture allowed to stir at room temperature for 1.75 hours. The mixture was cooled back down in ice-water and treated with a solution of 3-bromo-2-methylbenzaldehyde [J. Am. Chem. Soc. 2009, 131(4), 1410] (3.87 g) in THF (20 mL), added dropwise over 45 minutes. The reaction mixture was stirred for 2.5 hours, then poured into aqueous HCl (1M) and extracted twice with diethyl ether. The combined organic extracts were washed three times with water, once with brine, then dried ($MgSO_4$), filtered and concentrated in vacuo to afford a brown solid. The solid was purified by flash chromatography on silica eluted with 5% MeOH/DCM to remove most of the triphenylphosphine oxide, then again on silica eluted with 10% DCM/isohexane followed by 25% DCM/isohexane. Fractions containing the E/Z product mixture were combined and concentrated under reduced pressure to afford the subtitled compound as a colourless oil. Yield 1.76 g.

$^1$H NMR (400 MHz, $CDCl_3$) δ 7.72 (d, J=7.7 Hz, 0.5H), 7.38 (t, J=8.0 Hz, 1H), 7.18 (d, J=7.7 Hz, 0.5H), 6.97 (dt, J=13.6, 7.8 Hz, 1H), 6.80 (d, J=12.6 Hz, 0.5H), 6.19 (d, J=7.2 Hz, 0.5H), 5.93 (d, J=12.8 Hz, 0.5H), 5.34 (d, J=7.2 Hz, 0.5H), 3.74 (s, 1.5H), 3.70 (s, 1.5H), 2.40 (s, 1.5H), 2.39 (s, 1.5H).

b) 2-(3-Bromo-2-methylphenyl)ethanol

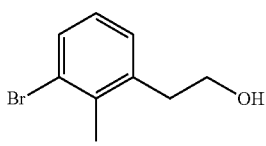

To an ice-cold solution of 1-bromo-3-(2-methoxyvinyl)-2-methylbenzene [Aromatic Intermediate 22, step a] (1.75 g) in THF (25 mL) was added a solution of mercury(II) acetate (2.95 g) in water (30 mL) and the resulting solution was stirred in ice-water for 2.75 hours. Meanwhile, potassium carbonate (35 g) was dissolved in water (30 mL) and the solution was filtered. Sodium borohydride (1.17 g) was part dissolved/part suspended in 35 mL of the resulting potassium carbonate solution, and added to the reaction mixture from above. A grey, cloudy, two-phase mixture was formed, that was stirred at room temperature for 2.5 hours, then poured into water and extracted twice with ethyl acetate. The combined organic phases were washed with brine, dried ($MgSO_4$), filtered and concentrated in vacuo to afford the subtitled compound as a colourless oil. Yield 1.67 g.

$^1$H NMR (400 MHz, $CDCl_3$) δ 7.45 (dd, J=7.9, 1.0 Hz, 1H), 7.12 (d, J=7.4 Hz, 1H), 6.99 (t, J=7.8 Hz, 1H), 3.83 (dd, J=12.3, 6.7 Hz, 2H), 2.96 (t, J=6.9 Hz, 2H), 2.42 (s, 3H), 1.37 (t, J=5.8 Hz, 1H).

c) (3-Bromo-2-methylphenethoxy)(tert-butyl)dimethylsilane

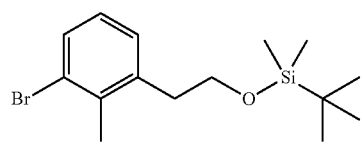

A solution of 2-(3-bromo-2-methylphenyl)ethanol [Aromatic Intermediate 22, step b] (1.67 g) and imidazole (1.60 g) in DMF (20 mL) was cooled in ice-water, treated with tert-butyldimethylchlorosilane (1.31 g), then removed from the cooling bath and stirred at room temperature overnight. The solution was poured into water and extracted twice with diethyl ether. The combined organic extracts were washed twice with water, once with brine, then dried over anhydrous magnesium sulphate and purified by flash chromatography on silica eluted with 10% dichloromethane in isohexane to afford the subtitled compound as a colourless oil. Yield 2.06 g.

$^1$H NMR (400 MHz, $CDCl_3$) δ 7.43 (dd, J=7.9, 1.3 Hz, 1H), 7.11 (dd, J=0.4, 7.3 Hz, 1H), 6.98 (t, J=7.8 Hz, 1H), 3.78 (t, J=7.2 Hz, 2H), 2.91 (t, J=7.2 Hz, 2H), 2.43 (s, 3H), 0.88 (s, 9H), 0.00 (s, 6H).

d) 3-(2-(tert-Butyldimethylsilyloxy)ethyl)-2-methylbenzaldehyde

A colourless solution of (3-bromo-2-methylphenethoxy)(tert-butyl)dimethylsilane [Aromatic Intermediate 22, step c] (2.06 g) in THF (40 mL) was cooled to −78° C. under an atmosphere of nitrogen and treated with butyllithium (2.1M in hexanes, 3.3 mL), added dropwise over 3 minutes. The resulting pale yellow solution was stirred at −78° C. for 30 minutes, treated with N,N-dimethylformamide (0.73 mL) added dropwise over 2 minutes to give a colourless solution, stirred at −78° C. for a further 30 minutes, then removed from the cooling bath and allowed to warm to room temperature over 45 minutes. The solution was quenched by the addition of 10% aqueous ammonium chloride (100 mL), and the resulting mixture was extracted twice with diethyl ether. The combined organic phases were washed with brine, dried over anhydrous magnesium sulphate and concentrated in vacuo to afford the titled compound as a pale yellow oil. Yield 1.74 g.

$^1$H NMR (400 MHz, $CDCl_3$) δ 10.35 (s, 1H), 7.71 (dd, J=7.7, 1.3 Hz, 1H), 7.44 (dd, J=7.6, 1.4 Hz, 1H), 7.32 (t, J=7.6

Hz, 1H), 3.82 (t, J=7.0 Hz, 2H), 2.97 (t, J=7.0 Hz, 2H), 2.68 (s, 3H), 0.89 (t, J=2.8 Hz, 9H), 0.00 (t, J=3.1 Hz, 6H).

$^1$H NMR (400 MHz, D$_6$-DMSO) δ 7.07 (s, 2H), 6.97 (s, 1H), 4.61 (s, 2H), 3.58 (t, J=7.6 Hz, 2H), 2.67 (t, J=7.0 Hz, 2H), 2.27 (s, 3H). One exchangeable proton not observed.

Aromatic Intermediate 23

Aromatic Intermediate 24

2-(3-(Bromomethyl)-5-methylphenyl)ethanol 3-(3-(tert-Butyldimethylsilyloxy)propyl)-2-fluorobenzaldehyde

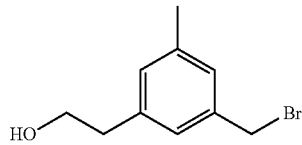

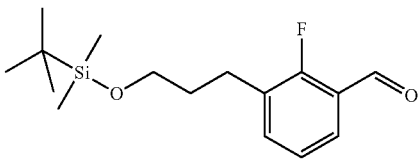

a) 2-(3-(Bromomethyl)-5-methylphenyl)acetic acid a) 3-(2-Fluorophenyl)propan-1-ol

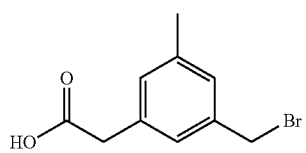

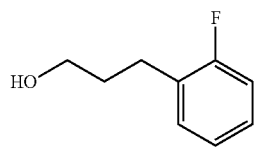

NBS (3.12 g) was added portionwise over 1 hour to a solution of 2-(3,5-dimethylphenyl)acetic acid (3.6 g) and AIBN (0.015 g) in ethyl acetate (100 mL) at 50° C. under nitrogen. More AIBN (0.015 g) was added and the mixture was heated to reflux for 3 hours. The reaction mixture was washed with 10% aqueous sodium chloride solution (2×200 mL), dried over magnesium sulphate, filtered and evaporated. The crude material was purified by flash silica chromatography using 20% ethyl acetate in isohexane containing 1% acetic acid as solvent. Fractions containing the product were evaporated to dryness to afford a solid which was triturated with cyclohexane (10 mL) to yield the subtitled compound as a white solid. Yield 2.10 g.

$^1$H NMR (400 MHz, D$_6$-DMSO) δ 7.15-7.11 (m, 2H), 7.01 (s, 1H), 4.64 (s, 2H), 3.52 (s, 2H), 2.28 (s, 3H). One exchangeable proton not observed.

b) 2-(3-(Bromomethyl)-5-methylphenyl)ethanol

Borane dimethyl sulfide complex (2M in THF, 8.6 mL) was added dropwise to a solution of 2-(3-(bromomethyl)-5-methylphenyl)acetic acid [Aromatic Intermediate 23, step a] (2.1 g) in THF (50 mL) at 0° C. and the mixture stirred for 10 minutes at this temperature and then at room temperature for 1 hour. The reaction mixture was quenched by dropwise addition of methanol, the solvents were evaporated under reduced pressure and the residue was purified by flash silica chromatography using 30% ethyl acetate in isohexane as solvent. Fractions containing the product were evaporated to dryness to afford the titled compound. Yield 1.40 g.

Borane dimethyl sulfide complex (2M in THF, 27.6 mL) was added dropwise to a solution of 3-(2-fluorophenyl)propanoic acid (3.09 g) in tetrahydrofuran (25 mL) and the resulting mixture was allowed to warm to RT and stirred overnight. The reaction was cautiously quenched with methanol and when bubbling had ceased, evaporated. The residue was purified by flash silica chromatography eluting with 4:1 to 1:1 isohexane:ethyl acetate gradient to give the subtitled compound as a clear oil. Yield 2.72 g.

$^1$H NMR (300 MHz, CDCl$_3$) δ 7.24-7.13 (m, 2H), 7.09-6.97 (m, 2H), 3.67 (t, J=6.3 Hz, 2H), 2.74 (t, J=7.6 Hz, 2H), 1.95-1.83 (m, 2H). One exchangeable proton not observed.

b) tert-Butyl(3-(2-fluorophenyl)propoxy)dimethylsilane

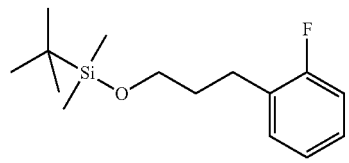

Prepared by the method of Aromatic Intermediate 5, step a using 3-(2-fluorophenyl)propan-1-ol [Aromatic Intermediate 24, step a] (2.72 g) in place of 2-(2-fluorophenyl)ethanol. Yield 4.4 g.

$^1$H NMR (300 MHz, CDCl$_3$) δ 7.23-7.09 (m, 2H), 7.09-6.94 (m, 2H), 3.64 (t, J=6.3 Hz, 2H), 2.75-2.66 (m, 2H), 1.89-1.76 (m, 2H), 0.91 (s, 9H), 0.05 (s, 6H).

c) 3-(3-(tert-Butyldimethylsilyloxy)propyl)-2-fluorobenzaldehyde tert-Butyl(3-(2-fluorophenyl)propoxy)dimethylsilane [Aromatic Intermediate 24, step b] (4.4 g) was added dropwise over 5 min to a solution of sec-butyllithium (1.4M in cyclohexane, 11.7 mL) and 1,1,4,7,7-pentamethyldiethylenetriamine (3.4 mL) in THF (25 mL) at −78° C. The resulting mixture was stirred for 2 h, then DMF (6.4 mL) was cautiously added and the resulting mixture allowed to warm to RT and stirred overnight. The reaction was quenched with water (100 mL) and then ethyl acetate (250 mL) was added. The phases were separated and the organic phase washed with water (2×100 mL), aqueous HCl (2M, 2×50 mL), and brine (100 mL), then dried over magnesium sulphate, filtered and evaporated. Purification was by silica gel chromatography eluting with isohexane to 10% ether in isohexane gradient. The fractions containing product were combined and evaporated to give the titled compound as a clear oil. Yield 1.0 g.

$^1$H NMR (400 MHz, CDCl$_3$) δ 10.38 (s, 1H), 7.73-7.67 (m, 1H), 7.48 (td, J=7.4, 1.8 Hz, 1H), 7.18 (t, J=7.7 Hz, 1H), 3.66 (t, J=6.0 Hz, 2H), 2.82-2.75 (m, 2H), 1.90-1.80 (m, 2H), 0.91 (s, 9H), 0.06 (s, 6H).

Aromatic Intermediate 25

3-((2-(tert-Butyldimethylsilyloxy)ethoxy)methyl)benzaldehyde

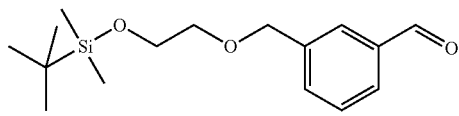

a) 2-(3-Bromobenzyloxy)ethanol

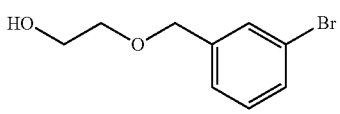

Sodium hydride (60% suspension in mineral oil, 1.23 g) was added portionwise to a solution of ethane-1,2-diol (4.7 mL) in THF (70 mL) and the mixture was stirred at RT for 30 min. 1-Bromo-3-(bromomethyl)benzene (7 g) was added, followed by tetrabutylammonium iodide (1.03 g) and the reaction mixture was heated at reflux for 90 min. The mixture was diluted with water and extracted into ethyl acetate (×2). The combined organics were dried over MgSO$_4$, filtered and evaporated. The crude product was purified by silica chromatography using 30% ethyl acetate in isohexane as solvent to afford the subtitled compound as a colourless oil. Yield 4.90 g.

$^1$H NMR (400 MHz, D$_6$-DMSO) δ 7.56-7.53 (m, 1H), 7.47 (dt, J=7.3, 1.9 Hz, 1H), 7.36-7.28 (m, 2H), 4.66 (t, J=5.5 Hz, 1H), 4.50 (s, 2H), 3.58-3.52 (m, 2H), 3.49-3.44 (m, 2H).

b) (2-(3-Bromobenzyloxy)ethoxy)(tert-butyl)dimethylsilane

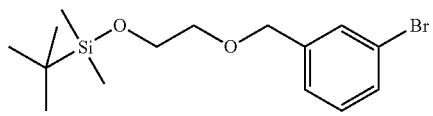

A solution of 2-(3-bromobenzyloxy)ethanol [Aromatic Intermediate 25, step a] (3 g), imidazole (2.2 g) and tert-butyldimethylchlorosilane (2.2 g) in DCM (50 mL) was stirred at RT for 17 hours. The reaction mixture was partitioned between ethyl acetate and water. The aqueous layer was extracted with ethyl acetate (×2). The combined organic phases were dried and evaporated in vacuo. The crude product was purified by silica gel chromatography, gradient elution 10 to 40% ethyl acetate in isohexane. Fractions containing the product were evaporated to dryness to afford the subtitled compound as a colourless oil. Yield 3.8 g.

$^1$H NMR (400 MHz, D$_6$-DMSO) δ 7.54-7.52 (m, 1H), 7.49-7.45 (m, 1H), 7.34-7.28 (m, 2H), 4.51 (s, 2H), 3.74 (t, J=5.0 Hz, 2H), 3.50 (t, J=4.9 Hz, 2H), 0.89-0.85 (m, 9H), 0.07-0.02 (m, 6H).

c) 3-((2-(tert-Butyldimethylsilyloxy)ethoxy)methyl)benzaldehyde (2-(3-Bromobenzyloxy)ethoxy)(tert-butyl)dimethylsilane [Aromatic Intermediate 25, step b] (2.3 g) was dissolved in THF (15 mL) and the solution cooled to −10° C. Isopropylmagnesium chloride (2M in THF, 1.2 mL) was added, followed by butyllithium (2.1M in hexanes, 2.4 mL). The mixture was stirred for 10 min before being added to a solution of morpholine-4-carbaldehyde (1.4 mL) in THF (15 mL). The mixture was stirred for 1 hour, then poured onto ammonium chloride solution (30 mL) and extracted into ether (2×30 mL). The combined ether extracts were washed with water and dried over sodium sulphate. The solvent was evaporated in vacuo to give the titled compound as a colourless oil. Yield 1.8 g.

$^1$H NMR (400 MHz, D$_6$-DMSO) δ 10.02 (s, 1H), 7.86 (s, 1H), 7.83 (d, J=7.4 Hz, 1H), 7.66 (d, J=7.7 Hz, 1H), 7.59 (t, J=7.4 Hz, 1H), 4.61 (s, 2H), 3.76 (t, J=4.9 Hz, 2H), 3.53 (t, J=5.0 Hz, 2H), 0.86 (s, 9H), 0.29 (s, 6H).

Aromatic Intermediate 26

3-(2-(tert-Butyldimethylsilyloxy)ethyl)-2-methoxybenzaldehyde

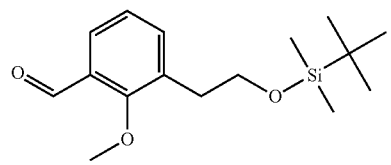

a) tert-Butyl(2-methoxyphenethoxy)dimethylsilane

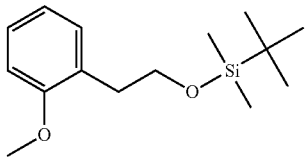

Prepared by the method of Aromatic Intermediate 5, step a using 2-(2-methoxyphenyl)ethanol (3 g) in place of 2-(2-fluorophenyl)ethanol. Yield 5.1 g.

$^1$H NMR (400 MHz, CDCl$_3$) δ 7.22-7.14 (m, 2H), 6.90-6.82 (m, 2H), 3.82 (s, 3H), 3.79 (t, J=7.3 Hz, 2H), 2.86 (t, J=7.3 Hz, 2H), 0.88 (s, 9H), 0.00 (s, 6H).

b) 3-(2-(tert-Butyldimethylsilyloxy)ethyl)-2-methoxybenzaldehyde tert-Butyl(2-methoxyphenethoxy)dimethylsilane [Aromatic Intermediate 26, step a] (2.0 g), as a solution in THF (1 mL), was added dropwise over 5 min to a stirred solution of butyllithium (2.5M in hexanes, 4.5 mL) and TMEDA (1.7 mL) in tetrahydrofuran (20 mL) at 0° C. The resulting mixture was stirred for 4 hours, and then DMF (2.9 mL) was added. The mixture was stirred for a further 30 min and allowed to warm to RT. The reaction was poured into aqueous HCl (0.5M, 20 mL) and extracted with ether (2×50 mL). The combined organic solutions were washed with water (50 mL) and brine (50 mL), dried over magnesium sulphate, filtered and evaporated. The resulting gum was purified by silica gel chromatography eluting with isohexane to 4:1 isohexane:ethyl acetate gradient to give the titled compound as a clear oil. Yield 0.40 g.

$^1$H NMR (300 MHz, CDCl$_3$) δ 10.37 (s, 1H), 7.73 (dd, J=7.7, 1.7 Hz, 1H), 7.53 (dd, J=7.5, 1.5 Hz, 1H), 7.18 (t, J=7.6 Hz, 1H), 3.92 (s, 3H), 3.86 (t, J=6.9 Hz, 2H), 2.92 (t, J=6.9 Hz, 2H), 0.87 (s, 9H), −0.01 (s, 6H).

B) Preparation of Carboxylic Acids

Carboxylic Acid 1

2-Ethylthiazole-4-carboxylic acid

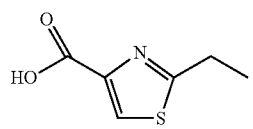

a) Propanethioamide

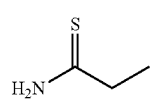

Phosphorus pentasulfide (15.2 g) was added to a suspension of propionamide (20 g) in methyl t-butyl ether (900 mL) and the mixture stirred for 18 hours. The mixture was filtered through Celite and concentrated in vacuo to afford the subtitled compound as a yellow oil. Yield 15.8 g.

$^1$H NMR (300 MHz, CDCl$_3$) δ 7.59 (s, 1H), 6.88 (s, 1H), 2.70 (q, J=7.5 Hz, 2H), 1.32 (t, J=7.5 Hz, 3H).

b) Ethyl 2-ethylthiazole-4-carboxylate

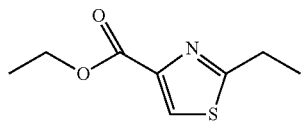

Ethyl 3-bromo-2-oxopropanoate (24.7 mL) was added dropwise over 10 min to a solution of propanethioamide [Carboxylic Acid 1, step a] (15.8 g) in ethanol (150 mL) at 0-10° C. under nitrogen. When the addition was complete the mixture was stirred at ambient temperature for 18 hours. The mixture was concentrated in vacuo, the residue diluted with water and extracted into ethyl acetate (×3). The combined extracts were washed with brine, dried over magnesium sulfate, filtered and the solvent removed. The crude product was purified by flash silica chromatography, elution gradient 10, 15 and 20% ethyl acetate in isohexane. Fractions containing the product were evaporated to dryness to afford the subtitled compound as a pale green solid. Yield 16.0 g.

$^1$H NMR (400 MHz, CDCl$_3$) δ 8.06 (s, 1H), 4.42 (q, J=7.1 Hz, 2H), 3.10 (q, J=7.5 Hz, 2H), 1.44-1.38 (m, 6H).

c) 2-Ethylthiazole-4-carboxylic acid

Concentrated HCl (75 mL) was added to a suspension of ethyl 2-ethylthiazole-4-carboxylate [Carboxylic Acid 1, step b] (16 g) in water (75 mL) and the mixture stirred at 100° C. for 24 hours. The mixture was cooled and concentrated in vacuo. The residue was triturated with acetone, the solid collected by filtration and dried in vacuo to afford the titled compound as a grey solid. Yield 14.4 g.

M/Z 158 (M+H)$^+$/156 (M−H)$^−$ (APCI).

$^1$H NMR (400 MHz, D$_6$-DMSO) δ 8.31 (s, 1H), 3.01 (q, J=7.5 Hz, 2H), 1.31 (t, J=7.6 Hz, 3H). One exchangeable proton not observed.

Carboxylic Acid 2

2-Cyclopentylthiazole-4-carboxylic acid

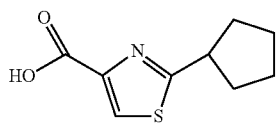

a) Ethyl 2-(cyclopentanecarboxamido)-3-mercaptopropanoate

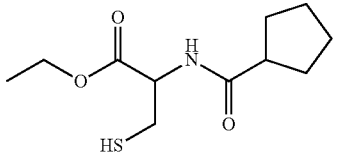

CDI (8.5 g) was added to a solution of cyclopentanecarboxylic acid (5.2 mL) in DMF (40 mL). The resulting mixture was stirred for 1 h and cooled in an ice bath. Ethyl 2-amino-3-mercaptopropanoate hydrochloride (8.88 g) was added, followed by triethylamine (10 mL). The resulting mixture was allowed to warm to RT and stirred overnight. The reaction was quenched with saturated sodium bicarbonate solution (50 mL) and the layers separated. The aqueous was extracted with DCM (2×100 mL). The combined organic solutions were washed with brine (100 mL), dried over sodium sulphate, filtered and evaporated. The resulting solid was purified by silica gel chromatography eluting with 4:1 to 1:1 isohexane:ethyl acetate gradient. The fractions containing the product were combined and evaporated to give the subtitled compound as a white solid. Yield 7.7 g.

$^1$H NMR (400 MHz, $D_6$-DMSO) δ 8.15 (d, J=7.7 Hz, 1H), 4.41-4.34 (m, 1H), 4.14-4.05 (m, 2H), 2.89-2.61 (m, 3H), 1.81-1.45 (m, 9H), 1.18 (t, J=7.0 Hz, 3H).

b) Ethyl 2-cyclopentyl-4,5-dihydrothiazole-4-carboxylate

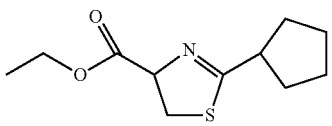

Tosic acid monohydrate (0.78 g) was added to a solution of ethyl 2-(cyclopentanecarboxamido)-3-mercaptopropanoate [Carboxylic Acid 2, step a] (5 g) in toluene (40 mL). The resulting mixture was heated at reflux under Dean and Stark conditions for 6 h. The reaction was allowed to cool, then the toluene solution was washed with saturated sodium bicarbonate solution (20 mL) and the solvent evaporated. The residue was azeotroped with toluene. The resulting white solid was purified by silica gel chromatography eluting with 9:1 isohexane:ethyl acetate. The fractions containing the product were combined and evaporated to give the subtitled compound as a clear oil. Yield 3.2 g.

$^1$H NMR (400 MHz, CDCl$_3$) δ 5.08-4.99 (m, 1H), 4.26 (q, J=7.2 Hz, 2H), 3.56-3.44 (m, 2H), 3.08-2.99 (m, 1H), 2.03-1.93 (m, 2H), 1.83-1.70 (m, 4H), 1.64-1.59 (m, 2H), 1.31 (t, J=7.2 Hz, 3H).

c) Ethyl 2-cyclopentylthiazole-4-carboxylate

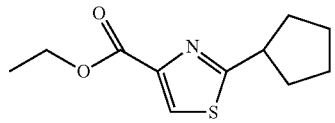

Manganese dioxide (24 g) was added to a solution of ethyl 2-cyclopentyl-4,5-dihydrothiazole-4-carboxylate [Carboxylic Acid 2, step b] (3.2 g) in acetonitrile (100 mL) and the resulting mixture heated at reflux overnight. The reaction was allowed to cool and filtered through a pad of Celite. The filter pad was washed with acetonitrile (2×100 mL) and the combined filtrate and washings evaporated. The residue was purified by silica gel chromatography eluting with 9:1 isohexane: ethyl acetate. The fractions containing the product were combined, evaporated and redissolved in ethanol (20 mL). A slurry of palladium on carbon (5%, 0.66 g) in water (0.5 mL) was added and the resulting suspension stirred under an atmosphere of hydrogen at 5 bar pressure for 2 h. The mixture was filtered through a pad of Celite which was washed with ethanol (3×50 mL). The combined filtrate and washings were evaporated to give the subtitled compound as a clear oil. Yield 0.9 g.

$^1$H NMR (400 MHz, CDCl$_3$) δ 8.04 (s, 1H), 4.41 (q, J=7.2 Hz, 2H), 3.60-3.48 (m, 1H), 2.29-2.18 (m, 2H), 1.89-1.67 (m, 6H), 1.40 (t, J=7.0 Hz, 3H).

d) 2-Cyclopentylthiazole-4-carboxylic acid

Lithium hydroxide monohydrate (0.67 g) was added to solution of ethyl 2-cyclopentylthiazole-4-carboxylate [Carboxylic Acid 2, step c] (0.9 g) in a mixture of THF (40 mL) and water (10 mL). The resulting mixture was stirred overnight. The reaction was acidified with aqueous HCl (2M, 10 mL) and the solvent evaporated. The residue was partitioned between brine (50 mL) and ethyl acetate (50 mL) and the layers separated. The aqueous phase was extracted with ethyl acetate (2×50 mL). The combined organic solutions were dried over sodium sulphate, filtered and evaporated to give the titled compound as a pale yellow solid. Yield 0.77 g.

$^1$H NMR (400 MHz, $D_6$-DMSO) δ 12.89 (s, 1H), 8.30 (s, 1H), 3.51-3.41 (m, 1H), 2.17-2.07 (m, 2H), 1.82-1.59 (m, 6H).

Carboxylic Acid 3

2-(Pentan-3-yl)thiazole-4-carboxylic acid

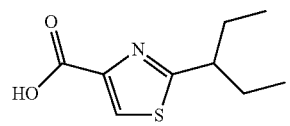

a) 2-Ethylbutanamide

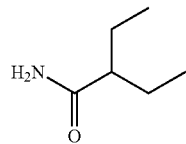

2-Ethylbutanoyl chloride (5 g) was cautiously added dropwise to ice cold 35% aqueous ammonia (50 mL) and the resulting suspension stirred for 1 h. The reaction mixture was extracted with DCM (3×100 mL). The combined organic phases were washed with brine (100 mL), dried over sodium sulphate, filtered and evaporated to give the subtitled compound as a white solid. Yield 3.4 g.

$^1$H NMR (400 MHz, D$_6$-DMSO) δ 7.23 (s, 1H), 6.71 (s, 1H), 1.98-1.88 (m, 1H), 1.50-1.27 (m, 4H), 0.81 (t, J=7.4 Hz, 6H).

b) 2-Ethylbutanethioamide

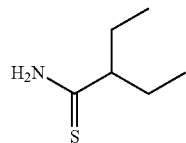

Prepared by the method of Carboxylic Acid 1, step a using 2-ethylbutanamide [Carboxylic Acid 3, step a] (3.4 g) in place of propionamide. Yield 3.8 g. Used directly.

c) Ethyl 2-(pentan-3-yl)thiazole-4-carboxylate

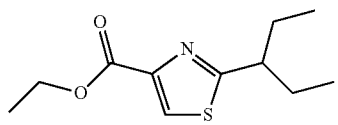

Prepared by the method of Carboxylic Acid 1, step b using 2-ethylbutanethioamide [Carboxylic Acid 3, step b] (3.8 g) in place of propanethioamide. Yield 2.8 g.

$^1$H NMR (400 MHz, D$_6$-DMSO) δ 8.42 (s, 1H), 4.29 (q, J=7.1 Hz, 2H), 2.99-2.89 (m, 1H), 1.82-1.58 (m, 4H), 1.30 (t, J=7.0 Hz, 3H), 0.81 (t, J=7.4 Hz, 6H).

d) 2-(Pentan-3-yl)thiazole-4-carboxylic acid

Prepared by the method of Carboxylic Acid 2, step d using ethyl 2-(pentan-3-yl)thiazole-4-carboxylate [Carboxylic Acid 3, step c] (2.8 g) in place of ethyl 2-cyclopentylthiazole-4-carboxylate. Yield 2.3 g.

$^1$H NMR (300 MHz, D$_6$-DMSO) δ 12.91 (s, 1H), 8.34 (s, 1H), 2.98-2.86 (m, 1H), 1.84-1.56 (m, 4H), 0.81 (t, J=7.3 Hz, 6H).

Carboxylic Acid 4

2-Isobutylthiazole-4-carboxylic acid

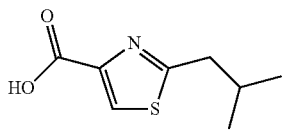

Prepared by the method of Carboxylic Acid 3, using 3-methylbutanoyl chloride (10 mL) in place of 2-ethylbutanoyl chloride in step a. Yield 3.8 g.

$^1$H NMR (300 MHz, D$_6$-DMSO) δ 12.90 (s, 1H), 8.32 (s, 1H), 2.87 (d, J=7.1 Hz, 2H), 2.11-1.96 (m, 1H), 0.94 (d, J=6.7 Hz, 6H).

Carboxylic Acid 5

2-Butylthiazole-4-carboxylic acid

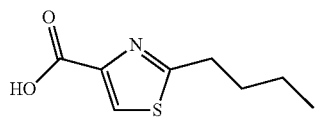

Prepared by the method of Carboxylic Acid 3, from step b using pentanamide (10 g) in place of 2-ethylbutanamide in step b. Yield 4.6 g.

$^1$H NMR (300 MHz, CDCl$_3$) δ 8.18 (s, 1H), 3.11-3.03 (m, 2H), 1.88-1.78 (m, 2H), 1.52-1.38 (m, 2H), 0.97 (t, J=7.2 Hz, 3H). One exchangeable proton not observed.

C) Preparation of amines

Amine 1

N-(2,2-Diethoxyethyl)tetrahydro-2H-pyran-4-amine

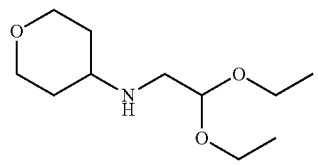

Sodium triacetoxyborohydride (10.6 g) was added to a cooled (0° C.) solution of aminoacetaldehyde diethyl acetal (5.8 mL) and tetrahydro-4H-pyran-4-one (3.7 mL) in dichloromethane (100 mL). The reaction was stirred for 18 h, allowing the temperature to warm to ambient conditions. Water (100 mL) was added, followed by portionwise addition of sodium bicarbonate (16.8 g), causing effervescence. The mixture was stirred vigorously for 1 h, and then allowed to partition. The phases were then separated and the aqueous phase extracted with more dichloromethane (50 mL). The combined organic extracts were dried over sodium sulfate, filtered and concentrated in vacuo to afford the titled compound as a colourless oil. Yield 8.3 g.

$^1$H NMR (300 MHz, CDCl$_3$) δ 4.59 (t, J=5.7 Hz, 1H), 3.97 (ddd, J=11.8, 3.8, 2.5 Hz, 2H), 3.77-3.66 (m, 2H), 3.61-3.50 (m, 2H), 3.39 (td, J=11.7, 2.1 Hz, 2H), 2.76 (d, J=5.6 Hz, 2H), 2.67 (tt, J=10.6, 4.0 Hz, 1H), 1.86-1.77 (m, 2H), 1.48-1.34 (m, 3H), 1.22 (t, J=7.1 Hz, 6H).

Amine 2

(R)—N-(2,2-Dimethoxyethyl)-3-methylbutan-2-amine

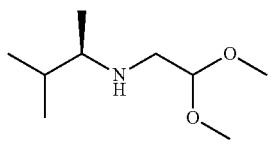

2,2-Dimethoxyacetaldehyde (60% in water, 8.7 mL) was added to (R)-3-methylbutan-2-amine (5.0 g) in methanol (25 mL) and the mixture stirred at ambient temperature overnight. A slurry of palladium on carbon (5%, 1.2 g) in water (10 mL) was added and the mixture was hydrogenated at 5 bar pressure with stirring for 3 hours. The mixture was filtered through Celite and the filter pad washed with methanol (3×100 mL). The combined filtrate and washings were concentrated to a volume of ~10 mL and then toluene (200 mL) was added. The mixture was concentrated, more toluene (200 mL) was added and the mixture was concentrated once more to give the titled compound as a yellow oil. Yield 8.0 g.

$^1$H NMR (300 MHz, CDCl$_3$) δ 4.46 (t, J=2.4 Hz, 1H), 3.38 (s, 6H), 2.78 (dd, J=5.5, 11.9 Hz, 1H), 2.67 (dd, J=5.5, 11.6 Hz, 1H), 2.49-2.39 (m, 1H), 1.76-1.62 (m, 1H), 0.96 (d, J=6.7 Hz, 3H), 0.90 (d, J=6.7 Hz, 3H), 0.85 (d, J=6.7 Hz, 3H). One exchangeable proton not observed.

Amine 3

N-(2,2-Dimethoxyethyl)propan-2-amine

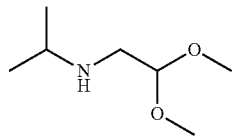

Prepared by the method of Amine 2 using propan-2-amine (5.0 g) in place of (R)-3-methylbutan-2-amine. Yield 3.0 g.

$^1$H NMR (400 MHz, CDCl$_3$) δ 4.48 (t, J=2.8 Hz, 1H), 3.39 (s, 6H), 2.84-2.78 (m, 1H), 2.73 (d, J=5.5 Hz, 2H), 1.07 (d, J=6.3 Hz, 6H). One exchangeable proton not observed.

Amine 4

N-(2,2-Dimethoxyethyl)-3,3-dimethylbutan-1-amine

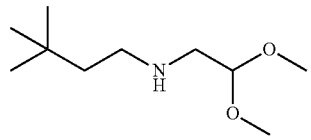

Prepared by the method of Amine 2 using 3,3-dimethylbutan-1-amine (1.0 g) in place of (R)-3-methylbutan-2-amine. Yield 1.85 g.

$^1$H NMR (300 MHz, CDCl$_3$) δ 4.47 (t, J=5.6 Hz, 1H), 3.40 (s, 6H), 2.75 (d, J=5.8 Hz, 2H), 2.65-2.57 (m, 2H), 1.45-1.35 (m, 3H), 0.90 (s, 9H). One exchangeable proton not observed.

Amine 5

(R)—N-(2,2-Dimethoxyethyl)-3,3-dimethylbutan-2-amine

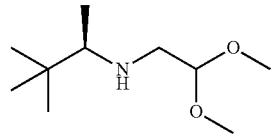

Prepared by the method of Amine 2 using (R)-3,3-dimethylbutan-2-amine (5.1 g) in place of (R)-3-methylbutan-2-amine. Yield 8.7 g.

$^1$H NMR (400 MHz, CDCl$_3$) δ 4.47 (t, J=5.6 Hz, 1H), 3.38 (d, J=4.1 Hz, 6H), 2.86 (dd, J=12.2, 5.5 Hz, 1H), 2.58 (dd, J=12.0, 5.6 Hz, 1H), 2.23 (q, J=6.4 Hz, 1H), 0.97 (d, J=6.4 Hz, 3H), 0.89 (s, 9H). One exchangeable proton not observed.

Amine 6

N-(2,2-Dimethoxyethyl)cyclopentanamine

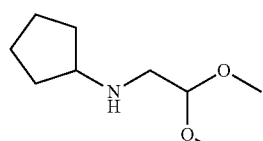

Prepared by the method of Amine 2 using cyclopentanamine (5.0 g) in place of (R)-3-methylbutan-2-amine. Yield 9.4 g.

$^1$H NMR (400 MHz, CDCl$_3$) δ 4.47 (t, J=5.6 Hz, 1H), 3.39 (s, 6H), 3.05 (quintet, J=6.8 Hz, 1H), 2.72 (d, J=5.4 Hz, 2H), 1.89-1.80 (m, 2H), 1.73-1.62 (m, 2H), 1.58-1.48 (m, 2H), 1.36-1.27 (m, 2H). One exchangeable proton not observed.

Amine 7

N-(2,2-Dimethoxyethyl)-3,3,3-trifluoropropan-1-amine

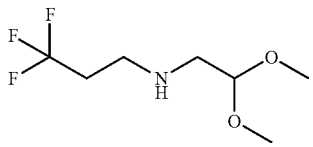

To a stirred solution of 3,3,3-trifluoropropan-1-amine hydrochloride (0.165 g) in methanol (3 mL) was added 2,2-dimethoxyacetaldehyde (60% in water, 0.17 mL) followed by sodium bicarbonate (0.093 g) and the mixture was stirred at ambient temperature overnight. A slurry of palladium on carbon 10% (50 mg) in methanol (1 mL) was added and the mixture was hydrogenated at 5 bar pressure for 4 hours. The mixture was filtered and concentrated in vacuo. The resulting gummy solid was suspended in DCM (5 mL) and dried over sodium sulphate, filtered and evaporated to give the titled compound as a yellow gum. Yield 0.152 g.

$^1$H NMR (500 MHz, CDCl$_3$) δ 4.45 (t, J=5.4 Hz, 1H), 3.40 (s, 6H), 2.89 (t, J=7.3 Hz, 2H), 2.75 (d, J=5.4 Hz, 2H), 2.36-2.23 (m, 2H). One exchangeable proton not observed.

Amine 8

N-(2,2-Dimethoxyethyl)-2-methylpropan-1-amine

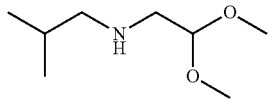

Prepared by the method of Amine 2 using 2-methylpropan-1-amine (10 mL) in place of (R)-3-methylbutan-2-amine. Instead of being dried by co-evaporation from toluene, the crude product was dissolved in DCM (500 mL), dried over sodium sulphate, filtered and evaporated Yield 14.2 g.

$^1$H NMR (400 MHz, CDCl$_3$) δ 4.45 (t, J=5.6 Hz, 1H), 3.36 (s, 6H), 2.69 (d, J=5.6 Hz, 2H), 2.40 (d, J=6.7 Hz, 2H), 1.78-1.64 (m, 1H), 0.87 (d, J=6.7 Hz, 6H). One exchangeable proton not observed.

Amine 9

N-(2,2-Dimethoxyethyl)-3-methoxypropan-1-amine

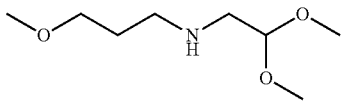

Prepared by the method of Amine 2 using 3-methoxypropan-1-amine (5 g) in place of (R)-3-methylbutan-2-amine. Yield 8.4 g.

$^1$H NMR (400 MHz, CDCl$_3$) δ 4.47 (t, J=5.5 Hz, 1H), 3.44 (t, J=6.3 Hz, 2H), 3.39 (s, 6H), 3.33 (d, J=2.6 Hz, 3H), 2.74 (d, J=5.4 Hz, 2H), 2.71 (t, J=7.0 Hz, 2H), 1.76 (quintet, J=6.7 Hz, 2H). One exchangeable proton not observed.

Amine 10

5-(2,2-Dimethoxyethylamino)pentan-1-ol

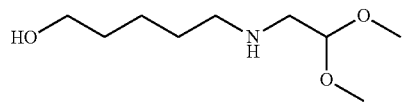

Prepared by the method of Amine 2 using 5-aminopentan-1-ol (5.2 g) in place of (R)-3-methylbutan-2-amine. Yield 9.9 g.

$^1$H NMR (400 MHz, CDCl$_3$) δ 4.47 (t, J=5.5 Hz, 1H), 3.65 (t, J=6.5 Hz, 2H), 3.39 (s, 6H), 2.73 (d, J=5.6 Hz, 2H), 2.63 (t, J=7.0 Hz, 2H), 1.63-1.36 (m, 6H). Two exchangeable protons not observed.

Amine 11

6-(2,2-Dimethoxyethylamino)hexan-1-ol

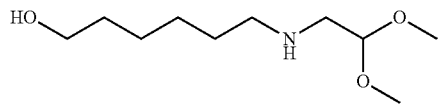

Prepared by the method of Amine 2 using 6-aminohexan-1-ol (4.8 g) in place of (R)-3-methylbutan-2-amine. Yield 7.3 g.

$^1$H NMR (400 MHz, CDCl$_3$) δ 4.47 (t, J=5.5 Hz, 1H), 3.64 (t, J=6.5 Hz, 2H), 3.39 (s, 6H), 2.73 (d, J=5.6 Hz, 2H), 2.62 (t, J=7.2 Hz, 2H), 1.61-1.31 (m, 8H). Two exchangeable protons not observed.

Amine 12

N-(2-Fluoroethyl)-2,2-dimethoxyethanamine

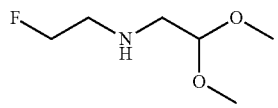

Prepared by the method of Amine 7 using 2-fluoroethanamine hydrochloride (1 g) in place of 3,3,3-trifluoropropan-1-amine hydrochloride. Yield 0.8 g.

¹H NMR (400 MHz, CDCl₃) δ 4.66 (t, J=5.2 Hz, 1H), 4.55 (q, J=5.1 Hz, 2H), 3.41 (s, 6H), 3.34 (s, 1H), 3.06 (t, J=4.7 Hz, 1H), 2.99 (t, J=4.7 Hz, 1H), 2.86 (d, J=5.4 Hz, 2H).

Amine 13

N-(2,2-Difluoroethyl)-2,2-dimethoxyethanamine

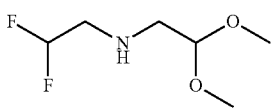

Prepared by the method of Amine 8 using 2,2-difluoroethanamine (1.1 g) in place of 2-methylpropan-1-amine. Yield 1.8 g.

¹H NMR (400 MHz, CDCl₃) δ 6.00-5.66 (m, 1H), 4.43 (t, J=5.2 Hz, 1H), 3.39 (s, 6H), 3.04-2.94 (m, 2H), 2.80 (d, J=5.1 Hz, 2H), 1.36 (s, 1H).

Amine 14

N-(2,2-Dimethoxyethyl)-2,2,2-trifluoroethanamine

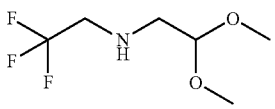

Prepared by the method of Amine 8 using 2,2,2-trifluoroethanamine (1 g) in place of 2-methylpropan-1-amine. Yield 1.2 g.

¹H NMR (400 MHz, CDCl₃) δ 4.42 (t, J=5.3 Hz, 1H), 3.39 (s, 6H), 3.21 (q, J=9.3 Hz, 2H), 2.85 (d, J=5.1 Hz, 2H), 1.49 (s, 1H).

Amine 15

N-(3-(tert-Butyldimethylsilyloxy)propyl)butan-1-amine

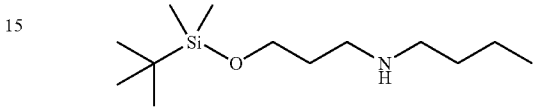

Butan-1-amine (8 mL) was added to (3-bromopropoxy)(tert-butyl)dimethylsilane (0.8 g) and the resulting mixture stirred overnight at RT. The volatiles were removed by concentration under reduced pressure and the residue was partitioned between saturated sodium bicarbonate solution (20 mL) and ethyl acetate (25 mL). The phases were separated and the aqueous phase was extracted with more ethyl acetate (2×25 mL). The combined organic phases were washed with brine (25 mL), dried over sodium sulphate, filtered and evaporated to give the titled compound as a clear oil. Yield 0.75 g.

¹H NMR (400 MHz, CDCl₃) δ 3.64 (t, J=6.2 Hz, 2H), 2.64 (t, J=6.9 Hz, 2H), 2.55 (t, J=7.3 Hz, 2H), 1.66 (quintet, J=6.5 Hz, 2H), 1.46-1.26 (m, 5H), 0.90-0.82 (m, 12H), 0.00 (s, 5H). One exchangeable proton not observed.

Preparation of Final Compounds:

All of the following final compounds were isolated as their ditrifluoroacetate salts, unless otherwise stated.

EXAMPLE 1

N-Ethyl-N-(2-(2-(4-hydroxy-2-oxo-2,3-dihydrobenzo[d]thiazol-7-yl)ethylamino)ethyl)-3-(4-(2-(4-(2-isopropylthiazole-4-carbonyl)-1-oxa-4,9-diazaspiro[5.5]undecan-9-yl)ethyl)phenethoxy)propanamide ditrifluoroacetate

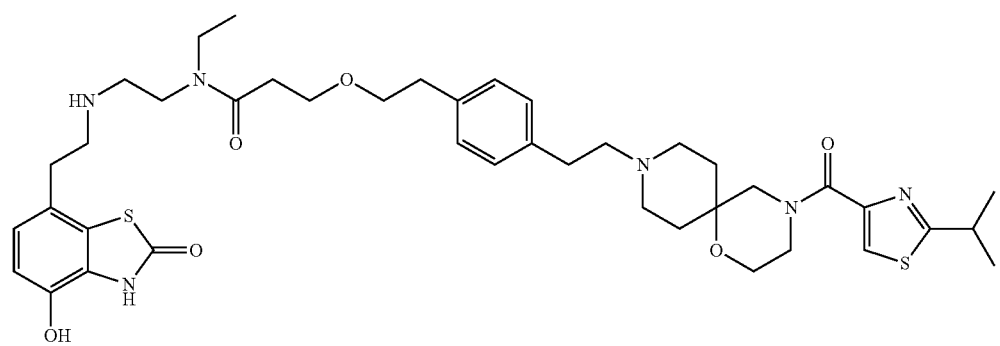

Tosic acid monohydrate (0.54 g) was added in one portion to a solution of N-(2,2-dimethoxyethyl)-N-ethyl-3-(4-(2-(4-(2-isopropylthiazole-4-carbonyl)-1-oxa-4,9-diazaspiro[5.5]undecan-9-yl)ethyl)phenethoxy)propanamide (0.26 g) in DCM (7 mL). The mixture was stirred for 2 hours at 20° C. Saturated sodium bicarbonate solution (10 mL) was added cautiously and the resultant mixture was stirred vigorously for 10 minutes. The mixture was extracted with DCM and the organic layer washed with saturated sodium bicarbonate solution (×2) and brine, then dried, filtered and concentrated under reduced pressure. The residue was dissolved in methanol (10 mL) and treated with acetic acid (0.023 mL) followed by 7-(2-aminoethyl)-4-hydroxybenzo[d]thiazol-2(3H)-one hydrochloride [Org. Proc. Res. Dev. 2004, 8(4), 628] (0.15 g). This mixture was stirred at 20° C. for 10 minutes and then cooled in an ice bath. Sodium cyanoborohydride (0.038 g) was added and the reaction mixture stirred at 20° C. for 18 hours. The solvent was evaporated under reduced pressure and the residue purified by flash silica chromatography, using 8% methanol in dichloromethane with 1% '880' aqueous ammonia as solvent. The residue was further purified by preparative HPLC (Sunfire™, Gradient: 40-70% methanol in 0.2% aqueous TFA). The fractions containing the desired product were evaporated to dryness to afford the titled compound as a white solid. Yield 0.105 g.

m/z 793 M$^+$ (MultiMode+).

$^1$H NMR (400 MHz, D$_6$-DMSO, 90° C.) δ 7.96 (s, 1H), 7.17 (s, 4H), 6.85 (d, J=8.2 Hz, 1H), 6.75 (d, J=8.2 Hz, 1H), 3.77-3.52 (m, 12H), 3.43-3.27 (m, 7H), 3.20-3.08 (m, 6H), 3.00-2.93 (m, 2H), 2.87-2.82 (m, 2H), 2.80-2.75 (m, 2H), 2.59-2.53 (m, 2H), 2.13-2.02 (m, 2H), 1.88-1.73 (m, 2H), 1.36 (d, J=6.9 Hz, 6H), 1.09 (t, J=6.7 Hz, 3H). Five exchangeable protons not observed.

The N-(2,2-dimethoxyethyl)-N-ethyl-3-(4-(2-(4-(2-isopropylthiazole-4-carbonyl)-1-oxa-4,9-diazaspiro[5.5]undecan-9-yl)ethyl)phenethoxy)propanamide used as a starting material was prepared as follows:

a) tert-Butyl 4-(2-isopropylthiazole-4-carbonyl)-1-oxa-4,9-diazaspiro[5.5]undecane-9-carboxylate

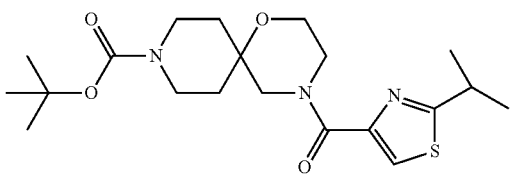

A solution of 2-isopropylthiazole-4-carboxylic acid (1 g) and tert-butyl 1-oxa-4,9-diazaspiro[5.5]undecane-9-carboxylate hydrochloride [WuXi PharmaTech] (1.71 g) in DMF (30 mL) was cooled in an ice bath and treated with triethylamine (2.44 mL) followed by HATU (2.89 g). The ice bath was removed and the mixture was stirred at 20° C. for 1 hour. The mixture was partitioned between ethyl acetate and brine, the organic layer was washed twice with brine, dried over sodium sulphate, filtered and the solvent evaporated under reduced pressure. The crude product was purified by flash silica chromatography using 70% ethyl acetate in isohexane as solvent. Fractions containing the product were evaporated to dryness to afford the subtitled compound. Yield 2.0 g.

$^1$H NMR (400 MHz, D$_6$-DMSO, 90° C.) δ 7.93 (s, 1H), 3.71-3.63 (m, 6H), 3.51-3.44 (m, 2H), 3.35-3.26 (m, 1H), 3.18-3.10 (m, 2H), 1.74-1.67 (m, 2H), 1.49-1.41 (m, 2H), 1.39 (s, 9H), 1.34 (d, J=7.6 Hz, 6H).

b) (2-Isopropylthiazol-4-yl)(1-oxa-4,9-diazaspiro[5.5]undecan-4-yl)methanone trifluoroacetate

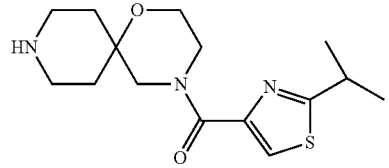

A solution of tert-butyl 4-(2-isopropylthiazole-4-carbonyl)-1-oxa-4,9-diazaspiro[5.5]undecane-9-carboxylate [Example 1, step a] (2.3 g) in a mixture of dichloromethane (40 mL) and trifluoroacetic acid (10 mL) was allowed to stand at 20° C. for 30 minutes. Toluene (50 mL) was added and the solvents were evaporated, then this process was repeated with further toluene (50 mL). The residue was triturated with ether. The gum was then dissolved in acetonitrile and the solvent evaporated to afford the subtitled compound. Yield 1.64 g.

m/z 310 (M+H)$^+$ (APCI).

c) (9-(4-(2-Hydroxyethyl)phenethyl)-1-oxa-4,9-diazaspiro[5.5]undecan-4-yl)(2-isopropylthiazol-4-yl)methanone

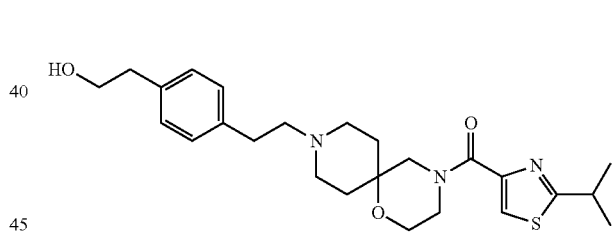

Potassium carbonate (0.634 g) was added to a solution of (2-isopropylthiazol-4-yl)(1-oxa-4,9-diazaspiro[5.5]undecan-4-yl)methanone trifluoroacetate [Example 1, step b] (0.971 g) and 4-(2-hydroxyethyl)phenethyl methanesulfonate [Aromatic Intermediate 10] (0.56 g) in acetonitrile (20 mL) and water (0.3 mL). The reaction mixture was heated at 60° C. for 1 day. The solvent was evaporated under reduced pressure and the residue partitioned between water and ethyl acetate. The aqueous layer was re-extracted with ethyl acetate and the combined organic phases were dried, filtered and the solvent evaporated under reduced pressure. The crude product was purified by flash silica chromatography, using 2% methanol in dichloromethane with 1% triethylamine as solvent. Fractions containing the product were evaporated to dryness to afford the subtitled compound. Yield 0.68 g.

$^1$H NMR (500 MHz, D$_6$-DMSO, 90° C.) δ 7.91 (s, 1H), 7.08 (s, 4H), 4.20 (t, J=4.7 Hz, 1H), 3.70-3.58 (m, 8H), 3.35-3.27 (m, 1H), 2.71-2.65 (m, 4H), 2.57-2.32 (m, 6H), 1.75-1.67 (m, 2H), 1.59-1.52 (m, 2H), 1.36 (d, J=6.8 Hz, 6H).

d) tert-Butyl 3-(4-(2-(4-(2-isopropylthiazole-4-carbonyl)-1-oxa-4,9-diazaspiro[5.5]undecan-9-yl)ethyl)phenethoxy)propanoate

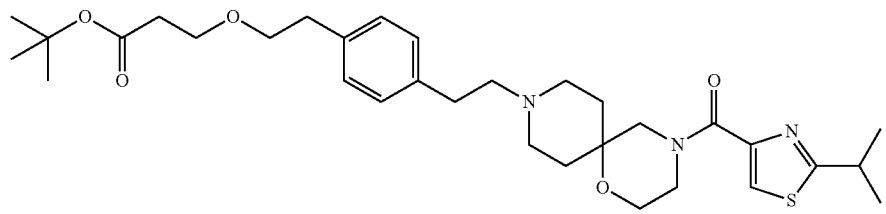

Benzyltrimethylammonium hydroxide (40% in methanol, 0.031 mL) was added to a solution of (9-(4-(2-hydroxyethyl)phenethyl)-1-oxa-4,9-diazaspiro[5.5]undecan-4-yl)(2-isopropylthiazol-4-yl)methanone [Example 1, step c] (0.62 g) in toluene (20 mL). The solvent was removed under reduced pressure and the residue azeotroped with toluene. The resultant liquid, which was just mobile with traces of toluene, was treated dropwise with tert-butyl acrylate (0.225 g). The reaction mixture was stirred at 20° C. for 18 hours. The mixture was purified by flash silica chromatography using 2% methanol in dichloromethane with 1% triethylamine as solvent. Fractions containing the product were evaporated to dryness to afford the subtitled compound. Yield 0.550 g.

m/z 586 (M+H)$^+$ (APCI).

e) 3-(4-(2-(4-(2-Isopropylthiazole-4-carbonyl)-1-oxa-4,9-diazaspiro[5.5]undecan-9-yl)ethyl)phenethoxy)propanoic acid

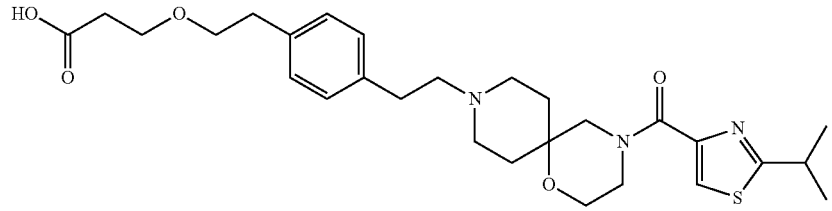

Trifluoroacetic acid (10 mL) was added to a solution of tert-butyl 3-(4-(2-(4-(2-isopropylthiazole-4-carbonyl)-1-oxa-4,9-diazaspiro[5.5]undecan-9-yl)ethyl)phenethoxy)propanoate [Example 1, step d] (0.55 g) in DCM (20 mL) and the resultant solution allowed to stand at 20° C. for 1 hour. Toluene (30 mL) was added and the solvents were evaporated under reduced pressure. The residue was azeotroped with acetonitrile (×2) to yield the subtitled compound. Yield 0.60 g.

m/z 530 (M+H)$^+$ (APCI).

f) N-(2,2-Dimethoxyethyl)-N-ethyl-3-(4-(2-(4-(2-isopropylthiazole-4-carbonyl)-1-oxa-4,9-diazaspiro[5.5]undecan-9-yl)ethyl)phenethoxy)propanamide

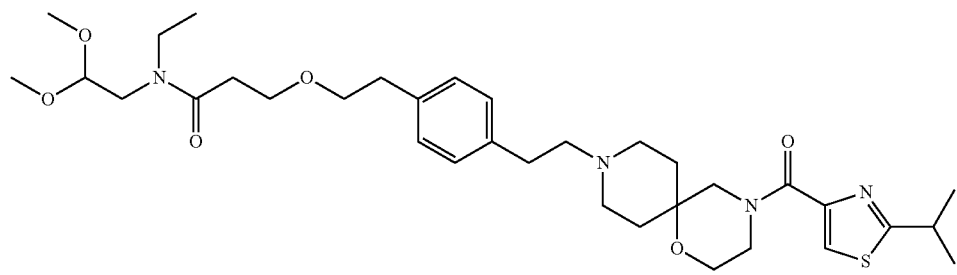

T3P (1.6M in THF, 0.33 mL) was added dropwise to a stirred solution of 3-(4-(2-(4-(2-isopropylthiazole-4-carbonyl)-1-oxa-4,9-diazaspiro[5.5]undecan-9-yl)ethyl)phenethoxy)propanoic acid [Example 1, step e] (0.3 g) and N-ethyl-2,2-dimethoxyethanamine [U.S. Pat. No. 2,707,186] (0.062 g) and triethylamine (0.46 mL) in DMF (7 mL). The reaction mixture was stirred at 20° C. for 3 hours. The mixture was partitioned between ethyl acetate and brine, the organic layer was washed with brine (×2), dried, filtered and the solvent evaporated under reduced pressure to yield the subtitled compound.

Yield 0.26 g.

m/z 645 (M+H)$^+$ (APCI).

EXAMPLE 2

N-Cyclohexyl-N-(2-(2-(5-hydroxy-3-oxo-3,4-dihydro-2H-benzo[b][1,4]oxazin-8-yl)ethylamino)ethyl)-3-(4-(2-(4-(2-isopropylthiazole-4-carbonyl)-1-oxa-4,9-diazaspiro[5.5]undecan-9-yl)ethyl)phenethoxy)propanamide ditrifluoroacetate

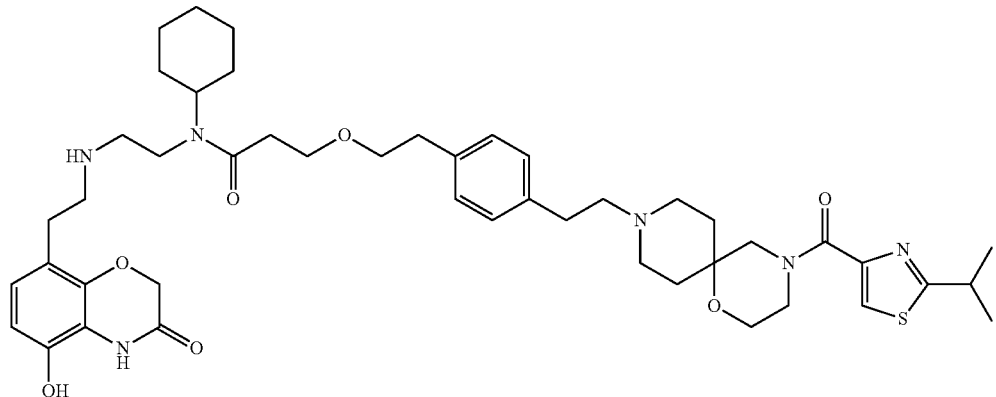

Prepared by the method of Example 1 using N-cyclohexyl-N-(2,2-dimethoxyethyl)-3-(4-(2-(4-(2-isopropylthiazole-4-carbonyl)-1-oxa-4,9-diazaspiro[5.5]undecan-9-yl)ethyl)phenethoxy)propanamide (0.32 g) in place of N-(2,2-dimethoxyethyl)-N-ethyl-3-(4-(2-(4-(2-isopropylthiazole-4-carbonyl)-1-oxa-4,9-diazaspiro[5.5]undecan-9-yl)ethyl)phenethoxy)propanamide, and 8-(2-aminoethyl)-5-hydroxy-2H-benzo[b][1,4]oxazin-3(4H)-one hydrochloride [WO 2008075025] (0.17 g) in place of 7-(2-aminoethyl)-4-hydroxybenzo[d]thiazol-2(3H)-one hydrochloride. Yield 0.102 g.

m/z 845 M$^+$ (MultiMode+).

$^1$H NMR (400 MHz, D$_6$-DMSO, 90° C.) δ 9.39 (s, 1H), 7.96 (s, 1H), 7.17 (s, 4H), 6.66 (d, J=8.5 Hz, 1H), 6.49 (d, J=8.2 Hz, 1H), 4.52 (s, 2H), 3.73-3.57 (m, 11H), 3.50-3.26 (m, 7H), 3.19-3.06 (m, 4H), 3.02-2.93 (m, 4H), 2.84-2.74 (m, 4H), 2.61-2.56 (m, 2H), 2.12-2.00 (m, 2H), 1.86-1.71 (m, 4H), 1.67-1.56 (m, 3H), 1.47-1.39 (m, 2H), 1.37-1.26 (m, 8H), 1.11-1.05 (m, 1H). Four exchangeable protons not observed. The N-cyclohexyl-N-(2,2-dimethoxyethyl)-3-(4-(2-(4-(2-isopropylthiazole-4-carbonyl)-1-oxa-4,9-diazaspiro[5.5]undecan-9-yl)ethyl)phenethoxy)propanamide used as a starting material was prepared as follows:

a) N-cyclohexyl-N-(2,2-dimethoxyethyl)-3-(4-(2-(4-(2-isopropylthiazole-4-carbonyl)-1-oxa-4,9-diazaspiro[5.5]undecan-9-yl)ethyl)phenethoxy)propanamide

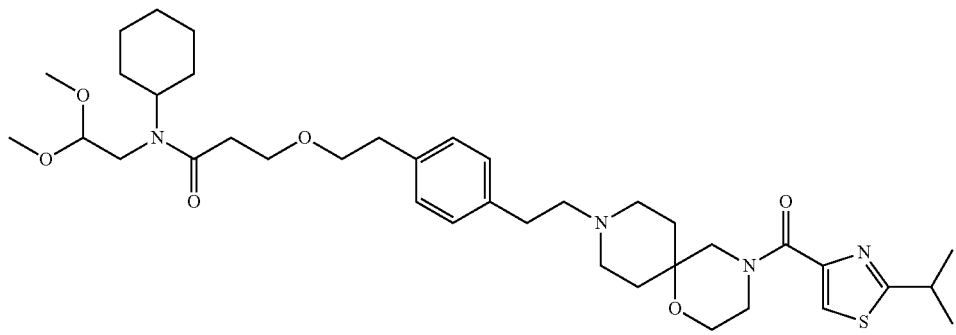

HATU (0.23 g) was added in one portion to an ice cold solution of 3-(4-(2-(4-(2-isopropylthiazole-4-carbonyl)-1-oxa-4,9-diazaspiro[5.5]undecan-9-yl)ethyl)phenethoxy)propanoic acid [Example 1, step e] (0.3 g) and N-(2,2-dimethoxyethyl)cyclohexanamine [WO 2008075025] (0.087 g) and triethylamine (0.26 mL) in DMF (10 mL). The mixture was stirred at 20° C. for 1 hour before being partitioned between ethyl acetate and brine. The organic layer was washed with brine (×2), dried, filtered and the solvent evaporated under reduced pressure to afford the subtitled compound. Yield 0.32 g.

m/z 699 (M+H)$^+$ (APCI).

EXAMPLE 3

3-(4-(2-(4-(2-Ethylthiazole-4-carbonyl)-1-oxa-4,9-diazaspiro[5.5]undecan-9-yl)ethyl)phenethoxy)-N-(2-(2-(4-hydroxy-2-oxo-2,3-dihydrobenzo[d]thiazol-7-yl)ethylamino)ethyl)-N-propylpropanamide ditrifluoroacetate

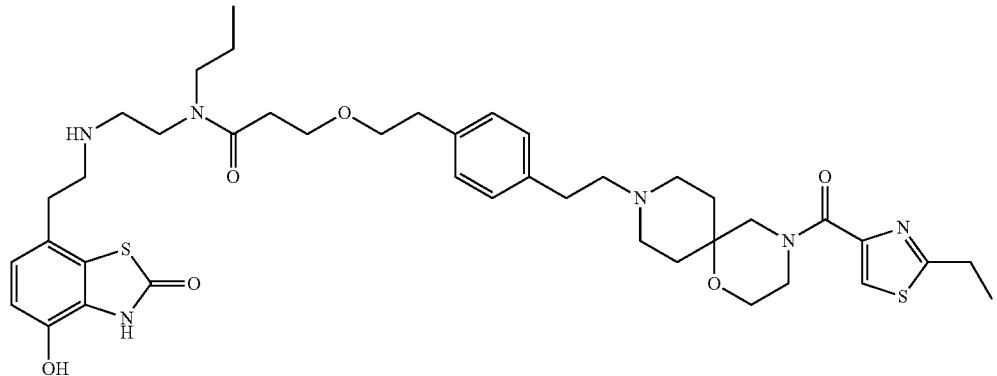

Prepared by the method of Example 1 using N-(2,2-dimethoxyethyl)-3-(4-(2-(4-(2-ethylthiazole-4-carbonyl)-1-oxa-4,9-diazaspiro[5.5]undecan-9-yl)ethyl)phenethoxy)-N-propylpropanamide (0.43 g) in place of N-(2,2-dimethoxyethyl)-N-ethyl-3-(4-(2-(4-(2-isopropylthiazole-4-carbonyl)-1-oxa-4,9-diazaspiro[5.5]undecan-9-yl)ethyl)phenethoxy)propanamide. Yield 0.11 g.

m/z 793 M$^+$ (MultiMode+).

$^1$H NMR (400 MHz, CD$_3$OD) δ 7.92 (s, 1H), 7.21-7.14 (m, 4H), 6.89 (d, J=8.2 Hz, 1H), 6.73 (d, J=8.2 Hz, 1H), 3.91-2.96 (m, 28H), 2.89 (t, J=8.0 Hz, 2H), 2.81 (t, J=7.1 Hz, 2H), 2.62 (t, J=6.6 Hz, 2H), 2.30-2.21 (m, 2H), 1.85-1.72 (m, 2H), 1.65-1.54 (m, 2H), 1.38 (t, J=7.6 Hz, 3H), 0.91 (t, J=7.3 Hz, 3H). Five exchangeable protons not observed.

The N-(2,2-dimethoxyethyl)-3-(4-(2-(4-(2-ethylthiazole-4-carbonyl)-1-oxa-4,9-diazaspiro[5.5]undecan-9-yl)ethyl)phenethoxy)-N-propylpropanamide used as a starting material was prepared as follows:

a) tert-Butyl 4-(2-ethylthiazole-4-carbonyl)-1-oxa-4,9-diazaspiro[5.5]undecane-9-carboxylate

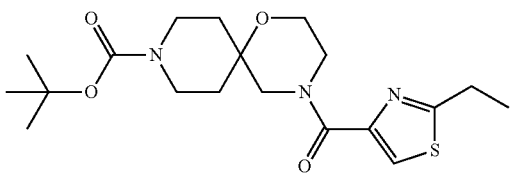

T3P (1.6M in THF, 51.3 mL) was added dropwise to a stirred suspension of tert-butyl 1-oxa-4,9-diazaspiro[5.5]undecane-9-carboxylate hydrochloride [WuXi PharmaTech] (18.1 g), 2-ethylthiazole-4-carboxylic acid [Carboxylic Acid 1] (12 g) and triethylamine (52 mL) in DMF (120 mL) under nitrogen and the mixture stirred at ambient temperature for 20 hours. It was diluted with water and extracted into ethyl acetate (×3). The combined extracts were washed successively with 10% brine, 30% brine and saturated brine, dried over magnesium sulfate, filtered and the solvent removed. The crude product was purified by flash silica chromatography, eluting with ethyl acetate. Fractions containing the product were evaporated to dryness to afford the subtitled compound as a yellow oil. Yield 24.0 g.

m/z 340 (M-tBu+H)$^+$ (APCI).

b) (2-Ethylthiazol-4-yl)(1-oxa-4,9-diazaspiro[5.5]undecan-4-yl)methanone trifluoroacetate

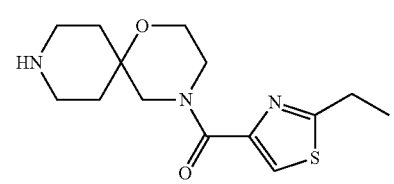

Prepared by the method of Example 1, step b using tert-butyl 4-(2-ethylthiazole-4-carbonyl)-1-oxa-4,9-diazaspiro[5.5]undecane-9-carboxylate [Example 3, step a] (24.0 g) in place of tert-butyl 4-(2-isopropylthiazole-4-carbonyl)-1-oxa-4,9-diazaspiro[5.5]undecane-9-carboxylate. Trituration with ether afforded a white solid, which was collected by filtration and dried to give the subtitled compound. Yield 27.7 g.

$^1$H NMR (400 MHz, D$_6$-DMSO) δ 8.55 (s, 1H), 8.39 (s, 1H), 8.04-8.00 (m, 1H), 3.81-3.51 (m, 6H), 3.18-2.91 (m, 6H), 2.00-1.90 (m, 2H), 1.72-1.56 (m, 2H), 1.32 (t, J=7.2 Hz, 3H).

c) (2-Ethylthiazol-4-yl)(9-(4-(2-hydroxyethyl)phenethyl)-1-oxa-4,9-diazaspiro[5.5]undecan-4-yl)methanone

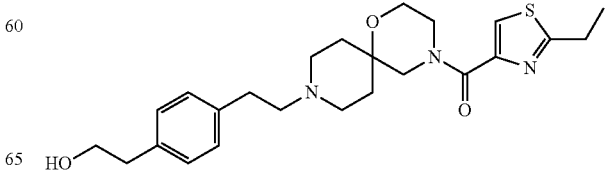

A solution of 2-(4-(2-bromoethyl)phenyl)ethanol [Organometallics 2002, 21(20), 4217] (1.71 g) in NMP (5 mL) was added to a suspension of (2-ethylthiazol-4-yl)(1-oxa-4,9-diazaspiro[5.5]undecan-4-yl)methanone trifluoroacetate [Example 3, step b] (3.0 g) and cesium carbonate (5.60 g) in NMP (10 mL) and the mixture stirred at 75° C. under nitrogen for 4 hours. More 2-(4-(2-bromoethyl)phenyl)ethanol (0.65 g) was added and the mixture stirred at 75° C. for 18 hours. The mixture was cooled, diluted with water and extracted into ethyl acetate (×3). The combined extracts were washed with 10% brine, 30% brine and saturated brine, dried over magnesium sulfate, filtered and the solvent removed. The crude product was purified by flash silica chromatography, successively eluted with 50% ethyl acetate in isohexane with 5% triethylamine, then 100% ethyl acetate with 5% triethylamine, then 10% methanol in ethyl acetate with 5% triethylamine. Fractions containing the product were evaporated to dryness to afford the subtitled compound as a yellow oil. Yield 1.90 g.

m/z 444 (M+H)+ (APCI).

d) tert-Butyl 3-(4-(2-(4-(2-ethylthiazole-4-carbonyl)-1-oxa-4,9-diazaspiro[5.5]undecan-9-yl)ethyl) phenethoxy)propanoate

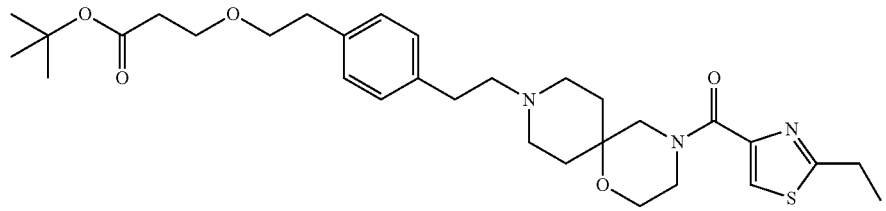

N,N,N-Trimethyl-1-phenylmethanaminium hydroxide (40% in water, 0.51 mL) was added to a solution of (2-ethylthiazol-4-yl)(9-(4-(2-hydroxyethyl)phenethyl)-1-oxa-4,9-diazaspiro[5.5]undecan-4-yl)methanone [Example 3, step c] (1.9 g) and tert-butyl acrylate (1.32 mL) in acetonitrile (1.5 mL) and the mixture stirred at ambient temperature for 4 hours. The mixture was concentrated in vacuo and the crude product purified by flash silica chromatography, elution gradient 50 to 75% ethyl acetate in isohexane with 5% triethylamine. Fractions containing the product were evaporated to dryness to afford the subtitled compound as a colourless oil. Yield 2.19 g.

m/z 572 (M+H)+ (APCI).

e) 3-(4-(2-(4-(2-Ethylthiazole-4-carbonyl)-1-oxa-4,9-diazaspiro[5.5]undecan-9-yl)ethyl)phenethoxy) propanoic acid

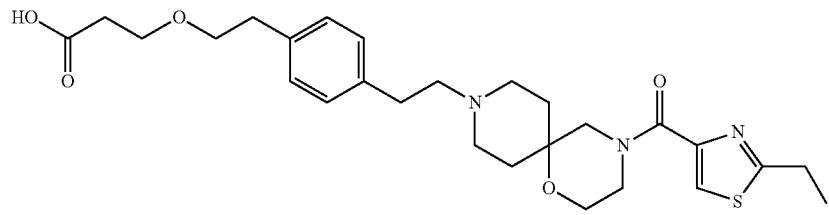

Prepared by the method of Example 1, step e using tert-butyl 3-(4-(2-(4-(2-ethylthiazole-4-carbonyl)-1-oxa-4,9-diazaspiro[5.5]undecan-9-yl)ethyl)phenethoxy)propanoate [Example 3, step d] (2.2 g) in place of tert-butyl 3-(4-(2-(4-(2-isopropylthiazole-4-carbonyl)-1-oxa-4,9-diazaspiro[5.5]undecan-9-yl)ethyl)phenethoxy)propanoate. Yield 3.36 g.

$^1$H NMR (400 MHz, CDCl$_3$) δ 7.90 (s, 1H), 7.13 (dd, J=29.9, 8.1 Hz, 4H), 3.97-3.92 (m, 1H), 3.82-3.77 (m, 3H), 3.74-3.67 (m, 4H), 3.64-3.56 (m, 1H), 3.35-3.27 (m, 1H), 3.10-3.00 (m, 6H), 2.85 (t, J=6.5 Hz, 2H), 2.61-2.55 (m, 2H), 2.21-2.13 (m, 2H), 2.03-1.92 (m, 6H), 1.45-1.34 (m, 3H). One exchangeable proton not observed.

f) N-(2,2-Dimethoxyethyl)-3-(4-(2-(4-(2-ethylthiazole-4-carbonyl)-1-oxa-4,9-diazaspiro[5.5]undecan-9-yl)ethyl)phenethoxy)-N-propylpropanamide

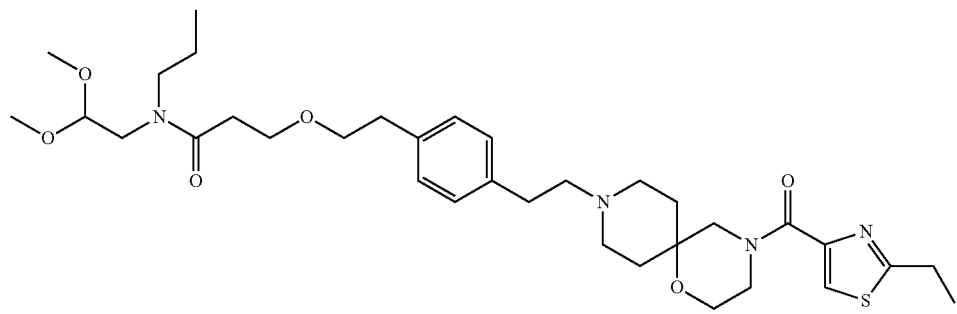

HATU (0.33 g) was added to a solution of 3-(4-(2-(4-(2-ethylthiazole-4-carbonyl)-1-oxa-4,9-diazaspiro[5.5]undecan-9-yl)ethyl)phenethoxy)propanoic acid [Example 3, step e] (0.50 g), N-(2,2-dimethoxyethyl)propan-1-amine [Liebigs Annalen der Chemie 1979, 11, 1818] (0.12 g) and triethylamine (0.56 mL) in dichloromethane (5 mL) at 0° C. under nitrogen, and the mixture stirred at ambient temperature for 2 hours. The mixture was washed with water, the organic phase was separated, dried, filtered and concentrated in vacuo to afford the subtitled compound as an orange oil. Yield 0.43 g.

m/z 645 (M+H)$^+$ (APCI).

The following compounds were prepared from the appropriate Carboxylic Acids and Amines using methods analogous to those described for Examples 1 to 3.

EXAMPLE 4

N-Butyl-N-(2-(2-(5-hydroxy-3-oxo-3,4-dihydro-2H-benzo[b][1,4]oxazin-8-yl)ethylamino)ethyl)-3-(4-(2-(4-(2-isopropylthiazole-4-carbonyl)-1-oxa-4,9-diazaspiro[5.5]undecan-9-yl)ethyl)phenethoxy)propanamide ditrifluoroacetate

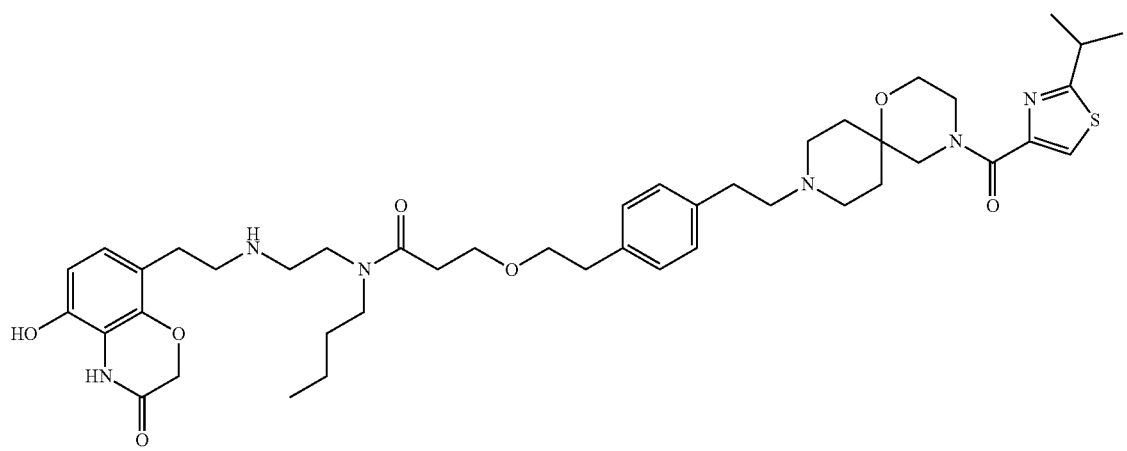

m/z 819 M$^+$ (MultiMode+).

$^1$H NMR (400 MHz, CD$_3$OD) δ 7.92 (s, 1H), 7.22-7.15 (m, 4H), 6.70 (s, 1H), 6.47 (d, J=8.5 Hz, 1H), 4.59-4.52 (m, 2H), 3.95-3.09 (m, 25H), 3.03-2.96 (m, 2H), 2.88 (t, J=7.1 Hz, 2H), 2.81 (t, J=7.1 Hz, 2H), 2.60 (t, J=6.0 Hz, 2H), 2.30-2.22 (m, 2H), 1.84-1.72 (m, 2H), 1.59-1.50 (m, 2H), 1.41-1.27 (m, 8H), 0.95 (t, J=7.4 Hz, 3H). Five exchangeable protons not observed.

EXAMPLE 5

N-Cycloheptyl-N-(2-(2-(5-hydroxy-3-oxo-3,4-dihydro-2H-benzo[b][1,4]oxazin-8-yl)ethylamino)ethyl)-3-(4-(2-(4-(2-methylthiazole-4-carbonyl)-1-oxa-4,9-diazaspiro[5.5]undecan-9-yl)ethyl)phenethoxy)propanamide ditrifluoroacetate

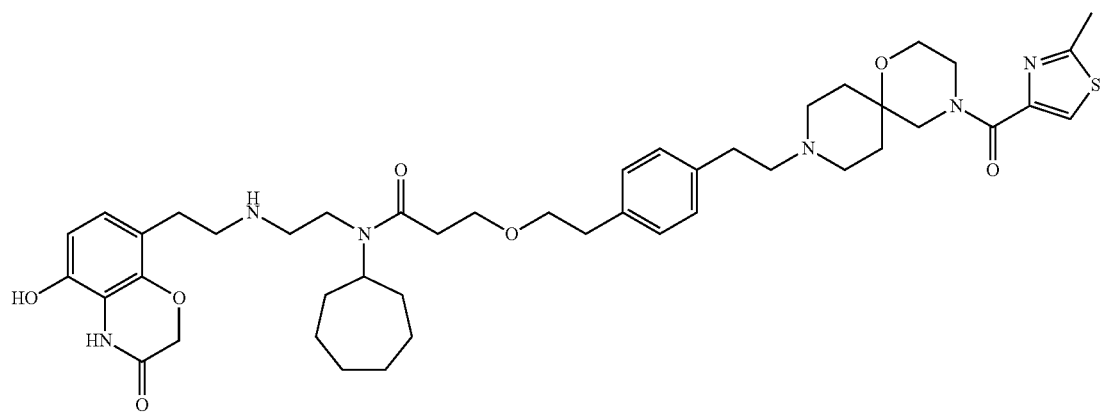

m/z 831 M$^+$ (MultiMode+).

$^1$H NMR (400 MHz, CD$_3$OD) δ 7.89 (s, 1H), 7.21-7.16 (m, 4H), 6.71 (d, J=8.5 Hz, 1H), 6.48 (d, J=8.5 Hz, 1H), 4.59 (s, 2H), 3.90-2.96 (m, 23H), 2.89 (t, J=7.3 Hz, 2H), 2.81 (t, J=7.1 Hz, 2H), 2.71 (s, 3H), 2.65 (t, J=6.3 Hz, 2H), 2.29-2.21 (m, 2H), 1.84-1.44 (m, 16H). Five exchangeable protons not observed.

EXAMPLE 6

(R)—N-(Hexan-2-yl)-N-(2-(2-(5-hydroxy-3-oxo-3,4-dihydro-2H-benzo[b][1,4]oxazin-8-yl)ethylamino)ethyl)-3-(4-(2-(4-(2-methylthiazole-4-carbonyl)-1-oxa-4,9-diazaspiro[5.5]undecan-9-yl)ethyl)phenethoxy)propanamide ditrifluoroacetate

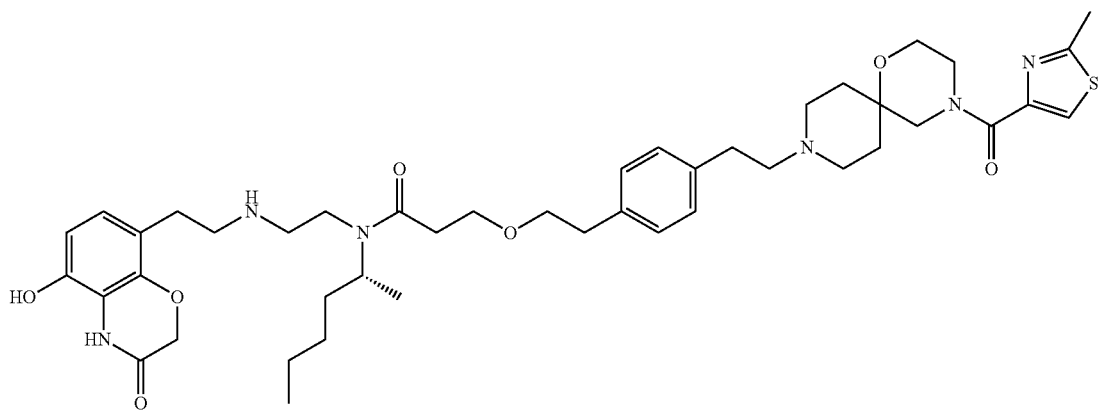

m/z 819 M$^+$ (MultiMode+).

¹H NMR (400 MHz, CD₃OD) δ 7.89 (s, 1H), 7.22-7.16 (m, 4H), 6.72 (d, J=8.5 Hz, 1H), 6.48 (d, J=8.2 Hz, 1H), 4.59 (s, 2H), 4.03-2.97 (m, 27H), 2.89 (t, J=7.1 Hz, 2H), 2.81 (t, J=7.1 Hz, 2H), 2.71 (s, 3H), 2.70-2.54 (m, 2H), 2.29-2.20 (m, 2H), 1.84-1.73 (m, 2H), 1.53-1.46 (m, 2H), 1.36-1.19 (m, 2H), 1.15 (t, J=7.0 Hz, 3H), 0.90 (t, J=7.2 Hz, 3H). Five exchangeable protons not observed.

Examples 4 to 6 were prepared using the following Carboxylic Acids and Amines:

| Example Number | Carboxylic Acid | Amine |
|---|---|---|
| 4 | 2-isopropylthiazole-4-carboxylic acid | N-(2,2-dimethoxyethyl)butan-1-amine [Note 1] |
| 5 | 2-methylthiazole-4-carboxylic acid | N-(2,2-dimethoxyethyl)-cycloheptanamine [Note 2] |
| 6 | 2-methylthiazole-4-carboxylic acid | R)-N-(2,2-dimethoxyethyl)hexan-2-amine [Note 2] |

[Note 1]: J. Am. Chem. Soc. 1949, 71(6), 2272.
[Note 2]: WO 2008075025.

EXAMPLE 7

N-Cycloheptyl-3-(2-fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

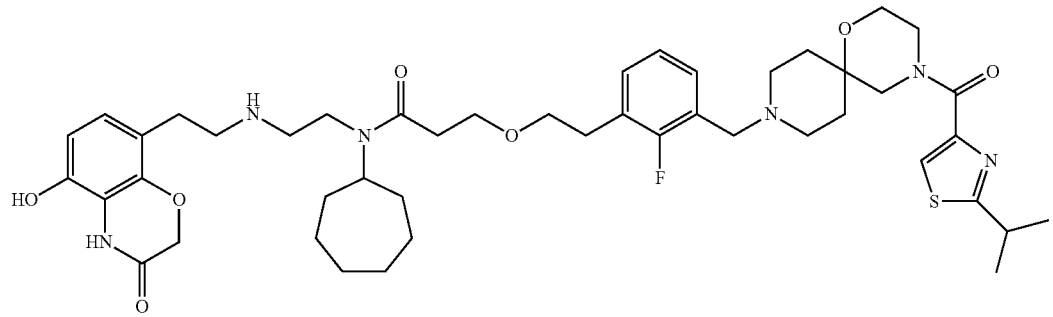

p-Toluenesulfonic acid monohydrate (0.219 g) was added to a solution of N-cycloheptyl-N-(2,2-dimethoxyethyl)-3-(2-fluoro-3-((4-(2-isopropylthiazole-4-carbonyl)-1-oxa-4,9-diazaspiro[5.5]undecan-9-yl)methyl)phenethoxy)propanamide (0.165 g) in tetrahydrofuran (2 mL) and the resulting mixture stirred overnight at RT. The solution was then added to a suspension of 8-(2-aminoethyl)-5-hydroxy-2H-benzo[b][1,4]oxazin-3(4H)-one hydrochloride [WO 2008075025] (0.056 g) and sodium bicarbonate (0.116 g) in a mixture of NMP (2 mL) and water (0.2 mL). The resulting cloudy solution was stirred for 10 min. Acetic acid (0.013 mL) was then added, followed by sodium triacetoxyborohydride (0.122 g) and the resulting mixture was stirred overnight. The reaction mixture was partitioned between 2-methyltetrahydrofuran (15 mL) and saturated sodium bicarbonate solution (15 mL). The organic phase was separated, washed with 10% aqueous brine (2×15 mL), dried over sodium sulphate, filtered and evaporated. The residue was purified by flash silica chromatography, elution gradient 97.25:2.5:0.25 to 92.3:7:0.7 dichloromethane:methanol:'880' aqueous ammonia. The fractions containing the product were combined and evaporated. The resulting gum was further purified by preparative HPLC (Sunfire™, Gradient: 35-60% methanol in 0.2% aqueous TFA). The fractions containing the product were combined, evaporated and triturated with ether to give the titled compound as a white solid. Yield 0.069 g.

m/z 863 M⁺ (MultiMode+).

¹H NMR (500 MHz, D₆-DMSO, 90° C.) δ 9.39-9.29 (m, 1H), 8.81-8.40 (m, 2H), 7.99-7.87 (m, 1H), 7.49-7.37 (m, 2H), 7.24-7.12 (m, 1H), 6.73-6.61 (m, 1H), 6.56-6.44 (m, 1H), 4.58-4.48 (m, 2H), 4.38-4.29 (m, 2H), 3.86-3.59 (m, 11H), 3.49-3.00 (m, 11H), 2.91-2.78 (m, 4H), 2.64-2.55 (m, 2H), 2.10-1.98 (m, 2H), 1.85-1.30 (m, 19H), 1.13-1.04 (m, 1H). Two exchangeable protons not observed.

The N-cycloheptyl-N-(2,2-dimethoxyethyl)-3-(2-fluoro-3-((4-(2-isopropylthiazole-4-carbonyl)-1-oxa-4,9-diazaspiro[5.5]undecan-9-yl)methyl)phenethoxy)propanamide used as a starting material was prepared as follows:

a) (9-(3-(2-(tert-Butyldimethylsilyloxy)ethyl)-2-fluorobenzyl)-1-oxa-4,9-diazaspiro[5.5]undecan-4-yl)(2-isopropylthiazol-4-yl)methanone

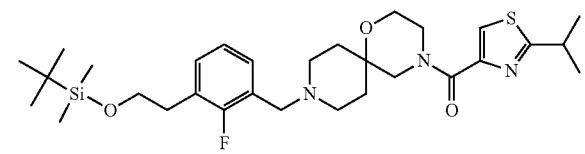

3-(2-(tert-Butyldimethylsilyloxy)ethyl)-2-fluorobenzaldehyde [Aromatic Intermediate 5] (4.07 g) was added to (2-isopropylthiazol-4-yl)(1-oxa-4,9-diazaspiro[5.5]undecan-4-yl)methanone trifluoroacetate [Example 1, step b] (6.10 g) in a mixture of N-methyl-2-pyrrolidinone (50 mL) and acetic acid (0.83 mL) and stirred for 30 min. Sodium triacetoxyborohydride (4.58 g) was then added and the mixture stirred overnight. The reaction mixture was poured into water (100 mL), the pH was adjusted to 8 using saturated sodium bicarbonate solution, and the mixture was extracted with ethyl acetate (3×100 mL). The combined organic phases were washed with water (3×100 mL) and brine (100 mL), dried over sodium sulphate, filtered and evaporated. The residue was purified by flash silica chromatography using 77.5:17.5:5 isohexane:ethyl acetate:triethylamine as solvent to give the subtitled compound as a clear oil. Yield 5.35 g.

$^1$H NMR (400 MHz, D$_6$-DMSO, 90° C.) δ 7.96 (s, 1H), 7.29-7.18 (m, 2H), 7.09 (t, J=7.4 Hz, 1H), 3.85 (t, J=6.5 Hz, 2H), 3.74-3.67 (m, 6H), 3.54 (s, 2H), 3.37 (septet, J=6.9 Hz, 1H), 2.88-2.82 (m, 2H), 2.50-2.34 (m, 4H), 1.79-1.71 (m, 2H), 1.63-1.54 (m, 2H), 1.42 (d, J=6.9 Hz, 6H), 0.87 (s, 9H), 0.00 (s, 6H).

b) (9-(2-Fluoro-3-(2-hydroxyethyl)benzyl)-1-oxa-4,9-diazaspiro[5.5]undecan-4-yl)(2-isopropylthiazol-4-yl)methanone

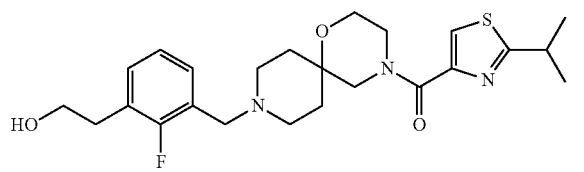

TBAF (1M in THF, 13.9 mL) was added to a solution of (9-(3-(2-(tert-butyldimethylsilyloxy)ethyl)-2-fluorobenzyl)-1-oxa-4,9-diazaspiro[5.5]undecan-4-yl)(2-isopropylthiazol-4-yl)methanone [Example 7, step a] (5.35 g) in THF (50 mL) and the resulting mixture was stirred for 1 h. The solvent was evaporated and the residue partitioned between ethyl acetate (100 mL) and water (100 mL). The layers were separated and the aqueous phase was extracted with ethyl acetate (2×100 mL). The combined organic phases were washed with brine (100 mL), dried over sodium sulphate, filtered and evaporated. The crude material was purified by flash silica chromatography, elution gradient 4:1 isohexane:ethyl acetate to 100% ethyl acetate to give the subtitled compound as a clear oil. Yield 3.90 g.

$^1$H NMR (300 MHz, D$_6$-DMSO) δ 7.93 (s, 1H), 7.23-7.14 (m, 2H), 7.03 (t, J=7.5 Hz, 1H), 4.48-4.40 (m, 1H), 3.69-3.56 (m, 8H), 3.48 (s, 2H), 3.38-3.24 (m, 1H), 2.75 (t, J=6.9 Hz, 2H), 2.45-2.23 (m, 4H), 1.76-1.62 (m, 2H), 1.60-1.47 (m, 2H), 1.35 (d, J=6.9 Hz, 6H).

c) tert-Butyl 3-(2-fluoro-3-((4-(2-isopropylthiazole-4-carbonyl)-1-oxa-4,9-diazaspiro[5.5]undecan-9-yl)methyl)phenethoxy)propanoate

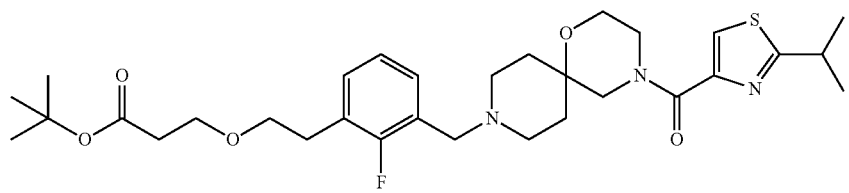

Prepared by the method of Example 1, step d using (9-(2-fluoro-3-(2-hydroxyethyl)benzyl)-1-oxa-4,9-diazaspiro[5.5]undecan-4-yl)(2-isopropylthiazol-4-yl)methanone [Example 7, step b] (3.85 g) in place of (9-(4-(2-hydroxyethyl)phenethyl)-1-oxa-4,9-diazaspiro[5.5]undecan-4-yl)(2-isopropylthiazol-4-yl)methanone. The crude product was purified by flash silica chromatography, elution gradient 1:1 ethyl acetate:isohexane with 5% triethylamine to 95:5 ethyl acetate:triethylamine. Fractions containing the product were evaporated to dryness to afford the subtitled compound. Yield 3.95 g.

m/z 590 (M+H)$^+$ (APCI).

d) 3-(2-Fluoro-3-((4-(2-isopropylthiazole-4-carbonyl)-1-oxa-4,9-diazaspiro[5.5]undecan-9-yl)methyl)phenethoxy)propanoic acid

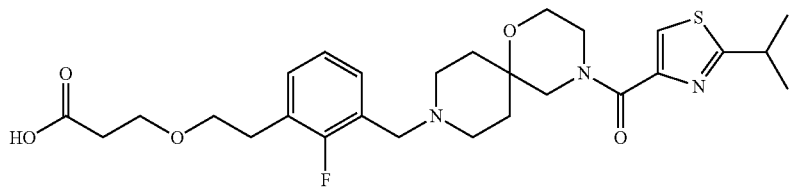

TFA (10 mL) was cautiously added to a solution of tert-butyl 3-(2-fluoro-3-((4-(2-isopropylthiazole-4-carbonyl)-1-oxa-4,9-diazaspiro[5.5]undecan-9-yl)methyl)phenethoxy)propanoate [Example 7, step c] (3.95 g) in DCM (40 mL). The resulting mixture was stirred for 2 h. The solvent was evaporated and the residue azeotroped twice with acetonitrile. The residue was dissolved in freshly distilled 2-methyltetrahydrofuran (100 mL) and washed 3 times with a mixture of brine and saturated sodium bicarbonate solution (10:1, 100 mL). The organic phase was dried over sodium sulphate, filtered and evaporated. The residue was azeotroped 3 times with isohexane to give the subtitled compound as a white foam. Yield 2.92 g.

m/z 534 (M+H)$^+$ (APCI).

e) N-Cycloheptyl-N-(2,2-dimethoxyethyl)-3-(2-fluoro-3-((4-(2-isopropylthiazole-4-carbonyl)-1-oxa-4,9-diazaspiro[5.5]undecan-9-yl)methyl)phenethoxy)propanamide

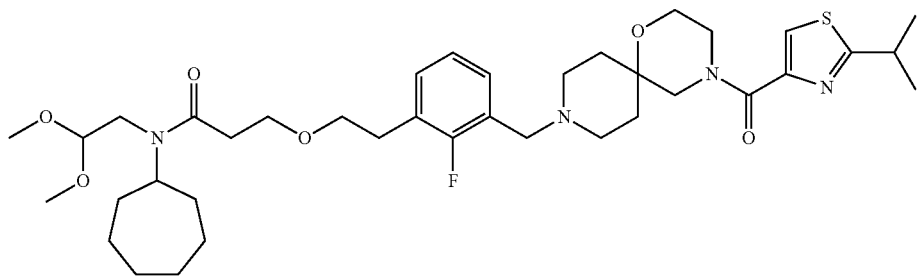

A solution of HATU (0.143 g) in DMF (0.5 mL) was added to a solution of 3-(2-fluoro-3-((4-(2-isopropylthiazole-4-carbonyl)-1-oxa-4,9-diazaspiro[5.5]undecan-9-yl)methyl)phenethoxy)propanoic acid [Example 7, step d] (0.133 g), Hunig's base (0.22 mL) and N-(2,2-dimethoxyethyl)cycloheptanamine [WO 2008075025] (0.050 g) in DMF (0.5 mL). The resulting dark solution was stirred overnight at RT. The solvent was evaporated and the residue partitioned between ethyl acetate (25 mL) and 20% aqueous brine (25 mL). The organic layer was separated and washed with 20% aqueous brine (2×25 mL). The organic solution was evaporated and the residue purified by silica gel chromatography, elution gradient 65:30:5 to 47.5:47.5:5 isohexane:ethyl acetate:triethylamine. The fractions containing the product were combined and evaporated to give the subtitled compound as an oil. Yield 0.165 g.

m/z 717 (M+H)$^+$ (APCI).

EXAMPLE 8

N-Benzyl-3-(2-fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

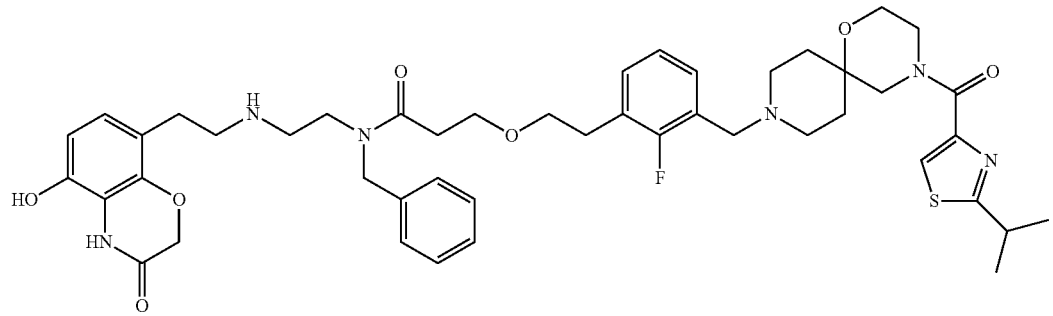

A solution of N-benzyl-N-(2,2-dimethoxyethyl)-3-(2-fluoro-3-((4-(2-isopropylthiazole-4-carbonyl)-1-oxa-4,9-diazaspiro[5.5]undecan-9-yl)methyl)phenethoxy)propanamide (0.114 g) in a mixture of water (1 mL) and acetic acid (1 mL) was heated at 50° C. for 2 h. The mixture was cautiously added to saturated sodium bicarbonate solution (30 mL) and the resulting aqueous mixture was extracted with ethyl acetate (3×25 mL). The combined organic phases were washed with brine, dried over sodium sulphate, filtered and evaporated. The residue was dissolved in NMP (1 mL) and added to a solution of 8-(2-aminoethyl)-5-hydroxy-2H-benzo[b][1,4]oxazin-3(4H)-one hydrochloride [WO 2008075025] (0.039 g) and sodium bicarbonate (0.013 g) in a mixture of NMP (1 mL) and water (0.2 mL). Acetic acid (1 mL) was then added and the mixture was stirred for 10 min. Sodium triacetoxyborohydride (0.085 g) was then added and the mixture was stirred overnight at RT. The reaction mixture was partitioned between 2-methyltetrahydrofuran (15 mL) and saturated sodium bicarbonate solution (15 mL). The organic phase was separated, washed with 10% aqueous brine (2×15 mL), dried over sodium sulphate, filtered and evaporated. The residue was purified by flash silica chromatography, elution gradient 97.25:2.5:0.25 to 92.3:7:0.7 dichloromethane:methanol: '880' aqueous ammonia. The fractions containing the product were combined and evaporated. The resulting gum was further purified by preparative HPLC (Sunfire™, Gradient: 35-60% methanol in 0.2% aqueous TFA). The fractions containing the product were combined, evaporated and triturated with ether to give the titled compound as a white solid. Yield 0.029 g.

m/z 857 M$^+$ (MultiMode+).

$^1$H NMR (500 MHz, D$_6$-DMSO, 90° C.) δ 9.34 (s, 1H), 8.64-8.27 (m, 1H), 7.93 (s, 1H), 7.42-7.14 (m, 8H), 6.64 (d, J=8.4 Hz, 1H), 6.48 (d, J=8.3 Hz, 1H), 4.60 (s, 2H), 4.49 (s, 2H), 4.27-4.20 (m, 2H), 3.73-2.98 (m, 21H), 2.88-2.78 (m, 4H), 2.66-2.59 (m, 2H), 2.04-1.95 (m, 2H), 1.81-1.70 (m, 2H), 1.35 (d, J=6.8 Hz, 6H). Three exchangeable protons not observed.

The N-benzyl-N-(2,2-dimethoxyethyl)-3-(2-fluoro-3-((4-(2-isopropylthiazole-4-carbonyl)-1-oxa-4,9-diazaspiro[5.5]undecan-9-yl)methyl)phenethoxy)propanamide used as a starting material was prepared as follows:

a) N-Benzyl-N-(2,2-dimethoxyethyl)-3-(2-fluoro-3-((4-(2-isopropylthiazole-4-carbonyl)-1-oxa-4,9-diazaspiro[5.5]undecan-9-yl)methyl)phenethoxy)propanamide

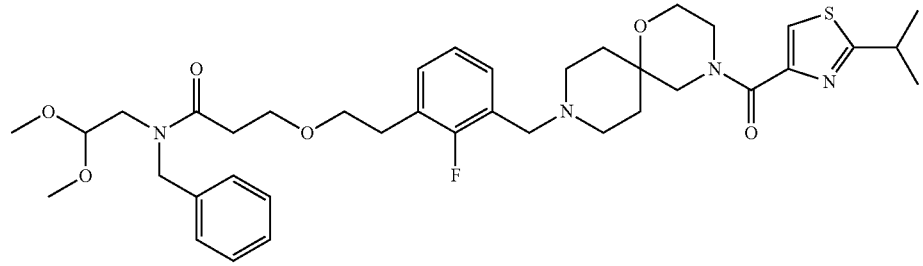

Prepared by the method of Example 7, step e using N-benzyl-2,2-dimethoxyethanamine [J. Chem. Soc., Perkin Trans. 1, 1974, 19, 2185] (0.049 g) in place of N-(2,2-dimethoxyethyl)cycloheptanamine. Yield 0.114 g.

m/z 711 (M+H)$^+$ (APCI).

EXAMPLE 9

N-Ethyl-3-(2-fluoro-3-((4-(2-(pentan-3-yl)thiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

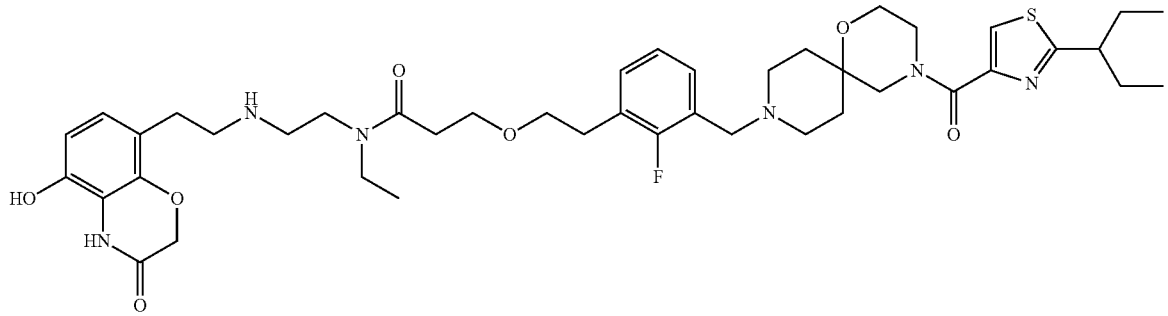

Prepared from (9-(2-fluoro-3-(2-hydroxyethyl)benzyl)-1-oxa-4,9-diazaspiro[5.5]undecan-4-yl)(2-(pentan-3-yl)thiazol-4-yl)methanone (0.32 g) using methods analogous to those described for Examples 1 to 3. Yield 0.11 g.

m/z 823 M$^+$ (MultiMode+).

$^1$H NMR (400 MHz, D$_6$-DMSO, 90° C.) δ 9.40 (s, 1H), 7.96 (s, 1H), 7.41 (t, J=7.2 Hz, 2H), 7.19 (t, J=7.7 Hz, 1H), 6.66 (d, J=8.5 Hz, 1H), 6.48 (d, J=8.5 Hz, 1H), 4.53 (s, 2H), 4.34-4.20 (m, 2H), 3.72-3.61 (m, 10H), 3.52 (t, J=6.5 Hz, 2H), 3.32 (q, J=7.0 Hz, 2H), 3.14-3.03 (m, 8H), 2.97-2.90 (m, 1H), 2.87 (t, J=6.9 Hz, 2H), 2.82 (t, J=7.8 Hz, 2H), 2.55 (t, J=6.7 Hz, 2H), 2.08-1.95 (m, 2H), 1.82-1.64 (m, 6H), 1.13-1.02 (m, 3H), 0.84 (t, J=7.4 Hz, 6H). Four exchangeable protons not observed.

The (9-(2-fluoro-3-(2-hydroxyethyl)benzyl)-1-oxa-4,9-diazaspiro[5.5]undecan-4-yl)(2-(pentan-3-yl)thiazol-4-yl)methanone used as a starting material was prepared as follows:

a) 2,2,2-Trifluoro-1-(1-oxa-4,9-diazaspiro[5.5]undecan-4-yl)ethanone trifluoroacetate

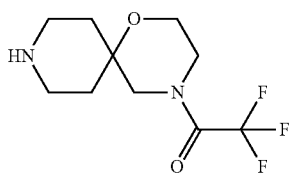

A solution of trifluoroacetic anhydride (9.6 mL) in DCM (10 mL) was added dropwise, over a period of 15 minutes, to a stirred solution of triethylamine (15.2 mL) and tert-butyl 1-oxa-4,9-diazaspiro[5.5]undecane-9-carboxylate hydrochloride [WuXi PharmaTech] (9.95 g) in DCM (100 mL) at 0° C. under nitrogen. The resulting solution was stirred at 0° C. for 30 minutes. More triethylamine (2.5 mL) was added, followed by more trifluoroacetic anhydride (1.6 mL) in DCM (10 mL), and stirring at 0° C. was continued for 1 hour. Water (100 mL) was added and the mixture was vigorously stirred for 10 minutes. The organic layer was separated, dried, and the solvent evaporated under reduced pressure. The residue was dissolved in DCM (100 mL) and the solution treated with trifluoroacetic acid (25 mL). This mixture was allowed to stand at 20° C. for 10 minutes and then diluted with toluene (40 mL). The solvents were removed under reduced pressure and the residue azeotroped with more toluene (×2) to yield the subtitled compound. Yield 14.0 g.

m/z 253 (M+H)$^+$ (APCI).

b) 2-(3-(1-Oxa-4,9-diazaspiro[5.5]undecan-9-ylmethyl)-2-fluorophenyl)ethanol

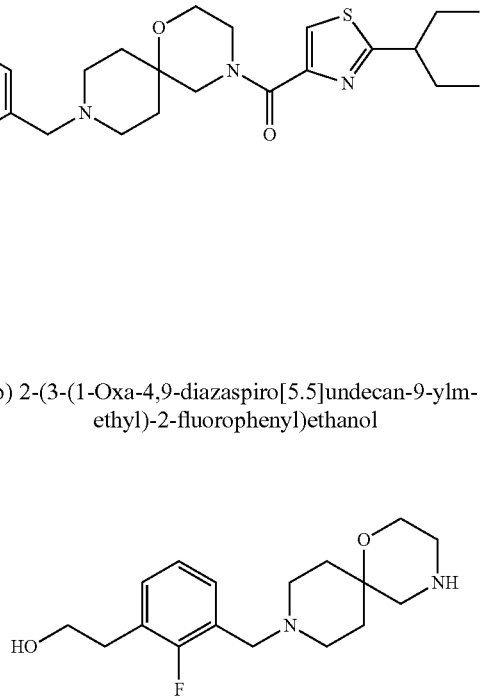

3-(2-(tert-Butyldimethylsilyloxy)ethyl)-2-fluorobenzaldehyde [Aromatic Intermediate 5] (5.0 g) was added to a solution of 2,2,2-trifluoro-1-(1-oxa-4,9-diazaspiro[5.5]undecan-4-yl)ethanone trifluoroacetate [Example 9, step a] (9.3 g) and acetic acid (1.0 mL) in N-methyl-2-pyrrolidinone (50 mL). The resulting mixture was stirred for 15 min, then cooled in an ice bath. Sodium triacetoxyborohydride (5.64 g) was then added and the mixture was stirred overnight. The reaction mixture was quenched by the addition of saturated sodium bicarbonate solution:brine (1:5) and extracted four times with ethyl acetate. The combined organic phases were dried (MgSO$_4$), filtered and concentrated in vacuo to afford an oil. The oil was dissolved in THF (100 mL) and treated with TBAF (1M in THF, 18.0 mL). The resulting solution was stirred at room temperature for 50 minutes, then more TBAF (1M in THF, 18.0 mL) was added and the mixture was stirred for a further 100 minutes. The solution was then concentrated in vacuo to afford an oil. The oil was dissolved in methanol (100 mL), the solution was treated with '880' aqueous ammonia (20 mL), stirred at room temperature for 50 minutes, then concentrated in vacuo to give an oil. The oil was dissolved in methanol and concentrated onto flash silica in vacuo. The resulting powder was purified by flash chromatography on silica eluted with '880' aqueous ammonia:methanol:dichloromethane (1:10:89) to afford the subtitled compound as a yellow oil. Yield 5.8 g, 60% pure. Used crude.

m/z 309 (M+H)$^+$ (APCI).

c) (9-(2-Fluoro-3-(2-hydroxyethyl)benzyl)-1-oxa-4, 9-diazaspiro[5.5]undecan-4-yl)(2-(pentan-3-yl)thiazol-4-yl)methanone

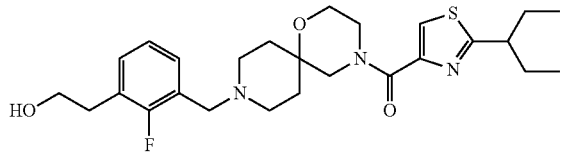

HATU (0.35 g) was added to a colourless solution of 2-(3-(1-oxa-4,9-diazaspiro[5.5]undecan-9-ylmethyl)-2-fluorophenyl)ethanol [Example 9, step b] (0.364 g), 2-(pentan-3-yl)thiazole-4-carboxylic acid [Carboxylic Acid 3] (0.141 g) and triethylamine (0.30 mL) in DMF (10 mL), pre-cooled in ice-water. The resulting yellow mixture was stirred in ice-water for 1 hour, then at room temperature for 1 hour. The solution was poured into a mixture of water and brine and extracted twice with ethyl acetate. The combined organic extracts were washed three times with water, once with brine, then dried (MgSO$_4$), filtered and concentrated onto flash silica in vacuo. The resulting powder was purified by flash chromatography on silica eluted with triethylamine:methanol:dichloromethane (1:2:97) to afford the subtitled compound. Yield 0.324 g.

m/z 490 (M+H)$^+$ (APCI).

The following compounds were prepared from the appropriate Carboxylic Acids and Amines using methods analogous to those described for Examples 13 to 15.

EXAMPLE 10

N-Ethyl-3-(2-fluoro-3-((4-(2-isopropylthiazole-4-carbonyl)-1-oxa-4,9-diazaspiro[5.5]undecan-9-yl)methyl)phenethoxy)-N-(2-(2-(4-hydroxy-2-oxo-2,3-dihydrobenzo[d]thiazol-7-yl)ethylamino)ethyl)propanamide ditrifluoroacetate

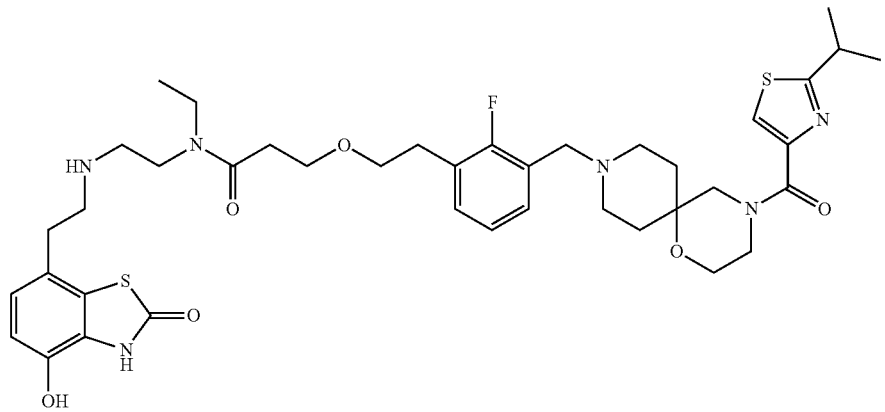

m/z 797 M$^+$ (MultiMode+).

$^1$H NMR (400 MHz, D$_6$-DMSO, 90° C.) δ 7.94 (s, 1H), 7.45-7.36 (m, 2H), 7.18 (t, J=7.6 Hz, 1H), 6.85 (d, J=8.2 Hz, 1H), 6.75 (d, J=8.2 Hz, 1H), 4.30 (s, 2H), 3.77-3.48 (m, 12H), 3.36-3.02 (m, 11H), 2.93-2.77 (m, 4H), 2.55 (t, J=6.4 Hz, 2H), 2.10-1.96 (m, 2H), 1.87-1.73 (m, 2H), 1.35 (d, J=6.7 Hz, 6H), 1.13-1.01 (m, 3H). Five exchangeable protons not observed.

EXAMPLE 11

3-(2-Fluoro-3-((4-(2-isopropylthiazole-4-carbonyl)-1-oxa-4,9-diazaspiro[5.5]undecan-9-yl)methyl)phenethoxy)-N-(2-(2-(4-hydroxy-2-oxo-2,3-dihydrobenzo[d]thiazol-7-yl)ethylamino)ethyl)-N-(tetrahydro-2H-pyran-4-yl)propanamide ditrifluoroacetate

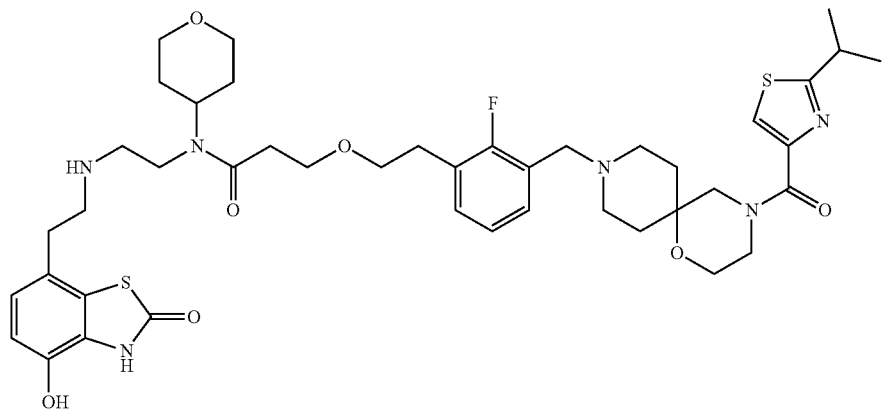

m/z 853 M+ (MultiMode+).

$^1$H NMR (500 MHz, D$_6$-DMSO, 90° C.) δ 8.70 (s, 1H), 7.93 (s, 1H), 7.48-7.38 (m, 2H), 7.22-7.15 (m, 1H), 6.86 (d, J=8.0 Hz, 1H), 6.76 (d, J=8.0 Hz, 1H), 4.31 (s, 2H), 4.06-3.84 (m, 3H), 3.76-3.60 (m, 10H), 3.54-3.46 (m, 2H), 3.43-3.27 (m, 3H), 3.25-2.99 (m, 8H), 2.92-2.81 (m, 4H), 2.68-2.59 (m, 2H), 2.09-1.98 (m, 2H), 1.86-1.67 (m, 4H), 1.60-1.49 (m, 2H), 1.35 (d, J=6.7 Hz, 6H). Four exchangeable protons not observed.

EXAMPLE 12

R)-3-(2-Fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)-N-(3-methylbutan-2-yl)propanamide ditrifluoroacetate

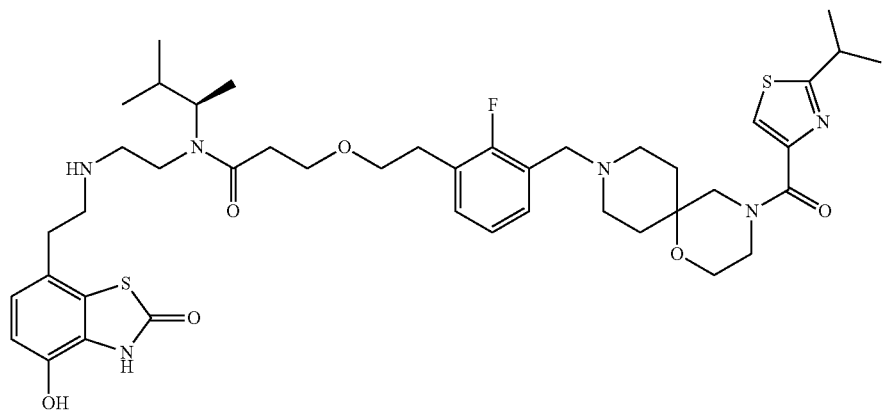

m/z 837 M+ (MultiMode+).

$^1$H NMR (500 MHz, D$_6$-DMSO, 90° C.) δ 9.33 (s, 1H), 8.52 (s, 1H), 7.93 (s, 1H), 7.43-7.35 (m, 2H), 7.21-7.13 (m, 1H), 6.67 (d, J=8.0 Hz, 1H), 6.49 (d, J=8.1 Hz, 1H), 4.53 (s, 2H), 4.24-4.15 (m, 2H), 3.75-3.26 (m, 14H), 3.16-2.95 (m, 8H), 2.90-2.80 (m, 4H), 2.66-2.54 (m, 2H), 2.05-1.94 (m, 2H), 1.82-1.69 (m, 3H), 1.35 (d, J=6.7 Hz, 6H), 1.17-1.11 (m, 3H), 0.96-0.88 (m, 3H), 0.82-0.74 (m, 3H). Three exchangeable protons not observed.

EXAMPLE 13

3-(2-Fluoro-3-((4-(2-isopropylthiazole-4-carbonyl)-1-oxa-4,9-diazaspiro[5.5]undecan-9-yl)methyl)phenethoxy)-N-(2-(2-(4-hydroxy-2-oxo-2,3-dihydrobenzo[d]thiazol-7-yl)ethylamino)ethyl)-N-methylpropanamide ditrifluoroacetate

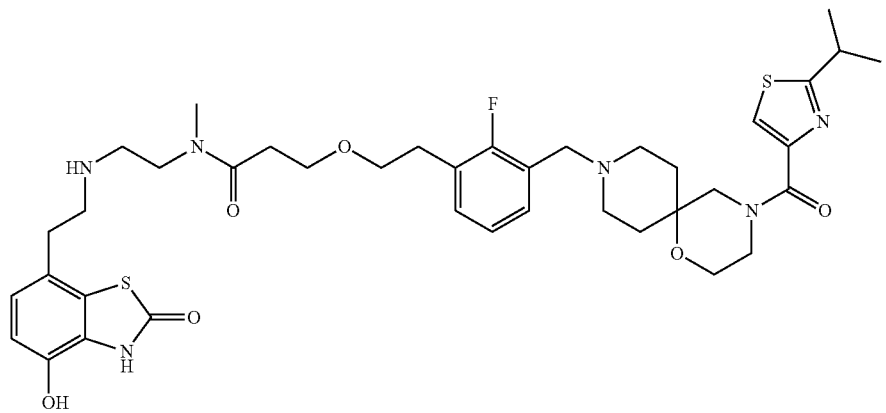

m/z 783 M$^+$ (MultiMode+).
$^1$H NMR (500 MHz, D$_6$-DMSO, 90° C.) δ 7.93 (s, 1H), 7.45-7.38 (m, 2H), 7.21-7.15 (m, 1H), 6.84 (d, J=7.8 Hz, 1H), 6.75 (d, J=8.2 Hz, 1H), 4.33-4.24 (m, 2H), 3.74-3.53 (m, 12H), 3.34-3.26 (m, 1H), 3.22-2.80 (m, 15H), 2.60-2.52 (m, 2H), 2.08-1.96 (m, 2H), 1.86-1.71 (m, 2H), 1.35 (d, J=6.7 Hz, 6H). Five exchangeable protons not observed.

EXAMPLE 14

(R)-3-(2-Fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)-N-(1-phenylethyl)propanamide ditrifluoroacetate

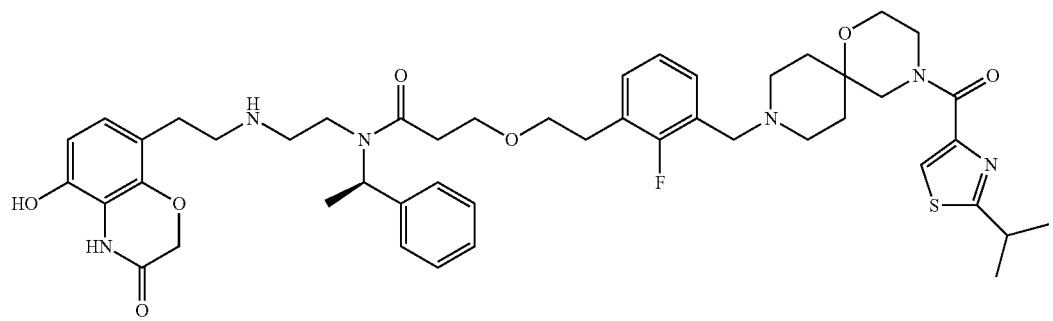

m/z 871 M$^+$ (MultiMode+).

$^1$H NMR (500 MHz, D$_6$-DMSO, 90° C.) δ 9.33 (s, 1H), 8.73-8.24 (m, 2H), 7.98-7.89 (m, 1H), 7.48-7.13 (m, 9H), 6.68-6.58 (m, 1H), 6.48 (s, 1H), 5.50-5.12 (m, 1H), 4.50 (d, J=2.8 Hz, 2H), 4.27 (s, 2H), 3.79-2.66 (m, 28H), 2.07-1.95 (m, 2H), 1.83-1.70 (m, 2H), 1.61-1.48 (m, 3H), 1.41-1.29 (m, 6H).

EXAMPLE 15

N-Ethyl-3-(2-fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

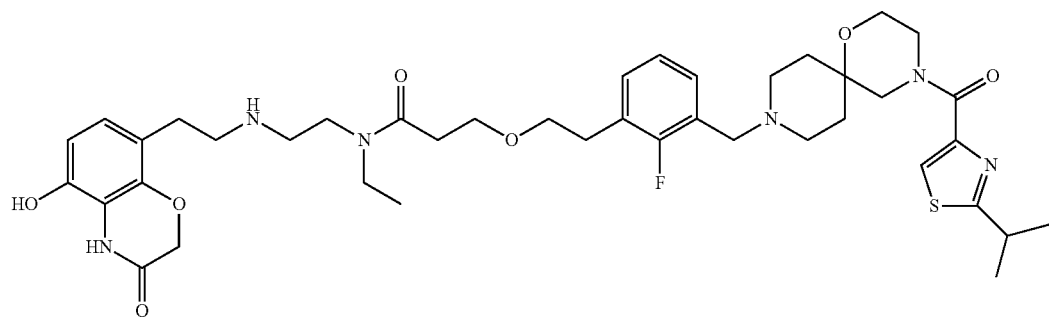

m/z 795 M$^+$ (MultiMode+).

$^1$H NMR (500 MHz, D$_6$-DMSO, 90° C.) δ 9.39-9.33 (m, 1H), 8.54-8.24 (m, 1H), 7.96-7.91 (m, 1H), 7.45-7.38 (m, 2H), 7.23-7.16 (m, 1H), 6.70-6.63 (m, 1H), 6.52-6.45 (m, 1H), 4.59-4.50 (m, 2H), 4.27 (s, 2H), 3.66-2.80 (m, 27H), 2.57-2.49 (m, 2H), 2.07-1.97 (m, 2H), 1.83-1.69 (m, 2H), 1.41-1.33 (m, 6H), 1.14-1.04 (m, 3H). Three exchangeable protons not observed.

EXAMPLE 16

3-(2-Fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)-N-isopropylpropanamide ditrifluoroacetate

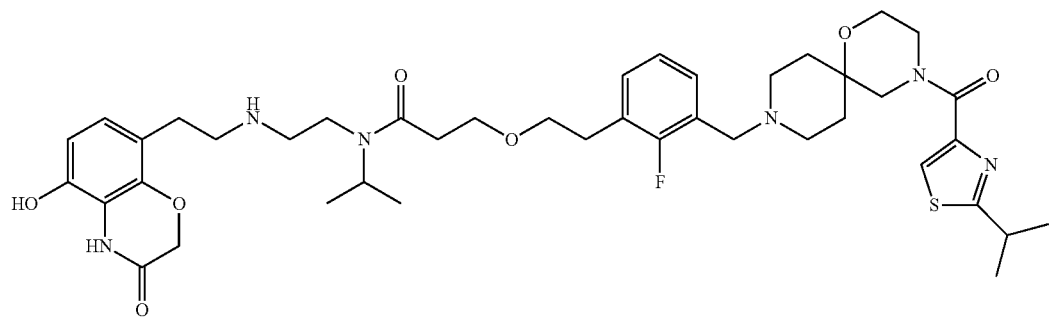

m/z 809 M$^+$ (MultiMode+).

$^1$H NMR (500 MHz, D$_6$-DMSO, 90° C.) δ 9.41-9.26 (m, 1H), 8.73-8.33 (m, 1H), 7.98-7.88 (m, 1H), 7.46-7.36 (m, 2H), 7.24-7.14 (m, 1H), 6.72-6.62 (m, 1H), 6.55-6.45 (m, 1H), 4.62-4.48 (m, 2H), 4.31-2.55 (m, 30H), 2.10-1.94 (m, 2H), 1.87-1.71 (m, 2H), 1.47-1.31 (m, 6H), 1.21-1.05 (m, 6H). Three exchangeable protons not observed.

EXAMPLE 17

N-(3,3-Dimethylbutyl)-3-(2-fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

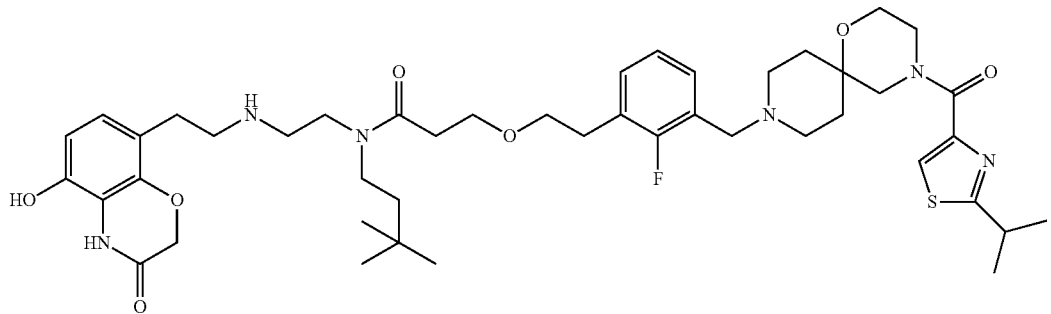

m/z 851 M$^+$ (MultiMode+).

$^1$H NMR (500 MHz, D$_6$-DMSO, 90° C.) δ 9.37 (s, 1H), 7.95 (s, 1H), 7.40-7.31 (m, 2H), 7.19-7.11 (m, 1H), 6.69-6.60 (m, 1H), 6.54-6.45 (m, 1H), 4.53 (s, 2H), 4.25-3.95 (m, 1H), 3.76-2.77 (m, 30H), 2.01-1.86 (m, 2H), 1.78-1.63 (m, 2H), 1.46-1.31 (m, 8H), 0.91 (s, 9H). Four exchangeable protons not observed.

EXAMPLE 18

(R)-3-(2-Fluoro-3-((4-(2-isopropylthiazole-4-carbonyl)-1-oxa-4,9-diazaspiro[5.5]undecan-9-yl)methyl)phenethoxy)-N-(hexan-2-yl)-N-(2-(2-(5-hydroxy-3-oxo-3,4-dihydro-2H-benzo[b][1,4]oxazin-8-yl)ethylamino)ethyl)propanamide ditrifluoroacetate

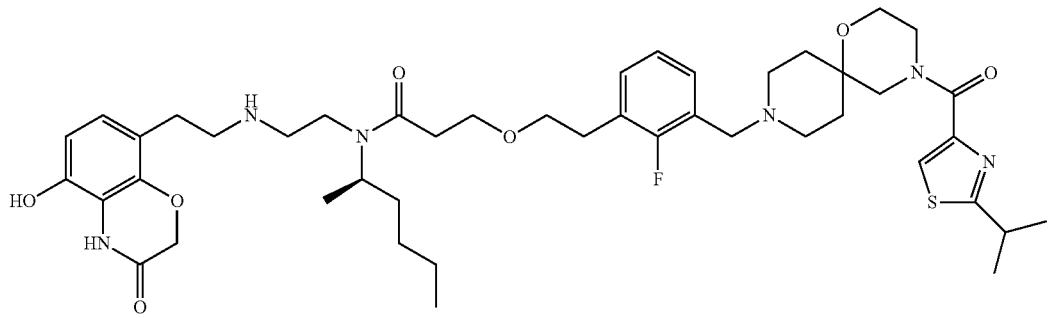

m/z 851 M$^+$ (MultiMode+).

¹H NMR (500 MHz, D₆-DMSO, 90° C.) δ 9.38-9.29 (m, 1H), 8.58 (s, 1H), 7.98-7.91 (m, 1H), 7.45-7.33 (m, 2H), 7.22-7.13 (m, 1H), 6.72-6.62 (m, 1H), 6.54-6.44 (m, 1H), 4.59-4.48 (m, 2H), 4.26-4.10 (m, 2H), 3.95-2.79 (m, 26H), 2.65-2.55 (m, 2H), 2.04-1.91 (m, 2H), 1.81-1.68 (m, 2H), 1.52-1.07 (m, 15H), 0.93-0.81 (m, 3H). Three exchangeable protons not observed.

EXAMPLE 19

(R)—N-(3,3-Dimethylbutan-2-yl)-3-(2-fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

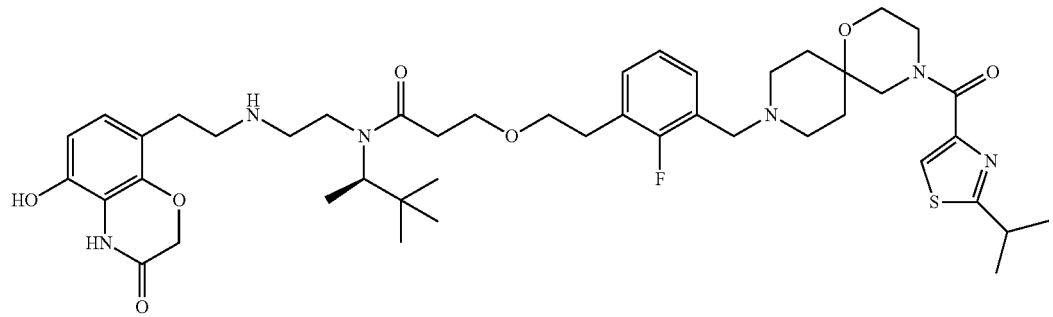

m/z 851 M⁺ (MultiMode+).

¹H NMR (500 MHz, D₆-DMSO, 90° C.) δ 9.36 (s, 1H), 8.59 (s, 1H), 7.93 (s, 1H), 7.43-7.37 (m, 2H), 7.18 (t, J=7.5 Hz, 1H), 6.67 (d, J=8.3 Hz, 1H), 6.49 (d, J=8.4 Hz, 1H), 4.53 (s, 2H), 4.28-4.18 (m, 2H), 3.81-3.54 (m, 13H), 3.33-3.24 (m, 1H), 3.16-2.97 (m, 8H), 2.89-2.80 (m, 4H), 2.73-2.52 (m, 2H), 2.04-1.95 (m, 2H), 1.80-1.71 (m, 2H), 1.35 (d, J=6.9 Hz, 6H), 1.16 (d, J=5.9 Hz, 3H), 0.90 (s, 9H). Three exchangeable protons not observed.

EXAMPLE 20

3-(2-Fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)-N-(3,3,3-trifluoropropyl)propanamide ditrifluoroacetate

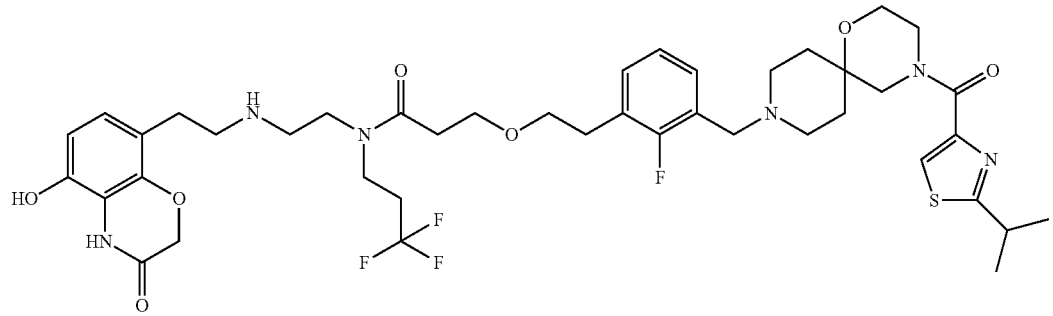

m/z 863 M⁺ (MultiMode+).

$^1$H NMR (500 MHz, D$_6$-DMSO, 90° C.) δ 9.35 (s, 1H), 7.93 (s, 1H), 7.44-7.34 (m, 2H), 7.16 (t, J=7.6 Hz, 1H), 6.66 (d, J=8.3 Hz, 1H), 6.49 (d, J=8.4 Hz, 1H), 4.52 (s, 2H), 4.22-4.11 (m, 2H), 3.75-2.80 (m, 29H), 2.58 (t, J=6.5 Hz, 2H), 2.04-1.92 (m, 2H), 1.80-1.68 (m, 2H), 1.35 (d, J=6.9 Hz, 6H). Four exchangeable protons not observed.

EXAMPLE 21

3-(2-Fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)-N-(2-methylbenzyl)propanamide ditrifluoroacetate

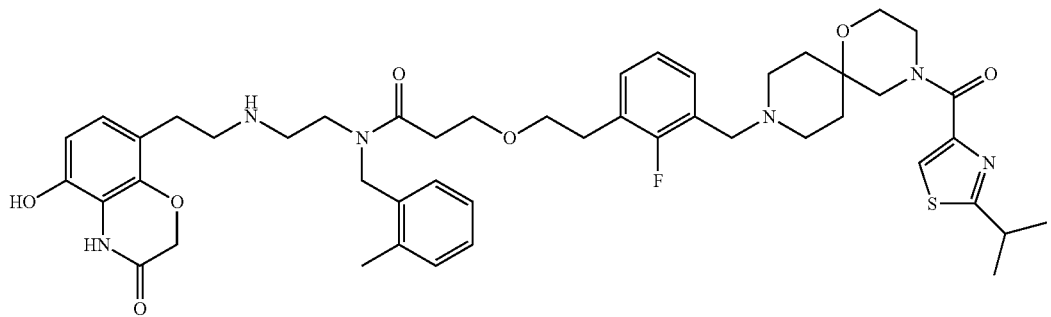

m/z 871 M$^+$ (MultiMode+).

$^1$H NMR (500 MHz, D$_6$-DMSO, 90° C.) δ 9.35 (s, 1H), 7.93 (s, 1H), 7.42-7.34 (m, 2H), 7.20-7.13 (m, 4H), 7.02-6.97 (m, 1H), 6.64 (d, J=8.3 Hz, 1H), 6.48 (d, J=8.3 Hz, 1H), 4.55 (s, 2H), 4.51 (s, 2H), 4.27-4.17 (m, 2H), 3.74-3.50 (m, 14H), 3.35-3.27 (m, 1H), 3.13-2.96 (m, 8H), 2.88-2.78 (m, 4H), 2.26 (s, 3H), 2.03-1.95 (m, 2H), 1.80-1.69 (m, 2H), 1.35 (d, J=6.9 Hz, 6H). Four exchangeable protons not observed.

EXAMPLE 22

3-(2-Fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)-N-(4-methylbenzyl)propanamide ditrifluoroacetate

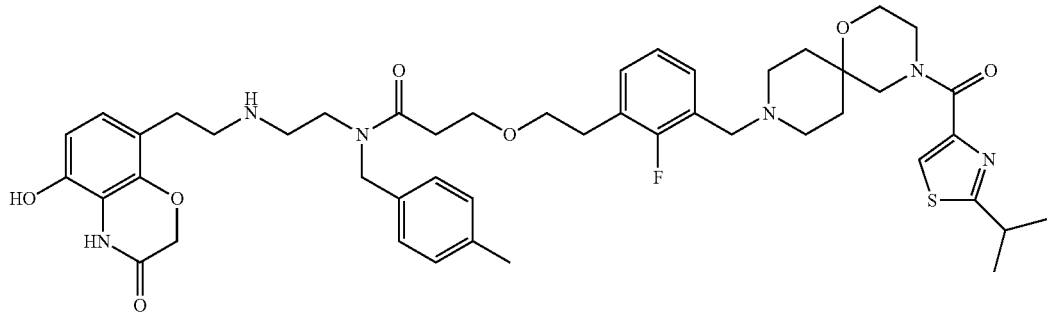

m/z 871 M$^+$ (MultiMode+).

¹H NMR (500 MHz, D₆-DMSO, 90° C.) δ 9.35 (s, 1H), 7.96 (s, 1H), 7.45-7.35 (m, 2H), 7.22-7.07 (m, 5H), 6.64 (d, J=8.4 Hz, 1H), 6.48 (d, J=8.3 Hz, 1H), 4.51 (s, 4H), 4.23 (s, 2H), 3.81-2.57 (m, 27H), 2.28 (s, 3H), 2.08-1.94 (m, 2H), 1.84-1.68 (m, 2H), 1.42-1.31 (m, 6H). Four exchangeable protons not observed.

EXAMPLE 23

3-(2-Fluoro-3-((4-(2-isopropylthiazole-4-carbonyl)-1-oxa-4,9-diazaspiro[5.5]undecan-9-yl)methyl) phenethoxy)-N-(2-(2-(5-hydroxy-3-oxo-3,4-dihydro-2H-benzo[b][1,4]oxazin-8-yl)ethylamino)ethyl)-N-(3-methoxybenzyl)propanamide ditrifluoroacetate

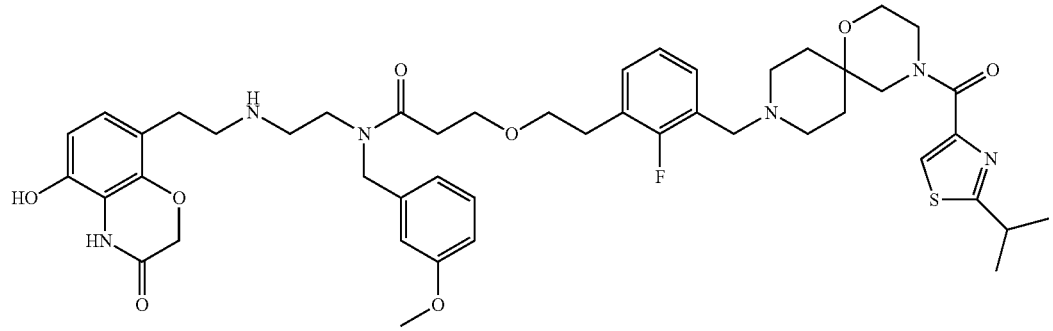

m/z 887 M⁺ (MultiMode+).

¹H NMR (500 MHz, D₆-DMSO, 90° C.) δ 9.34 (s, 1H), 7.93 (s, 1H), 7.42-7.35 (m, 2H), 7.28-7.22 (m, 1H), 7.16 (t, J=7.5 Hz, 1H), 6.88-6.83 (m, 1H), 6.80-6.75 (m, 2H), 6.64 (d, J=8.3 Hz, 1H), 6.48 (d, J=8.3 Hz, 1H), 4.57-4.48 (m, 4H), 4.27-4.17 (m, 2H), 3.80-2.58 (m, 30H), 2.05-1.95 (m, 2H), 1.80-1.65 (m, 2H), 1.35 (d, J=6.9 Hz, 6H). Four exchangeable protons not observed.

EXAMPLE 24

N-Ethyl-3-(3-((4-(5-ethylthiophene-3-carbonyl)-1-oxa-4,9-diazaspiro[5.5]undecan-9-yl)methyl)-2-fluorophenethoxy)-N-(2-(2-(5-hydroxy-3-oxo-3,4-dihydro-2H-benzo[b][1,4]oxazin-8-yl)ethylamino)ethyl) propanamide ditrifluoroacetate

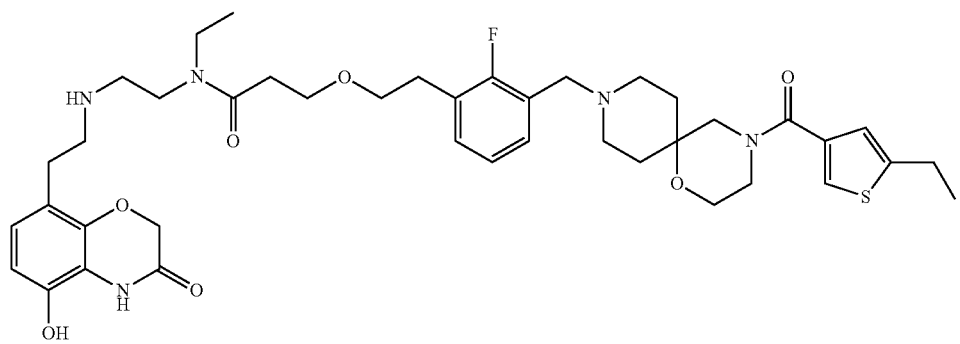

m/z 780 M⁺ (MultiMode+).

¹H NMR (400 MHz, D₆-DMSO, 90° C.) δ 9.39 (s, 1H), 7.49-7.40 (m, 3H), 7.19 (t, J=7.6 Hz, 1H), 6.89 (s, 1H), 6.66 (d, J=8.2 Hz, 1H), 6.49 (d, J=8.2 Hz, 1H), 4.52 (s, 2H), 4.34 (s, 2H), 3.71-3.61 (m, 6H), 3.56-3.50 (m, 4H), 3.47-3.36 (m, 2H), 3.35-3.28 (m, 2H), 3.24-3.17 (m, 2H), 3.14-3.05 (m, 6H), 2.90-2.77 (m, 6H), 2.55 (t, J=6.1 Hz, 2H), 2.09-1.99 (m, 2H), 1.81-1.70 (m, 2H), 1.25 (t, J=7.4 Hz, 3H), 1.12-1.02 (m, 3H). Four exchangeable protons not observed.

EXAMPLE 25

3-(3-((4-(2-Cyclopentylthiazole-4-carbonyl)-1-oxa-4,9-diazaspiro[5.5]undecan-9-yl)methyl)-2-fluorophenethoxy)-N-ethyl-N-(2-(2-(5-hydroxy-3-oxo-3,4-dihydro-2H-benzo[b][1,4]oxazin-8-yl)ethylamino)ethyl)propanamide ditrifluoroacetate

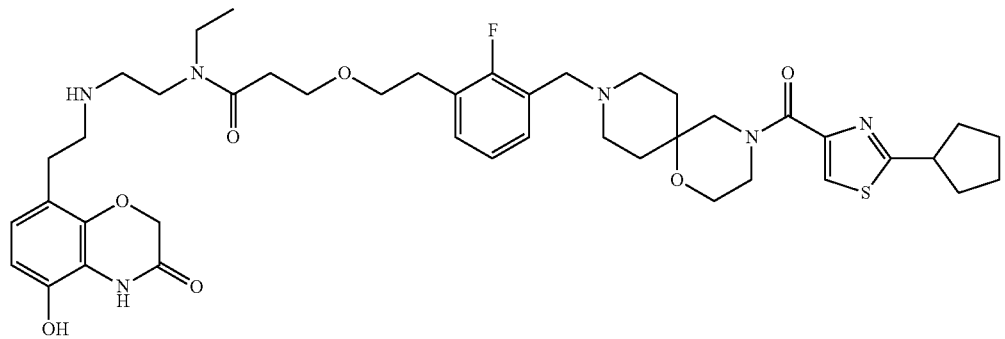

m/z 821 M⁺ (MultiMode+).

¹H NMR (400 MHz, D₆-DMSO, 90° C.) δ 9.39 (s, 1H), 7.92 (s, 1H), 7.44-7.38 (m, 2H), 7.20 (d, J=7.4 Hz, 1H), 6.66 (d, J=8.2 Hz, 1H), 6.48 (d, J=8.2 Hz, 1H), 4.53 (s, 2H), 4.27 (s, 2H), 3.75-3.60 (m, 12H), 3.56-3.28 (m, 5H), 3.14-3.03 (m, 6H), 2.91-2.79 (m, 4H), 2.55 (t, J=7.2 Hz, 2H), 2.18-2.09 (m, 2H), 2.04-1.95 (m, 2H), 1.83-1.62 (m, 8H), 1.11-1.05 (m, 3H). Four exchangeable protons not observed.

Examples 10 to 25 were prepared using the following Carboxylic Acids and Amines:

| Example Number | Carboxylic Acid | Amine |
|---|---|---|
| 10 | 2-isopropylthiazole-4-carboxylic acid | N-ethyl-2,2-dimethoxyethanamine [Note 1] |
| 11 | 2-isopropylthiazole-4-carboxylic acid | Amine 1 |
| 12 | 2-isopropylthiazole-4-carboxylic acid | Amine 2 |
| 13 | 2-isopropylthiazole-4-carboxylic acid | N-methyl-2,2-dimethoxyethanamine |
| 14 | 2-isopropylthiazole-4-carboxylic acid | (R)-2,2-dimethoxy-N-(1-phenylethyl)ethanamine [Note 2] |
| 15 | 2-isopropylthiazole-4-carboxylic acid | N-ethyl-2,2-dimethoxyethanamine [Note 1] |
| 16 | 2-isopropylthiazole-4-carboxylic acid | Amine 3 |
| 17 | 2-isopropylthiazole-4-carboxylic acid | Amine 4 |
| 18 | 2-isopropylthiazole-4-carboxylic acid | (R)-N-(2,2-dimethoxyethyl)hexan-2-amine [Note 3] |
| 19 | 2-isopropylthiazole-4-carboxylic acid | Amine 5 |
| 20 | 2-isopropylthiazole-4-carboxylic acid | Amine 7 |
| 21 | 2-isopropylthiazole-4-carboxylic acid | 2,2-dimethoxy-N-(2-methylbenzyl)ethanamine [Note 4] |
| 22 | 2-isopropylthiazole-4-carboxylic acid | 2,2-dimethoxy-N-(4-methylbenzyl)ethanamine [Note 4] |
| 23 | 2-isopropylthiazole-4-carboxylic acid | 2,2-dimethoxy-N-(3-methoxybenzyl)ethanamine [Note 4] |
| 24 | 5-ethylthiophene-3-carboxylic acid | N-ethyl-2,2-dimethoxyethanamine [Note 1] |
| 25 | Carboxylic Acid 2 | N-ethyl-2,2-dimethoxyethanamine [Note 1] |

[Note 1]: U.S. Pat. No. 2,707,186.
[Note 2]: WO 2005085226.
[Note 3]: WO 2008075025.
[Note 4]: J. Chem. Soc., Perkin Trans. 1, 1974, 19, 2185.

EXAMPLE 26

3-(2-Chloro-3-((4-(2-ethylthiazole-4-carbonyl)-1-oxa-4,9-diazaspiro[5.5]undecan-9-yl)methyl)phenethoxy)-N-ethyl-N-(2-(2-(4-hydroxy-2-oxo-2,3-dihydrobenzo[d]thiazol-7-yl)ethylamino)ethyl)propanamide ditrifluoroacetate

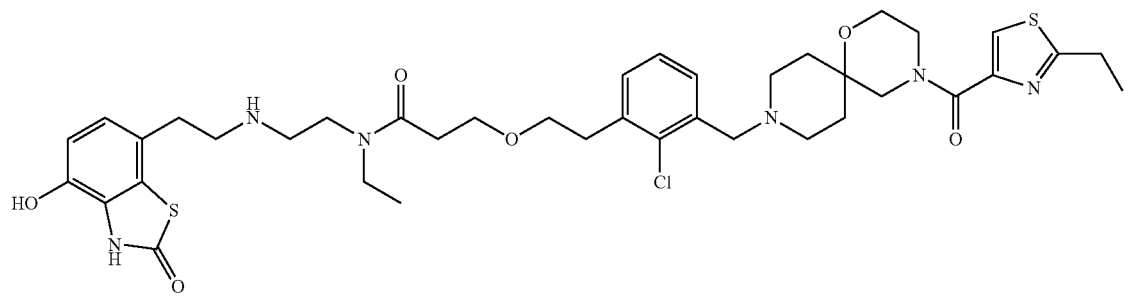

p-Toluenesulfonic acid monohydrate (0.51 g) was added to a solution of 3-(2-chloro-3-((4-(2-ethylthiazole-4-carbonyl)-1-oxa-4,9-diazaspiro[5.5]undecan-9-yl)methyl)phenethoxy)-N-(2,2-dimethoxyethyl)-N-ethylpropanamide (0.35 g) in THF (5 mL) and the resulting mixture stirred for 15 min at RT. The solution was then added to a suspension of 7-(2-aminoethyl)-4-hydroxybenzo[d]thiazol-2(3H)-one hydrochloride [Org. Proc. Res. Dev. 2004, 8(4), 628] (0.20 g) and sodium bicarbonate (0.29 g) in a mixture of NMP (2 mL) and water (0.2 mL). The resulting cloudy solution was stirred for 10 min, then sodium triacetoxyborohydride (0.34 g) was added and the resulting mixture was stirred overnight. The reaction mixture was partitioned between ethyl acetate (15 mL) and saturated sodium bicarbonate solution (15 mL). The organic phase was separated, washed with 10% brine (2×15 mL), dried over sodium sulphate, filtered and evaporated. The residue was purified by flash silica chromatography, elution gradient 97.25:2.5:0.25 to 92.3:7:0.7 dichloromethane: methanol: '880' aqueous ammonia. The fractions containing the product were combined and evaporated. The resulting gum was further purified by preparative HPLC (Gemini™ NX, Gradient: 27-62% methanol in 0.1% aqueous TFA). The fractions containing the product were combined and evaporated to give the titled compound as a white foam. Yield 0.17 g.

m/z 799 M (MultiMode+).

$^1$H NMR (500 MHz, D$_6$-DMSO, 90° C.) δ 11.35 (s, 1H), 7.95-7.90 (m, 1H), 7.53-7.47 (m, 1H), 7.44-7.38 (m, 1H), 7.36-7.30 (m, 1H), 6.87-6.81 (m, 1H), 6.77-6.71 (m, 1H), 4.36-4.23 (m, 2H), 3.75-2.54 (m, 30H), 2.06-1.94 (m, 2H), 1.83-1.68 (m, 2H), 1.38-1.29 (m, 3H), 1.16-1.03 (m, 3H). Four exchangeable protons not observed.

The 3-(2-chloro-3-((4-(2-ethylthiazole-4-carbonyl)-1-oxa-4,9-diazaspiro[5.5]undecan-9-yl)methyl)phenethoxy)-N-(2,2-dimethoxyethyl)-N-ethylpropanamide used as a starting material was prepared as follows:

a) tert-Butyl 4-(2-ethylthiazole-4-carbonyl)-1-oxa-4,9-diazaspiro[5.5]undecane-9-carboxylate

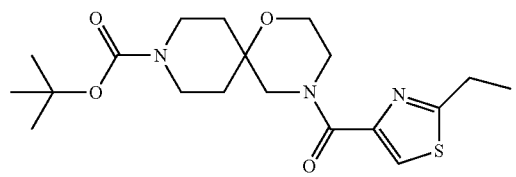

T3P (1.6M in THF, 51 mL) was added dropwise to a stirred suspension of tert-butyl 1-oxa-4,9-diazaspiro[5.5]undecane-9-carboxylate hydrochloride [WuXi PharmaTech] (18 g), 2-ethylthiazole-4-carboxylic acid [Carboxylic Acid 1] (12.0 g) and triethylamine (52 mL) in DMF (120 mL) under nitrogen and the mixture stirred at ambient temperature for 20 hours. The mixture was diluted with water and extracted into ethyl acetate (×3). The combined extracts were washed successively with 10% brine, 30% brine and saturated brine, dried over magnesium sulfate, filtered and the solvent removed. The crude product was purified by flash silica chromatography, eluting with ethyl acetate. Pure fractions were evaporated to dryness to afford the subtitled compound as a yellow oil. Yield 24 g.

m/z 340 (M-tBu+H)$^+$ (APCI).

b) (2-Ethylthiazol-4-yl)(1-oxa-4,9-diazaspiro[5.5]undecan-4-yl)methanone trifluoroacetate

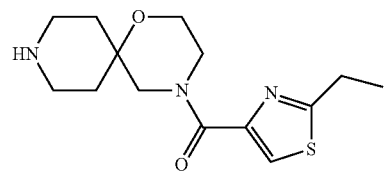

Trifluoroacetic acid (20 mL) was added to a solution of tert-butyl 4-(2-ethylthiazole-4-carbonyl)-1-oxa-4,9-diazaspiro[5.5]undecane-9-carboxylate [Example 26, step a] (24 g) in dichloromethane (100 mL) and the mixture stirred at ambient temperature for 18 hours. The reaction mixture was diluted with toluene (50 mL) and concentrated in vacuo. The residue was dissolved in dichloromethane (50 mL), TFA (50 mL) was added and the mixture was stirred for 4 hours. The mixture was diluted with toluene (50 mL), concentrated in vacuo, the residue triturated with ether and the precipitated solid collected by filtration and dried to afford the subtitled compound as a white solid. Yield 28 g.

$^1$H NMR (400 MHz, D$_6$-DMSO) δ 8.55 (s, 1H), 8.39 (s, 1H), 8.04-8.00 (m, 1H), 3.81-3.51 (m, 6H), 3.18-2.91 (m, 6H), 2.00-1.90 (m, 2H), 1.72-1.56 (m, 2H), 1.32 (t, J=7.2 Hz, 3H).

c) (9-(2-Chloro-3-(2-hydroxyethyl)benzyl)-1-oxa-4,9-diazaspiro[5.5]undecan-4-yl)(2-ethylthiazol-4-yl)methanone

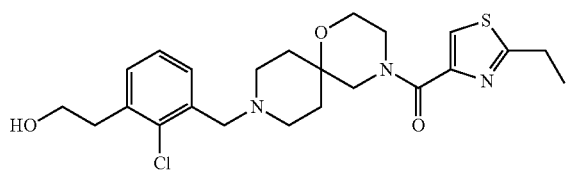

To a suspension of 2-chloro-3-(2-hydroxyethyl)benzaldehyde [Aromatic Intermediate 11] (1.5 g) and (2-ethylthiazol-4-yl)(1-oxa-4,9-diazaspiro[5.5]undecan-4-yl)methanone trifluoroacetate [Example 26, step b] (4.25 g) in tetrahydrofuran (50 mL) was added triethylamine (2.5 mL) in one portion. The mixture was stirred for 0.5 h, sodium triacetoxyborohydride (2.58 g) was then added in one portion and the resultant solution was stirred for 2 h. The reaction mixture was partitioned between ethyl acetate (100 mL) and saturated sodium bicarbonate solution (50 mL). The mixture was shaken vigorously for 10 min and the layers were separated. The aqueous phase was extracted with ethyl acetate (100 mL). The combined organic solutions were washed with brine, dried over sodium sulphate, filtered and evaporated. The residue was purified by flash silica chromatography using 95:5 ethyl acetate:triethylamine as solvent. The fractions containing the product were combined and evaporated to give the subtitled compound as a clear oil. Yield 3.40 g.

$^1$H NMR (400 MHz, D$_6$-DMSO, 90° C.) δ 7.89 (s, 1H), 7.33-7.28 (m, 1H), 7.24-7.16 (m, 2H), 4.35 (t, J=5.4 Hz, 1H), 3.68-3.60 (m, 8H), 3.55 (s, 2H), 3.02 (q, J=7.5 Hz, 2H), 2.89 (t, J=6.9 Hz, 2H), 2.46-2.31 (m, 4H), 1.75-1.67 (m, 2H), 1.59-1.51 (m, 2H), 1.33 (t, J=7.6 Hz, 3H).

d) tert-Butyl 3-(2-chloro-3-((4-(2-ethylthiazole-4-carbonyl)-1-oxa-4,9-diazaspiro[5.5]undecan-9-yl)methyl)phenethoxy)propanoate

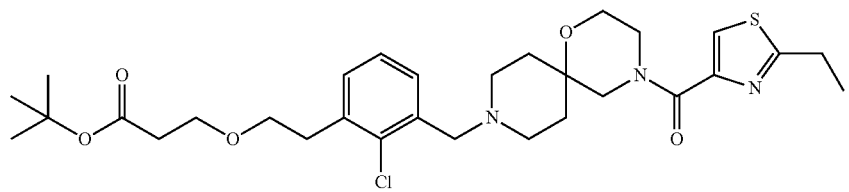

Triton-B (40% in water, 0.94 mL) was added to a solution of (9-(2-chloro-3-(2-hydroxyethyl)benzyl)-1-oxa-4,9-diazaspiro[5.5]undecan-4-yl)(2-ethylthiazol-4-yl)methanone [Example 26, step c] (3.2 g) and tert-butyl acrylate (1.5 mL) in acetonitrile (1 mL) and the resulting mixture stirred overnight at RT. The solvent was evaporated and the residue was purified by flash silica chromatography, elution gradient 1:1:0.05 ethyl acetate:isohexane:triethylamine to 95:5 ethyl acetate:triethylamine to give the subtitled compound as a clear oil. Yield 3.2 g.

m/z 592 M$^+$ (APCI).

e) 3-(2-Chloro-3-((4-(2-ethylthiazole-4-carbonyl)-1-oxa-4,9-diazaspiro[5.5]undecan-9-yl)methyl)phenethoxy)propanoic acid

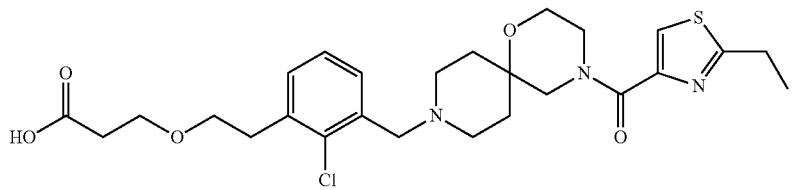

TFA (10 mL) was added to a solution of tert-butyl 3-(2-chloro-3-((4-(2-ethylthiazole-4-carbonyl)-1-oxa-4,9-diazaspiro[5.5]undecan-9-yl)methyl)phenethoxy)propanoate [Example 26, step d] (3.1 g) in DCM (30 mL) and the resulting mixture stirred for 2 h, then evaporated. The residue was partitioned between ethyl acetate (100 mL) and saturated sodium bicarbonate solution (50 mL). The phases were separated and the aqueous phase was washed with more ethyl acetate (2×100 mL). The aqueous phase was then acidified with acetic acid and extracted with ethyl acetate (3×100 mL). The combined organic solutions were dried over sodium sulphate, filtered and evaporated to give the subtitled compound as a white foam. Yield 2.7 g.

$^1$H NMR (400 MHz, D$_6$-DMSO, 90° C.) δ 7.92 (s, 1H), 7.60-7.53 (m, 1H), 7.44-7.39 (m, 1H), 7.32 (t, J=7.6 Hz, 1H), 3.76-3.56 (m, 12H), 3.12-2.92 (m, 8H), 2.42 (t, J=6.4 Hz, 2H), 2.01-1.73 (m, 4H), 1.33 (t, J=7.6 Hz, 3H). One exchangeable proton not observed.

f) 3-(2-Chloro-3-((4-(2-ethylthiazole-4-carbonyl)-1-oxa-4,9-diazaspiro[5.5]undecan-9-yl)methyl)phenethoxy)-N-(2,2-dimethoxyethyl)-N-ethylpropanamide

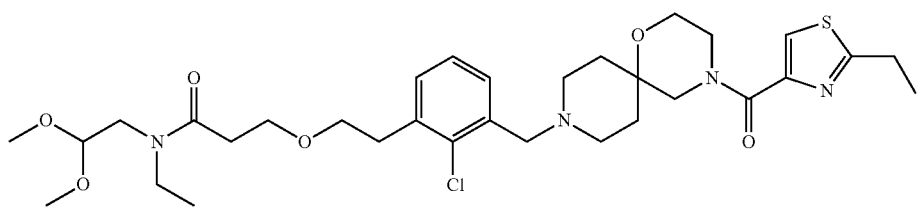

HATU (1.06 g) was added to a solution of 3-(2-chloro-3-((4-(2-ethylthiazole-4-carbonyl)-1-oxa-4,9-diazaspiro[5.5]undecan-9-yl)methyl)phenethoxy)propanoic acid [Example 26, step e] (0.75 g), Hunig's base (1.22 mL) and N-ethyl-2,2-dimethoxyethanamine [U.S. Pat. No. 2,707,186] (0.37 g) in DMF (5 mL). The resulting dark solution was stirred overnight at RT. The reaction mixture was partitioned between ethyl acetate (25 mL) and 20% brine (25 mL). The organic layer was separated and washed with 20% brine (2×25 mL). The organic solution was evaporated and the residue purified by silica gel chromatography, gradient elution isohexane:triethylamine 95:5 to ethyl acetate:triethylamine 95:5. The fractions containing the product were combined and evaporated to give the subtitled compound as an oil. Yield 0.70 g.

m/z 651 M$^+$ (APCI).

EXAMPLE 27

3-(2-Chloro-3-((4-(2-isopropylthiazole-4-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide ditrifluoroacetate

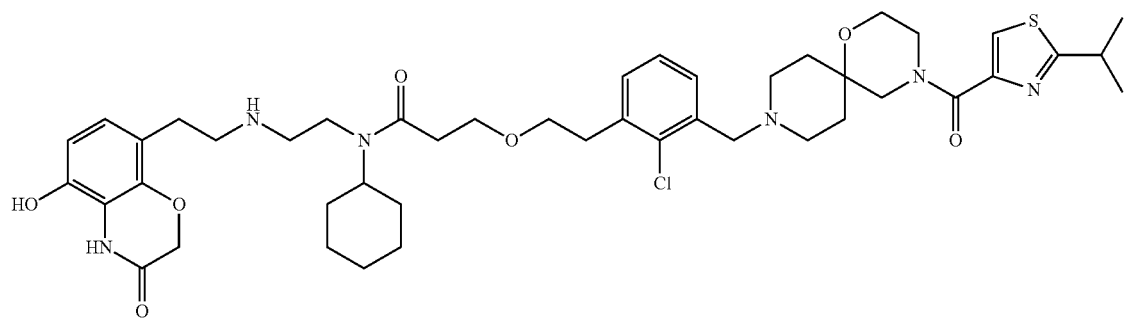

p-Toluenesulfonic acid monohydrate (0.29 g) was added to a solution of 3-(2-chloro-3-((4-(2-isopropylthiazole-4-carbonyl)-1-oxa-4,9-diazaspiro[5.5]undecan-9-yl)methyl)phenethoxy)-N-cyclohexyl-N-(2,2-dimethoxyethyl)propanamide (0.22 g) in DCM (5 mL) and the resulting mixture stirred for 3 h at RT. The solution was then added to a suspension of 8-(2-aminoethyl)-5-hydroxy-2H-benzo[b][1,4]oxazin-3(4H)-one hydrochloride [WO 2008075025] (0.11 g) and sodium bicarbonate (0.17 g) in a mixture of NMP (2 mL) and water (0.2 mL) and the resulting cloudy solution was stirred for 10 min. Acetic acid (0.018 mL) was then added, followed by sodium triacetoxyborohydride (0.16 g), and the resulting mixture was stirred overnight. The reaction mixture was partitioned between 2-methyltetrahydrofuran (15 mL) and saturated sodium bicarbonate solution (15 mL). The organic phase was separated, washed with 10% brine (2×15 mL), dried over sodium sulphate, filtered and evaporated. The residue was purified by flash silica chromatography, elution gradient 97.25:2.5:0.25 to 92.3:7:0.7 dichloromethane:methanol: '880' aqueous ammonia. The fractions containing the product were combined and evaporated. The resulting gum was further purified by preparative HPLC (Sunfire™, Gradient: 35-60% methanol in 0.2% aqueous TFA). The fractions containing the product were combined, evaporated and triturated with ether to give the titled compound as a white solid. Yield 0.037 g.

m/z 865 M⁺ (MultiMode+).

$^1$H NMR (400 MHz, D$_6$-DMSO, 90° C.) δ 9.40 (br s, 1H), 8.40 (br s, 1H), 7.93 (s, 1H), 7.49 (d, J=7.2 Hz, 1H), 7.41 (d, J=6.9 Hz, 1H), 7.32 (t, J=7.4 Hz, 1H), 6.66 (d, J=8.2 Hz, 1H), 6.49 (d, J=8.2 Hz, 1H), 4.53 (s, 2H), 4.26 (br s, 2H), 3.75-3.60 (m, 11H), 3.51-2.93 (m, 13H), 2.82 (t, J=7.6 Hz, 2H), 2.60 (t, J=6.4 Hz, 2H), 2.03-1.89 (m, 2H), 1.82-1.69 (m, 4H), 1.68-1.56 (m, 4H), 1.50-1.23 (m, 4H), 1.35 (d, J=6.9 Hz, 6H). Three exchangeable protons not observed.

The 3-(2-chloro-3-((4-(2-isopropylthiazole-4-carbonyl)-1-oxa-4,9-diazaspiro[5.5]undecan-9-yl)methyl)phenethoxy)-N-cyclohexyl-N-(2,2-dimethoxyethyl)propanamide used as a starting material was prepared as follows:

a) (2-Isopropylthiazol-4-yl)(1-oxa-4,9-diazaspiro[5.5]undecan-4-yl)methanone hydrochloride

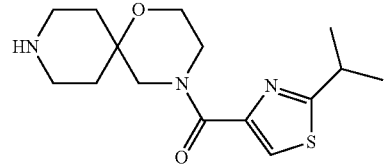

A solution of 2-isopropylthiazole-4-carboxylic acid (12 g) and tert-butyl 1-oxa-4,9-diazaspiro[5.5]undecane-9-carboxylate hydrochloride [WuXi PharmaTech] (20 g) in 2-methyltetrahydrofuran (140 mL) was cooled in ice-water and treated with triethylamine (47 mL), followed by T3P (1.6M in THF, 54 mL). The mixture was allowed to warm to RT and was stirred for 1 h. Water (140 mL) was added with stirring, then the phases were separated. The organic phase was washed with water (80 mL), and then concentrated to a volume of (~100 mL) under reduced pressure using a temperature of <30° C. IPA (75 mL) was added, and the mixture was concentrated to a volume of (~100 mL). More IPA (75 mL) was added, and the mixture was again concentrated to a volume of (~100 mL). A solution of hydrogen chloride in IPA (~6M, 81 mL) was added with cooling in ice-water, then the mixture was warmed to 40° C. and stirred for 3.5 h. The mixture was cooled to RT, diluted with MTBE (34 mL) and stirred for 30 min. The resulting precipitated solid was removed by filtration and dried in a vacuum oven at 55° C. overnight. Yield 20.5 g.

$^1$H NMR (400 MHz, D$_6$-DMSO) δ 8.88 (d, J=41.0 Hz, 2H), 8.05 (s, 1H), 3.86-3.46 (m, 6H), 3.32 (quintet, J=6.7 Hz, 1H), 3.17-3.02 (m, 2H), 3.01-2.85 (m, 2H), 1.96 (d, J=14.1 Hz, 2H), 1.81-1.55 (m, 2H), 1.35 (d, J=6.9 Hz, 6H).

b) (9-(2-Chloro-3-(2-hydroxyethyl)benzyl)-1-oxa-4,9-diazaspiro[5.5]undecan-4-yl)(2-isopropylthiazol-4-yl)methanone

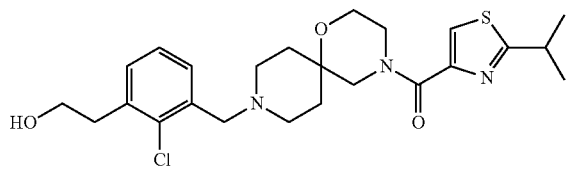

Prepared by the method of Example 26, step c using (2-isopropylthiazol-4-yl)(1-oxa-4,9-diazaspiro[5.5]undecan-4-yl)methanone hydrochloride [Example 27, step a] (1.37 g) in place of (2-ethylthiazol-4-yl)(1-oxa-4,9-diazaspiro[5.5]undecan-4-yl)methanone trifluoroacetate, and 2-methyltetrahydrofuran (50 mL) in place of tetrahydrofuran. Yield 1.00 g.

$^1$H NMR (400 MHz, D$_6$-DMSO 90° C.) δ 7.91 (d, J=1.3 Hz, 1H), 7.30 (d, J=7.2 Hz, 1H), 7.24-7.16 (m, 2H), 4.36 (t, J=5.1 Hz, 1H), 3.73-3.59 (m, 8H), 3.55 (s, 2H), 3.32 (septet, J=6.8 Hz, 1H), 2.89 (t, J=7.0 Hz, 2H), 2.46-2.40 (m, 1H), 2.40-2.28 (m, 1H), 2.17 (t, J=8.1 Hz, 1H), 1.91 (quintet, J=7.5 Hz, 1H), 1.77-1.65 (m, 2H), 1.62-1.50 (m, 2H), 1.36 (d, J=6.5 Hz, 6H).

c) tert-Butyl 3-(2-chloro-3-((4-(2-isopropylthiazole-4-carbonyl)-1-oxa-4,9-diazaspiro[5.5]undecan-9-yl)methyl)phenethoxy)propanoate

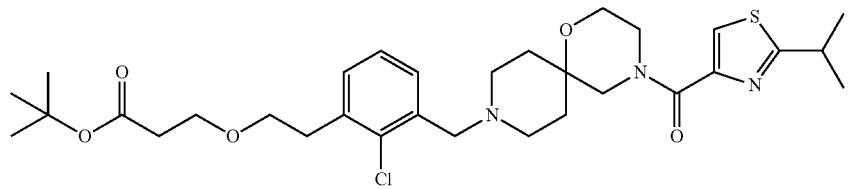

Prepared by the method of Example 7, step c using (9-(2-chloro-3-(2-hydroxyethyl)benzyl)-1-oxa-4,9-diazaspiro[5.5]undecan-4-yl)(2-isopropylthiazol-4-yl)methanone [Example 27, step b] (1.0 g) in place of (9-(2-fluoro-3-(2-hydroxyethyl)benzyl)-1-oxa-4,9-diazaspiro[5.5]undecan-4-yl)(2-isopropylthiazol-4-yl)methanone. Yield 0.93 g.

m/z 606 M$^+$ (APCI).

d) 3-(2-chloro-3-((4-(2-isopropylthiazole-4-carbonyl)-1-oxa-4,9-diazaspiro[5.5]undecan-9-yl)methyl)phenethoxy)propanoic acid

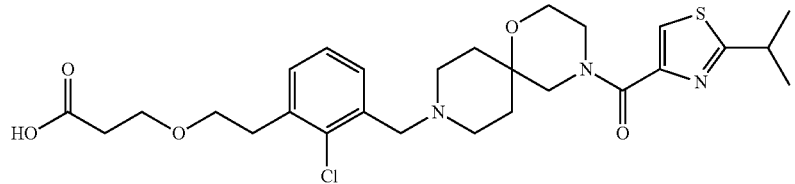

Prepared by the method of Example 7, step d using tert-butyl 3-(2-chloro-3-((4-(2-isopropylthiazole-4-carbonyl)-1-oxa-4,9-diazaspiro[5.5]undecan-9-yl)methyl)phenethoxy)propanoate [Example 27, step c] (0.93 g) in place of tert-butyl 3-(2-fluoro-3-((4-(2-isopropylthiazole-4-carbonyl)-1-oxa-4,9-diazaspiro[5.5]undecan-9-yl)methyl)phenethoxy)propanoate. Yield 0.76 g.

m/z 550 M$^+$ (APCI).

e) 3-(2-Chloro-3-((4-(2-isopropylthiazole-4-carbonyl)-1-oxa-4,9-diazaspiro[5.5]undecan-9-yl)methyl)phenethoxy)-N-cyclohexyl-N-(2,2-dimethoxyethyl)propanamide

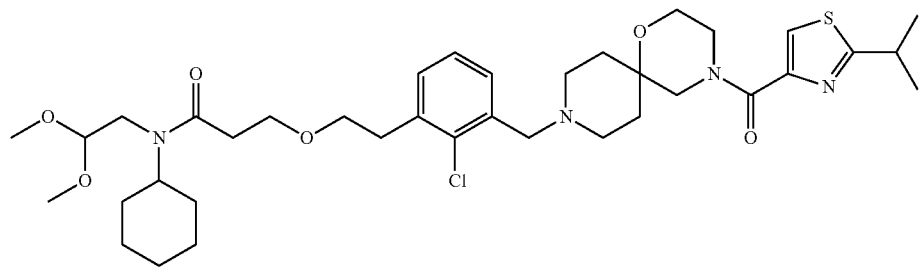

Prepared by the method of Example 7, step e using 3-(2-chloro-3-((4-(2-isopropylthiazole-4-carbonyl)-1-oxa-4,9-diazaspiro[5.5]undecan-9-yl)methyl)phenethoxy)propanoic acid [Example 27, step d] (0.28 g) in place of 3-(2-fluoro-3-((4-(2-isopropylthiazole-4-carbonyl)-1-oxa-4,9-diazaspiro[5.5]undecan-9-yl)methyl)phenethoxy)propanoic acid, and N-(2,2-dimethoxyethyl)cyclohexanamine [WO 2008075025] (0.10 g) in place of N-(2,2-dimethoxyethyl)cycloheptanamine. Yield 0.11 g.

m/z 719 M$^+$ (APCI).

The following compounds were prepared from the appropriate Carboxylic Acids and Amines using methods analogous to those described above.

EXAMPLE 28

3-(2-Chloro-3-((4-(2-isopropylthiazole-4-carbonyl)-1-oxa-4,9-diazaspiro[5.5]undecan-9-yl)methyl)phenethoxy)-N-ethyl-N-(2-(2-(4-hydroxy-2-oxo-2,3-dihydrobenzo[d]thiazol-7-yl)ethylamino)ethyl)propanamide ditrifluoroacetate

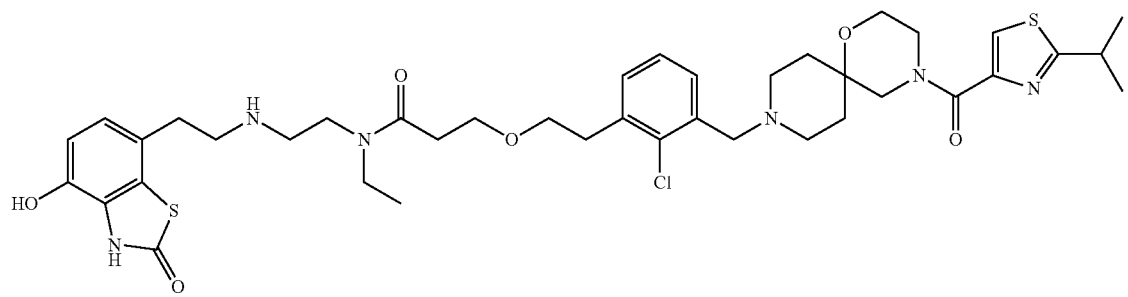

m/z 813 M$^+$ (MultiMode+).

$^1$H NMR (400 MHz, D$_6$-DMSO, 90° C.) δ 7.94 (s, 1H), 7.50 (d, J=6.9 Hz, 1H), 7.43 (d, J=7.2 Hz, 1H), 7.33 (t, J=7.6 Hz, 1H), 6.85 (d, J=8.2 Hz, 1H), 6.74 (d, J=8.2 Hz, 1H), 4.32 (br s, 2H), 3.78-3.59 (m, 10H), 3.53 (t, J=6.7 Hz, 2H), 3.44-3.24 (m, 5H), 3.22-3.04 (m, 6H), 2.99 (t, J=6.9 Hz, 2H), 2.83 (t, J=7.9 Hz, 2H), 2.56 (t, J=6.5 Hz, 2H), 2.06-1.91 (m, 2H), 1.84-1.67 (m, 2H), 1.35 (d, J=6.9 Hz, 6H), 1.09 (t, J=6.9 Hz, 3H). Five exchangeable protons not observed.

EXAMPLE 29

3-(2-Chloro-3-((4-(2-isopropylthiazole-4-carbonyl)-1-oxa-4,9-diazaspiro[5.5]undecan-9-yl)methyl) phenethoxy)-N-(2-(2-(5-hydroxy-3-oxo-3,4-dihydro-2H-benzo[b][1,4]oxazin-8-yl)ethylamino)ethyl)-N-propylpropanamide ditrifluoroacetate

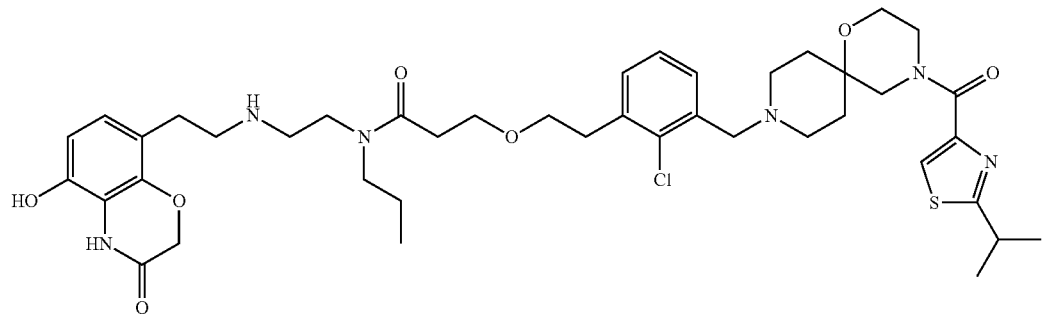

m/z 825 M$^+$ (MultiMode+).

$^1$H NMR (500 MHz, D$_6$-DMSO, 90° C.) δ 9.33 (s, 1H), 8.45 (s, 1H), 7.93 (s, 1H), 7.56-7.49 (m, 1H), 7.43 (d, J=7.5 Hz, 1H), 7.33 (t, J=7.6 Hz, 1H), 6.66 (d, J=8.3 Hz, 1H), 6.49 (d, J=8.3 Hz, 1H), 4.55 (s, 2H), 4.36 (s, 2H), 3.73-3.62 (m, 10H), 3.56-3.51 (m, 3H), 3.34-3.21 (m, 2H), 3.15-3.05 (m, 8H), 2.99 (t, J=6.8 Hz, 2H), 2.83 (t, J=7.7 Hz, 2H), 2.55 (t, J=6.5 Hz, 2H), 2.04-1.96 (m, 2H), 1.83-1.73 (m, 2H), 1.57-1.45 (m, 2H), 1.35 (d, J=6.9 Hz, 6H), 0.85 (t, J=7.2 Hz, 3H). Three exchangeable protons not observed.

EXAMPLE 30

3-(2-Chloro-3-((4-(2-ethylthiazole-4-carbonyl)-1-oxa-4,9-diazaspiro[5.5]undecan-9-yl)methyl) phenethoxy)-N-ethyl-N-(2-(2-(5-hydroxy-3-oxo-3,4-dihydro-2H-benzo[b][1,4]oxazin-8-yl)ethylamino) ethyl)propanamide ditrifluoroacetate

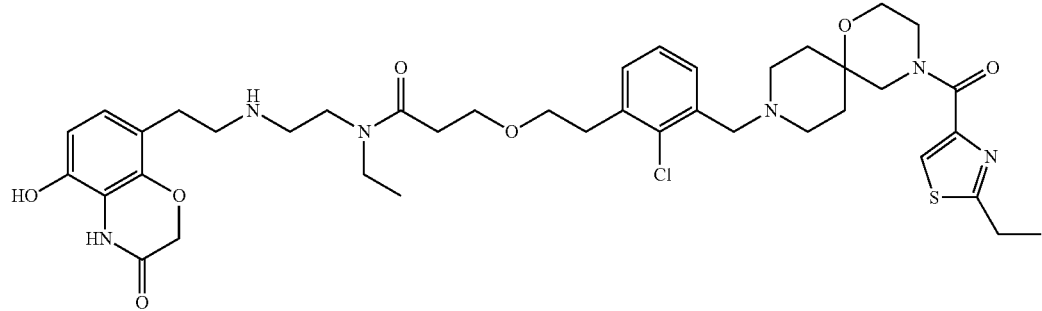

m/z 797 M$^+$ (MultiMode+).

$^1$H NMR (500 MHz, D$_6$-DMSO, 90° C.) δ 9.36 (s, 1H), 8.33 (s, 1H), 7.92 (s, 1H), 7.51-7.46 (m, 1H), 7.45-7.41 (m, 1H), 7.36-7.31 (m, 1H), 6.68-6.63 (m, 1H), 6.50-6.45 (m, 1H), 4.53 (s, 2H), 4.31 (s, 2H), 3.72-2.96 (m, 26H), 2.86-2.77 (m, 2H), 2.59-2.54 (m, 2H), 2.05-1.93 (m, 2H), 1.84-1.69 (m, 2H), 1.37-1.28 (m, 3H), 1.15-1.04 (m, 3H). Three exchangeable protons not observed.

EXAMPLE 31

(R)—N-sec-Butyl-3-(2-chloro-3-((4-(2-ethylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

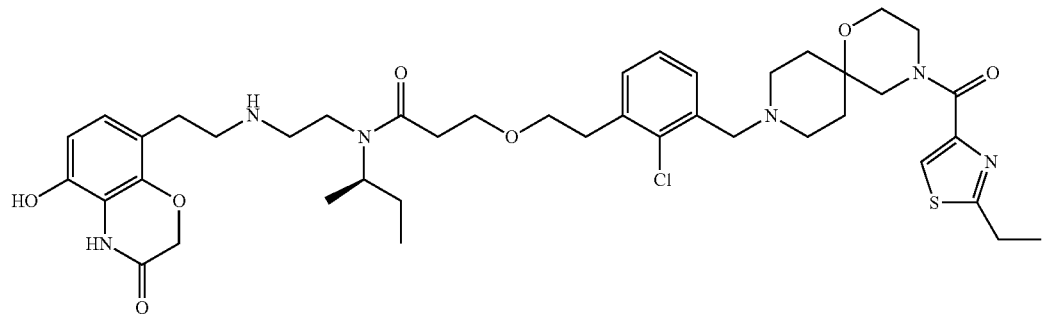

m/z 825 M⁺ (MultiMode+).

$^1$H NMR (500 MHz, D$_6$-DMSO, 90° C.) δ 9.34 (s, 1H), 8.53 (s, 1H), 7.92 (s, 1H), 7.54 (d, J=7.6 Hz, 1H), 7.45 (d, J=7.5 Hz, 1H), 7.34 (t, J=7.6 Hz, 1H), 6.67 (d, J=8.3 Hz, 1H), 6.49 (d, J=8.3 Hz, 1H), 4.53 (s, 3H), 4.41 (s, 3H), 3.73-3.62 (m, 10H), 3.53-3.42 (m, 1H), 3.23-3.09 (m, 6H), 3.07-2.97 (m, 6H), 2.83 (t, J=7.5 Hz, 2H), 2.63-2.56 (m, 2H), 2.05-1.98 (m, 2H), 1.87-1.75 (m, 2H), 1.48 (quintet, J=7.3 Hz, 2H), 1.32 (t, J=7.5 Hz, 3H), 1.12 (d, J=6.4 Hz, 3H), 0.81 (t, J=7.0 Hz, 3H). Three exchangeable protons not observed.

EXAMPLE 32

N-Butyl-3-(2-chloro-3-((4-(2-ethylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

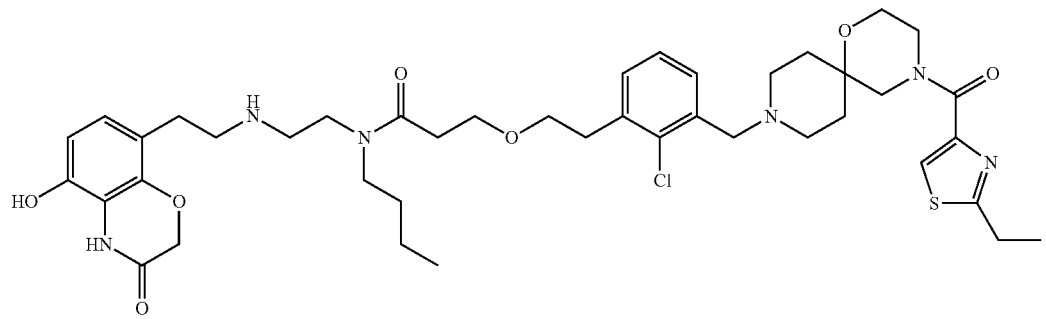

m/z 825 M⁺ (MultiMode+).

$^1$H NMR (500 MHz, D$_6$-DMSO, 90° C.) δ 9.34 (s, 1H), 8.45 (s, 1H), 7.92 (s, 1H), 7.53 (d, J=7.4 Hz, 1H), 7.44 (d, J=7.5 Hz, 1H), 7.33 (t, J=7.5 Hz, 1H), 6.66 (d, J=8.2 Hz, 1H), 6.49 (d, J=8.2 Hz, 1H), 4.52 (s, 2H), 4.38 (s, 2H), 3.73-3.63 (m, 10H), 3.56-3.51 (m, 2H), 3.29-3.23 (m, 2H), 3.21-3.06 (m, 8H), 3.04-2.97 (m, 4H), 2.83 (t, J=7.6 Hz, 2H), 2.55 (t, J=6.4 Hz, 2H), 2.04-1.96 (m, 2H), 1.85-1.75 (m, 2H), 1.54-1.44 (m, 2H), 1.36-1.23 (m, 5H), 0.90 (t, J=7.3 Hz, 3H). Three exchangeable protons not observed.

EXAMPLE 33

3-(2-Chloro-3-((4-(2-ethylthiazole-4-carbonyl)-1-oxa-4,9-diazaspiro[5.5]undecan-9-yl)methyl) phenethoxy)-N-cyclopentyl-N-(2-(2-(5-hydroxy-3-oxo-3,4-dihydro-2H-benzo[b][1,4]oxazin-8-yl) ethylamino)ethyl)propanamide ditrifluoroacetate

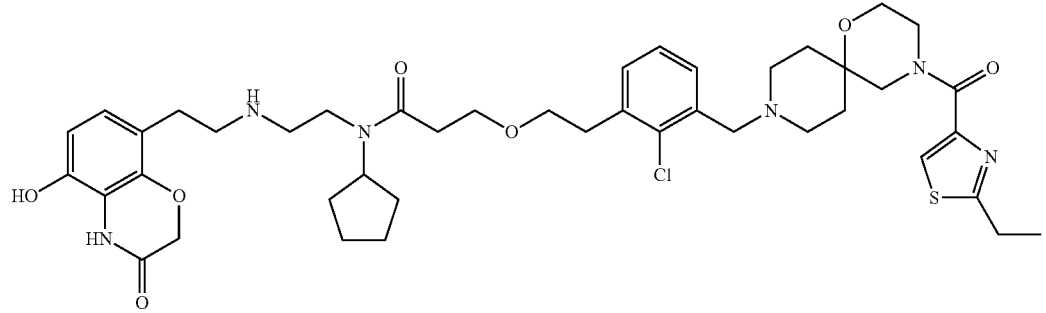

m/z 837 M+ (MultiMode+).

$^1$H NMR (500 MHz, D$_6$-DMSO, 90° C.) δ 9.37 (s, 1H), 8.41 (s, 1H), 7.92 (s, 1H), 7.52-7.48 (m, 1H), 7.44-7.39 (m, 1H), 7.36-7.30 (m, 1H), 6.66 (d, J=8.3 Hz, 1H), 6.48 (d, J=8.3 Hz, 1H), 4.53 (s, 2H), 4.34-4.16 (m, 2H), 3.74-2.96 (m, 25H), 2.82 (t, J=7.6 Hz, 2H), 2.62 (t, J=6.2 Hz, 2H), 2.02-1.41 (m, 12H), 1.32 (t, J=7.5 Hz, 3H). Three exchangeable protons not observed.

EXAMPLE 33a 3-(2-chloro-3-((4-(2-ethylthiazole-4-carbonyl)-1-oxa-4,9-diazaspiro[5.5]undecan-9-yl)methyl) phenethoxy)-N-cyclopentyl-N-(2-(2-(5-hydroxy-3-oxo-3,4-dihydro-2H-benzo[b][1,4]oxazin-8-yl) ethylamino)ethyl)propanamide, sulphate salt

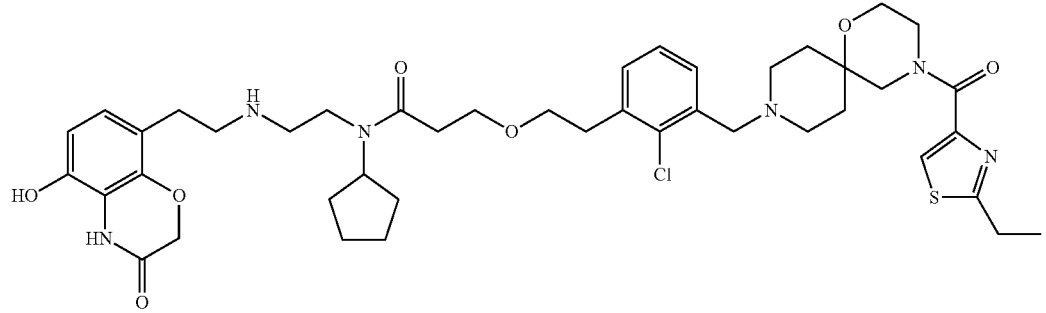

To a solution of 3-(2-chloro-3-((4-(2-ethylthiazole-4-carbonyl)-1-oxa-4,9-diazaspiro[5.5]undecan-9-yl)methyl) phenethoxy)-N-cyclopentyl-N-(2,2-dimethoxyethyl)propanamide (9.6 g) in THF (80 mL) and NMP (8.0 mL) was added tosic acid.H$_2$O (13.25 g) and the reaction was stirred at ambient temperature for 30 mins.

Meanwhile, to a solution of 8-(2-aminoethyl)-5-hydroxy-2H-benzo[b][1,4]oxazin-3(4H)-one.HCl (4.09 g) in NMP (48.0 mL) and water (4.8 mL) was added sodium bicarbonate (7.84 g) and the reaction was stirred at ambient temperature for 30 mins.

The above solution of aldehyde was added to the solution of amine and the reaction was stirred for 15 mins before the addition of sodium triacetoxyborohydride (8.86 g). The reaction was then stirred at ambient temperature for 90 mins.

The reaction mixture was diluted with EtOAc (300 mL) and washed with sat sodium bicarbonate (2×300 mL) and brine. The ethyl acetate solution was then evaporated in vacuo. The crude product was purified by silica chromatography, eluting with DCM (300 mL) followed by 6-9% 7N NH$_3$/methanol in dichloromethane to afford 3-(2-chloro-3-((4-(2-ethylthiazole-4-carbonyl)-1-oxa-4,9-diazaspiro[5.5] undecan-9-yl)methyl)phenethoxy)-N-cyclopentyl-N-(2-(2-(5-hydroxy-3-oxo-3,4-dihydro-2H-benzo[b][1,4]oxazin-8-yl)ethylamino)ethyl)propanamide (4.90 g).

To a solution of 3-(2-chloro-3-((4-(2-ethylthiazole-4-carbonyl)-1-oxa-4,9-diazaspiro[5.5]undecan-9-yl)methyl) phenethoxy)-N-cyclopentyl-N-(2-(2-(5-hydroxy-3-oxo-3,4-dihydro-2H-benzo[b][1,4]oxazin-8-yl)ethylamino)ethyl) propanamide (4.9 g) in ethanol (50 mL) was added sulfuric acid (0.5 Molar aq.) (10.62 mL). The reaction was stirred at ambient temperature for 5 min.

The reaction mixture was evaporated in vacuo to ca. 5-10 ml, MeCN was added and the solvent was evaporated (×2) to yield a white solid 5.2 g.

The above material (5.2 g) was dissolved in MeOH (100 mL), seeded with crystalline material (see below)* and stirred at ambient temperature for 72 hours. The solid was filtered, washed with MeOH and dried in vacuo at ambient temperature overnight to yield 3-(2-chloro-3-((4-(2-ethylthiazole-4-carbonyl)-1-oxa-4,9-diazaspiro[5.5]undecan-9-yl)methyl) phenethoxy)-N-cyclopentyl-N-(2-(2-(5-hydroxy-3-oxo-3,4-dihydro-2H-benzo[b][1,4]oxazin-8-yl)ethylamino)ethyl) propanamide, sulphate salt (3.04 g) as a crystalline white solid.

[M+H]+=837 (calc=837) (MultiMode+)

$^1$H NMR (400 MHz, D$_6$-DMSO) δ 9.96-9.90 (m, 1H), 9.82 (s, 1H), 7.98 (s, 1H), 7.40-7.18 (m, 3H), 6.69-6.63 (m, 1H), 6.51-6.45 (m, 1H), 4.54 (s, 2H), 4.17 (quintet, J=8.5 Hz, 1H), 3.75-3.45 (m, 12H), 3.37 (t, J=7.1 Hz, 2H), 3.09-2.90 (m, 8H), 2.77 (t, J=7.6 Hz, 2H), 2.69-2.22 (m, 8H), 1.84-1.21 (m, 16H)

*Some of the ditrifluoroacetate salt (1.05 g) (example 33) was partitioned between DCM (30 mL) and saturated sodium bicarbonate (30 mL). The aqueous layer was further extracted with DCM. The combined organics were dried over Na$_2$SO$_4$ and evaporated in vacuo to yield 3-(2-chloro-3-((4-(2-ethylthiazole-4-carbonyl)-1-oxa-4,9-diazaspiro[5.5]undecan-9-yl)methyl)phenethoxy)-N-cyclopentyl-N-(2-(2-(5-hydroxy-3-oxo-3,4-dihydro-2H-benzo[b][1,4]oxazin-8-yl)ethylamino)ethyl)propanamide (0.82 g) as a white foam.

To a solution of 3-(2-chloro-3-((4-(2-ethylthiazole-4-carbonyl)-1-oxa-4,9-diazaspiro[5.5]undecan-9-yl)methyl)phenethoxy)-N-cyclopentyl-N-(2-(2-(5-hydroxy-3-oxo-3,4-dihydro-2H-benzo[b][1,4]oxazin-8-yl)ethylamino)ethyl)propanamide (230 mg) in ethanol (5 mL) was added sulfuric acid (0.5 Molar aq.) (0.549 mL). After 5 min the mixture was evaporated in vacuo and azeotroped with MeCN (×2) to yield a white solid (280 mg). 50 mg of this material was dissolved in methanol (5 mL) and under vapour diffusion experiment conditions (using diethyl ether as antisolvent) 15 mL of diethyl ether added over 6 days. The crystalline solid (20 mg) was collected by filtration.

3-(2-chloro-3-((4-(2-ethylthiazole-4-carbonyl)-1-oxa-4,9-diazaspiro[5.5]undecan-9-yl)methyl)phenethoxy)-N-cyclopentyl-N-(2,2-dimethoxyethyl)propanamide

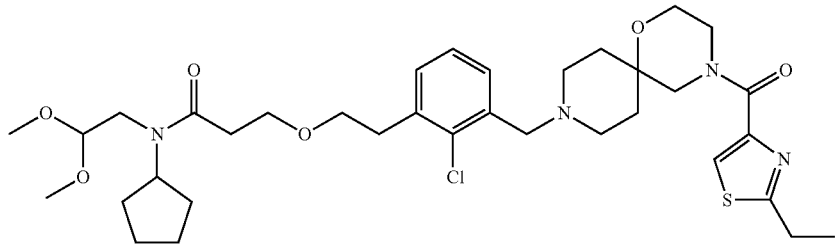

To a solution of 3-(2-chloro-3-((4-(2-ethylthiazole-4-carbonyl)-1-oxa-4,9-diazaspiro[5.5]undecan-9-yl)methyl)phenethoxy)propanoic acid (9.8 g) in DCM (100 mL) was added Hunig's Base (9.58 mL). The reaction was stirred for 10 mins before the addition of N-(2,2-dimethoxyethyl)cyclopentanamine (4.12 g) followed by HATU (7.65 g). After 1 h, the reaction mixture was diluted with DCM (200 mL) and washed with saturated sodium bicarbonate (300 mL) followed by water (300 mL). The DCM solution was dried over Na$_2$SO$_4$, filtered and evaporated in vacuo. The crude product was purified by silica chromatography, eluting with 2 to 5% 7N/NH$_3$/methanol in dichloromethane to afford 3-(2-chloro-3-((4-(2-ethylthiazole-4-carbonyl)-1-oxa-4,9-diazaspiro[5.5]undecan-9-yl)methyl)phenethoxy)-N-cyclopentyl-N-(2,2-dimethoxyethyl)propanamide (12.0 g) as a pale yellow gum.

m/z=691 [M+H]$^+$

EXAMPLE 33b 3-(2-Chloro-3-((4-(2-ethylthiazole-4-carbonyl)-1-oxa-4,9-diazaspiro[5.5]undecan-9-yl)methyl)phenethoxy)-N-cyclopentyl-N-(2-(2-(5-hydroxy-3-oxo-3,4-dihydro-2H-benzo[b][1,4]oxazin-8-yl)ethylamino)ethyl)propanamide

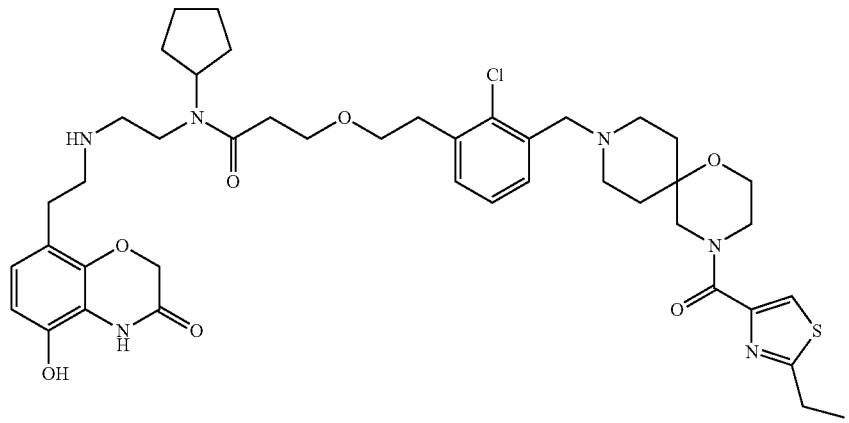

a) tert-Butyl 4-(4-ethylthiazole-2-carbonyl)-1-oxa-4,9-diazaspiro[5.5]undecane-9-carboxylate

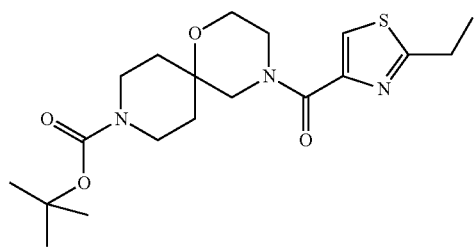

A mixture of tert-butyl 1-oxa-4,9-diazaspiro[5.5]undecane-9-carboxylate hydrochloride (limiting reagent), and 4-ethylthiazole-2-carboxylic acid (1 molar equivalent) was suspended in DCM (4.5 volumes) and cooled to 16° C. To this was added triethylamine (5 molar equivalents) in portions. The thick suspension was cooled to 6° C. and T3P (1.1 molar equivalents of a 1.57M in THF) was added drop-wise at 5-15° C. over 0.5 hr. The reaction mixture was allowed to warm to 22° C. and stirred at 22° C. for 2 hr. The mixture was diluted with water (6.5 volumes, 4° C. exotherm) and the mixture was stirred for 10 mins; the aqueous was separated and extracted with DCM (4.5 volumes). The combined organics were washed saturated aq sodium bicarbonate solution (5.5 volumes) and 20% brine solution (1.5 volumes). The organics were dried over anhydrous sodium sulphate, filtered and evaporated to give a brown oil. Yield: 96% of theoretical.

m/z [M+H]+=296-boc (calc=396) (Multimode+)

$^1$H NMR (500 MHz, CDCl$_3$) δ 7.84 (s, 1H), 4.08-3.51 (m, 10H), 3.22 (dd, J=15.0, 25.7 Hz, 2H), 3.04 (q, J=7.6 Hz, 2H), 1.88-1.78 (m, 2H), 1.55 (d, J=26.2 Hz, 1H), 1.45 (s, 9H), 1.40 (t, J=7.6 Hz, 3H).

b) (2-Ethylthiazol-4-yl)(1-oxa-4,9-diazaspiro[5.5]undecan-4-yl)methanone

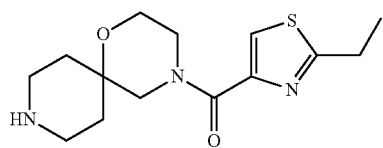

To a solution of tert-butyl 4-(2-ethylthiazole-4-carbonyl)-1-oxa-4,9-diazaspiro[5.5]undecane-9-carboxylate (limiting reagent) (step a) in iPrOH (3 volumes) was added hydrogen chloride (2 molar equivalents of a 5-6N solution in iPrOH). The reaction mixture was heated and stirred at 49° C. (internal) for 18 hr before being cooled to 22° C. TBME (4.3 volumes) was added and the suspension was stirred at 22° C. for 3 days. The solid was collected by filtration, washed with TBME (3.5 volumes) and air dried for 2 days to give an off white solid. Yield 95% of theoretical.

m/z [M+H]+=295 (calc=295) (Multimode+)

$^1$H NMR (400 MHz, DMSO) δ 8.03 (s, 1H), 3.82-3.50 (m, 8H), 3.14-2.86 (m, 8H), 1.32 (t, J=7.5 Hz, 3H).

c) (9-(2-Chloro-3-(2-hydroxyethyl)benzyl)-1-oxa-4,9-diazaspiro[5.5]undecan-4-yl)(2-ethylthiazol-4-yl)methanone

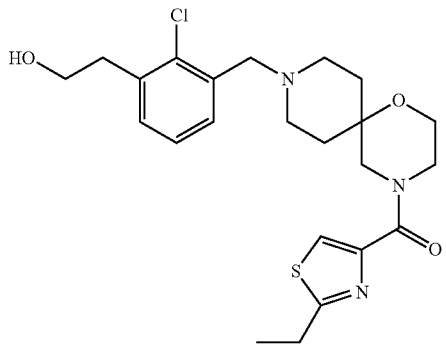

To a solution of 2-chloro-3-(2-hydroxyethyl)benzaldehyde (1.1 molar equivalents) in DCM (12 volumes) was added to (2-ethylthiazol-4-yl)(1-oxa-4,9-diazaspiro[5.5]undecan-4-yl)methanone ((limiting reagent) (step b). Triethylamine (2 molar equivalents) was added and the mixture was stirred for 1.15 hr. Sodium triacetoxyborohydride (2.5 molar equivalents) was added portion-wise over 15 minutes maintaining the temperature below 25° C. The reaction mixture was stirred at ambient temperature for 22.5 hr. Saturated aq. sodium bicarbonate solution (8 volumes) was added slowly and the mixture was stirred vigorously for 1 hr; the aqueous was separated and extracted with DCM (5.3 volumes). The combined organics were washed with 20% brine solution (5.3 volumes), dried over anhydrous sodium sulfate, filtered and evaporated to give a brown oil. Yield 107% of theoretical.

m/z [M+H]+=465 (calc=465) (Multimode+)

$^1$H NMR (400 MHz, CDCL$_3$) δ 7.80 (s, 1H), 7.38 (d, J=4.7 Hz, 1H), 7.17 (d, J=4.3 Hz, 2H), 3.89 (dd, J=15.4, 22.0 Hz, 4H), 3.78 (s, 2H), 3.63 (d, J=11.9 Hz, 3H), 3.04 (t, J=6.6 Hz, 4H), 2.49 (s, 4H), 1.85 (s, 3H), 1.66 (d, J=74.8 Hz, 2H), 1.42 (d, J=6.5 Hz, 3H).

d) tert-Butyl 3-(2-chloro-3-((4-(2-ethylthiazole-4-carbonyl)-1-oxa-4,9-diazaspiro[5.5]undecan-9-yl)methyl)phenethoxy)propanoate

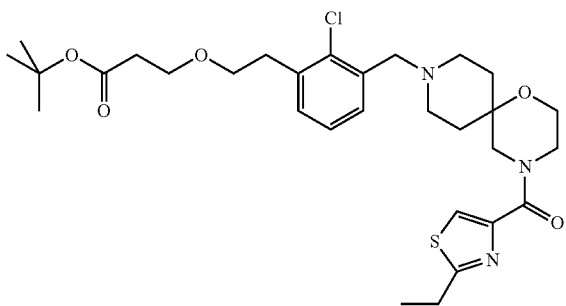

Triton-B (0.3 molar equivalents of a 40% solution in water) was added to a solution of (9-(2-chloro-3-(2-hydroxyethyl)benzyl)-1-oxa-4,9-diazaspiro[5.5]undecan-4-yl)(2-ethylthi-azol-4-yl)methanone (limiting reagent) (step c) and tert-butyl acrylate (5 molar equivalents) in acetonitrile (3.4 volumes). The reaction was stirred at ambient temperature for 1 hr. The solvent was evaporated and the residue was partitioned between water (2 volumes) and 2-MeTHF (2 volumes). The layers were separated and the organics were dried over anhydrous sodium sulfate, filtered and evaporated to give a brown oil. Yield: 94% of theoretical.

$^1$H NMR (500 MHz, CDCl$_3$) δ 7.80 (s, 1H), 7.44-7.31 (m, 1H), 7.22-7.09 (m, 2H), 4.01-3.48 (m, 11H), 3.10-2.95 (m, 4H), 2.62-2.39 (m, 6H), 1.94-1.63 (m, 2H), 1.63-1.50 (m, 2H), 1.47-1.35 (m, 13H).

e) 3-(2-Chloro-3-((4-(2-ethylthiazole-4-carbonyl)-1-oxa-4,9-diazaspiro[5.5]undecan-9-yl)methyl)phenethoxy)propanoic acid

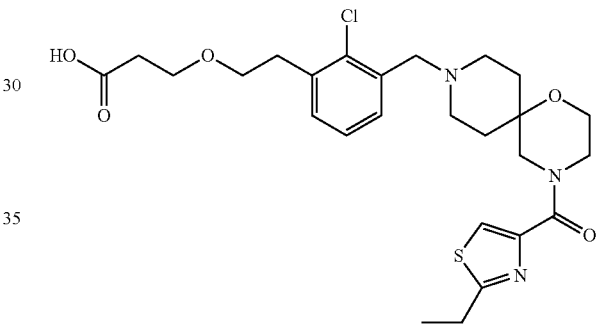

A solution of tert-butyl 3-(2-chloro-3-((4-(2-ethylthiazole-4-carbonyl)-1-oxa-4,9-diazaspiro[5.5]undecan-9-yl)methyl)phenethoxy)propanoate (limiting reagent) (step d) in DCM (2.8 volumes) was cooled to 5° C. Trifluoroacetic acid (10 molar equivalents) was added over 20 min (exotherm to 15° C.). The reaction mixture was warmed to ambient and stirred for 18 hr. Toluene (3 volumes) was added and the mixture was evaporated. The resulting gum was triturated with toluene (2×1.5 volumes) and evaporated to give a brown gum. Yield: 200% of theoretical. (carried through crude—NMR assay shows ~45% by weight purity with remaining weight due to TFA trapped in the gum)

$^1$H NMR (500 MHz, CDCl$_3$) δ 7.88 (s, 1H), 7.40-7.33 (m, 2H), 7.27-7.22 (m, 1H), 4.42 (d, J=5.0 Hz, 2H), 3.90 (d, J=8.6 Hz, 2H), 3.82 (d, J=6.8 Hz, 2H), 3.77 (dd, J=5.9, 10.6 Hz, 4H), 3.69 (dd, J=6.2, 11.8 Hz, 2H), 3.65 (s, 2H), 3.26-3.13 (m, 2H), 3.09-2.98 (m, 4H), 2.67 (dt, J=5.8, 11.6 Hz, 1H), 2.49 (t, J=5.7 Hz, 2H), 2.16 (t, J=14.1 Hz, 2H), 1.98 (dd, J=8.5, 19.8 Hz, 2H), 1.45-1.31 (m, 3H).

f) 3-(2-Chloro-3-((4-(2-ethylthiazole-4-carbonyl)-1-oxa-4,9-diazaspiro[5.5]undecan-9-yl)methyl)phenethoxy)-N-cyclopentyl-N-(2,2-dimethoxyethyl)propanamide

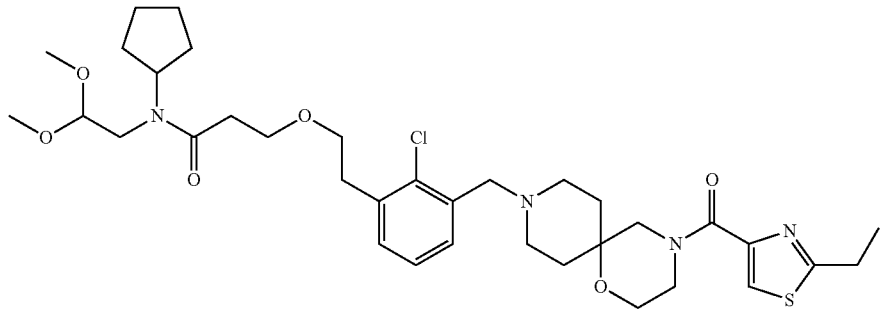

A solution of 3-(2-chloro-3-((4-(2-ethylthiazole-4-carbonyl)-1-oxa-4,9-diazaspiro[5.5]undecan-9-yl)methyl)phenethoxy)propanoic acid (limiting reagent) (step e) in DCM (6.4 volumes) was cooled to 13° C. Triethylamine (15 molar equivalents) was added over 80 mins (exotherm of 5° C.). N-(2,2-dimethoxyethyl)cyclopentanamine (1.3 molar equivalents) was added over 5 mins (no exotherm). The mixture was allowed to warm to ambient temperature and was stirred for 45 mins at 22° C. T3P (2 molar equivalents of a 1.57M solution in THF) was added portion-wise over 10 mins (exotherm 8° C.). The reaction mixture was stirred at 22° C. for 1.5 hr. Saturated sodium bicarbonate solution was added (4.2 volumes) and the mixture was stirred for 5 mins. The layers were partitioned and the aqueous was extracted with DCM (1.4 volumes). The combined organics were washed with 20% brine solution (1.4 volumes), dried over anhydrous sodium sulphate, filtered and evaporated. The crude residue was purified by Si column chromatography (1500 g biotage snap cartridge) eluting product with 95% DCM: 5% (9:1 MeOH:aq NH3) to give a yellow oil. Yield: 79% of theoretical.

m/z [M+H]+=691 (calc=691) (Multimode+)

$^1$H NMR (500 MHz, CDCl$_3$) δ 7.81 (s, 1H), 7.41-7.26 (m, 1H), 7.15 (d, J=3.4 Hz, 2H), 4.69-4.62 (m, 1H), 4.37 (dd, J=6.8, 12.0 Hz, 1H), 4.21-4.08 (m, 1H), 3.99-3.52 (m, 12H), 3.45-3.36 (m, 8H), 3.28 (t, J=7.8 Hz, 2H), 3.11-2.97 (m, 4H), 2.70 (t, J=6.9 Hz, 2H), 2.63-2.36 (m, 4H), 1.93-1.32 (m, 16H)

g) 3-(2-Chloro-3-((4-(2-ethylthiazole-4-carbonyl)-1-oxa-4,9-diazaspiro[5.5]undecan-9-yl)methyl)phenethoxy)-N-cyclopentyl-N-(2-(2-(5-hydroxy-3-oxo-3,4-dihydro-2H-benzo[b][1,4]oxazin-8-yl)ethylamino)ethyl)propanamide

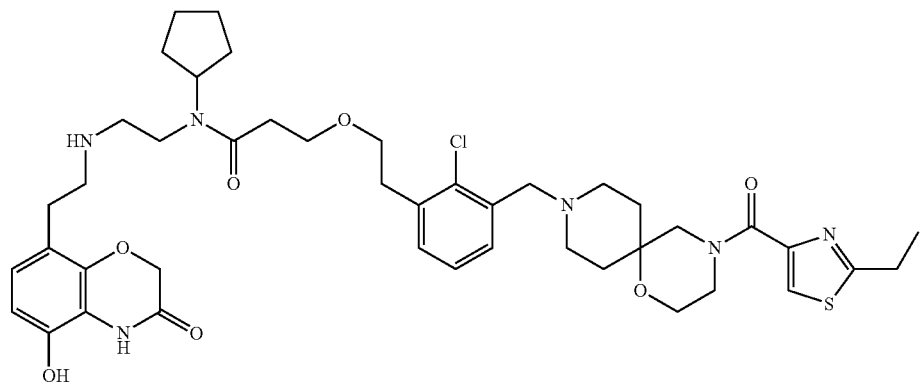

A solution of 3-(2-chloro-3-((4-(2-ethylthiazole-4-carbonyl)-1-oxa-4,9-diazaspiro[5.5]undecan-9-yl)methyl)phenethoxy)-N-cyclopentyl-N-(2,2-dimethoxyethyl)propanamide (limiting reagent) (step f) in THF (9.5 volumes) was heated to 40° C. P-Toluenesulfonic acid monohydrate (5 molar equivalents) was added and the mixture was held at 40° C. for 10 min. A solution of sodium bicarbonate (8 molar equivalents) in water (16 volumes) was added slowly to the reaction mixture. Once effervescence had ceased, the aqueous was extracted with ethyl acetate (2×16 volumes). The combined organics were dried over anhydrous sodium sulfate, filtered and evaporated. The residue was dissolved in NMP (4 volumes) and added to a suspension of 8-(2-aminoethyl)-5-hydroxy-2H-benzo[b][1,4]oxazin-3(4H)-one.HCl (1.2 molar equivalents) in NMP (4 volumes), water (0.4 volumes) and sodium bicarbonate (3 molar equivalents) which had been previously stirring for 3 hr at ambient temperature. The reaction mixture was stirred at ambient temperature for 30 mins. Sodium triacetoxyborohydride (3 molar equivalents) was added in one portion and the mixture was stirred for 90 mins at ambient temperature. To the reaction mixture was added slowly a saturated sodium bicarbonate solution (16 volumes) (much-effervescence and exotherm of 10° C.). 2-MeTHF (16 volumes) was added. The layers were separated and the aqueous was extracted with 2-MeTHF (16 volumes). The combined organics were washed with water containing sodium bicarbonate (pH8) (2×16 volumes of a solution of 15 g sodium bicarbonate in 2000 mL water). The organics were dried over anhydrous sodium sulphate, filtered and evaporated. The crude residue was purified by Si silica chromatography (750 g snap biotage column) elution gradient 1% ammonia/3% methanol in DCM increasing to 1% ammonia/5% methanol in DCM to elute product. Pure fractions were evaporated to dryness to afford an off white crunchy foam. Yield: 33% of theoretical.

m/z [M+H]+=837 (calc=837) (Multimode+)

$^1$H NMR (400 MHz, DMSO, 90° C.) δ 7.89 (d, J=1.7 Hz, 1H), 7.31 (d, J=7.1 Hz, 1H), 7.20 (dt, J=7.3, 14.7 Hz, 2H), 6.61 (d, J=8.2 Hz, 1H), 6.43 (d, J=8.2 Hz, 1H), 4.46 (d, J=1.4 Hz, 2H), 4.29-4.13 (m, 1H), 3.71-3.49 (m, 12H), 3.18 (t, J=7.2 Hz, 2H), 3.08-2.90 (m, 7H), 2.71-2.29 (m, 12H), 1.67 (d, J=14.9 Hz, 6H), 1.51 (d, J=23.5 Hz, 6H), 1.33 (dd, J=6.0, 7.5 Hz, 3H).

h) 3-(2-Chloro-3-((4-(2-ethylthiazole-4-carbonyl)-1-oxa-4,9-diazaspiro[5.5]undecan-9-yl)methyl)phenethoxy)-N-cyclopentyl-N-(2-(2-(5-hydroxy-3-oxo-3,4-dihydro-2H-benzo[b][1,4]oxazin-8-yl)ethylamino)ethyl)propanamide.sulfuric acid monohydrate salt A solution of 3-(2-chloro-3-((4-(2-ethylthiazole-4-carbonyl)-1-oxa-4,9-diazaspiro[5.5]undecan-9-yl)methyl)phenethoxy)-N-cyclopentyl-N-(2-(2-(5-hydroxy-3-oxo-3,4-dihydro-2H-benzo[b][1,4]oxazin-8-yl)ethylamino)ethyl)propanamide (limiting reagent) (step g) 37.85 g, 45.20 mmol) in methanol (6 volumes) was heated to 50° C. and sulfuric acid (1 molar equivalent) in methanol (6 volumes) was added dropwise over 10 mins. The mixture was seeded and stirred at 50° C. for 1 hr. The mixture was cooled to ambient temperature over 2 hrs and stirred for 18 hrs. The precipitate was collected by filtration and the dried in the oven under vacuum (no heat) to give a white solid. Yield: 76% of theoretical.

m/z [M+H]+=837 (calc=837) (Multimode+)

$^1$H NMR (500 MHz, DMSO) δ 7.99 (s, 1H), 7.43-7.16 (m, 3H), 6.67 (t, J=7.7 Hz, 1H), 6.48 (t, J=7.3 Hz, 1H), 4.59-4.36 (m, 2H), 4.23-4.13 (m, 1H), 3.63 (dt, J=27.8, 53.1 Hz, 12H), 3.37 (dd, J=9.0, 16.1 Hz, 6H), 3.11-2.89 (m, 8H), 2.77 (t, J=7.6 Hz, 2H), 2.64 (t, J=6.3 Hz, 2H), 2.38 (dd, J=33.4, 51.6 Hz, 4H), 1.83-1.38 (m, 12H), 1.32 (s, 3H).

Examples 28 to 33a were prepared using the following Carboxylic Acids and Amines:

| Example Number | Carboxylic Acid | Amine |
|---|---|---|
| 28 | 2-isopropylthiazole-4-carboxylic acid | N-ethyl-2,2-dimethoxyethanamine [Note 1] |
| 29 | 2-isopropylthiazole-4-carboxylic acid | N-(2,2-dimethoxyethyl)propan-1-amine [Note 2] |
| 30 | Carboxylic Acid 1 | N-ethyl-2,2-dimethoxyethanamine [Note 1] |
| 31 | Carboxylic Acid 1 | (R)-N-(2,2-dimethoxyethyl)butan-2-amine [Note 3] |
| 32 | Carboxylic Acid 1 | N-(2,2-dimethoxyethyl)butan-1-amine [Note 4] |
| 33, 33a | Carboxylic Acid 1 | Amine 6 |

[Note 1]: U.S. Pat. No. 2,707,186.
[Note 2]: Liebigs Annalen der Chemie 1979, 11, 1818.
[Note 3]: WO 2008075025.
[Note 4]: J. Am. Chem. Soc. 1949, 71(6), 2272.

EXAMPLE 34

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide ditrifluoroacetate

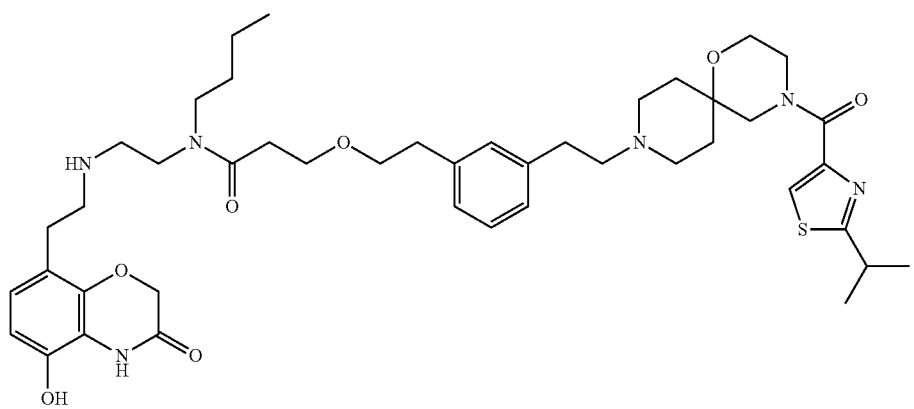

N-Butyl-N-(2,2-dimethoxyethyl)-3-(3-(2-(4-(2-isopropylthiazole-4-carbonyl)-1-oxa-4,9-diazaspiro[5.5]undecan-9-yl)ethyl)phenethoxy)propanamide (0.45 g) was dissolved in tetrahydrofuran (10 mL) and tosic acid (0.28 g) was added. The mixture was stirred at room temperature for 1 hour, then added to a mixture of 8-(2-aminoethyl)-5-hydroxy-2H-m benzo[b][1,4]oxazin-3(4H)-one hydrochloride [WO 2008075025] (0.245 g) and sodium bicarbonate (0.20 g) in NMP (4 mL) and water (0.5 mL) and stirred for 15 minutes. Sodium triacetoxyborohydride (0.35 g) and acetic acid (0.5 mL) were then added and the mixture was stirred at room temperature for 16 hours. The mixture was poured onto saturated sodium bicarbonate solution and extracted with ethyl acetate. The extracts were combined and evaporated under reduced pressure. The residue was purified by flash silica chromatography using 8% methanol in dichloromethane containing 1% '880' aqueous ammonia as solvent. Further purification by preparative HPLC (Sunfire™, Gradient: 33-68% methanol in 0.1% aqueous TFA) afforded the titled compound as a white solid. Yield 0.194 g.

m/z 819 M$^+$ (MultiMode+).

$^1$H NMR (400 MHz, D$_6$-DMSO, 90° C.) δ 9.44-9.34 (m, 1H), 8.36-8.27 (m, 1H), 7.97 (s, 1H), 7.26-7.19 (m, 1H), 7.15-7.08 (m, 3H), 6.68-6.63 (m, 1H), 6.51-6.45 (m, 1H), 4.53 (s, 2H), 3.73-3.48 (m, 14H), 3.37-2.52 (m, 20H), 2.15-1.41 (m, 6H), 1.36 (d, J=6.9 Hz, 6H), 1.32-1.25 (m, 2H), 0.91 (t, J=7.4 Hz, 3H). Two exchangeable protons not observed.

The N-butyl-N-(2,2-dimethoxyethyl)-3-(3-(2-(4-(2-isopropylthiazole-4-carbonyl)-1-oxa-4,9-diazaspiro[5.5]undecan-9-yl)ethyl)phenethoxy)propanamide used as a starting material was prepared as follows:

a) (9-(3-(2-Hydroxyethyl)phenethyl)-1-oxa-4,9-diazaspiro[5.5]undecan-4-yl)(2-isopropylthiazol-4-yl)methanone

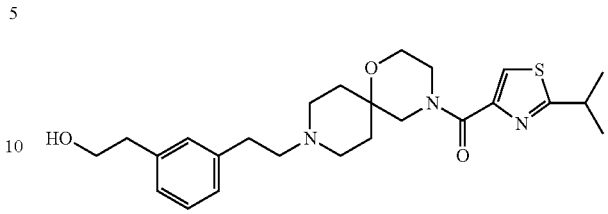

A mixture of (2-isopropylthiazol-4-yl)(1-oxa-4,9-diazaspiro[5.5]undecan-4-yl)methanone hydrochloride [Example 27, step a] (10 g) and 2-(3-(2-bromoethyl)phenyl)ethanol [Organometallics 2002, 21(20), 4217] (10 g) and potassium carbonate (16 g) in acetonitrile (600 mL) and water (10 mL) was heated at 60° C. for 36 hours. The solvent was decanted off and evaporated under reduced pressure. The residue was partitioned between ethyl acetate and brine, the aqueous layer was re-extracted with ethyl acetate, and the combined organic layers were dried, filtered and the solvent evaporated under reduced pressure. The residue was purified by flash silica chromatography, using 5% methanol in ethyl acetate containing 1% triethylamine as solvent. Fractions containing the product were evaporated to dryness to afford the subtitled compound. Yield 11 g.

m/z 458 (M+H)$^+$ (APCI).

b) tert-Butyl 3-(3-(2-(4-(2-isopropylthiazole-4-carbonyl)-1-oxa-4,9-diazaspiro[5.5]undecan-9-yl)ethyl)phenethoxy)propanoate

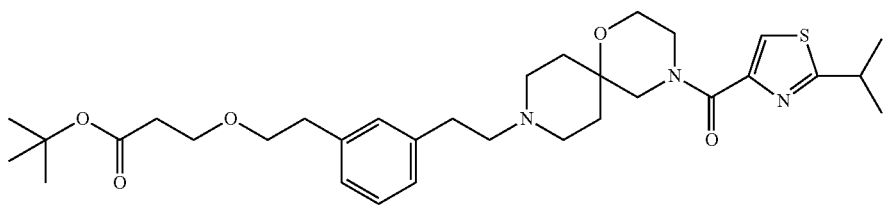

(9-(3-(2-Hydroxyethyl)phenethyl)-1-oxa-4,9-diazaspiro[5.5]undecan-4-yl)(2-isopropylthiazol-4-yl)methanone [Example 34, step a] (2.4 g) was dissolved in acetonitrile (2 mL) and tert-butyl acrylate (1.7 mL) added, followed by benzyltrimethylammonium hydroxide (40% in water, 0.72 mL). The mixture was stirred at ambient temperature for 3 hours. The volatiles were removed under reduced pressure and the residue purified by flash silica chromatography eluting with 3% methanol in dichloromethane containing 1% '880' aqueous ammonia to afford the subtitled compound Yield 2.7 g.

m/z 586 (M+H)$^+$ (APCI).

c) 3-(3-(2-(4-(2-Isopropylthiazole-4-carbonyl)-1-oxa-4,9-diazaspiro[5.5]undecan-9-yl)ethyl)phenethoxy)propanoic acid

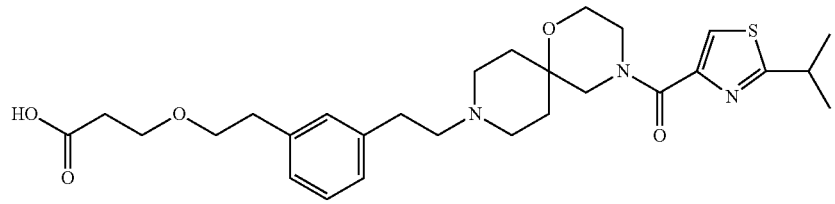

tert-Butyl 3-(3-(2-(4-(2-isopropylthiazole-4-carbonyl)-1-oxa-4,9-diazaspiro[5.5]undecan-9-yl)ethyl)phenethoxy)propanoate [Example 34, step b] (0.70 g) was stirred in dichloromethane (8 mL) and trifluoroacetic acid (2 mL) was added. The solution was stirred for 18 hours, then the volatiles were removed under reduced pressure to afford the subtitled compound. Yield 1.0 g.

m/z 530 (M+H)$^+$ (APCI).

d) N-Butyl-N-(2,2-dimethoxyethyl)-3-(3-(2-(4-(2-isopropylthiazole-4-carbonyl)-1-oxa-4,9-diazaspiro[5.5]undecan-9-yl)ethyl)phenethoxy)propanamide

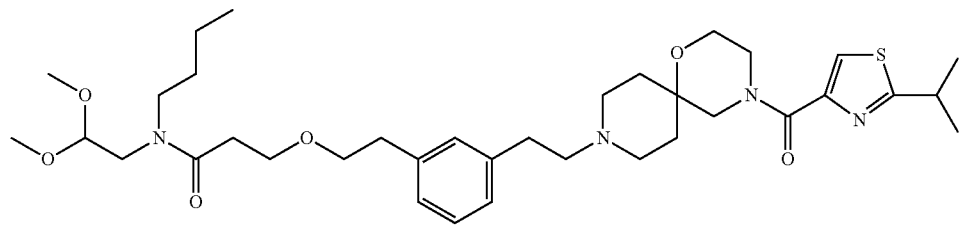

3-(3-(2-(4-(2-Isopropylthiazole-4-carbonyl)-1-oxa-4,9-diazaspiro[5.5]undecan-9-yl)ethyl)phenethoxy)propanoic acid [Example 34, step c] (0.50 g), Hunig's base (0.58 mL), and N-(2,2-dimethoxyethyl)butan-1-amine [J. Am. Chem. Soc. 1949, 71(6), 2272] (0.12 g) were dissolved in dichloromethane (10 mL). HATU (0.33 g) was then added and the mixture was stirred at room temperature for 24 hours. The mixture was poured into water and extracted with dichloromethane. The organic extracts were combined and evaporated under reduced pressure to give the subtitled compound. Yield 0.45 g.

m/z 673 (M+H)$^+$ (APCI).

EXAMPLE 34a

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide Sulphate salt Modification A To a solution of N-butyl-N-(2-(2-(5-hydroxy-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (100 mg) (see below for preparation) in ethanol (20 mL) was added sulfuric acid (244 μA of 0.5 M solution in water). Half of this solution was left for 16 h and N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide Sulphate salt Modification A collected by filtration. Yield 5 mg.

Tosic acid monohydrate (4.24 g) was added to a solution of N-butyl-N-(2,2-dimethoxyethyl)-3-(3-(2-(4-(2-isopropylthiazole-4-carbonyl)-1-oxa-4,9-diazaspiro[5.5]undecan-9-yl)ethyl)phenethoxy)propanamide (3 g) in THF (30 mL) and the resulting mixture stirred for 1 hour at RT. NMP (1 mL) was added and the solution was then added to a suspension of 8-(2-aminoethyl)-5-hydroxy-2H-benzo[b][1,4]oxazin-3(4H)-one HCl (1.636 g) and sodium bicarbonate (3.00 g) in a mixture of NMP (16 mL) and water (1.6 mL) which had been stirring for 45 min. The flask in which the aldehyde was formed was rinsed with NMP (2 mL) and the washings added to the suspension and the resulting cloudy solution was stirred for 20 min. Sodium triacetoxyborohydride (2.83 g) was then added and the resulting mixture stirred for 1 hr.

The reaction mixture was partitioned between 2-methylTHF (200 mL) and saturated sodium bicarbonate solution (150 mL). Water (~100 mL) was added until the precipitates had dissolved. The mixture was shaken for 10 min (until gas evolution had ceased). The 2-methylTHF solution was separated, dried over sodium sulphate, filtered and evaporated. The residue was purified by flash silica chromatography eluting with 8% methanol in dichloromethane with 1% 880 ammonia. Pure fractions were evaporated to dryness. This gum was dissolved in ethanol (30 mL) and treated with 1 equiv of sulfuric acid (from a 0.5 molar aq solution). The solvents were evaporated and the residue azeotroped with acetonitrile (×2). The resultant gum was dissolved in ethanol (15 mL) and seeded with the sulphate modification A (Example 34a, 10 mg). The mixture was stirred at RT for 2 days, filtered off under nitrogen and washed with ethanol (5 mL) followed by acetonitrile (5 mL) followed by ether (10 mL). Yield 1.8 g.

m/z 819.4 (multimode+)

a) (9-(3-(2-Hydroxyethyl)phenethyl)-1-oxa-4,9-diazaspiro[5.5]undecan-4-yl)(2-isopropylthiazol-4-yl)methanone

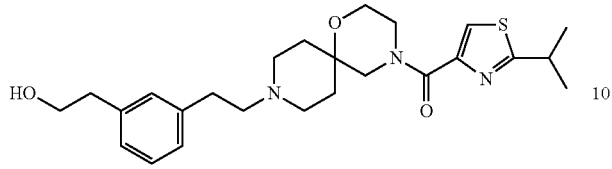

A mixture of (2-isopropylthiazol-4-yl)(1-oxa-4,9-diazaspiro[5.5]undecan-4-yl)methanone hydrochloride [Example 27, step a] (13.6 g) and 2-(3-(2-bromoethyl)phenyl)ethanol [Organometallics 2002, 21(20), 4217] (13.51 g) and potassium carbonate (21.7 g) in acetonitrile (700 mL) and water (13 mL) was heated at 60° C. for 36 hours. The solvent was decanted off and evaporated under reduced pressure. The residue was partitioned between ethyl acetate and brine, the aqueous layer was re-extracted with ethyl acetate, and the combined organic layers were dried, filtered and the solvent evaporated under reduced pressure. The residue was purified by flash silica chromatography, using 5% methanol in ethyl acetate containing 1% triethylamine as solvent. Fractions containing the product were evaporated to dryness to afford the subtitled compound.

Yield 13.2 g.

m/z 458 (M+H)+ (APCI).

b) tert-Butyl 3-(3-(2-(4-(2-isopropylthiazole-4-carbonyl)-1-oxa-4,9-diazaspiro[5.5]undecan-9-yl)ethyl)phenethoxy)propanoate

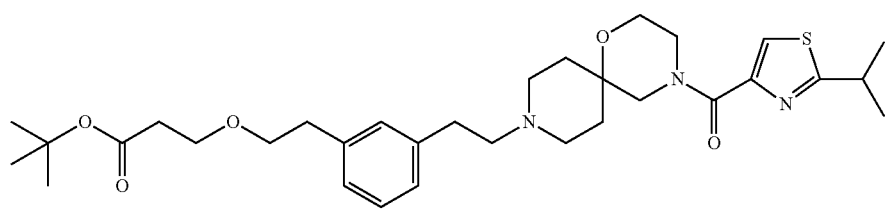

(9-(3-(2-Hydroxyethyl)phenethyl)-1-oxa-4,9-diazaspiro[5.5]undecan-4-yl)(2-isopropylthiazol-4-yl)methanone [Example 34a, step a] (13.2 g) was dissolved in acetonitrile (20 mL) and tert-butyl acrylate (8.13 g) added, followed by benzyltrimethylammonium hydroxide (40% in water, 3.93 mL). The mixture was stirred at ambient temperature for 3 hours. The volatiles were removed under reduced pressure and the residue purified by flash silica chromatography eluting with 5% methanol and 1% triethylamine in ethyl acetate to afford the subtitled compound Yield 13.2 g.

m/z 586 (M+H)+ (APCI).

c) 3-(3-(2-(4-(2-Isopropylthiazole-4-carbonyl)-1-oxa-4,9-diazaspiro[5.5]undecan-9-yl)ethyl)phenethoxy)propanoic acid trifluoroacetate salt

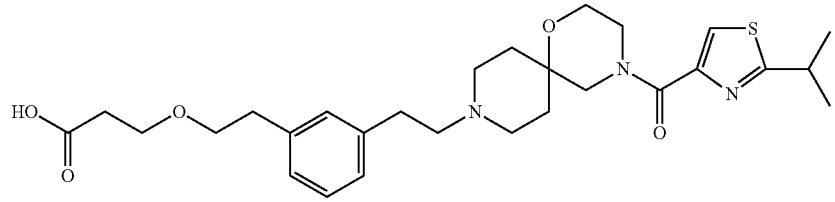

tert-Butyl 3-(3-(2-(4-(2-isopropylthiazole-4-carbonyl)-1-oxa-4,9-diazaspiro[5.5]undecan-9-yl)ethyl)phenethoxy)propanoate [Example 34a, step b] (13.2 g) was stirred in dichloromethane (150 mL) and trifluoroacetic acid (50 mL) was added. The solution was stirred for 1 hour. The solvents were evaporated under reduced pressure and the residue dissolved in acetonitrile and the solution evaporated under reduced pressure to afford the subtitled compound. Yield 14.4 g.

m/z 530 (M+H)$^+$ (APCI).

d) N-Butyl-N-(2,2-dimethoxyethyl)-3-(3-(2-(4-(2-isopropylthiazole-4-carbonyl)-1-oxa-4,9-diazaspiro[5.5]undecan-9-yl)ethyl)phenethoxy)propanamide

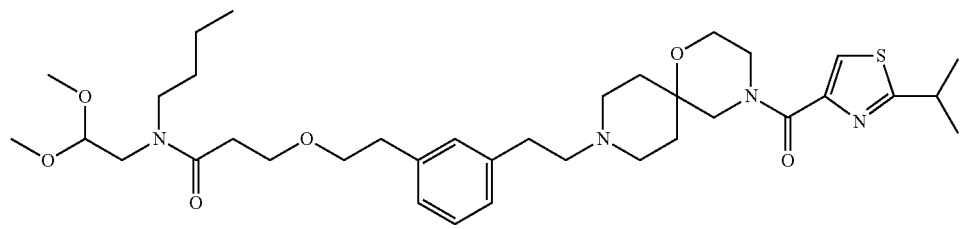

T3P (15.67 mL of 1.57M solution in THF) was added dropwise over 15 minutes to a stirred solution of 3-(3-(2-(4-(2-isopropylthiazole-4-carbonyl)-1-oxa-4,9-diazaspiro[5.5]undecan-9-yl)ethyl)phenethoxy)propanoic acid trifluoroacetate salt [Example 34a, step c] (14.4 g) and N-(2,2-dimethoxyethyl)butan-1-amine [J. Am. Chem. Soc. 1949, 71(6), 2272] (3.97 g) and triethylamine (21.83 mL) in DMF (180 mL). The mixture was stirred at 20° C. for 3 hours and then partitioned between ethyl acetate and aqueous brine. The organic layer was washed with aqueous brine (×2), dried over sodium sulphate, filtered and the solvent evaporated under reduced pressure to give the subtitled compound. Yield 15.00 g.

m/z 673.4 (M+H)$^+$

EXAMPLE 34b

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide Sulphate salt Modification A (Example 34a) (1.73 g) was dissolved in DCM/methanol, filtered and evaporated to dryness. The resultant gum was partitioned between sat aq bicarb (100 mL) and freshly distilled MeTHF (150 mL) and the mixture stirred vigorously for 10 mins. The organic layer was separated, washed with fresh sodium bicarbonate (×2), dried over sodium sulphate, filtered and evaporated under reduced pressure to give the title compound as a foam. Yield 1.2 g.

m/z 819.4 (multimode+)

$^1$H NMR (400 MHz, D$_6$-DMSO, 90° C.) δ 7.93 (s, 1H), 7.13 (t, 1H), 7.03-6.99 (m, 3H), 6.60 (d, 1H), 6.42 (d, 1H), 4.45 (s, 2H), 3.66-3.56 (m, 10H), 3.31-3.20 (m, 5H), 2.74 (t, 2H), 2.70-2.36 (m, 16H), 1.69-1.65 (m, 2H), 1.55-1.53 (m, 2H), 1.43 (s, 2H), 1.35 (d, 6H), 1.25-1.23 (m, 2H), 0.87 (t, 3H). plus 3 exchangeables not observed

EXAMPLE 34c

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide sulphate salt Modification B N-butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (Example 34b)(0.1 g) in ethanol (5 mL) was treated with sulfuric acid (0.244 ml of 0.5M aqueous solution). The solvents were evaporated under reduced vacuum and the residue triturated with diethyl ether to give a white solid.

10 mg of this solid was suspended in a mixture of ethanol and ethyl acetate (9:1, 1 mL) and stirred at RT for 1 week. The resulting solid was collected by filtration to give N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide sulphate salt Modification B as a white solid. Yield 3 mg.

m/z 819.3 (M+H)$^+$

EXAMPLE 34d

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl) ethyl)phenethoxy) propanamide sulphate salt Modification C N-butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (Example 34b)(0.1 g) in ethanol (5 mL) was treated with sulfuric acid (0.244 ml of 0.5M aqueous solution). The solvents were evaporated under reduced vacuum and the residue triturated with diethyl ether to give a white solid.

10 mg of this solid was suspended in a mixture of Dioxane and ethyl acetate (9:1, 1 mL) and stirred at RT for 1 week. The resulting solid was collected by filtration to give N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide sulphate salt Modification C as a white solid. Yield 3 mg m/z 819.3 (M+H)$^+$

EXAMPLE 34e

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy) propanamide sulphate salt Modification D N-butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (Example 34b)(0.1 g) in ethanol (5 mL) was treated with sulfuric acid (0.244 ml of 0.5M aqueous solution). The solvents were evaporated under reduced vacuum and the residue triturated with diethyl ether to give a white solid.

10 mg of this solid was suspended in 1,4-dioxane (1 mL) and stirred at RT for 12 days. The resulting solid was collected by filtration to give N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide sulphate salt Modification D as a white solid. Yield 3 mg.

m/z 819.3 (M+H)$^+$

EXAMPLE 34f

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy) propanamide sulphate salt Modification E N-butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (Example 34b)(0.1 g) in ethanol (5 mL) was treated with sulfuric acid (0.244 ml of 0.5M aqueous solution). The solvents were evaporated under reduced vacuum and the residue triturated with diethyl ether to give a white solid.

10 mg of this solid was suspended in a mixture of Dioxane and DMF (9:1, 1 mL) and stirred at RT for 12 days. The resulting solid was collected by filtration to give N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl) ethyl)phenethoxy)propanamide sulphate salt Modification E as a white solid. Yield 3 mg.

m/z 819.3 (M+H)$^+$

EXAMPLE 34g

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy) propanamide sulphate salt Modification F N-butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (Example 34b)(0.1 g) in ethanol (5 mL) was treated with sulfuric acid (0.244 ml of 0.5M aqueous solution). The solvents were evaporated under reduced vacuum and the residue triturated with diethyl ether to give a white solid.

10 mg of this solid was suspended in a mixture of methanol and acetonitrile (9:1, 1 mL) and stirred at RT for 1 week. The resulting solid was collected by filtration to give N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl) ethyl)phenethoxy)propanamide sulphate salt Modification F as a white solid. Yield 3 mg.

m/z 819.3 (M+H)$^+$

EXAMPLE 34H

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy) propanamide sulphate salt Modification G N-butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (Example 34b)(0.1 g) in ethanol (5 mL) was treated with sulfuric acid (0.244 ml of 0.5M aqueous solution). The solvents were evaporated under reduced vacuum and the residue triturated with diethyl ether to give a white solid.

10 mg of this solid was dissolved in refluxing water (~0.2 mL) and acetonitrile (~4 mL) was slowly added. The resulting mixture was allowed to cool overnight. The resulting precipitate was isolated by filtration and dried under vacuum to give N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide sulphate salt modification G as a white solid. Yield 2 mg N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide sulphate salt Modification A (example 34a)(0.117 g) was seeded sulphate salt Modification G and 5% water in acetonitrile (3 mL) added. After 1 h of stirring a gum had formed and after 24 h a white suspension had formed. After 72 h N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)

phenethoxy)propanamide sulphate salt modification G as a white solid was collected by filtration. Yield 101 mg.

m/z 819.3 (M+H)+

$^1$H NMR (400 MHz, D$_6$-DMSO, 90° C.) δ 9.33 (s, 1H), 7.92 (s, 1H), 7.16 (t, 1H), 7.05-7.02 (m, 3H), 6.65 (d, 1H), 6.47 (d, 1H), 4.51 (s, 2H), 3.70-3.55 (m, 10H), 3.50-2.40 (m, 23H), 1.80-1.70 (m, 2H), 1.65-1.55 (m, 2H), 1.48 (s, 2H), 1.36 (d, 6H), 1.28-1.27 (m, 2H), 0.90 (t, 3H). plus 4 exchangeables not observed

EXAMPLE 34i

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide napadisylate salt Modification B N-butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (example 34b) (332 mg) was dissolved in IPA (3 mL) and a solution of 1,5-naphthalenedisulphonic acid tetrahydrate (144 mg) in IPA (8 mL) was added. After stirring for 10 minutes the resultant solid was filtered off and washed with a little IPA (1 mL) and then ether.

20 mg in methanol (1 mL), seeded with Example 39a (0.5 mg) and stirred for 1 day at RT. N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide napadisylate salt Modification B was filtered off. Yield 10 mg.

m/z 819.3 (M+H)+

1H NMR (400 MHz, D$_6$-DMSO, 90° C.) δ 9.36 (s, 1H), 8.96 (d, 2H), 8.30 (s, 1H), 7.97 (d, 2H), 7.35 (t, 2H), 7.21 (t, 1H), 7.10-7.06 (m, 3H), 6.65 (d, 1H), 6.48 (d, 1H), 4.53 (s, 2H), 3.72-3.50 (m, 12H), 3.40-2.45 (m, 21H), 2.07 (s, 2H), 1.75 (s, 2H), 1.46 (s, 2H), 1.36 (d, 6H), 1.29-1.26 (m, 2H), 0.89 (t, 3H). plus 3 exchange

EXAMPLE 34j

N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide a) tert-Butyl 4-(2-isopropylthiazole-4-carbonyl)-1-oxa-4,9-diazaspiro[5.5]undecane-9-carboxylate

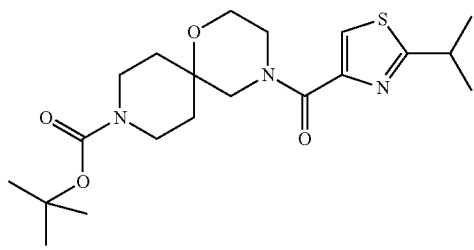

To a suspension of tert-butyl 1-oxa-4,9-diazaspiro[5.5]undecane-9-carboxylate hydrochloride and triethylamine (5 molar equivalents) in DCM (10 volumes under nitrogen was added 4-isopropylthiazole-2-carboxylic acid (1 molar equivalent) followed by a solution of T3P in THF (1.57M solution, 1.1 molar equivalents) added dropwise over 50 mins [exotherm of 23° C. was observed]. The mixture was stirred for 4 hours, washed with water (2×1 L), dried (Na$_2$SO$_4$), filtered and concentrated in vacuo to leave an orange syrup. Yield: 99% of theoretical.

$^1$H NMR (400 MHz, CDCl$_3$) δ 7.86 (s, 1H), 4.06-3.86 (m, 2H), 3.86-3.48 (m, 6H), 3.30 (septet, J=6.8 Hz, 1H), 3.32-3.10 (m, 2H), 1.87-1.79 (m, 2H), 1.64-1.52 (m, 1H), 1.52-1.40 (m, 1H) 1.45 (s, 9H) and 1.40 (d, J=6.8 Hz, 6H).

b) (2-Isopropylthiazol-4-yl)(1-oxa-4,9-diazaspiro[5.5]undecan-4-yl)methanone, hydrochloride salt

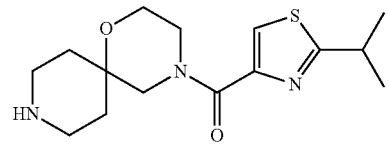

To a solution of tert-butyl 4-(2-isopropylthiazole-4-carbonyl)-1-oxa-4,9-diazaspiro[5.5]undecane-9-carboxylate in iPrOH (3 volumes) at 40° C. under nitrogen was added a solution of 5-6N HCl in isopropanol (2-2.4 molar equivalents). The mixture was stirred at 40° C. for 18 hours, cooled to room temp and diluted with TBME (4 volumes). Stirred at room temp for 2 hours, collected by filtration, washed with TBME and air dried to leave an off white powder. Yield: 97% of theoretical.

$^1$H NMR (400 MHz, CDCl$_3$) δ 9.74-9.59 (m, 1H), 9.59-9.44 (m, 1H), 7.88 (s, 1H), 4.06-3.86 (m, 2H), 3.86-3.58 (m, 4H), 3.40-3.12 (m, 5H), 2.28-2.06 (m, 2H), 2.06-1.84 (m, 2H) and 1.42 (d, J=6.4 Hz, 6H).

c) 2,2'-(1,3-phenylene)diethanol

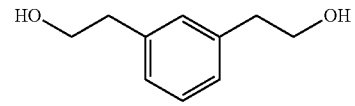

A solution of 2,2'-(1,3-phenylene)diacetic acid (1.50 kg, 7.72 mol, 1.0 equiv.) in Me-THF (21.0 L, 14.0 vols) was charged over 2 h 06 min to a suspension of lithium aluminium hydride pellets (1.25 kg, 32.81 mol, 4.25 equiv.) in Me-THF (12.00 L, 8 vols) while maintaining the temperature in the range 31-40° C. The reaction mixture was then heated to 50° C. over 2 h 10 min and held at 50° C. for a further 15 h 18 min. The mixture was cooled to 23° C. and the excess lithium aluminium hydride was quenched by the addition of water (1.25 L) over 2 h 21 mins, 15% w/v sodium hydroxide (1.25 L) over 41 min, and water (1.25 L) over 13 min, while maintaining the temperature below 30° C. throughout the additions. The suspension was filtered and the filter cake was re-slurried with DCM (2×15.00 L, 2×10 vols). The combined filtrates were concentrated at 45° C. to afford 1.18 kg of material. When corrected for toluene content this gave a yield of 1.12 kg (87% Th., 75 wt. %) of material was isolated as an off white solid.

¹H NMR (400 MHz, CD₃OD) δ 7.0-7.25 (m, 4H), 3.75 (t, 4H), 2.80 (t, 4H)

d) 2-(3-(2-bromoethyl)phenyl)ethanol

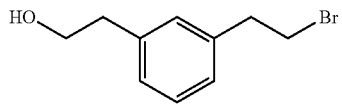

A suspension of 2,2'-(1,3-phenylene)diethanol (step c) (1.03 kg, 6.22 mol, 1.0 equiv.) in toluene (13.49 L, 15.0 vols) and 48% HBr (1.44 L, 12.75 mol, 2.05 equiv.) was heated at 87° C. for 14 h. Additional 48% w/w HBr (0.35 L 3.11 mol, 0.5 equiv.) was charged and the mixture was stirred at reflux for a further 24 h. The mixture was cooled to ambient and the layers were separated. The organic layer was concentrated to afford 1.39 kg of material. The purification was split into two equal batches of 800 g. The crude meta-bromoalcohol (800 g) was dissolved in DCM (1.6 L, 2 vols w.r.t. the mass of crude material) and charged to a dry pad of silica gel (3.6 kg, 4 wt equiv.). The pad was eluted with 10% IPAc/Heptane (16 L) to remove the fast running impurities then 50% IPAc/Heptane (20 L) to wash off the product. The product containing fractions from each of the silica pads were combined, concentrated at 40-45° C. and then dried to constant weight to afford 1.32 kg (81% Th.) of meta-bromoalcohol as a pale yellow oil.

¹H NMR (400 MHz, CD₃OD) δ 7.0-7.25 (m, 4H), 3.75 (t, 2H), 3.60 (t, 2H), 3.15 (t, 2H), 2.82 (t, 2H)

e) (9-(3-(2-Hydroxyethyl)phenethyl)-1-oxa-4,9-diazaspiro[5.5]undecan-4-yl)(2-isopropylthiazol-4-yl)methanone

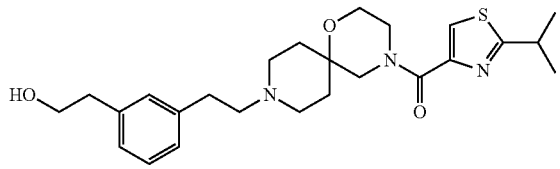

To a suspension of (2-isopropylthiazol-4-yl)(1-oxa-4,9-diazaspiro[5.5]undecan-4-yl)methanone hydrochloride in a solution of 2-(3-(2-bromoethyl)phenyl)ethanol (1.15 molar equivalents) in acetonitrile (10 volumes) at room temp was added potassium carbonate (4 molar equivalents) followed by water (0.167 volumes. The mixture was stirred at 60° C. for 66 hours, cooled to room temp, filtered, washed with MeCN and concentrated in vacuo to leave a crude orange gum. This gum was dissolved in EtOAc (3 volumes) and washed with 2N HCl (1.1 molar equivalents). The aqueous layer was bas- ified using 2N NaOH (1.5 molar equivalents) and extracted with TBME (2×2 volumes) [an oil appeared at the interface which would not dissolve in TBME]. The combined organics and oil were diluted with EtOAc (1 volume) [oil dissolved], dried (Na₂SO₄), filtered and concentrated in vacuo to leave an orange gum. Yield: 88% of theoretical.

¹H NMR (400 MHz, CDCl₃) δ 7.84 (s, 1H), 7.23 (t, J=8.0 Hz, 1H), 7.08-7.06 (m, 3H), 4.03-3.93 (m, 1H), 3.93-3.83 (m, 1H), 3.85 (t, J=6.4 Hz, 2H), 3.82-3.74 (m, 4H), 3.71-3.62 (m, 1H), 3.32 (septet, J=6.8 Hz, 1H), 2.87-2.76 (m, 2H), 2.84 (t, J=6.8 Hz, 2H), 2.70-2.40 (m, 6H), 1.96-1.85 (m, 2H), 1.85-1.71 (m, 2H), 1.71-1.53 (m, 2H) and 1.41 (d, J=6.8 Hz, 6H).

f) tert-Butyl 3-(3-(2-(4-(2-isopropylthiazole-4-carbonyl)-1-oxa-4,9-diazaspiro[5.5]undecan-9-yl)ethyl)phenethoxy)propanoate

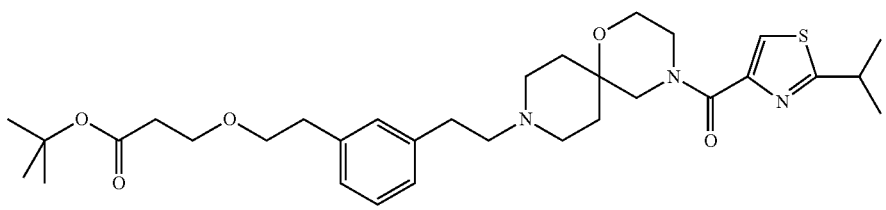

To a suspension of (9-(3-(2-hydroxyethyl)phenethyl)-1-oxa-4,9-diazaspiro[5.5]undecan-4-yl)(2-isopropylthiazol-4-yl)methanone (limiting reagent) in acetonitrile (5 volumes) was added tert-butyl acrylate (5 molar equivalents) followed by benzyltrimethylammonium hydroxide solution (40% by weight in water, 0.3 molar equivalents). The mixture was stirred at room temperature for 1 hour.

The mixture was concentrated in vacuo to leave a crude brown oil which was partitioned between MeTHF and water (5 volumes each). The organic layer was dried (Na₂SO₄), filtered and concentrated in vacuo to leave a pale yellow syrup. Yield: 106% of theoretical.

¹H NMR (400 MHz, CDCl₃) δ 7.83 (s, 1H), 7.19 (t, J=8.0 Hz, 1H), 7.07-7.00 (m, 3H), 4.03-3.92 (m, 1H), 3.92-3.84 (m, 1H), 3.82-3.72 (m, 3H), 3.684 (t, J=6.4 Hz, 2H), 3.675 (t, J=6.4 Hz, 2H), 3.64 (t, J=7.2 Hz, 2H), 3.31 (septet, J=6.8 Hz, 1H), 2.84 (t, J=7.2 Hz, 2H), 2.81-2.71 (m, 2H), 2.68-2.50 (m, 3H), 2.48 (t, J=6.8 Hz, 2H), 2.47 (t, J=6.4 Hz, 2H), 1.94-1.90 (m, 1H), 1.90-1.85 (m, 1H), 1.81-1.65 (m, 1H), 1.63-1.51 (m, 1H), 1.44 (s, 9H) and 1.41 (d, J=6.8 Hz, 6H).

g) N-(2,2-Dimethoxyethyl)butan-1-amine

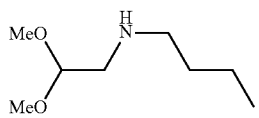

To a solution of butan-1-amine (limiting reagent) in EtOH (5 volumes) was added 2,2-dimethoxyacetaldehyde (60%) in water (1 molar equivalent) and the mixture was stirred at room temp for 4 days. A slurry of 5% palladium on carbon (0.01 molar equivalent) in EtOH (1 volume) was added and the mixture was hydrogenated at 3 bar pressure for 20 hours.

The mixture was filtered through a glass fibre filter paper, washed with EtOH (2×3 volumes) and the mother liquor was carefully concentrated to leave a cloudy brown oil. This oil was dissolved in DCM (15 volumes), dried (Na$_2$SO$_4$), filtered and carefully concentrated in vacuo to leave an orange oil. Yield: 101% of theoretical.

$^1$H NMR (400 MHz, CDCl$_3$) δ 4.48 (t, J=5.6 Hz, 1H), 3.39 (s, 6H), 2.74 (d, J=5.6 Hz, 2H), 2.62 (t, J=7.2 Hz, 2H), 1.48 (quintet, J=7.2 Hz, 2H), 1.31 (sextet, J=7.2 Hz, 2H) and 0.92 (t, J=7.2 Hz, 3H).

h) N-butyl-N-(2,2-dimethoxyethyl)-3-(3-(2-(4-(2-isopropylthiazole-4-carbonyl)-1-oxa-4,9-diazaspiro[5.5]undecan-9-yl)ethyl)phenethoxy)propanamide

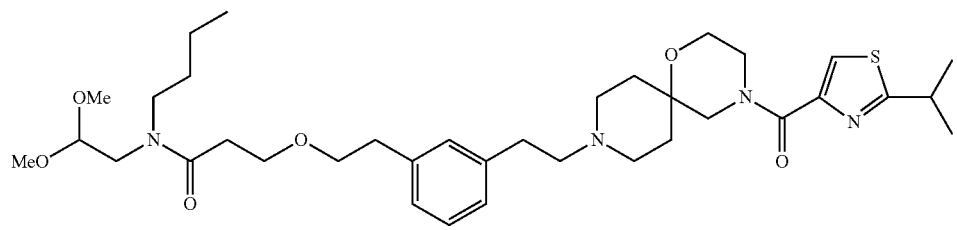

To a solution of tert-butyl 3-(3-(2-(4-(2-isopropylthiazole-4-carbonyl)-1-oxa-4,9-diazaspiro[5.5]undecan-9-yl)ethyl)phenethoxy)propanoate (limiting reagent) in dichloromethane (4 volumes) at 22° C. was added TFA (10 molar equivalents) dropwise over 1 hour [an exotherm of 8° C. occurred after about 5 mL of TFA had been added and after 1 hr the temp was down to 25° C.]. The mixture was stirred at ambient temperature for 72 hours, concentrated in vacuo, redissolved in acetonitrile (4 volumes) and cooled in an ice-bath. Triethylamine (10 molar equivalents) followed by N-(dimethoxyethyl)-N-butylamine (1.2 molar equivalents) were added before a 1.57M solution of T3P in THF (1.3 molar equivalents) was added dropwise. The mixture was stirred at 22° C. for 20 hours, concentrated in vacuo to leave a crude red oil. Redissolved in DCM (4 volumes) and washed with saturated sodium bicarbonate solution (4 volumes). Dried (Na$_2$SO$_4$), filtered and concentrated in vacuo to leave a red syrup. Yield: 106% of theoretical.

$^1$H NMR (400 MHz, CD$_3$OD) δ 7.90 (s, 1H), 7.17 (t, J=7.6 Hz, 1H), 7.11-6.98 (m, 3H), 4.50-4.43 (m, 1H), 3.90-3.59 (m, 10H), 3.41-3.32 (m, 13H), 2.78 (t, J=6.8 Hz, 4H), 2.68-2.54 (m, 8H), 2.00-1.86 (m, 1H), 1.80-1.43 (m, 3H), 1.40 (d, J=6.8 Hz, 6H), 1.35-1.22 (m, 2H) and 0.97-0.88 (m, 3H).

i) N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide

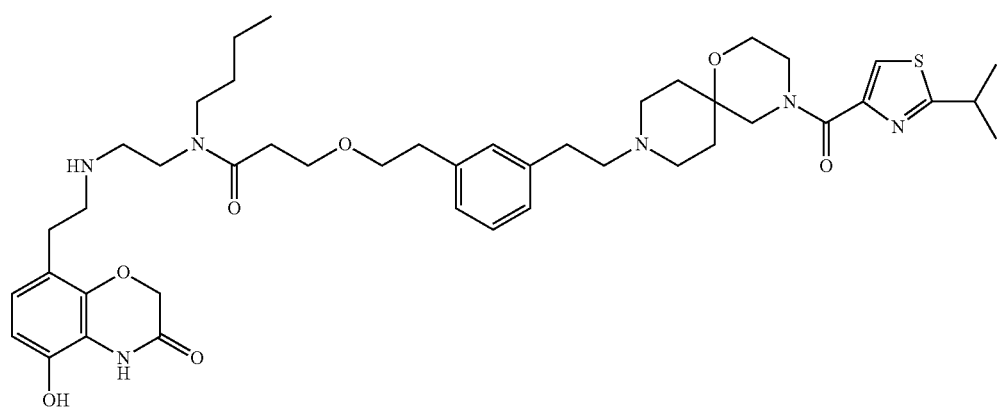

p-Toluenesulphonic acid monohydrate (4 molar equivalents) was added to a solution of N-butyl-N-(2,2-dimethoxyethyl)-3-(3-(2-(4-(2-isopropylthiazole-4-carbonyl)-1-oxa-4,9-diazaspiro[5.5]undecan-9-yl)ethyl)phenethoxy)propanamide (limiting reagent) in THF (10 volumes) and the resulting mixture stirred for 1 hour at room temperature. The solution was then added via a peristaltic pump to a suspension of 8-(2-aminoethyl)-5-hydroxy-2H-benzo[b][1,4]oxazin-3(4H)-one hydrochloride (1 molar equivalent) and sodium bicarbonate (6.5 molar equivalents) in a mixture of NMP (4 volumes) and water (0.45 volumes) which had been stirring at room temp for 1 hour. The resulting cloudy solution was stirred for 30 mins before sodium triacetoxyborohydride (3 molar equivalents) was added portionwise and the resulting mixture was stirred for 1 hour.

The reaction mixture was quenched with saturated sodium bicarbonate solution (10 volumes), water (5 volumes) was added until the precipitates had dissolved and gas evolution had ceased (~15 mins). Extracted with MeTHF (2×10 volumes) and the combined extracts were washed with water (10 volumes), dried ($Na_2SO_4$), filtered and concentrated in vacuo to give a brown syrup which was purified on silica (10 times weight of crude reaction mixture), eluent DCM/8% MeOH/1% ammonia.

Yield: 29% of theoretical.

$^1$H NMR (400 MHz, d6-DMSO) δ 9.82 (s, 1H), 8.01 (s, 1H), 7.20-7.10 (m, 1H), 7.10-6.95 (m, 3H), 6.60 (d, J=8.0 Hz, 1H), 6.41 (d, J=8.0 Hz, 1H), 4.46 (s, 1H), 3.80-3.45 (m, 9H), 3.40-3.15 (m, 12H), 2.78-2.17 (m, 14H), 1.77-1.37 (m, 4H), 1.34 (d, J=6.8 Hz, 6H), 1.30-1.14 (m, 2H) and 0.91-0.82 (m, 3H).

j) N-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide monosulphate salt

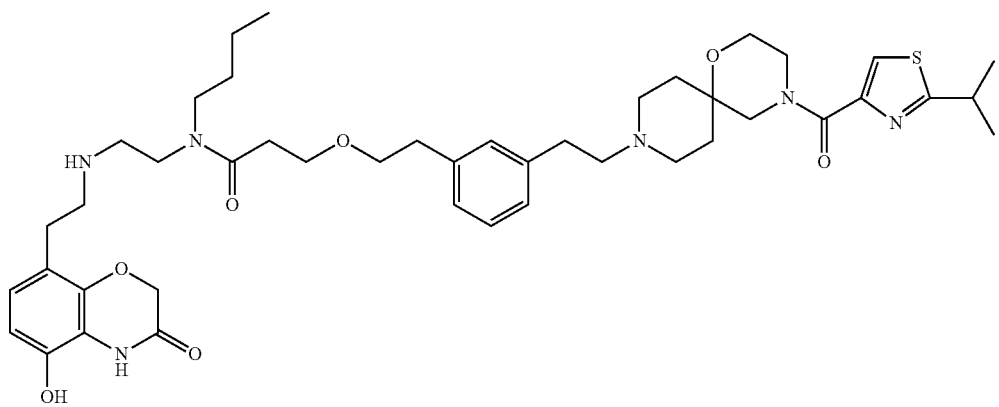

N-butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (limiting reagent) was dissolved in EtOH (15 vols) and 4.9M sulphuric acid (1 molar equivalent) was added and the solution was stirred at room temp for 48 hours. The precipitate was collected, washed with EtOH (1 voll) and vacuum dried (oven at 40° C., oil pump) to leave a white solid (70% recovery). 5% water in MeCN (20 volumes) was added and the mixture stirred for 6 days. Crystalline solid (form G) was then collect by filtration (95% recovery).

$^1$H NMR (400 MHz, d6-DMSO) δ (ppm) 9.92 (s, 1H), 8.02 (s, 1H), 7.22-7.13 (m, 1H), 7.12-6.98 (m, 3H), 6.65 (d, J=8.0 Hz, 1H), 6.47 (d, J=8.0 Hz, 1H), 4.52 (d, J=8.0 Hz, 2H), 3.82-3.14 (m, 20H), 3.04-2.90 (m, 4H), 2.83-2.64 (m, 7H), 2.63-2.47 (m, 4H), 1.85-1.37 (m, 4H), 1.35 (d, J=6.8 Hz, 6H), 1.32-1.16 (m, 2H) and 0.92-0.83 (m, 3H).

EXAMPLE 35

N-Ethyl-N-(2-(2-(4-hydroxy-2-oxo-2,3-dihydrobenzo[d]thiazol-7-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide ditrifluoroacetate

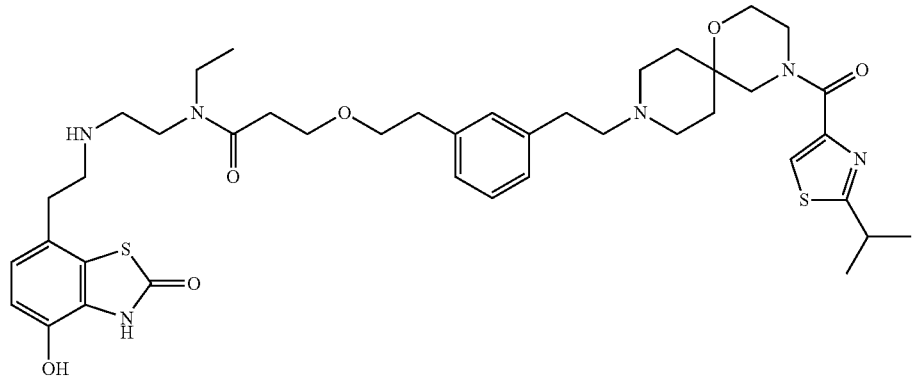

Prepared by the method of Example 1 using 3-(2-hydroxyethyl)phenethyl methanesulfonate [Aromatic Intermediate 9] in place of 4-(2-hydroxyethyl)phenethyl methanesulfonate in step c.

m/z 793 M$^+$ (MultiMode+).

$^1$H NMR (400 MHz, D$_6$-DMSO, 90° C.) δ 7.96 (s, 1H), 7.25-7.19 (m, 1H), 7.13-7.05 (m, 3H), 6.85 (d, J=8.2 Hz, 1H), 6.75 (d, J=8.2 Hz, 1H), 3.74-3.50 (m, 12H), 3.42-3.26 (m, 7H), 3.19-3.05 (m, 6H), 3.01-2.92 (m, 2H), 2.87-2.74 (m, 4H), 2.57-2.52 (m, 2H), 2.11-2.00 (m, 2H), 1.87-1.75 (m, 2H), 1.36 (d, J=6.9 Hz, 6H), 1.12-1.04 (m, 3H). Five exchangeable protons not observed.

The following compounds were prepared from the appropriate Carboxylic Acids and Amines using methods analogous to those described above.

EXAMPLE 36

N-Cyclohexyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide ditrifluoroacetate

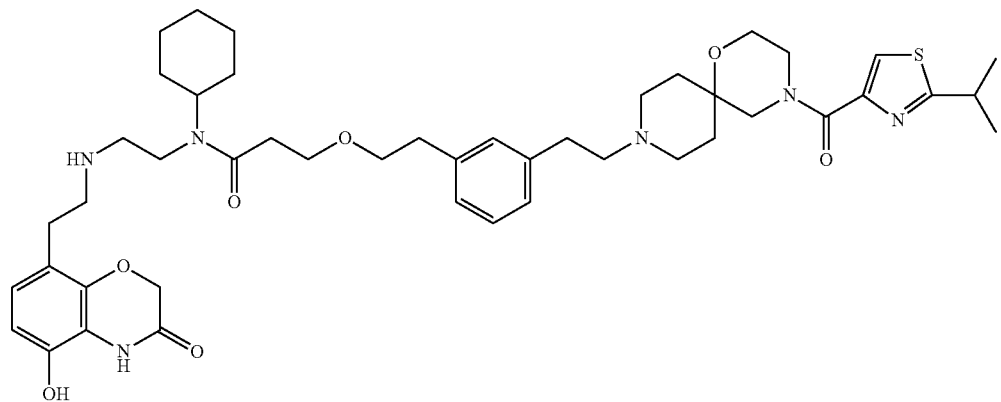

m/z 845 M$^+$ (MultiMode+).

$^1$H NMR (400 MHz, D$_6$-DMSO, 90° C.) δ 9.38 (s, 1H), 7.96 (s, 1H), 7.25-7.19 (m, 1H), 7.13-7.07 (m, 3H), 6.66 (d, J=8.5 Hz, 1H), 6.49 (d, J=8.2 Hz, 1H), 4.53 (s, 2H), 3.75-3.57 (m, 11H), 3.50-3.26 (m, 7H), 3.18-3.05 (m, 4H), 3.03-2.93 (m, 4H), 2.85-2.74 (m, 4H), 2.62-2.55 (m, 2H), 2.10-1.99 (m, 2H), 1.87-1.69 (m, 4H), 1.66-1.54 (m, 3H), 1.47-1.39 (m, 2H), 1.39-1.25 (m, 8H), 1.12-1.02 (m, 1H). Four exchangeable protons not observed.

EXAMPLE 37

(R)—N-sec-Butyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide ditrifluoroacetate

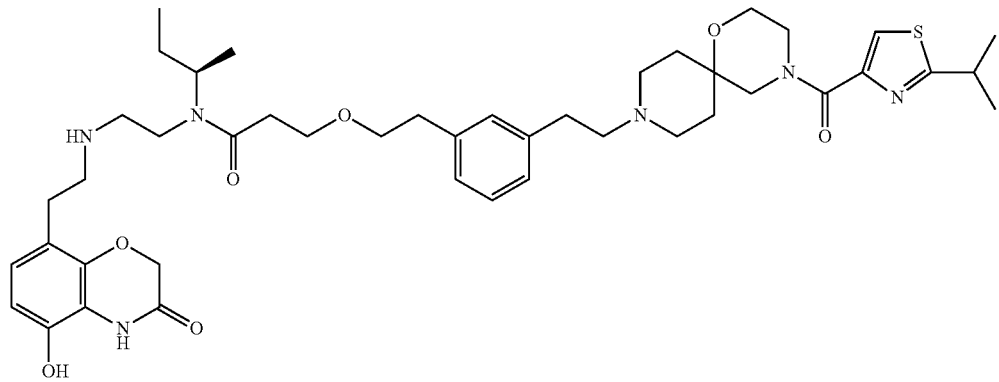

m/z 819 M⁺ (MultiMode+).

$^1$H NMR (400 MHz, D$_6$-DMSO) δ 9.81-9.76 (m, 1H), 8.01 (s, 1H), 7.17-7.09 (m, 1H), 7.07-6.98 (m, 3H), 6.61 (dd, J=8.3, 1.7 Hz, 1H), 6.42 (d, J=8.2 Hz, 1H), 4.47 (d, J=2.8 Hz, 2H), 4.22-4.15 (m, 1H), 4.11-4.06 (m, 1H), 3.77-3.50 (m, 12H), 3.34-3.27 (m, 6H), 3.21-3.00 (m, 11H), 2.44-2.34 (m, 2H), 1.73-1.38 (m, 7H), 1.34 (d, J=6.9 Hz, 6H), 1.10-1.00 (m, 3H), 0.81-0.70 (m, 3H). Two exchangeable protons not observed.

EXAMPLE 38

(R)—N-(Hexan-2-yl)-N-(2-(2-(5-hydroxy-3-oxo-3,4-dihydro-2H-benzo[b][1,4]oxazin-8-yl)ethylamino)ethyl)-3-(3-(2-(4-(2-methylthiazole-4-carbonyl)-1-oxa-4,9-diazaspiro[5.5]undecan-9-yl)ethyl)phenethoxy)propanamide ditrifluoroacetate

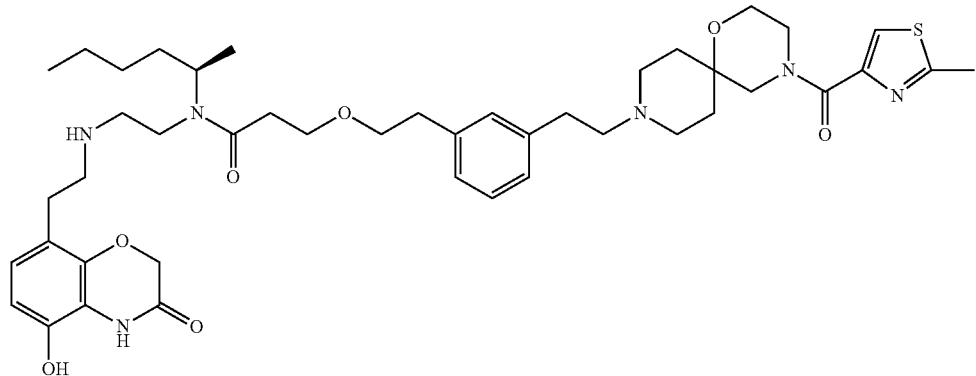

m/z 819 M⁺ (MultiMode+).

$^1$H NMR (400 MHz, CD$_3$OD) δ 7.89 (s, 1H), 7.26-7.21 (m, 1H), 7.16-7.10 (m, 3H), 6.74-6.69 (m, 1H), 6.51-6.45 (m, 1H), 4.61 (s, 2H), 4.01-3.31 (m, 14H), 3.25-2.56 (m, 20H), 2.29-2.20 (m, 3H), 1.84-1.74 (m, 2H), 1.53-1.45 (m, 2H), 1.35-1.22 (m, 3H), 1.16 (d, J=6.7 Hz, 3H), 0.90 (t, J=7.2 Hz, 3H). Five exchangeable protons not observed.

EXAMPLE 39

N-Cyclopentyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide ditrifluoroacetate N-cyclopentyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide trifluoroacetate salt (example 39) (700 mg) was partitioned between saturated aqueous sodium bicarbonate and freshly distilled 2-methyltetrahydrofuran. The organic phase was washed with saturated aqueous sodium bicarbonate (×2),

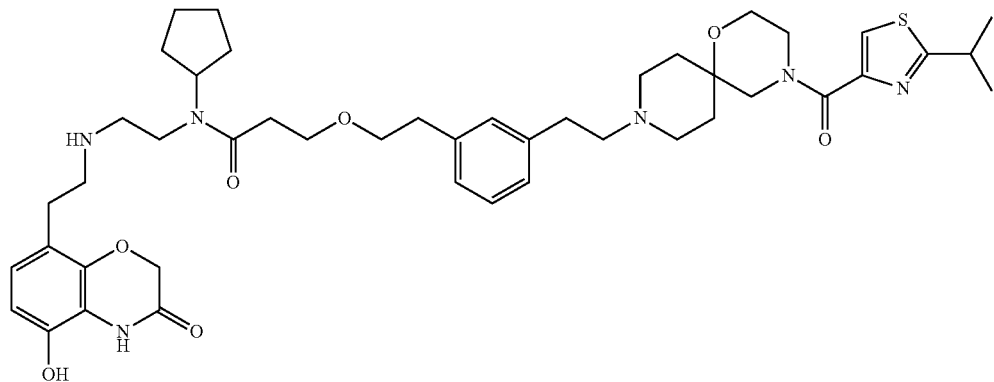

m/z 831 M⁺ (MultiMode+).

¹H NMR (400 MHz, CD₃OD) δ 7.95-7.91 (m, 1H), 7.27-7.21 (m, 1H), 7.17-7.08 (m, 3H), 6.73-6.69 (m, 1H), 6.49-6.46 (m, 1H), 4.60 (s, 2H), 4.28-4.19 (m, 1H), 3.94-3.61 (m, 10H), 3.53-3.45 (m, 3H), 3.36-3.30 (m, 2H), 3.26-3.13 (m, 6H), 3.12-3.08 (m, 2H), 3.04-2.99 (m, 2H), 2.92-2.87 (m, 2H), 2.85-2.81 (m, 2H), 2.70-2.66 (m, 2H), 2.29-2.22 (m, 2H), 1.91-1.71 (m, 6H), 1.63-1.56 (m, 2H), 1.52-1.44 (m, 2H), 1.40 (d, J=6.9 Hz, 6H). Five exchangeable protons not observed.

dried over sodium sulfate, filtered and the solvent removed to afford N-cyclopentyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide as a white foam. Yield 0.49 g. Naphthalene-1,5-disulfonic acid tetrahydrate (52.5 mg) was added to a solution of N-cyclopentyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide (121 mg) in methanol (5 mL). 0.55 mL of this solution was evaporated to dryness and ethanol (0.5 mL) added. The mixture was heated to 70° C. and allowed to cool to room temperature over 24 h. The mixture was then stirred at room temperature for 11 days. The white solid was then collected by filtration.

EXAMPLE 39a

N-Cyclopentyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy)propanamide napadisylate salt Modification A

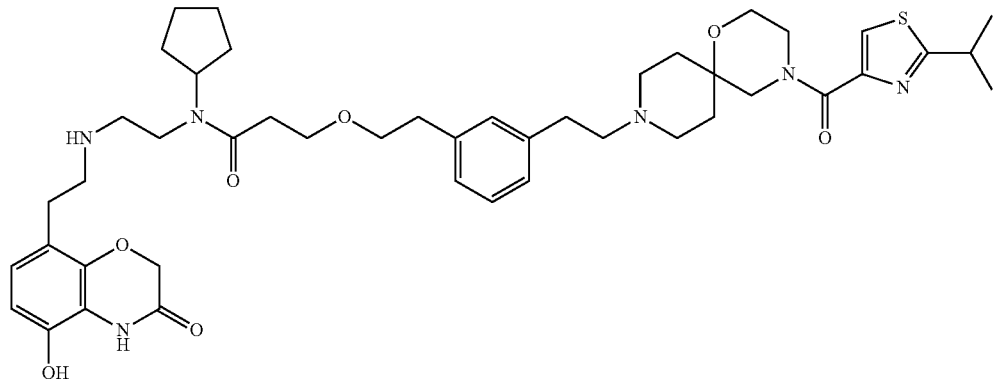

EXAMPLE 40

N-(2-(2-(5-Hydroxy-3-oxo-3,4-dihydro-2H-benzo[b] [1,4]oxazin-8-yl)ethylamino)ethyl)-N-isobutyl-3-(3-(2-(4-(2-isopropylthiazole-4-carbonyl)-1-oxa-4,9-diazaspiro[5.5]undecan-9-yl)ethyl)phenethoxy) propanamide ditrifluoroacetate

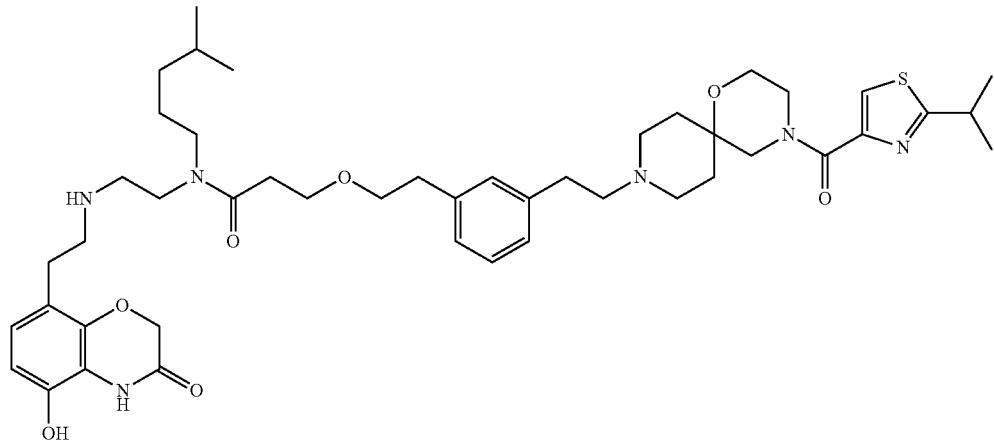

m/z 819 M⁺ (MultiMode+).

¹H NMR (400 MHz, CD$_3$OD) δ 7.96-7.88 (m, 1H), 7.26-7.20 (m, 1H), 7.15-7.08 (m, 3H), 6.73-6.69 (m, 1H), 6.50-6.46 (m, 1H), 4.60 (s, 2H), 3.95-3.30 (m, 16H), 3.26-2.97 (m, 8H), 3.05-2.98 (m, 2H), 2.91-2.86 (m, 2H), 2.84-2.78 (m, 2H), 2.63-2.57 (m, 2H), 2.30-2.22 (m, 2H), 1.96-1.89 (m, 2H), 1.84-1.74 (m, 2H), 1.39 (d, J=6.9 Hz, 6H), 0.91 (d, J=6.7 Hz, 6H). Five exchangeable protons not observed.

EXAMPLE 41

N-Benzyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethyl)phenethoxy) propanamide ditrifluoroacetate ¹H NMR (400 MHz, CD$_3$OD) δ 7.95-7.89 (m, 1H), 7.37-7.18 (m, 6H), 7.15-7.07 (m, 3H), 6.72-6.67 (m, 1H), 6.50-6.45 (m, 1H), 4.62 (s, 2H), 4.60 (s, 2H), 3.91-3.43 (m, 14H), 3.34-3.30 (m, 2H), 3.25-3.06 (m, 6H), 3.03-2.97 (m, 2H), 2.90-2.79 (m, 4H), 2.70-2.61 (m, 3H), 2.28-2.20 (m, 2H), 1.85-1.74 (m, 2H), 1.39 (d, J=6.9 Hz, 6H). Five exchangeable protons not observed.

Examples 36 to 41 were prepared using the following Carboxylic Acids and Amines:

| Example Number | Carboxylic Acid | Amine |
|---|---|---|
| 36 | 2-isopropylthiazole-4-carboxylic acid | N-(2,2-dimethoxyethyl)-cyclohexanamine [Note 1] |
| 37 | 2-isopropylthiazole-4-carboxylic acid | (R)-N-(2,2-dimethoxyethyl)butan-2-amine [Note 1] |
| 38 | 2-methylthiazole-4-carboxylic acid | (R)-N-(2,2-dimethoxyethyl)hexan-2-amine [Note 1] |

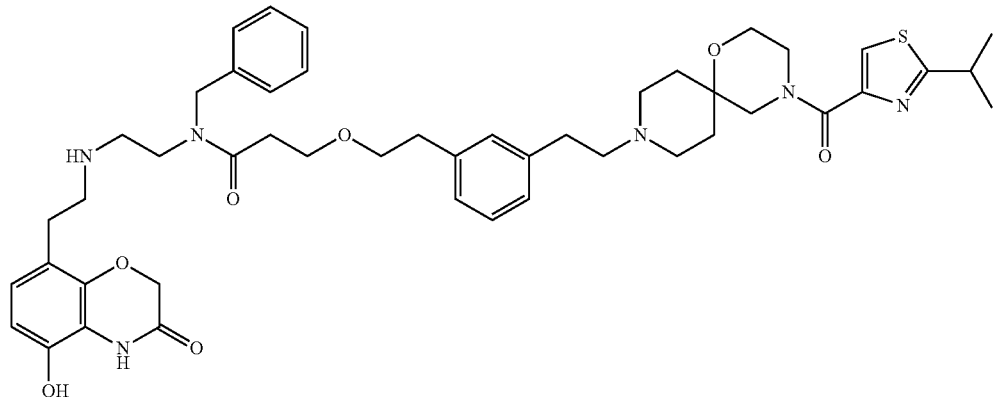

m/z 853 M⁺ (MultiMode+).

| Example Number | Carboxylic Acid | Amine |
|---|---|---|
| 39 | 2-isopropylthiazole-4-carboxylic acid | Amine 6 |
| 40 | 2-isopropylthiazole-4-carboxylic acid | Amine 8 |
| 41 | 2-isopropylthiazole-4-carboxylic acid | N-benzyl-2,2-dimethoxyethanamine [Note 2] |

[Note 1]: WO 2008075025.
[Note 2]: J. Chem. Soc., Perkin Trans. 1, 1974, 19, 2185.

EXAMPLE 42

N-Cyclohexyl-N-(2-(2-(8-hydroxy-2-oxo-1,2-dihydroquinolin-5-yl)ethylamino)ethyl)-3-(3-((4-(2-methylthiazole-4-carbonyl)-1-oxa-4,9-diazaspiro[5.5]undecan-9-yl)methyl)phenethoxy)propanamide ditrifluoroacetate

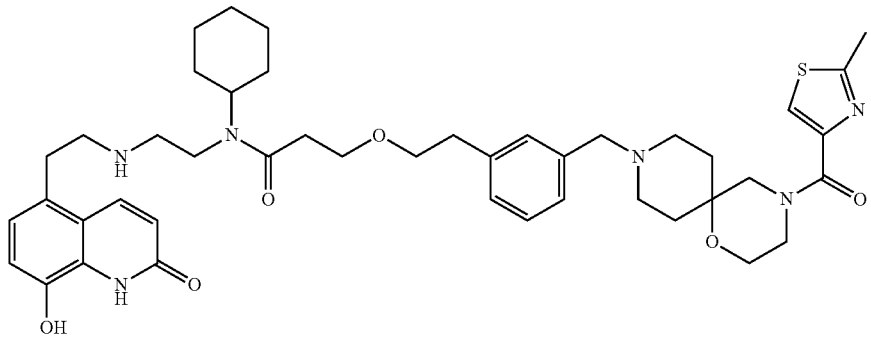

A solution of N-cyclohexyl-3-(3-((4-(2-methylthiazole-4-carbonyl)-1-oxa-4,9-diazaspiro[5.5]undecan-9-yl)methyl)phenethoxy)-N-(2-oxoethyl)propanamide (0.122 g) in NMP (2 mL) was added to a mixture of 5-(2-aminoethyl)-8-hydroxyquinolin-2(1H)-one hydrochloride [EP 0125052] (0.072 g) and acetic acid (0.011 mL). The resulting mixture was stirred for 5 min then cooled to 0° C. Sodium cyanoborohydride (0.019 g) was then added and the mixture allowed to warm to RT and stirred for 2 h. The solvent was evaporated and the residue purified by flash silica chromatography, elution gradient 95:5:0.5 to 89:10:1 DCM:MeOH: '880' aqueous ammonia. The fractions containing the product were combined, evaporated and further purified by preparative HPLC (Sunfire™, Gradient: 5-40% acetonitrile in 0.2% aqueous TFA). The fractions containing the product were combined, evaporated and triturated with ether to give the titled compound as a white solid. Yield 0.036 g.

m/z 799 (M+H)$^+$ (APCI).

$^1$H NMR (400 MHz, D$_6$-DMSO, 90° C.) δ 8.04 (d, J=9.7 Hz, 1H), 7.90 (s, 1H), 7.39-7.28 (m, 4H), 6.98-6.87 (m, 2H), 6.54 (d, J=9.7 Hz, 1H), 4.29 (s, 2H), 3.72-3.57 (m, 11H), 3.48 (t, J=6.9 Hz, 2H), 3.26-2.97 (m, 11H), 2.83 (t, J=6.8 Hz, 2H), 2.67 (s, 2H), 2.60 (t, J=6.3 Hz, 2H), 2.10-1.96 (m, 2H), 1.83-1.56 (m, 6H), 1.49-1.23 (m, 5H), 1.14-1.01 (m, 1H). Five exchangeable protons not observed.

The N-cyclohexyl-3-(3-((4-(2-methylthiazole-4-carbonyl)-1-oxa-4,9-diazaspiro[5.5]undecan-9-yl)methyl)phenethoxy)-N-(2-oxoethyl)propanamide used as a starting material was prepared as follows:

a) (2-Methylthiazol-4-yl)(1-oxa-4,9-diazaspiro[5.5]undecan-4-yl)methanone trifluoroacetate

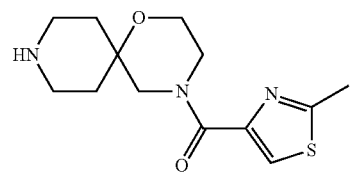

Prepared by the method of Example 3, steps a and b using 2-methylthiazole-4-carboxylic acid (1.9 g) in place of 2-ethylthiazole-4-carboxylic acid. Yield 4.6 g.

$^1$H NMR (300 MHz, D$_6$-DMSO) δ 8.59-8.18 (m, 2H), 8.00 (s, 1H), 3.86-3.49 (m, 6H), 3.22-2.86 (m, 4H), 2.69 (s, 3H), 2.00-1.90 (m, 2H), 1.74-1.58 (m, 2H).

b) 9-(3-(2-Hydroxyethyl)benzyl)-1-oxa-4,9-diazaspiro[5.5]undecan-4-yl)(2-methylthiazol-4-yl)methanone

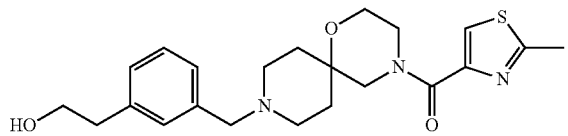

(2-Methylthiazol-4-yl)(1-oxa-4,9-diazaspiro[5.5]undecan-4-yl)methanone trifluoroacetate [Example 42, step a] (2.2 g) was added to a solution of 2-(3-(bromomethyl)phenyl)ethanol [EP 0472449] (1.2 g) and triethylamine (2.3 mL) in acetonitrile (30 mL). The resulting mixture was stirred overnight at RT under nitrogen. The solvent was evaporated and the residue purified by silica gel chromatography, gradient elution 99:1:0.1 to 97:3:0.3 DCM:MeOH:'880' aqueous ammonia to give the subtitled compound as a clear foam. Yield 1.72 g.

$^1$H NMR (400 MHz, D$_6$-DMSO) δ 7.85 (s, 1H), 7.18 (t, J=7.4 Hz, 1H), 7.12-7.04 (m, 3H), 4.24 (t, J=5.1 Hz, 1H), 3.71-3.54 (m, 8H), 3.42 (s, 2H), 2.71 (t, J=6.9 Hz, 2H), 2.68 (s, 3H), 2.38-2.27 (m, 4H), 1.74-1.64 (m, 2H), 1.57-1.47 (m, 2H).

c) N-Cyclohexyl-N-(2,2-dimethoxyethyl)-3-(3-((4-(2-methylthiazole-4-carbonyl)-1-oxa-4,9-diazaspiro[5.5]undecan-9-yl)methyl)phenethoxy)propanamide

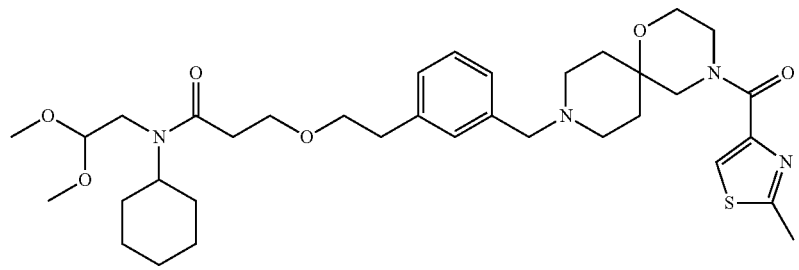

Prepared by the method of Example 1, steps d, e, and f using 94342-hydroxyethyl)benzyl)-1-oxa-4,9-diazaspiro[5.5]undecan-4-yl)(2-methylthiazol-4-yl)methanone [Example 42, step b] (1.72 g) in place of (9-(4-(2-hydroxyethyl)phenethyl)-1-oxa-4,9-diazaspiro[5.5]undecan-4-yl)(2-isopropylthiazol-4-yl)methanone and N-(2,2-dimethoxyethyl)cyclohexanamine [WO 2008075025] (0.93 g) in place of N-ethyl-2,2-dimethoxyethanamine. Yield 0.90 g.

m/z 657 (M+H)$^+$ (APCI).

d) N-Cyclohexyl-3-(3-((4-(2-methylthiazole-4-carbonyl)-1-oxa-4,9-diazaspiro[5.5]undecan-9-yl)methyl)phenethoxy)-N-(2-oxoethyl)propanamide

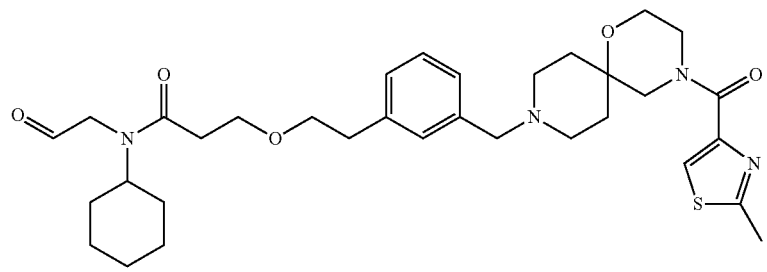

Tosic acid monohydrate (1.38 g) was added to a solution of N-cyclohexyl-N-(2,2-dimethoxyethyl)-3-(3-((4-(2-methylthiazole-4-carbonyl)-1-oxa-4,9-diazaspiro[5.5]undecan-9-yl)methyl)phenethoxy)propanamide (0.68 g) in DCM (10 mL) and the resulting mixture stirred at RT until consumption of the acetal was complete (4 h). Saturated sodium bicarbonate solution (10 mL) was cautiously added and the mixture was stirred until bubbling ceased (10 min). The reaction mixture was diluted with DCM (50 mL) and the aqueous phase separated. The organic phase was washed with saturated sodium bicarbonate solution (2×20 mL) and brine (20 mL), dried over sodium sulphate, filtered and evaporated to give the subtitled compound as a gum. Yield 0.61 g.

m/z 611 (M+H)$^+$ (APCI).

EXAMPLE 43

N-Ethyl-3-(2-fluoro-5-((4-(2-isopropylthiazole-4-carbonyl)-1-oxa-4,9-diazaspiro[5.5]undecan-9-yl)methyl)phenethoxy)-N-(2-(2-(4-hydroxy-2-oxo-2,3-dihydrobenzo[d]thiazol-7-yl)ethylamino)ethyl)propanamide ditrifluoroacetate

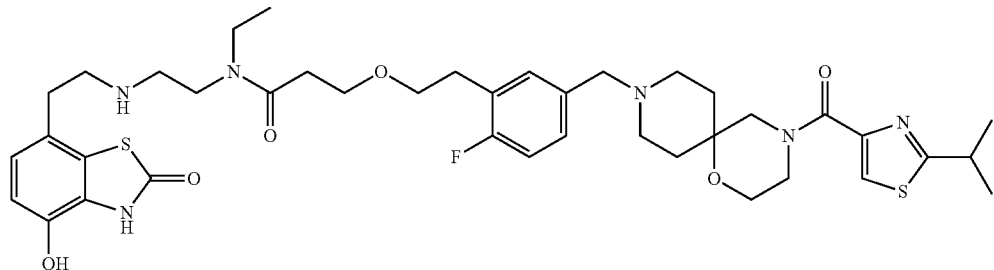

Prepared by the method of Example 1, from step d using (9-(4-fluoro-3-(2-hydroxyethyl)benzyl)-1-oxa-4,9-diazaspiro[5.5]undecan-4-yl)(2-isopropylthiazol-4-yl)methanone (0.25 g) in place of (9-(4-(2-hydroxyethyl)phenethyl)-1-oxa-4,9-diazaspiro[5.5]undecan-4-yl)(2-isopropylthiazol-4-yl)methanone in step d. Yield 0.13 g.

m/z 797 M$^+$ (MultiMode+).

$^1$H NMR (300 MHz, D$_6$-DMSO, 90° C.) δ 11.45 (s, 1H), 8.71 (s, 1H), 7.96 (s, 1H), 7.51-7.37 (m, 2H), 7.24-7.15 (m, 1H), 6.85 (d, J=8.3 Hz, 1H), 6.75 (d, J=8.3 Hz, 1H), 4.29 (s, 2H), 3.76-3.00 (m, 23H), 2.84 (t, J=7.0 Hz, 4H), 2.55 (t, J=6.9 Hz, 2H), 2.11-1.96 (m, 2H), 1.86-1.65 (m, 2H), 1.34 (d, J=6.9 Hz, 6H), 1.13-1.05 (m, 3H). Three exchangeable protons not observed.

The (9-(4-fluoro-3-(2-hydroxyethyl)benzyl)-1-oxa-4,9-diazaspiro[5.5]undecan-4-yl)(2-isopropylthiazol-4-yl)methanone used a starting material was prepared as follows:

a) (9-(4-Fluoro-3-(2-hydroxyethyl)benzyl)-1-oxa-4,9-diazaspiro[5.5]undecan-4-yl)(2-isopropylthiazol-4-yl)methanone

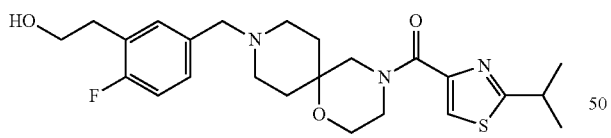

A solution of 2-(5-(bromomethyl)-2-fluorophenyl)ethanol [Aromatic Intermediate 2] (5.17 g) in ethanol (20 mL) was added dropwise to a suspension of (2-isopropylthiazol-4-yl)(1-oxa-4,9-diazaspiro[5.5]undecan-4-yl)methanone trifluoroacetate [Example 1, step b] (9.4 g) and potassium carbonate (6.75 g) in ethanol (75 mL) and the resulting mixture stirred overnight. The mixture was filtered, the filter cake was washed with ethanol (50 mL), and the filtrate and washings combined and evaporated. The residue was partitioned between water (100 mL) and ethyl acetate (250 mL). The phases were separated and the organic phase washed with brine (100 mL), dried over sodium sulphate, filtered and evaporated. The residue was purified by flash silica chromatography using 95:5 ethyl acetate:triethylamine as solvent to give the subtitled compound as a clear oil. Yield 7.9 g.

m/z 462 (M+H)$^+$ (APCI).

EXAMPLE 44

N-Ethyl-3-(4-fluoro-3-((4-(2-isopropylthiazole-4-carbonyl)-1-oxa-4,9-diazaspiro[5.5]undecan-9-yl)methyl)phenethoxy)-N-(2-(2-(4-hydroxy-2-oxo-2,3-dihydrobenzo[d]thiazol-7-yl)ethylamino)ethyl)propanamide

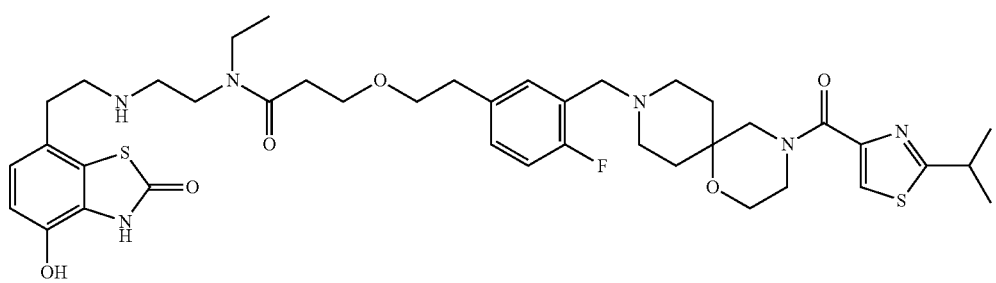

Prepared by the method of Example 1, from step d using (9-(2-fluoro-5-(2-hydroxyethyl)benzyl)-1-oxa-4,9-diazaspiro[5.5]undecan-4-yl)(2-isopropylthiazol-4-yl)methanone (0.19 g) in place of (9-(4-(2-hydroxyethyl)phenethyl)-1-oxa-4,9-diazaspiro[5.5]undecan-4-yl)(2-isopropylthiazol-4-yl) methanone in step d. Yield 0.12 g.

m/z 797 M+ (MultiMode+).

$^1$H NMR (400 MHz, D$_6$-DMSO, 90° C.) δ 7.94 (s, 1H), 7.44-7.32 (m, 2H), 7.21-7.14 (m, 1H), 6.85 (d, J=8.2 Hz, 1H), 6.74 (d, J=8.2 Hz, 1H), 4.24 (s, 2H), 3.76-3.50 (m, 12H), 3.41-3.28 (m, 3H), 3.20-3.00 (m, 8H), 2.88-2.77 (m, 4H), 2.59-2.52 (m, 2H), 2.07-1.96 (m, 2H), 1.81-1.70 (m, 2H), 1.35 (d, J=6.9 Hz, 6H), 1.13-1.05 (m, 3H). Five exchangeable protons not observed.

The (9-(2-fluoro-5-(2-hydroxyethyl)benzyl)-1-oxa-4,9-diazaspiro[5.5]undecan-4-yl)(2-isopropylthiazol-4-yl) methanone used a starting material was prepared as follows:

a) 1-(9-(5-(2-(tert-Butyldimethylsilyloxy)ethyl)-2-fluorobenzyl)-1-oxa-4,9-diazaspiro[5.5]undecan-4-yl)-2,2,2-trifluoroethanone

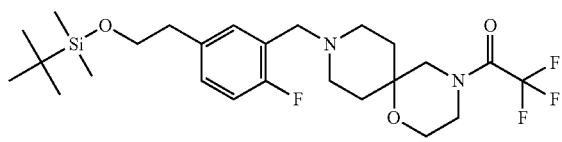

Methanesulphonyl chloride (1.3 mL) in DCM (20 mL) was added dropwise to a solution at 0° C. of (5-(2-(tert-butyldimethylsilyloxy)ethyl)-2-fluorophenyl)methanol [Aromatic Intermediate 3] (4.66 g) and triethylamine (2.5 mL) in DCM (100 mL). The mixture was stirred at 0° C. for 1 hour and then washed with water. The organic layer was dried, filtered and the solvent evaporated under reduced pressure. The resultant intermediate (5.9 g) was added portionwise over 30 minutes to a stirred solution at 20° C. of 2,2,2-trifluoro-1-(1-oxa-4,9-diazaspiro[5.5]undecan-4-yl)ethanone trifluoroacetate [Example 9, step a] (6 g) and triethylamine (9.1 mL) in acetonitrile (130 mL). The reaction mixture was stirred for 4 hours at 20° C. The solvent was evaporated under reduced pressure and the residue partitioned between ethyl acetate and brine. The organic layer was dried, filtered and the solvent evaporated under reduced pressure to give the subtitled compound. Yield 8.5 g.

m/z 519 (M+H)+ (APCI).

b) 2,2,2-Trifluoro-1-(9-(2-fluoro-5-(2-hydroxyethyl) benzyl)-1-oxa-4,9-diazaspiro[5.5]undecan-4-yl)ethanone

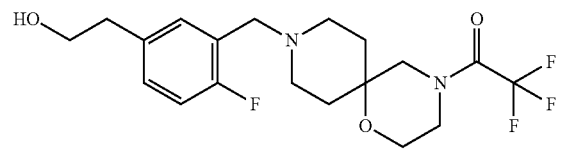

TBAF (1M in THF, 16.4 mL) was added to a solution of 1-(9-(5-(2-(tert-butyldimethylsilyloxy)ethyl)-2-fluorobenzyl)-1-oxa-4,9-diazaspiro[5.5]undecan-4-yl)-2,2,2-trifluoroethanone [Example 44, step a] (8.5 g) in THF (100 mL) and the resultant solution allowed to stand at 20° C. for 18 hours. The solvent was evaporated under reduced pressure and the residue was purified by flash silica chromatography, using 2% methanol in dichloromethane containing 1% triethylamine as solvent. Fractions containing the product were evaporated to dryness to afford the subtitled compound. Yield 4.2 g.

m/z 405 (M+H)+ (APCI).

c) 2-(3-(1-Oxa-4,9-diazaspiro[5.5]undecan-9-ylmethyl)-4-fluorophenyl)ethanol

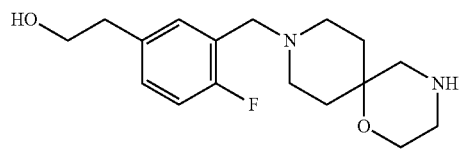

A solution of sodium carbonate (1.4 g) in water (40 mL) was added to a solution of 2,2,2-trifluoro-1-(9-(2-fluoro-5-(2-hydroxyethyl)benzyl)-1-oxa-4,9-diazaspiro[5.5]undecan-4-yl)ethanone [Example 44, step b] (4.2 g) in acetonitrile (40 mL). The reaction mixture was stirred at 20° C. for 20 hours. The acetonitrile was removed under reduced pressure and the remaining aqueous solution was extracted with DCM (×9). The combined DCM extracts were dried, filtered and the solvent removed under reduced pressure to yield the subtitled compound. Yield 2.7 g.

m/z 309 (M+H)+ (APCI).

d) (9-(2-Fluoro-5-(2-hydroxyethyl)benzyl)-1-oxa-4,9-diazaspiro[5.5]undecan-4-yl)(2-isopropylthiazol-4-yl)methanone

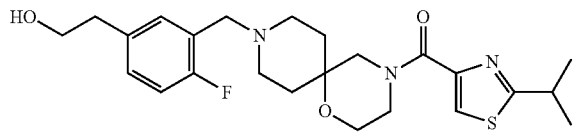

HATU (1.1 g) was added in one portion to a cooled solution of 2-(3-(1-oxa-4,9-diazaspiro[5.5]undecan-9-ylmethyl)-4-fluorophenyl)ethanol [Example 44, step c] (0.7 g) and 2-isopropylthiazole-4-carboxylic acid (0.39 g) and triethylamine (0.95 mL) in DMF (15 mL). The reaction mixture was stirred at 20° C. for 1 hour and then partitioned between ethyl acetate and brine. The organic layer was washed with brine (×2), dried, filtered and the solvent removed under reduced pressure. The crude product was purified by flash silica chromatography, using 3% methanol in ethyl acetate containing 1% triethylamine as solvent. Fractions containing the product were evaporated to dryness to afford the subtitled compound. Yield 0.61 g.

m/z 462 (M+H)+ (APCI).

The following compounds were prepared from the appropriate Aromatic Intermediates, Carboxylic Acids and Amines using methods analogous to all of those described above.

EXAMPLE 45

N-Cyclohexyl-N-(2-(2-(5-hydroxy-3-oxo-3,4-dihydro-2H-benzo[b][1,4]oxazin-8-yl)ethylamino)ethyl)-3-(4-((4-(2-methylthiazole-4-carbonyl)-1-oxa-4,9-diazaspiro[5.5]undecan-9-yl)methyl)phenethoxy)propanamide ditrifluoroacetate

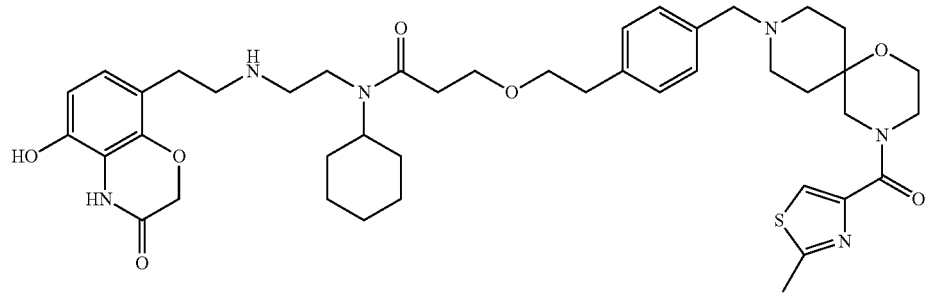

m/z 803 M⁺ (MultiMode+).

$^1$H NMR (400 MHz, D$_6$-DMSO, 90° C.) δ 9.40 (s, 1H), 7.90 (s, 1H), 7.41 (d, J=7.9 Hz, 2H), 7.30 (d, J=7.9 Hz, 2H), 6.66 (d, J=8.2 Hz, 1H), 6.49 (d, J=8.5 Hz, 1H), 4.53 (s, 2H), 4.27 (s, 2H), 3.73-3.56 (m, 12H), 3.50-3.43 (m, 2H), 3.23-2.96 (m, 8H), 2.85-2.79 (m, 4H), 2.67 (s, 2H), 2.60 (t, J=6.3 Hz, 2H), 2.10-1.92 (m, 2H), 1.81-1.55 (m, 6H), 1.49-1.23 (m, 5H), 1.13-1.03 (m, 1H). Four exchangeable protons not observed.

EXAMPLE 46

3-(2-Chloro-5-((4-(2-methylthiazole-4-carbonyl)-1-oxa-4,9-diazaspiro[5.5]undecan-9-yl)methyl)phenethoxy)-N-ethyl-N-(2-(2-(4-hydroxy-2-oxo-2,3-dihydrobenzo[d]thiazol-7-yl)ethylamino)ethyl)propanamide ditrifluoroacetate

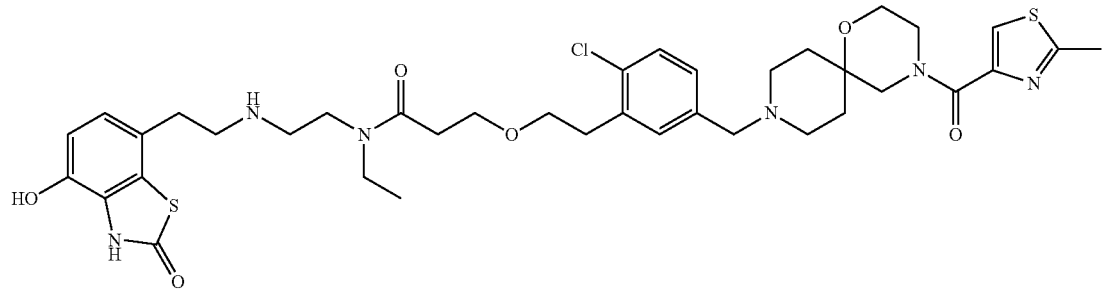

m/z 785 M⁺ (MultiMode+).

$^1$H NMR (400 MHz, D$_6$-DMSO, 90° C.) δ 7.89 (s, 1H), 7.52-7.42 (m, 2H), 7.35 (d, J=7.9 Hz, 1H), 6.85 (d, J=8.2 Hz, 1H), 6.74 (d, J=8.2 Hz, 1H), 4.20 (br s, 2H), 3.78-3.58 (m, 10H), 3.53 (t, J=6.5 Hz, 2H), 3.44-3.21 (m, 6H), 3.16 (t, J=8.0 Hz, 2H), 3.10 (t, J=6.2 Hz, 2H), 2.95 (t, J=6.9 Hz, 2H), 2.83 (t, J=8.0 Hz, 2H), 2.67 (s, 3H), 2.56 (t, J=6.5 Hz, 2H), 2.06-1.91 (m, 2H), 1.84-1.66 (m, 2H), 1.09 (t, J=6.9 Hz, 3H). Five exchangeable protons not observed.

EXAMPLE 47

N-Cyclohexyl-3-(3-fluoro-5-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

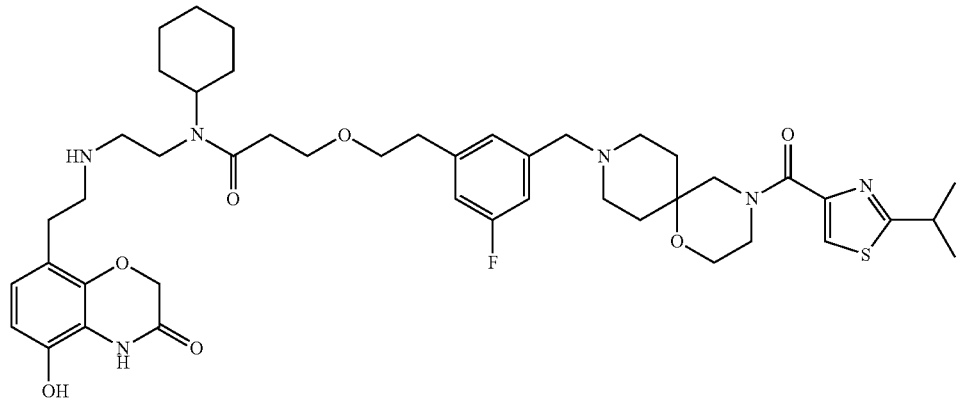

m/z 849 M⁺ (MultiMode+).

$^1$H NMR (500 MHz, D$_6$-DMSO, 90° C.) δ 9.35 (s, 1H), 8.40 (s, 1H), 7.93 (s, 1H), 7.19-7.09 (m, 3H), 6.66 (d, J=8.3 Hz, 1H), 6.49 (d, J=8.3 Hz, 1H), 4.53 (s, 2H), 4.19 (s, 2H), 3.73-3.62 (m, 11H), 3.48-3.43 (m, 2H), 3.33-3.27 (m, 1H), 3.13-2.97 (m, 8H), 2.86-2.80 (m, 4H), 2.61-2.56 (m, 2H), 2.04-1.94 (m, 2H), 1.79-1.71 (m, 4H), 1.65-1.57 (m, 3H), 1.48-1.38 (m, 2H), 1.38-1.26 (m, 8H), 1.12-1.06 (m, 1H). Three exchangeable protons not observed.

EXAMPLE 48

N-Ethyl-N-(2-(2-(4-hydroxy-2-oxo-2,3-dihydrobenzo[d]thiazol-7-yl)ethylamino)ethyl)-3-(2-(5-((4-(2-isopropylthiazole-4-carbonyl)-1-oxa-4,9-diazaspiro[5.5]undecan-9-yl)methyl)thiophen-3-yl)ethoxy)propanamide ditrifluoroacetate

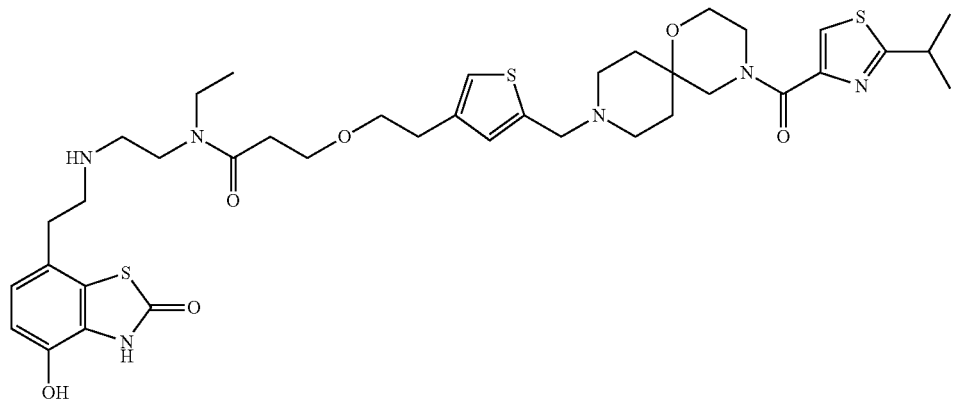

m/z 785 M⁺ (MultiMode+).

¹H NMR (400 MHz, D₆-DMSO, 90° C.) δ 7.94 (s, 1H), 7.29 (s, 1H), 7.13 (s, 1H), 6.84 (d, J=8.4 Hz, 1H), 6.74 (d, J=8.4 Hz, 1H), 4.50-4.38 (m, 2H), 3.78-3.50 (m, 12H), 3.40-3.25 (m, 3H), 3.25-2.95 (m, 8H), 2.90-2.78 (m, 4H), 2.60-2.55 (m, 2H), 2.11-1.95 (m, 2H), 1.82-1.62 (m, 2H), 1.35 (d, J=6.8 Hz, 6H), 1.09 (t, J=7.2 Hz, 3H). Five exchangeable protons not observed.

EXAMPLE 49

3-(4-Chloro-3-((4-(2-isopropylthiazole-4-carbonyl)-1-oxa-4,9-diazaspiro[5.5]undecan-9-yl)methyl) phenethoxy)-N-cyclohexyl-N-(2-(2-(5-hydroxy-3-oxo-3,4-dihydro-2H-benzo[b][1,4]oxazin-8-yl) ethylamino)ethyl)propanamide ditrifluoroacetate

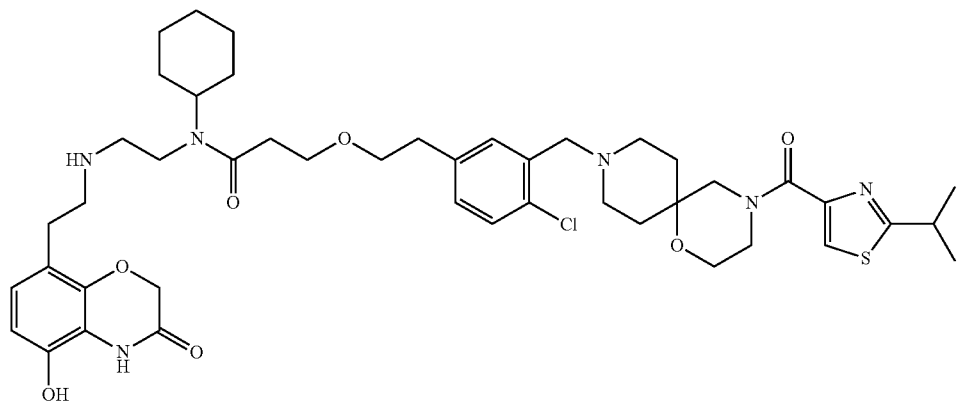

m/z 865 M⁺ (MultiMode+).

¹H NMR (500 MHz, D₆-DMSO, 90° C.) δ 9.34 (s, 1H), 8.59 (s, 2H), 7.93 (s, 1H), 7.53 (s, 1H), 7.42 (d, J=8.2 Hz, 1H), 7.33-7.29 (m, 1H), 6.66 (d, J=8.3 Hz, 1H), 6.49 (d, J=8.3 Hz, 1H), 4.53 (s, 2H), 4.30 (s, 2H), 3.73-3.61 (m, 11H), 3.49-3.44 (m, 2H), 3.34-3.26 (m, 1H), 3.19-3.06 (m, 6H), 3.03-2.98 (m, 2H), 2.85-2.78 (m, 4H), 2.60-2.55 (m, 2H), 2.04-1.97 (m, 2H), 1.84-1.72 (m, 4H), 1.65-1.57 (m, 3H), 1.48-1.39 (m, 2H), 1.36-1.26 (m, 8H), 1.13-1.03 (m, 1H). Two exchangeable protons not observed.

EXAMPLE 50

3-(3-Chloro-5-((4-(2-isopropylthiazole-4-carbonyl)-1-oxa-4,9-diazaspiro[5.5]undecan-9-yl)methyl)phenethoxy)-N-ethyl-N-(2-(2-(4-hydroxy-2-oxo-2,3-dihydrobenzo[d]thiazol-7-yl)ethylamino)ethyl)propanamide ditrifluoroacetate

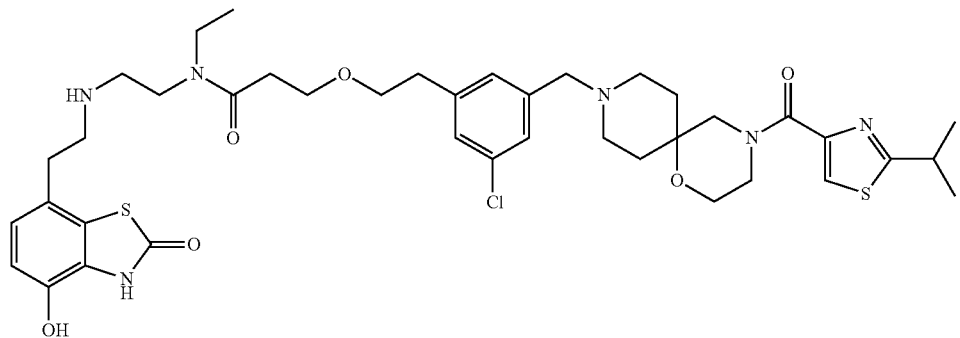

m/z 813 M+ (MultiMode+).

$^1$H NMR (500 MHz, D$_6$-DMSO, 90° C.) δ 7.93 (s, 1H), 7.42 (s, 1H), 7.36 (s, 1H), 7.32 (s, 1H), 6.85 (d, J=8.3 Hz, 1H), 6.75 (d, J=8.3 Hz, 1H), 4.24 (s, 2H), 3.73-3.61 (m, 10H), 3.54 (t, J=6.6 Hz, 2H), 3.35-3.27 (m, 3H), 3.19-3.03 (m, 8H), 2.87-2.80 (m, 4H), 2.55 (t, J=6.5 Hz, 2H), 2.06-1.99 (m, 2H), 1.82-1.73 (m, 2H), 1.35 (d, J=6.9 Hz, 6H), 1.12-1.06 (m, 3H). Five exchangeable protons not observed.

EXAMPLE 51

N-Cyclohexyl-N-(2-(2-(5-hydroxy-3-oxo-3,4-dihydro-2H-benzo[b][1,4]oxazin-8-yl)ethylamino)ethyl)-3-(4-(2-(4-(2-isopropylthiazole-4-carbonyl)-1-oxa-4,9-diazaspiro[5.5]undecan-9-yl)ethoxy)phenethoxy)propanamide ditrifluoroacetate

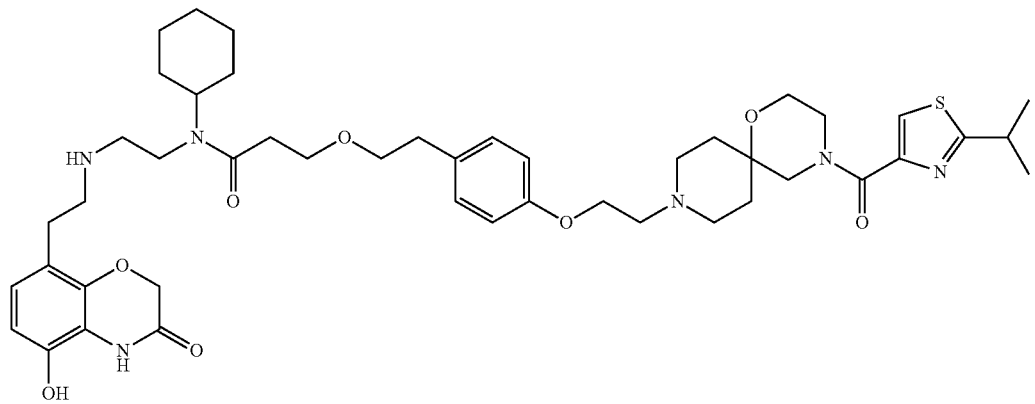

m/z 861 M+ (MultiMode+).

¹H NMR (500 MHz, D₆-DMSO, 90° C.) δ 9.34 (s, 1H), 8.52 (s, 1H), 7.95 (s, 1H), 7.15 (d, J=7.9 Hz, 2H), 6.89 (d, J=7.0 Hz, 2H), 6.66 (d, J=7.9 Hz, 1H), 6.49 (d, J=7.9 Hz, 1H), 4.53 (s, 2H), 4.30 (s, 2H), 3.77-3.64 (m, 9H), 3.62-3.56 (m, 2H), 3.52-3.45 (m, 4H), 3.41-3.29 (m, 3H), 3.25-3.17 (m, 2H), 3.15-3.09 (m, 2H), 3.04-2.99 (m, 2H), 2.87-2.81 (m, 2H), 2.78-2.72 (m, 2H), 2.63-2.56 (m, 2H), 2.09-2.02 (m, 2H), 1.89-1.71 (m, 4H), 1.68-1.57 (m, 3H), 1.49-1.40 (m, 2H), 1.39-1.28 (m, 8H), 1.14-1.05 (m, 1H). Three exchangeable protons not observed.

EXAMPLE 52

N-Ethyl-N-(2-(2-(4-hydroxy-2-oxo-2,3-dihydrobenzo[d]thiazol-7-yl)ethylamino)ethyl)-3-(2-(5-(2-(4-(2-isopropylthiazole-4-carbonyl)-1-oxa-4,9-diazaspiro[5.5]undecan-9-yl)ethyl)thiophen-2-yl)ethoxy)propanamide ditrifluoroacetate

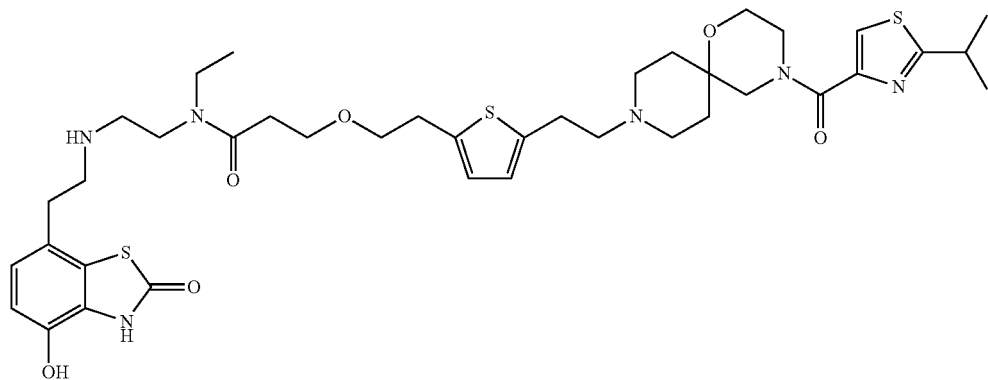

m/z 799 M⁺ (MultiMode+).

¹H NMR (500 MHz, D₆-DMSO, 90° C.) δ 11.26 (s, 1H), 8.70 (s, 1H), 7.95 (s, 1H), 6.90-6.83 (m, 1H), 6.80-6.69 (m, 3H), 3.76-3.64 (m, 8H), 3.63-3.50 (m, 4H), 3.44-3.27 (m, 7H), 3.23-3.07 (m, 8H), 2.98-2.92 (m, 2H), 2.89-2.82 (m, 2H), 2.62-2.56 (m, 2H), 2.10-2.00 (m, 2H), 1.87-1.74 (m, 2H), 1.36 (d, J=6.6 Hz, 6H), 1.15-1.06 (m, 3H). Three exchangeable protons not observed.

EXAMPLE 53

N-Cyclohexyl-N-(2-(2-(5-hydroxy-3-oxo-3,4-dihydro-2H-benzo[b][1,4]oxazin-8-yl)ethylamino)ethyl)-3-(3-(2-(4-(2-isopropylthiazole-4-carbonyl)-1-oxa-4,9-diazaspiro[5.5]undecan-9-yl)ethoxy)phenethoxy)propanamide ditrifluoroacetate

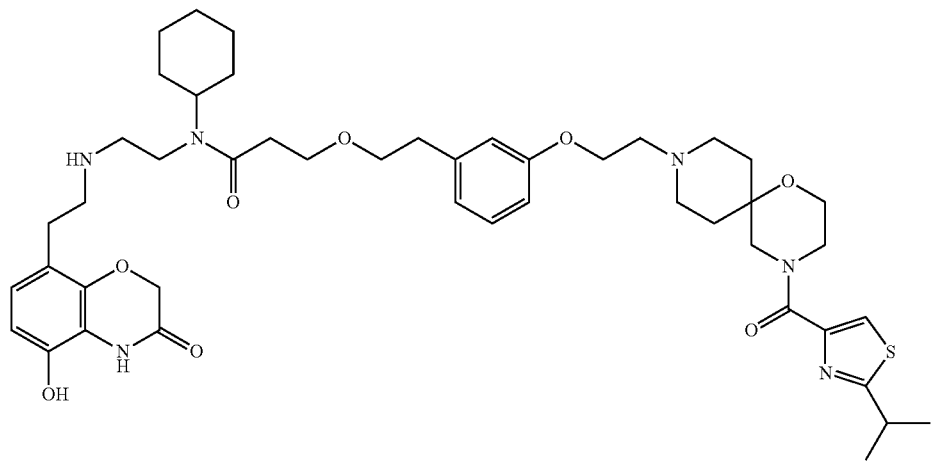

m/z 861 M⁺ (MultiMode+).

¹H NMR (400 MHz, D₆-DMSO, 90° C.) δ 9.42-9.37 (m, 1H), 8.50-8.41 (m, 1H), 7.96 (s, 1H), 7.24-7.18 (m, 1H), 6.88-6.80 (m, 3H), 6.66 (d, J=8.2 Hz, 1H), 6.49 (d, J=8.2 Hz, 1H), 4.54-4.52 (m, 2H), 4.35-4.30 (m, 2H), 3.74-3.59 (m, 11H), 3.54-3.17 (m, 10H), 3.13-3.08 (m, 2H), 3.03-2.98 (m, 2H), 2.85-2.75 (m, 4H), 2.62-2.57 (m, 2H), 2.12-2.01 (m, 2H), 1.88-1.72 (m, 4H), 1.67-1.55 (m, 3H), 1.49-1.25 (m, 10H), 1.13-1.02 (m, 1H). Two exchangeable protons not observed.

EXAMPLE 54

N-Cyclopentyl-N-(2-(2-(5-hydroxy-3-oxo-3,4-dihydro-2H-benzo[b][1,4]oxazin-8-yl)ethylamino)ethyl)-3-(3-(3-((4-(2-isopropylthiazole-4-carbonyl)-1-oxa-4,9-diazaspiro[5.5]undecan-9-yl)methyl)phenylthio)propoxy)propanamide ditrifluoroacetate

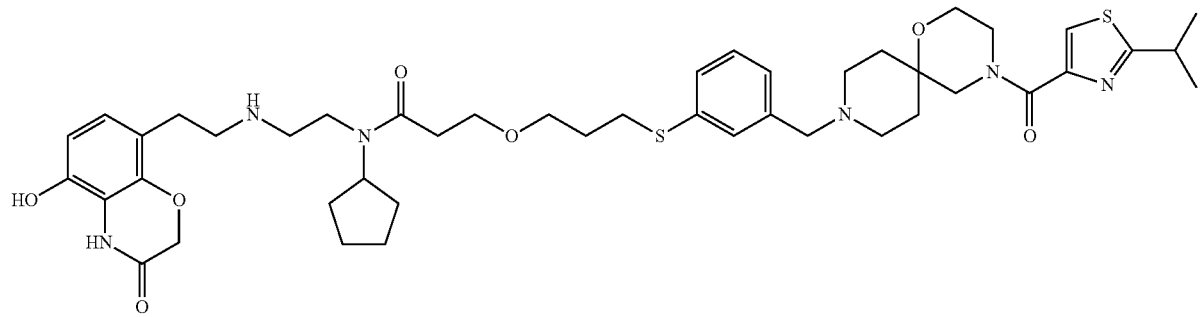

m/z 863 M⁺ (MultiMode+).

¹H NMR (400 MHz, D₆-DMSO, 90° C.) δ 9.40 (s, 1H), 7.94 (s, 1H), 7.45 (s, 1H), 7.41-7.33 (m, 2H), 7.32-7.25 (m, 1H), 6.66 (d, J=8.2 Hz, 1H), 6.48 (d, J=8.5 Hz, 1H), 4.53 (s, 2H), 4.30-4.15 (m, 3H), 3.75-3.58 (m, 8H), 3.53-3.23 (m, 7H), 3.17-2.93 (m, 8H), 2.82 (t, J=7.7 Hz, 2H), 2.62 (t, J=6.7 Hz, 2H), 2.10-1.91 (m, 2H), 1.81 (quintet, J=6.6 Hz, 2H), 1.74-1.60 (m, 6H), 1.60-1.39 (m, 4H), 1.35 (d, J=6.9 Hz, 6H). Four exchangeable protons not observed.

EXAMPLE 55

N-(2-(2-(4-Hydroxy-2-oxo-2,3-dihydrobenzo[d]thiazol-7-yl)ethylamino)ethyl)-3-(2-(3-04-(2-isopropylthiazole-4-carbonyl)-1-oxa-4,9-diazaspiro[5.5]undecan-9-yl)methyl)phenylthio)ethoxy)-N-methylpropanamide ditrifluoroacetate

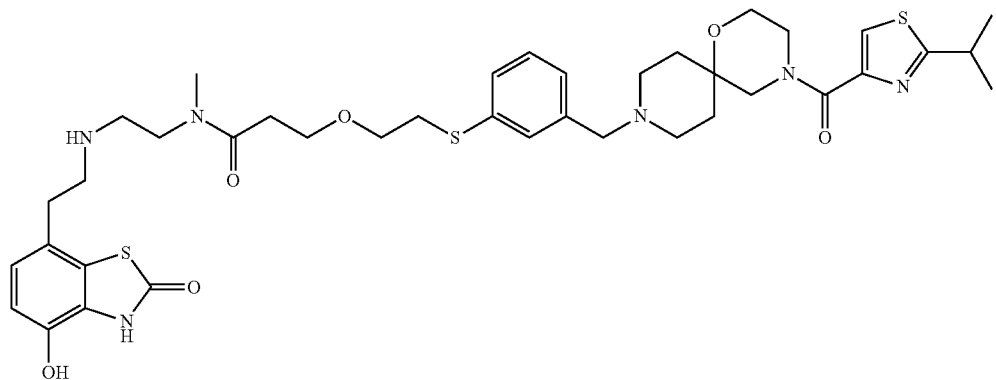

m/z 797 M⁺ (MultiMode+).

¹H NMR (400 MHz, D₆-DMSO, 90° C.) δ 7.94 (s, 1H), 7.48 (s, 1H), 7.43-7.34 (m, 2H), 7.32-7.26 (m, 1H), 6.84 (d, J=8.5 Hz, 1H), 6.74 (d, J=8.2 Hz, 1H), 4.23 (s, 2H), 3.73-3.60 (m, 10H), 3.57 (t, J=6.5 Hz, 2H), 3.54-3.23 (m, 3H), 3.22-2.88 (m, 11H), 2.88-2.79 (m, 2H), 2.57 (t, J=6.5 Hz, 2H), 2.10-1.92 (m, 2H), 1.83-1.62 (m, 2H), 1.35 (d, J=6.7 Hz, 6H). Five exchangeable protons not observed.

EXAMPLE 56

N-Cyclohexyl-N-(2-(2-(5-hydroxy-3-oxo-3,4-dihydro-2H-benzo[b][1,4]oxazin-8-yl)ethylamino)ethyl)-3-(2-(4-((4-(2-isopropylthiazole-4-carbonyl)-1-oxa-4,9-diazaspiro[5.5]undecan-9-yl)methyl)thiophen-2-yl)ethoxy)propanamide ditrifluoroacetate

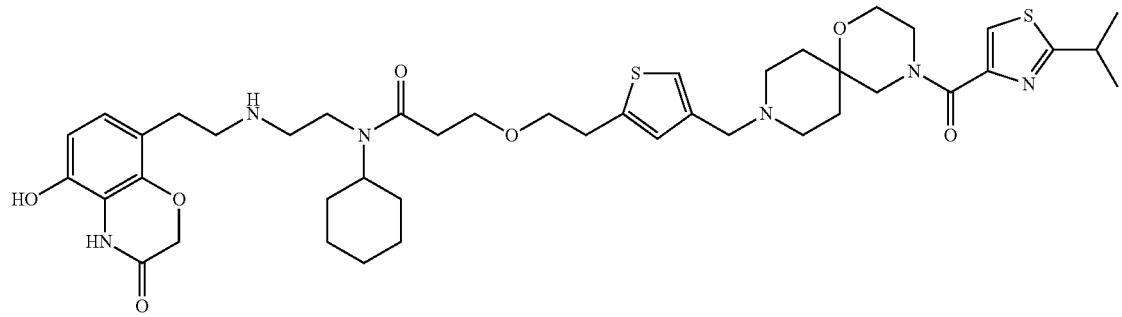

m/z 837 M⁺ (MultiMode+).

$^1$H NMR (500 MHz, D$_6$-DMSO, 90° C.) δ 9.42-9.33 (m, 1H), 8.66 (s, 1H), 7.96 (d, J=2.3 Hz, 1H), 7.49 (s, 1H), 6.99 (s, 1H), 6.69 (d, J=8.4 Hz, 1H), 6.52 (d, J=8.2 Hz, 1H), 4.61-4.54 (m, 2H), 4.33-4.22 (m, 2H), 3.82-3.00 (m, 24H), 2.92-2.83 (m, 2H), 2.70-2.62 (m, 2H), 2.16-2.00 (m, 2H), 1.88-1.61 (m, 6H), 1.54-1.31 (m, 11H), 1.18-1.09 (m, 1H). Three exchangeable protons not observed.

EXAMPLE 57

N-Cyclohexyl-N-(2-(2-(5-hydroxy-3-oxo-3,4-dihydro-2H-benzo[b][1,4]oxazin-8-yl)ethylamino)ethyl)-3-(3-(3-((4-(2-isopropylthiazole-4-carbonyl)-1-oxa-4,9-diazaspiro[5.5]undecan-9-yl)methyl)phenyl)propoxy)propanamide ditrifluoroacetate

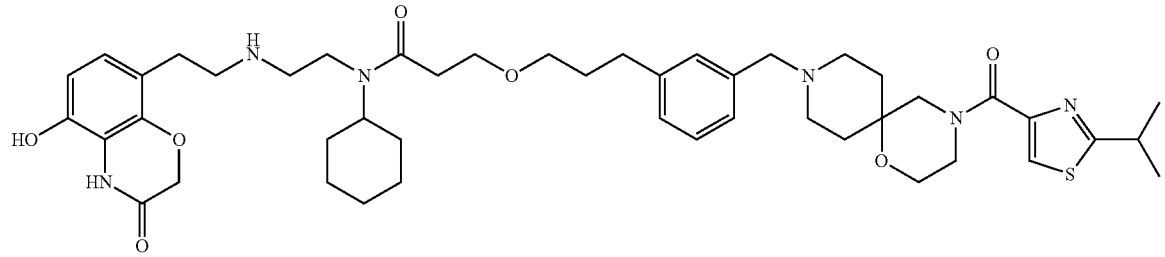

m/z 845 M$^+$ (MultiMode+).

$^1$H NMR (400 MHz, CD$_3$OD) δ 7.91 (s, 1H), 7.40-7.27 (m, 4H), 6.70 (d, J=8.5 Hz, 1H), 6.47 (d, J=8.2 Hz, 1H), 4.59-4.53 (m, 2H), 4.27 (s, 2H), 3.90-3.07 (m, 20H), 2.88 (s, 2H), 2.73-2.65 (m, 4H), 2.25-2.18 (m, 2H), 1.90-1.62 (m, 10H), 1.54-1.33 (m, 10H), 1.16 (t, J=7.0 Hz, 2H). Five exchangeable protons not observed.

EXAMPLE 58

N-Cyclohexyl-N-(2-(2-(5-hydroxy-3-oxo-3,4-dihydro-2H-benzo[b][1,4]oxazin-8-yl)ethylamino)ethyl)-3-(4-(3-((4-(2-isopropylthiazole-4-carbonyl)-1-oxa-4,9-diazaspiro[5.5]undecan-9-yl)methyl)phenyl)butoxy)propanamide ditrifluoroacetate

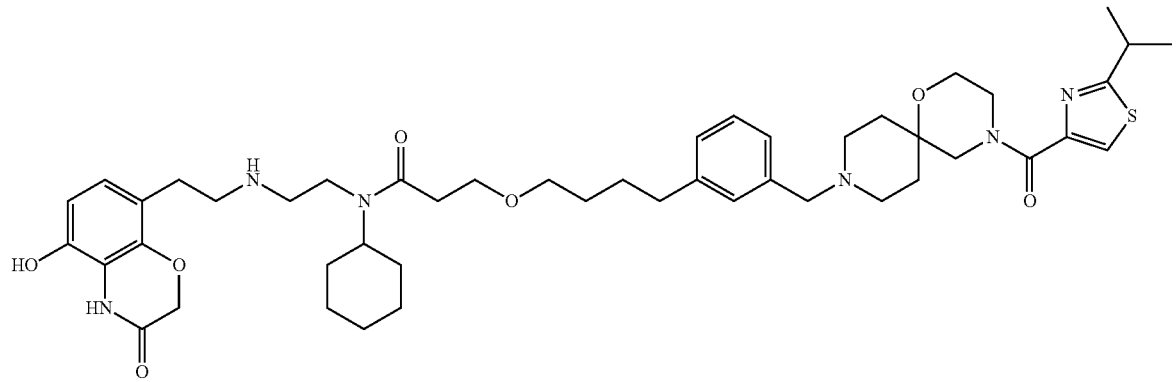

m/z 859 M$^+$ (MultiMode+).

¹H NMR (400 MHz, CD₃OD) δ 7.90 (s, 1H), 7.39-7.25 (m, 4H), 6.71 (d, J=8.5 Hz, 1H), 6.48 (d, J=8.5 Hz, 1H), 4.61-4.55 (m, 2H), 4.27 (s, 2H), 3.91-3.05 (m, 20H), 2.88 (s, 2H), 2.69-2.62 (m, 4H), 2.26-2.18 (m, 2H), 1.85-1.10 (m, 24H). Five exchangeable protons not observed.

EXAMPLE 59

N-Cyclohexyl-N-(2-(2-(5-hydroxy-3-oxo-3,4-dihydro-2H-benzo[b][1,4]oxazin-8-yl)ethylamino)ethyl)-3-(2-(3-((4-(2-isopropylthiazole-4-carbonyl)-1-oxa-4,9-diazaspiro[5.5]undecan-9-yl)methyl)phenoxy)ethoxy)propanamide ditrifluoroacetate

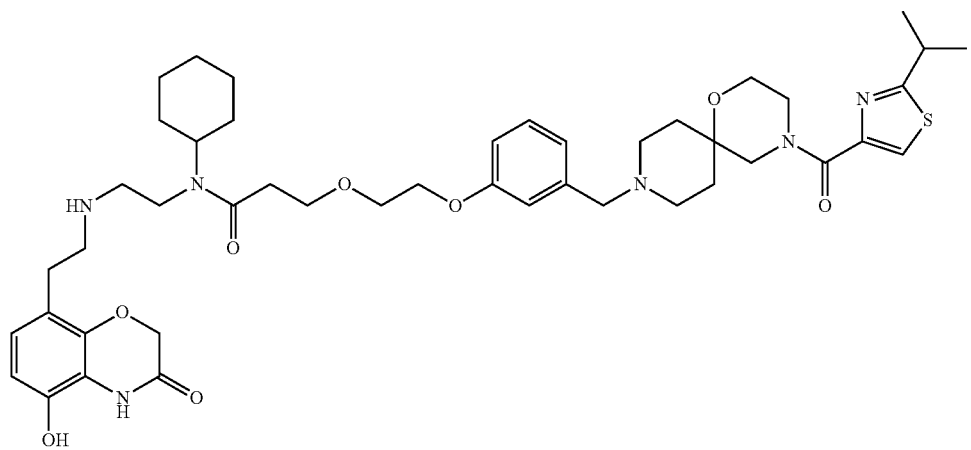

m/z 847 M⁺ (MultiMode+).

¹H NMR (400 MHz, D₆-DMSO, 90° C.) δ 9.37 (s, 1H), 7.94 (s, 1H), 7.33 (t, J=7.9 Hz, 1H), 7.11 (s, 1H), 7.07 (d, J=7.4 Hz, 1H), 7.01-6.97 (m, 1H), 6.66 (d, J=8.2 Hz, 1H), 6.49 (d, J=8.2 Hz, 1H), 4.52 (s, 2H), 4.25 (s, 2H), 4.10 (t, J=4.7 Hz, 2H), 3.76-3.62 (m, 11H), 3.47 (t, J=7.0 Hz, 2H), 3.34-3.26 (m, 1H), 3.21-2.98 (m, 8H), 2.82 (t, J=7.7 Hz, 2H), 2.63 (t, J=6.4 Hz, 2H), 2.08-1.97 (m, 2H), 1.83-1.54 (m, 7H), 1.49-1.37 (m, 2H), 1.36-1.23 (m, 8H), 1.13-1.04 (m, 1H). Four exchangeable protons not observed.

EXAMPLE 60

N-Cyclohexyl-N-(2-(2-(5-hydroxy-3-oxo-3,4-dihydro-2H-benzo[b][1,4]oxazin-8-yl)ethylamino)ethyl)-3-(3-(3-((4-(2-isopropylthiazole-4-carbonyl)-1-oxa-4,9-diazaspiro[5.5]undecan-9-yl)methyl)phenoxy)propoxy)propanamide ditrifluoroacetate

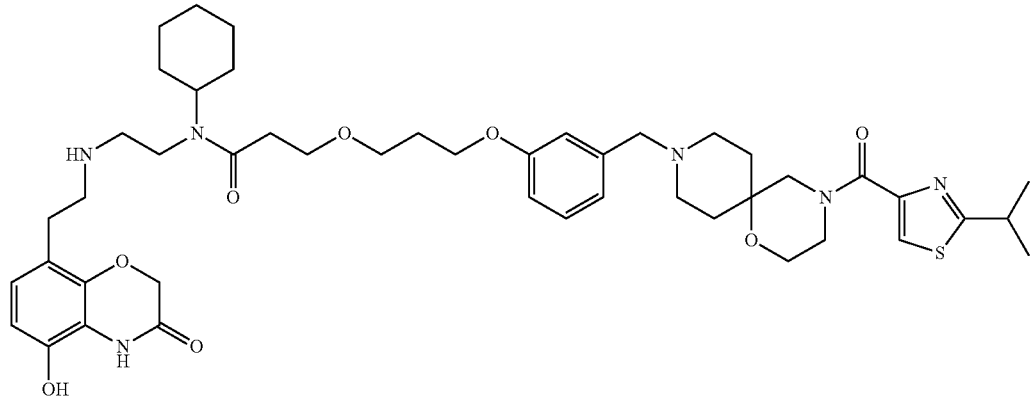

m/z 861 M+ (MultiMode+).

$^1$H NMR (400 MHz, D$_6$-DMSO, 90° C.) δ 9.37 (s, 1H), 7.94 (s, 1H), 7.33 (t, J=8.2 Hz, 1H), 7.10 (s, 1H), 7.06 (d, J=8.1 Hz, 1H), 7.01-6.96 (m, 1H), 6.66 (d, J=8.2 Hz, 1H), 6.49 (d, J=8.2 Hz, 1H), 4.53 (s, 2H), 4.26 (s, 2H), 4.05 (t, J=6.4 Hz, 2H), 3.73-3.61 (m, 9H), 3.54 (t, J=6.4 Hz, 2H), 3.48 (t, J=7.3 Hz, 2H), 3.34-3.26 (m, 1H), 3.22-2.98 (m, 8H), 2.84 (d, J=8.2 Hz, 2H), 2.61 (s, 2H), 2.08-1.99 (m, 2H), 1.98-1.89 (m, 2H), 1.85-1.55 (m, 7H), 1.50-1.38 (m, 2H), 1.37-1.25 (m, 8H), 1.12-1.04 (m, 1H). Four exchangeable protons not observed.

EXAMPLE 61

N-Ethyl-N-(2-(2-(4-hydroxy-2-oxo-2,3-dihydrobenzo[d]thiazol-7-yl)ethylamino)ethyl)-3-(3-(3-(4-(2-isopropylthiazole-4-carbonyl)-1-oxa-4,9-diazaspiro[5.5]undecan-9-yl)propoxy)phenethoxy)propanamide ditrifluoroacetate

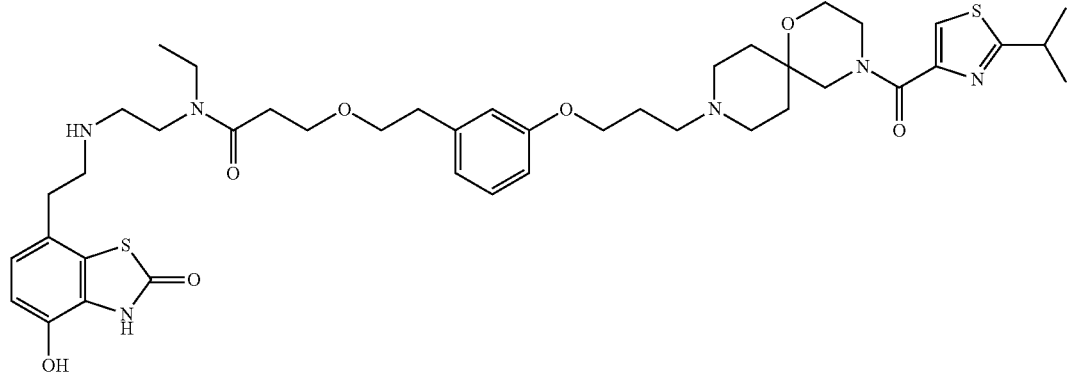

m/z 823 M+ (MultiMode+).

$^1$H NMR (400 MHz, D$_6$-DMSO, 90° C.) δ 11.36-11.28 (m, 1H), 8.56-8.51 (m, 1H), 7.97 (s, 1H), 7.20-7.15 (m, 1H), 6.87-6.73 (m, 5H), 4.04 (t, J=6.0 Hz, 2H), 3.74-3.51 (m, 14H), 3.39-3.01 (m, 14H), 2.87-2.73 (m, 4H), 2.56 (t, J=6.5 Hz, 2H), 2.17-2.03 (m, 3H), 1.82-1.69 (m, 1H), 1.36 (d, J=6.9 Hz, 6H), 1.13-1.05 (m, 3H). Two exchangeable protons not observed.

EXAMPLE 62

N-Ethyl-N-(2-(2-(4-hydroxy-2-oxo-2,3-dihydrobenzo[d]thiazol-7-yl)ethylamino)ethyl)-3-(4-(3-(4-(2-isopropylthiazole-4-carbonyl)-1-oxa-4,9-diazaspiro[5.5]undecan-9-yl)propoxy)phenethoxy)propanamide ditrifluoroacetate

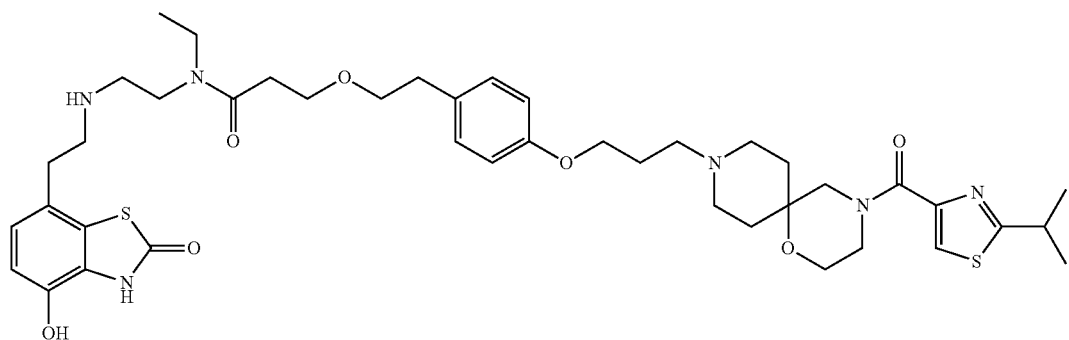

m/z 823 M$^+$ (MultiMode+).

$^1$H NMR (400 MHz, D$_6$-DMSO, 90° C.) δ 7.91 (s, 1H), 7.08 (d, J=8.5 Hz, 2H), 6.78 (d, J=8.5 Hz, 3H), 6.67 (d, J=8.2 Hz, 1H), 3.94 (t, J=6.4 Hz, 2H), 3.70-3.58 (m, 8H), 3.54 (t, J=6.9 Hz, 2H), 3.40 (q, J=6.9 Hz, 2H), 3.34-3.22 (m, 5H), 2.80-2.24 (m, 14H), 1.86-1.74 (m, 2H), 1.73-1.63 (m, 2H), 1.58-1.48 (m, 2H), 1.35 (d, J=6.9 Hz, 6H), 1.09 (t, J=6.9 Hz, 3H). Five exchangeable protons not observed.

EXAMPLE 63

N-Cyclohexyl-N-(2-(2-(5-hydroxy-3-oxo-3,4-dihydro-2H-benzo[b][1,4]oxazin-8-yl)ethylamino)ethyl)-3-(2-(5-(2-(4-(2-isopropylthiazole-4-carbonyl)-1-oxa-4,9-diazaspiro[5.5]undecan-9-yl)ethyl)thiophen-3-yl)ethoxy)propanamide ditrifluoroacetate

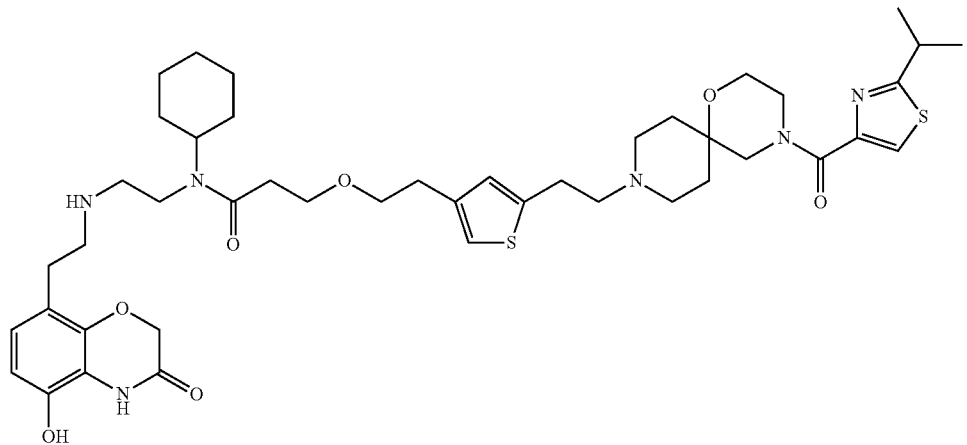

m/z 851 M⁺ (MultiMode+).

¹H NMR (500 MHz, D₆-DMSO, 90° C.) δ 9.33 (s, 1H), 7.96 (s, 1H), 7.00 (s, 1H), 6.82 (s, 1H), 6.66 (d, J=8.3 Hz, 1H), 6.49 (d, J=8.3 Hz, 1H), 4.52 (s, 2H), 3.76-3.65 (m, 9H), 3.59 (t, J=6.9 Hz, 2H), 3.48 (t, J=6.9 Hz, 2H), 3.41-3.28 (m, 5H), 3.22-3.09 (m, 6H), 3.01 (t, J=7.2 Hz, 2H), 2.83 (t, J=7.7 Hz, 2H), 2.74 (t, J=6.9 Hz, 2H), 2.60 (t, J=6.1 Hz, 2H), 2.10-2.01 (m, 2H), 1.86-1.73 (m, 4H), 1.68-1.58 (m, 3H), 1.50-1.40 (m, 2H), 1.39-1.28 (m, 8H), 1.14-1.05 (m, 1H). Four exchangeable protons not observed.

EXAMPLE 64

N-Cyclopentyl-N-(2-(2-(5-hydroxy-3-oxo-3,4-dihydro-2H-benzo[b][1,4]oxazin-8-yl)ethylamino)ethyl)-3-(3-((4-(2-isopropylthiazole-4-carbonyl)-1-oxa-4,9-diazaspiro[5.5]undecan-9-yl)methyl)-2-methylphenethoxy)propanamide ditrifluoroacetate

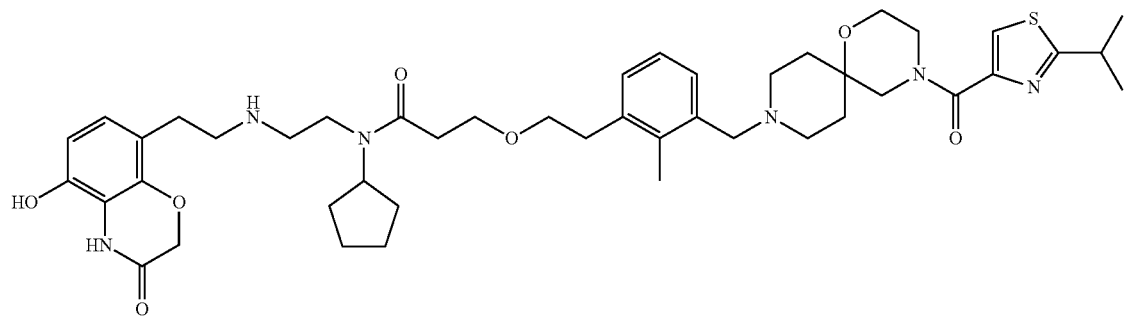

m/z 831 M⁺ (MultiMode+).

¹H NMR (400 MHz, D₆-DMSO, 90° C.) δ 9.40 (s, 1H), 7.94 (s, 1H), 7.31 (d, J=6.7 Hz, 1H), 7.25 (d, J=7.2 Hz, 1H), 7.17 (t, J=7.5 Hz, 1H), 6.66 (d, J=8.5 Hz, 1H), 6.49 (d, J=8.5 Hz, 1H), 4.53 (s, 2H), 4.39-4.15 (m, 3H), 3.71 (s, 4H), 3.70-3.62 (m, 4H), 3.60 (t, J=7.0 Hz, 2H), 3.47-3.37 (m, 3H), 3.36-3.20 (m, 4H), 3.11 (t, J=7.4 Hz, 2H), 3.03 (t, J=6.9 Hz, 2H), 2.90-2.78 (m, 4H), 2.62 (t, J=6.7 Hz, 2H), 2.32 (s, 3H), 2.09-1.91 (m, 2H), 1.86-1.75 (m, 2H), 1.74-1.62 (m, 4H), 1.60-1.41 (m, 4H), 1.35 (d, J=6.7 Hz, 6H). Four exchangeable protons not observed.

EXAMPLE 65

N-Butyl-N-(2-(2-(5-hydroxy-3-oxo-3,4-dihydro-2H-benzo[b][1,4]oxazin-8-yl)ethylamino)ethyl)-3-(3-((4-(2-isopropylthiazole-4-carbonyl)-1-oxa-4,9-diazaspiro[5.5]undecan-9-yl)methyl)-5-methylphenethoxy)propanamide ditrifluoroacetate

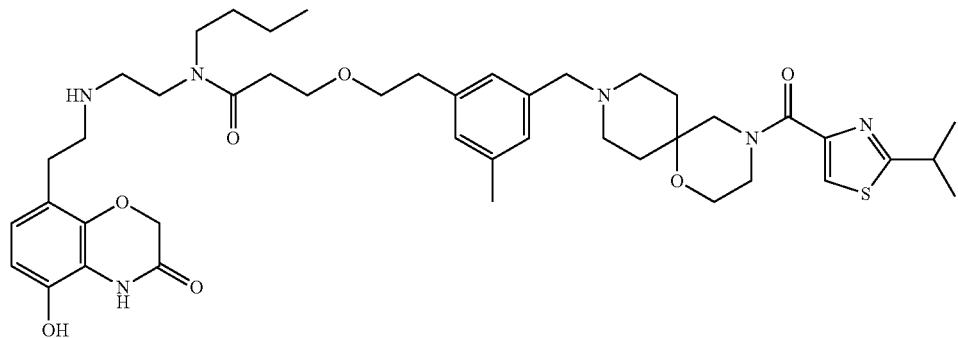

m/z 819 M⁺ (MultiMode+).

¹H NMR (400 MHz, D₆-DMSO, 90° C.) δ 9.40 (s, 1H), 7.94 (s, 1H), 7.16-7.11 (m, 3H), 6.66 (d, J=8.5 Hz, 1H), 6.48 (d, J=8.2 Hz, 1H), 4.53 (s, 2H), 4.21 (s, 2H), 3.74-3.02 (m, 23H), 2.86-2.76 (m, 4H), 2.58-2.52 (m, 2H), 2.31 (s, 3H), 2.11-1.97 (m, 2H), 1.77-1.60 (m, 2H), 1.54-1.43 (m, 2H), 1.35 (d, J=6.5 Hz, 6H), 1.32-1.25 (m, 2H), 0.90 (t, J=7.3 Hz, 3H). Four exchangeable protons not observed.

EXAMPLE 66

N-Ethyl-3-(3-(2-fluoro-3-((4-(2-isopropylthiazole-4-carbonyl)-1-oxa-4,9-diazaspiro[5.5]undecan-9-yl)methyl)phenyl)propoxy)-N-(2-(2-(4-hydroxy-2-oxo-2,3-dihydrobenzo[d]thiazol-7-yl)ethylamino)ethyl)propanamide ditrifluoroacetate

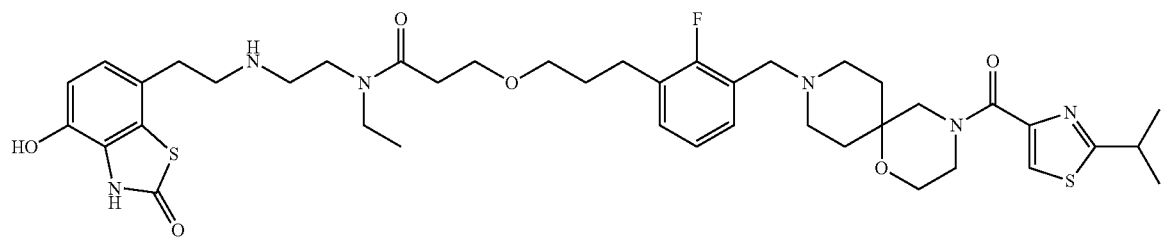

m/z 811 M⁺ (MultiMode+).

$^1$H NMR (400 MHz, CD$_3$OD) δ 7.91 (s, 1H), 7.44-7.33 (m, 2H), 7.20 (s, 1H), 6.88 (d, J=8.2 Hz, 1H), 6.73 (d, J=8.5 Hz, 1H), 4.39-4.33 (m, 2H), 3.91-3.18 (m, 23H), 2.92-2.86 (m, 2H), 2.75 (t, J=7.6 Hz, 2H), 2.67 (t, J=6.0 Hz, 2H), 2.27-2.17 (m, 2H), 1.89-1.68 (m, 4H), 1.38 (d, J=6.9 Hz, 6H), 1.21 (t, J=7.0 Hz, 3H). Five exchangeable protons not observed.

EXAMPLE 67

N-Cyclohexyl-N-(2-(2-(5-hydroxy-3-oxo-3,4-dihydro-2H-benzo[b][1,4]oxazin-8-yl)ethylamino)ethyl)-3-(2-(3-((4-(2-isopropylthiazole-4-carbonyl)-1-oxa-4,9-diazaspiro[5.5]undecan-9-yl)methyl)benzyloxy)ethoxy)propanamide ditrifluoroacetate

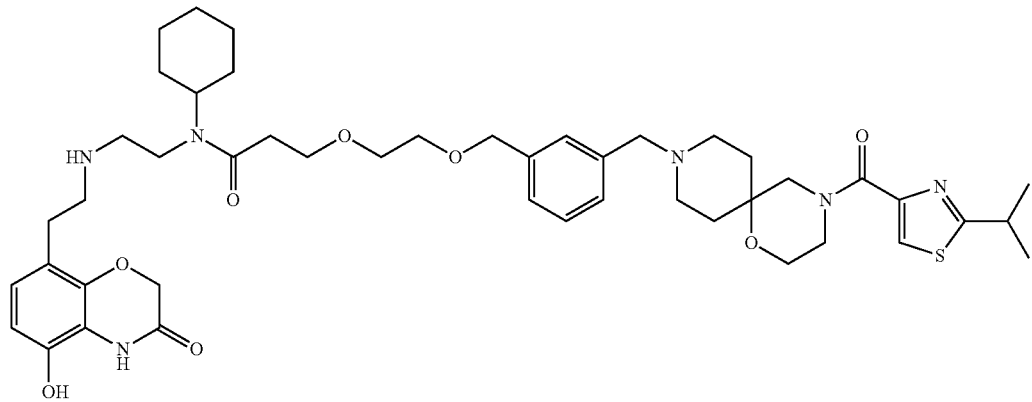

m/z 861 M$^+$ (MultiMode+).

$^1$H NMR (400 MHz, D$_6$-DMSO, 90° C.) δ 9.40 (s, 1H), 7.94 (s, 1H), 7.48-7.35 (m, 4H), 6.71-6.63 (m, 1H), 6.53-6.45 (m, 1H), 4.58-4.49 (m, 4H), 4.35-4.27 (m, 2H), 3.76-3.63 (m, 8H), 3.62-2.94 (m, 20H), 2.87-2.75 (m, 2H), 2.68-2.56 (m, 2H), 2.05-1.97 (m, 2H), 1.80-1.54 (m, 4H), 1.49-0.99 (m, 4H), 1.35 (d, J=7.2 Hz, 6H). Four exchangeable protons not observed.

EXAMPLE 68

N-Ethyl-N-(2-(2-(4-hydroxy-2-oxo-2,3-dihydrobenzo[d]thiazol-7-yl)ethylamino)ethyl)-3-(3-((4-(2-isopropylthiazole-4-carbonyl)-1-oxa-4,9-diazaspiro[5.5]undecan-9-yl)methyl)-2-methoxyphenethoxy)propanamide ditrifluoroacetate

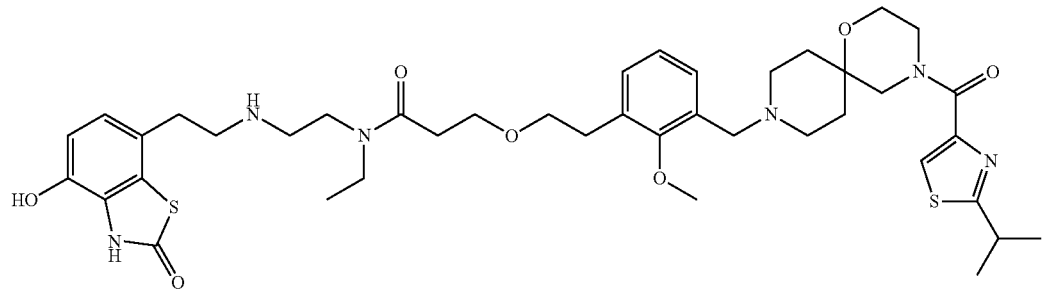

m/z 809 M$^+$ (MultiMode+).

¹H NMR (500 MHz, D₆-DMSO, 90° C.) δ 7.94 (s, 1H), 7.40-7.34 (m, 2H), 7.18-7.12 (m, 1H), 6.88-6.82 (m, 1H), 6.77-6.72 (m, 1H), 4.29-4.23 (m, 2H), 3.79-3.06 (m, 24H), 2.91-2.79 (m, 4H), 2.64-2.53 (m, 4H), 2.09-1.95 (m, 2H), 1.83-1.64 (m, 2H), 1.38-1.31 (m, 6H), 1.14-1.03 (m, 3H). Five exchangeable protons not observed.

EXAMPLE 69

N-Ethyl-3-(2-fluoro-3-((4-(2-isobutylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

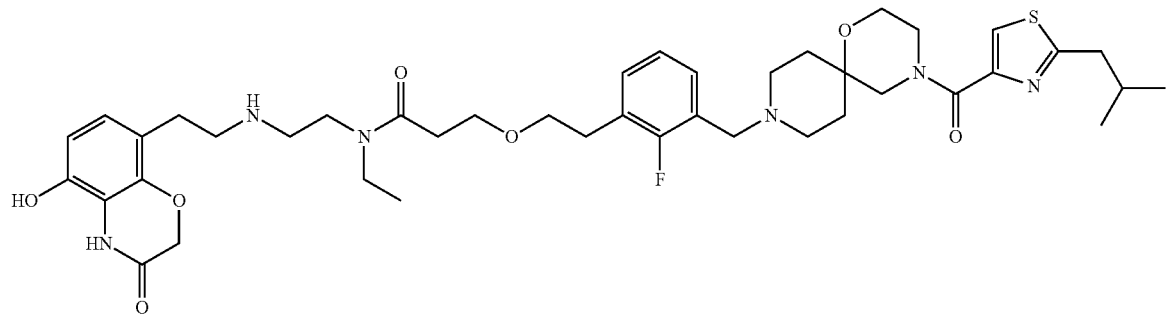

m/z 809 M⁺(MultiMode+).

¹H NMR (400 MHz, D₆-DMSO, 90° C.) δ 9.40 (s, 1H), 7.98-7.90 (m, 1H), 7.49-7.37 (m, 2H), 7.26-7.14 (m, 1H), 6.71-6.61 (m, 1H), 6.53-6.44 (m, 1H), 4.57-4.49 (m, 2H), 4.32 (s, 2H), 3.82-3.45 (m, 12H), 3.38-3.27 (m, 2H), 3.26-3.16 (m, 2H), 3.16-3.02 (m, 6H), 2.93-2.77 (m, 6H), 2.59-2.49 (m, 2H), 2.12-1.95 (m, 3H), 1.85-1.68 (m, 2H), 1.15-1.00 (m, 3H), 1.00-0.89 (m, 6H). Four exchangeable protons not observed.

EXAMPLE 70

3-(2-Chloro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)-N-(2-methoxyethyl)propanamide ditrifluoroacetate

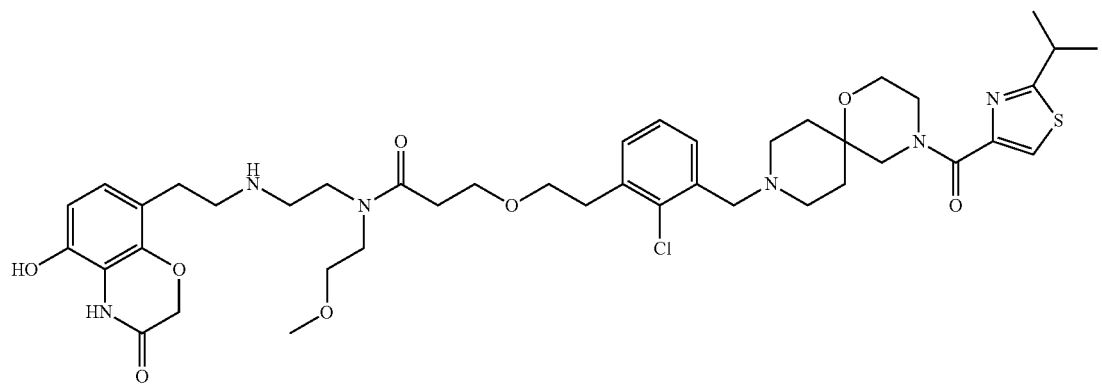

m/z 841 M⁺(MultiMode+).

$^1$H NMR (500 MHz, CD$_3$OD) δ 7.96 (s, 1H), 7.57-7.52 (m, 2H), 7.45-7.40 (m, 1H), 6.75 (d, J=8.4 Hz, 1H), 6.52 (d, J=8.3 Hz, 1H), 4.64 (s, 2H), 4.59-4.54 (m, 2H), 3.97-3.30 (m, 24H), 3.25-3.19 (m, 4H), 3.12 (t, J=6.8 Hz, 2H), 2.93 (t, J=7.2 Hz, 2H), 2.71 (t, J=6.1 Hz, 2H), 2.32-2.25 (m, 2H), 1.87-1.77 (m, 2H), 1.43 (d, J=6.3 Hz, 6H). Five exchangeable protons not observed.

EXAMPLE 71

3-(2-Chloro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)-N-(3-methoxypropyl)propanamide ditrifluoroacetate

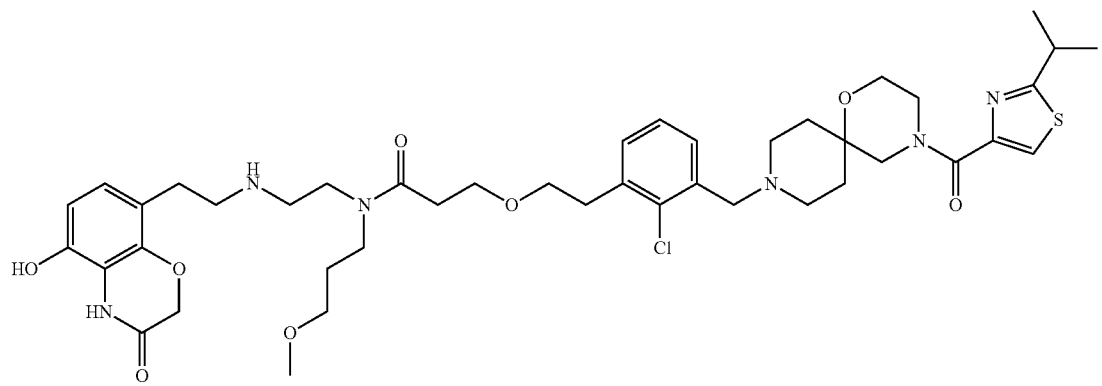

m/z 855 M$^+$(MultiMode+).

$^1$H NMR (300 MHz, CD$_3$OD) δ 7.95 (s, 1H), 7.56-7.49 (m, 2H), 7.43-7.37 (m, 1H), 6.74 (d, J=8.3 Hz, 1H), 6.51 (d, J=8.3 Hz, 1H), 4.64 (s, 2H), 4.56-4.52 (m, 2H), 3.95-3.38 (m, 24H), 3.24-3.16 (m, 4H), 3.10 (t, J=7.0 Hz, 2H), 2.92 (t, J=7.0 Hz, 2H), 2.67 (t, J=6.3 Hz, 2H), 2.31-2.21 (m, 2H), 1.89-1.77 (m, 4H), 1.41 (d, J=6.9 Hz, 6H). Five exchangeable protons not observed.

EXAMPLE 72

3-(2-Fluoro-3-((4-(2-isopropylthiazole-4-carbonyl)-1-oxa-4,9-diazaspiro[5.5]undecan-9-yl)methyl)phenethoxy)-N-(2-fluoroethyl)-N-(2-(2-(5-hydroxy-3-oxo-3,4-dihydro-2H-benzo[b][1,4]oxazin-8-yl)ethylamino)ethyl)propanamide ditrifluoroacetate

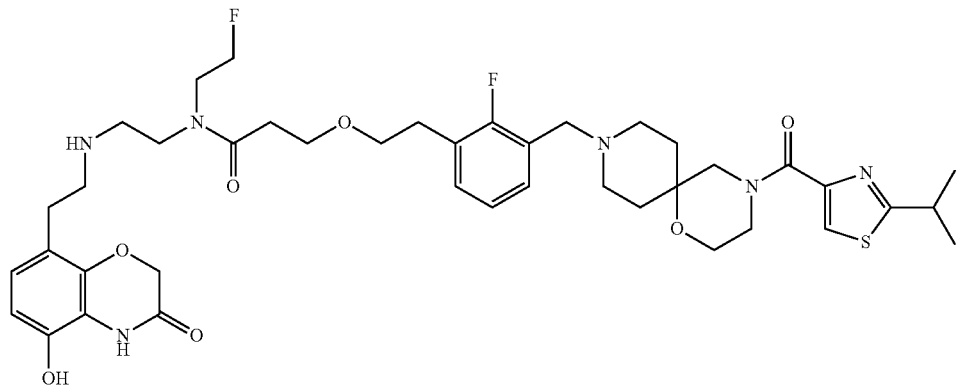

m/z 813 M⁺(MultiMode+).

$^1$H NMR (400 MHz, D$_6$-DMSO, 90° C.) δ 9.38 (s, 1H), 7.94 (s, 1H), 7.46-7.39 (m, 2H), 7.19 (t, J=7.7 Hz, 1H), 6.66 (d, J=8.5 Hz, 1H), 6.49 (d, J=8.5 Hz, 1H), 4.60 (s, 1H), 4.53 (s, 2H), 4.47 (s, 1H), 4.33 (s, 2H), 3.73-3.57 (m, 14H), 3.35-3.26 (m, 1H), 3.25-3.18 (m, 2H), 3.15-3.06 (m, 6H), 2.89-2.81 (m, 4H), 2.58 (t, J=6.5 Hz, 2H), 2.08-1.99 (m, 2H), 1.85-1.73 (m, 2H), 1.35 (d, J=6.9 Hz, 6H). Four exchangeable protons not observed.

EXAMPLE 73

N-(2,2-Difluoroethyl)-3-(2-fluoro-3-((4-(2-isopropylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

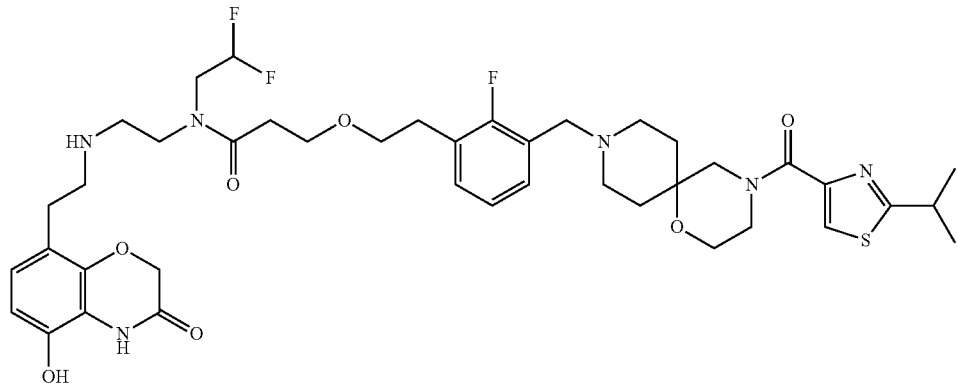

m/z 831 M⁺(MultiMode+).

$^1$H NMR (400 MHz, D$_6$-DMSO, 90° C.) δ 9.39 (s, 1H), 7.94 (s, 1H), 7.41 (t, J=7.4 Hz, 2H), 7.19 (t, J=7.6 Hz, 1H), 6.66 (d, J=8.2 Hz, 1H), 6.49 (d, J=8.2 Hz, 1H), 6.35-5.92 (m, 1H), 4.53 (s, 2H), 4.28 (s, 2H), 3.73-3.60 (m, 14H), 3.35-3.26 (m, 1H), 3.20-3.02 (m, 8H), 2.91-2.79 (m, 4H), 2.66-2.58 (m, 2H), 2.06-1.96 (m, 2H), 1.83-1.67 (m, 2H), 1.35 (d, J=6.9 Hz, 6H). Four exchangeable protons not observed.

EXAMPLE 74

N-Ethyl-3-(2-fluoro-3-((4-(5-isopropylthiophene-3-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide ditrifluoroacetate

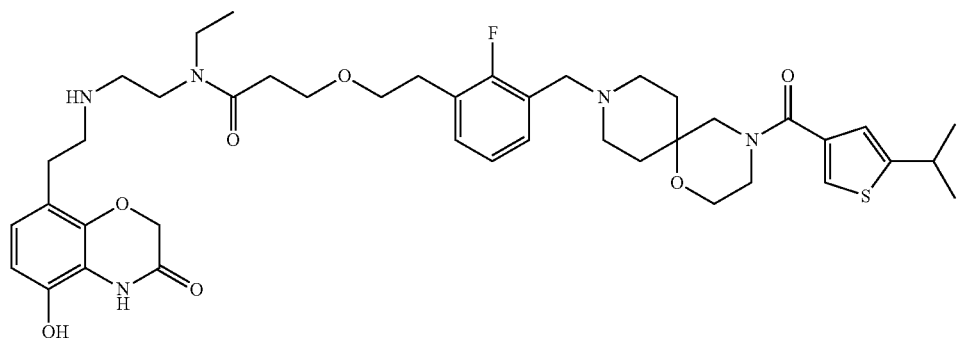

m/z 794 M$^+$(MultiMode+).

$^1$H NMR (400 MHz, CD$_3$OD) δ 7.49-7.43 (m, 2H), 7.42-7.36 (m, 1H), 7.25-7.18 (m, 1H), 6.91 (s, 1H), 6.74-6.68 (m, 1H), 6.50-6.45 (m, 1H), 4.60 (s, 2H), 4.40-4.35 (m, 2H), 3.75-3.10 (m, 25H), 2.97-2.85 (m, 4H), 2.64-2.58 (m, 2H), 2.26-2.16 (m, 2H), 1.30 (d, J=7.5 Hz, 6H), 1.16 (t, J=7.2 Hz, 3H). Five exchangeable protons not observed.

EXAMPLE 75

3-(4-(2-(4-(2-Ethylthiazole-4-carbonyl)-1-oxa-4,9-diazaspiro[5.5]undecan-9-yl)ethyl)phenethoxy)-N-(2-(2-(4-hydroxy-2-oxo-2,3-dihydrobenzo[d]thiazol-7-yl)ethylamino)ethyl)-N-(5-hydroxypentyl)propanamide diformate

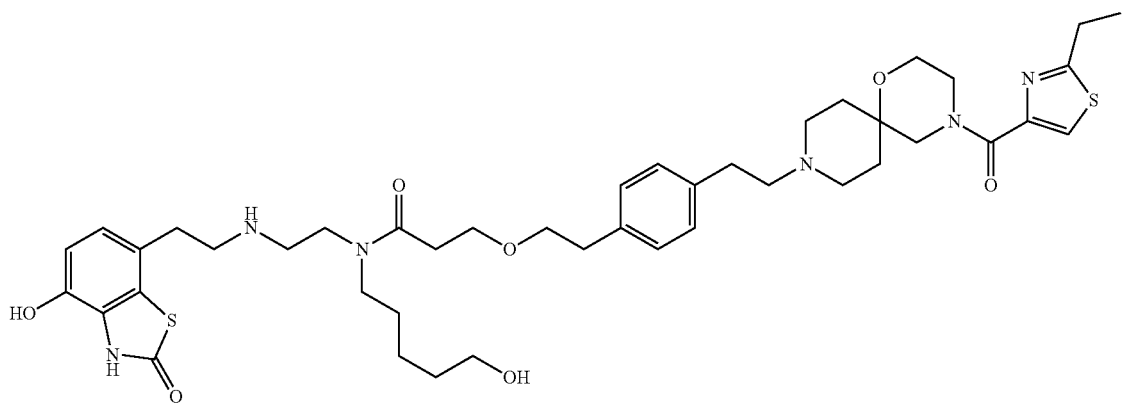

m/z 837 M$^+$(MultiMode+).

¹H NMR (400 MHz, CD₃OD) δ 8.40 (s, 2H), 7.90 (s, 1H), 7.16 (s, 4H), 6.90-6.84 (m, 1H), 6.75-6.70 (m, 1H), 3.88-2.84 (m, 32H), 2.80 (t, J=7.1 Hz, 2H), 2.61 (t, J=5.5 Hz, 2H), 2.20-2.10 (m, 2H), 1.88-1.69 (m, 2H), 1.64-1.48 (m, 4H), 1.41-1.29 (m, 5H). Four exchangeable protons not observed.

EXAMPLE 76

3-(4-(2-(4-(2-Ethylthiazole-4-carbonyl)-1-oxa-4,9-diazaspiro[5.5]undecan-9-yl)ethyl)phenethoxy)-N-(2-(2-(4-hydroxy-2-oxo-2,3-dihydrobenzo[d]thiazol-7-yl)ethylamino)ethyl)-N-(6-hydroxyhexyl)propanamide diformate

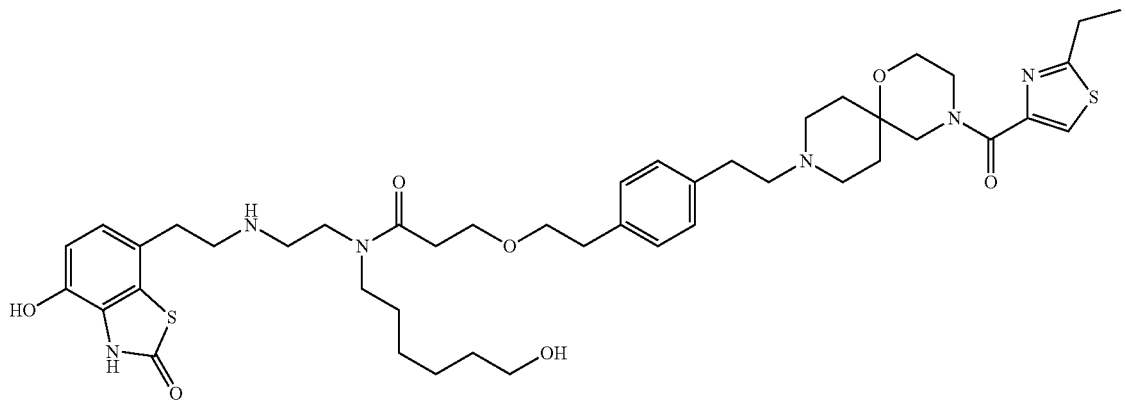

m/z 851 M⁺(MultiMode+).

¹H NMR (400 MHz, CD₃OD) δ 0.40 (s, 2H), 7.91 (s, 1H), 7.20-7.14 (m, 4H), 6.90-6.84 (m, 1H), 6.75-6.70 (m, 1H), 3.88-2.84 (m, 32H), 2.80 (t, J=6.5 Hz, 2H), 2.60 (t, J=6.2 Hz, 2H), 2.20-2.11 (m, 2H), 1.88-1.73 (m, 2H), 1.62-1.47 (m, 4H), 1.43-1.26 (m, 7H). Four exchangeable protons not observed.

EXAMPLE 77

3-(3-((4-(2-Butylthiazole-4-carbonyl)-1-oxa-4,9-diazaspiro[5.5]undecan-9-yl)methyl)-2-chlorophenethoxy)-N-ethyl-N-(2-(2-(5-hydroxy-3-oxo-3,4-dihydro-2H-benzo[b][1,4]oxazin-8-yl)ethylamino)ethyl)propanamide ditrifluoroacetate

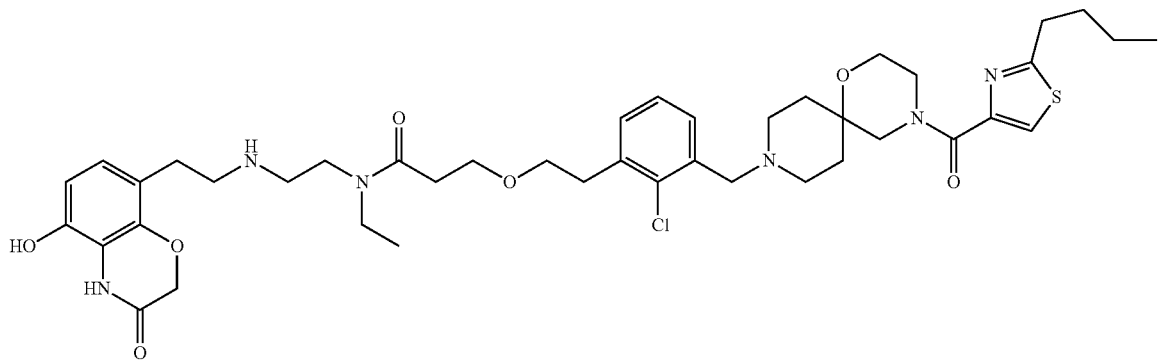

m/z 825 M⁺ (MultiMode+).

$^1$H NMR (400 MHz, CD$_3$OD) 7.89 (s, 1H), 7.51-7.47 (m, 2H), 7.39-7.34 (m, 1H), 6.71 (d, J=8.0 Hz, 1H), 6.47 (d, J=8.0 Hz, 1H), 4.60 (s, 2H), 4.56-4.50 (m, 2H), 3.85-2.98 (m, 26H), 2.89 (t, J=7.1 Hz, 2H), 2.62 (t, J=6.0 Hz, 2H), 2.28-2.17 (m, 2H), 1.83-1.69 (m, 4H), 1.44-1.36 (m, 2H), 1.16 (t, J=7.4 Hz, 3H), 0.94 (t, J=7.4 Hz, 3H). Five exchangeable protons not observed.

Examples 45 to 77 were prepared using the following Aromatic Intermediates, Carboxylic Acids and Amines:

| Example Number | Aromatic Intermediate | Carboxylic Acid | Amine |
|---|---|---|---|
| 45 | 2-(4-(bromomethyl)phenyl)ethanol [Note 1] | 2-methylthiazole-4-carboxylic acid | N-(2,2-dimethoxyethyl)cyclohexanamine [Note 2] |
| 46 | Aromatic Intermediate 1 | 2-methylthiazole-4-carboxylic acid | N-ethyl-2,2-dimethoxyethanamine [Note 3] |
| 47 | Aromatic Intermediate 4 | 2-isopropylthiazole-4-carboxylic acid | N-(2,2-dimethoxyethyl)cyclohexanamine [Note 2] |
| 48 | Aromatic Intermediate 6 | 2-isopropylthiazole-4-carboxylic acid | N-ethyl-2,2-dimethoxyethanamine [Note 3] |
| 49 | Aromatic Intermediate 7 | 2-isopropylthiazole-4-carboxylic acid | N-(2,2-dimethoxyethyl)cyclohexanamine [Note 2] |
| 50 | Aromatic Intermediate 8 | 2-isopropylthiazole-4-carboxylic acid | N-ethyl-2,2-dimethoxyethanamine [Note 3] |
| 51 | Aromatic Intermediate 12 | 2-isopropylthiazole-4-carboxylic acid | N-(2,2-dimethoxyethyl)cyclohexanamine [Note 2] |
| 52 | Aromatic Intermediate 13 | 2-isopropylthiazole-4-carboxylic acid | N-ethyl-2,2-dimethoxyethanamine [Note 3] |
| 53 | Aromatic Intermediate 14 | 2-isopropylthiazole-4-carboxylic acid | N-(2,2-dimethoxyethyl)cyclohexanamine [Note 2] |
| 54 | Aromatic Intermediate 15 | 2-isopropylthiazole-4-carboxylic acid | Amine 6 |
| 55 | Aromatic Intermediate 16 | 2-isopropylthiazole-4-carboxylic acid | N-methyl-2,2-dimethoxyethanamine |
| 56 | Aromatic Intermediate 17 | 2-isopropylthiazole-4-carboxylic acid | N-(2,2-dimethoxyethyl)cyclohexanamine [Note 2] |
| 57 | Aromatic Intermediate 18 | 2-isopropylthiazole-4-carboxylic acid | N-(2,2-dimethoxyethyl)cyclohexanamine [Note 2] |
| 58 | Aromatic Intermediate 19 | 2-isopropylthiazole-4-carboxylic acid | N-(2,2-dimethoxyethyl)cyclohexanamine [Note 2] |
| 59 | 3-(2-hydroxyethoxy)benzaldehyde [Note 4] | 2-isopropylthiazole-4-carboxylic acid | N-(2,2-dimethoxyethyl)cyclohexanamine [Note 2] |
| 60 | 3-(3-hydroxypropoxy)benzaldehyde [Note 5] | 2-isopropylthiazole-4-carboxylic acid | N-(2,2-dimethoxyethyl)cyclohexanamine[Note 2] |
| 61 | 2-(3-(3-bromopropoxy)phenyl)ethanol [Note 6] | 2-isopropylthiazole-4-carboxylic acid | N-ethyl-2,2-dimethoxyethanamine [Note 3] |
| 62 | 2-(4-(3-bromopropoxy)phenyl)ethanol [Note 6] | 2-isopropylthiazole-4-carboxylic acid | N-ethyl-2,2-dimethoxyethanamine [Note 3] |
| 63 | Aromatic Intermediate 20 | 2-isopropylthiazole-4-carboxylic acid | N-(2,2-dimethoxyethyl)cyclohexanamine [Note 2] |
| 64 | Aromatic Intermediate 22 | 2-isopropylthiazole-4-carboxylic acid | Amine 6 |
| 65 | Aromatic Intermediate 23 | 2-isopropylthiazole-4-carboxylic acid | N-(2,2-dimethoxyethyl)butan-1-amine [Note 7] |
| 66 | Aromatic Intermediate 24 | 2-isopropylthiazole-4-carboxylic acid | N-ethyl-2,2-dimethoxyethanamine [Note 3] |
| 67 | Aromatic Intermediate 25 | 2-isopropylthiazole-4-carboxylic acid | N-(2,2-dimethoxyethyl)cyclohexanamine [Note 2] |
| 68 | Aromatic Intermediate 26 | 2-isopropylthiazole-4-carboxylic acid | N-ethyl-2,2-dimethoxyethanamine [Note 3] |
| 69 | Aromatic Intermediate 5 | Carboxylic Acid 4 | N-ethyl-2,2-dimethoxyethanamine [Note 3] |
| 70 | Aromatic Intermediate 11 | 2-isopropylthiazole-4-carboxylic acid | 2,2-dimethoxy-N-(2-methoxyethyl)ethanamine [Note 8] |
| 71 | Aromatic Intermediate 11 | 2-isopropylthiazole-4-carboxylic acid | Amine 9 |
| 72 | Aromatic Intermediate 5 | 2-isopropylthiazole-4-carboxylic acid | Amine 12 |
| 73 | Aromatic Intermediate 5 | 2-isopropylthiazole-4-carboxylic acid | Amine 13 |
| 74 | Aromatic Intermediate 5 | 5-isopropylthiophene-3-carboxylic acid | N-ethyl-2,2-dimethoxyethanamine [Note 3] |
| 75[Note 9] | 2-(4-(2-bromoethyl)phenyl)ethanol [Note 10] | Carboxylic Acid 1 | Amine 10 |

-continued

| Example Number | Aromatic Intermediate | Carboxylic Acid | Amine |
|---|---|---|---|
| 76[Note 9] | 2-(4-(2-bromoethyl)phenyl)ethanol [Note 10] | Carboxylic Acid 1 | Amine 11 |
| 77 | Aromatic Intermediate 11 | Carboxylic Acid 5 | N-ethyl-2,2-dimethoxyethanamine [Note 3] |

[Note 1]: Tet. Lett. 1987, 28(13), 1401.
[Note 2]: WO 2008075025.
[Note 3]: U.S. Pat. No. 2,707,186.
[Note 4]: WO 9733202.
[Note 5]: Org. Proc. Res. Dev. 2007, 11(6), 1043.
[Note 6]: WO 2008096127.
[Note 7]: J. Am. Chem. Soc. 1949, 71(6), 2272.
[Note 8]: EP 1852434.
[Note 9]: Purified by preparative HPLC (Sunfire ™, Gradient: 30-70% methanol in 0.2% aqueous formic acid).
[Note 10]: Organometallics 2002, 21(20), 4217.

EXAMPLE 78

N-Ethyl-N-(2-(2-(4-hydroxy-2-oxo-2,3-dihydrobenzo[d]thiazol-7-yl)ethylamino)ethyl)-3-(2-(4-(2-(4-(2-isopropylthiazole-4-carbonyl)-1-oxa-4,9-diazaspiro[5.5]undecan-9-yl)ethyl)thiophen-2-yl)ethoxy)propanamide ditrifluoroacetate

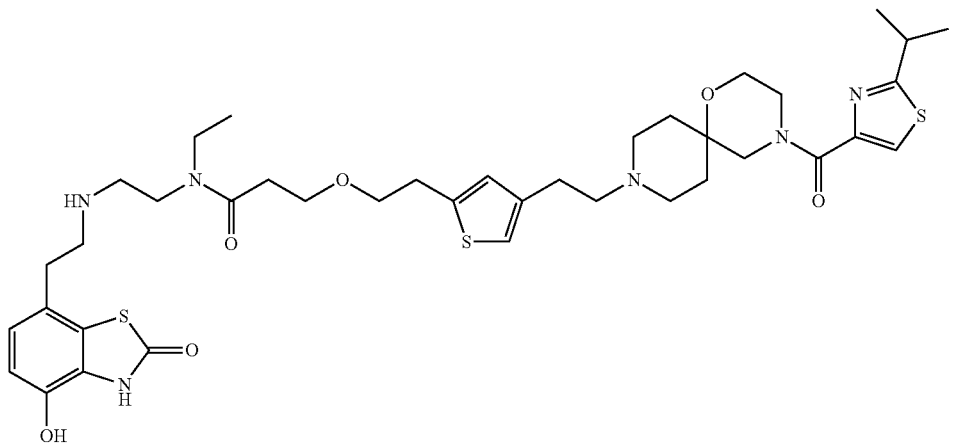

Prepared by the method of Example 1, from step e using tert-butyl 3-(2-(4-(2-(4-(2-isopropylthiazole-4-carbonyl)-1-oxa-4,9-diazaspiro[5.5]undecan-9-yl)ethyl)thiophen-2-yl)ethoxy)propanoate (0.84 g) in place of tert-butyl 3-(4-(2-(4-(2-isopropylthiazole-4-carbonyl)-1-oxa-4,9-diazaspiro[5.5]undecan-9-yl)ethyl)phenethoxy)propanoate in step e.

Yield 0.18 g.

m/z 799 M⁺ (MultiMode+).

$^1$H NMR (400 MHz, D$_6$-DMSO, 90° C.) δ 7.95 (s, 1H), 7.02 (s, 1H), 6.84 (d, J=8.2 Hz, 1H), 6.79-6.73 (m, 2H), 3.74-3.65 (m, 8H), 3.60 (t, J=6.7 Hz, 2H), 3.55 (t, J=5.5 Hz, 2H), 3.42-3.28 (m, 7H), 3.20-3.06 (m, 6H), 2.98-2.91 (m, 4H), 2.84 (t, J=8.0 Hz, 2H), 2.57 (t, J=7.0 Hz, 2H), 2.09-1.99 (m, 2H), 1.86-1.74 (m, 2H), 1.35 (d, J=6.9 Hz, 6H), 1.09 (t, J=6.9 Hz, 3H). Five exchangeable protons not observed.

The tert-butyl 3-(2-(4-(2-(4-(2-isopropylthiazole-4-carbonyl)-1-oxa-4,9-diazaspiro[5.5]undecan-9-yl)ethyl)thiophen-2-yl)ethoxy)propanoate used as a starting material was prepared as follows:

a) 2-(4-(2-(4-(2-Isopropylthiazole-4-carbonyl)-1-oxa-4,9-diazaspiro[5.5]undecan-9-yl)ethyl)thiophen-2-yl)ethyl acetate

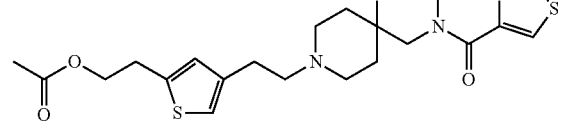

Prepared by the method of Example 1, step c using the hydrochloride salt of (2-isopropylthiazol-4-yl)(1-oxa-4,9- diazaspiro[5.5]undecan-4-yl)methanone [Example 27, step a] (1 g) in place of its trifluoroacetate salt, and 2-(4-(2-(methylsulfonyloxy)ethyl)thiophen-2-yl)ethyl acetate [Aromatic Intermediate 21] (0.8 g) in place of 4-(2-hydroxyethyl)phenethyl methanesulfonate. Yield 1 g.

m/z 506 (M+H)⁺ (APCI).

b) (9-(2-(5-(2-Hydroxyethyl)thiophen-3-yl)ethyl)-1-oxa-4,9-diazaspiro[5.5]undecan-4-yl)(2-isopropylthiazol-4-yl)methanone

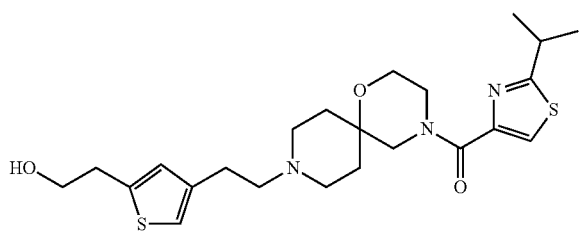

Aqueous sodium hydroxide (1M, 4.9 mL) was added to a solution of 2-(2-(4-(2-isopropylthiazole-4-carbonyl)-1-oxa-4,9-diazaspiro[5.5]undecan-9-yl)ethyl)thiophen-2-yl)ethyl acetate [Example 78, step a] (1.0 g) in methanol (20 mL) and the resulting mixture was stirred for 1 hour at 20° C. The mixture was partitioned between ethyl acetate and brine and separated. The organic phase was dried, filtered and the solvent evaporated under reduced pressure to afford the subtitled compound. Yield 0.92 g.

¹H NMR (400 MHz, D₆-DMSO, 90° C.) δ 7.91 (s, 1H), 6.86 (s, 1H), 6.70 (s, 1H), 4.39 (t, J=5.3 Hz, 1H), 3.70-3.58 (m, 8H), 3.35-3.27 (m, 1H), 2.86 (t, J=6.8 Hz, 2H), 2.63 (t, J=7.7 Hz, 2H), 2.52-2.30 (m, 6H), 1.73-1.65 (m, 2H), 1.58-1.50 (m, 2H), 1.36 (d, J=6.9 Hz, 6H).

c) tert-Butyl 3-(2-(4-(2-(4-(2-isopropylthiazole-4-carbonyl)-1-oxa-4,9-diazaspiro[5.5]undecan-9-yl)ethyl)thiophen-2-yl)ethoxy)propanoate

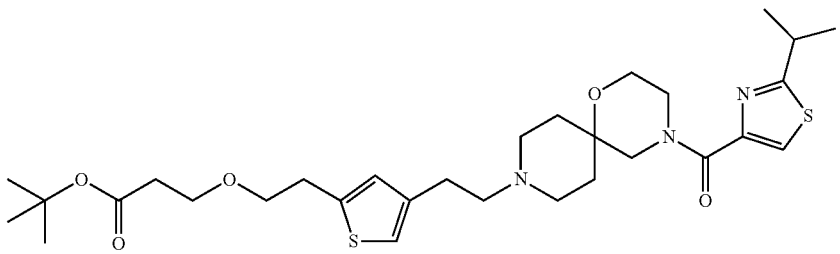

Benzyltrimethylammonium hydroxide (40% in water, 0.27 mL) was added in one portion to a stirred solution of (9-(2-(5-(2-hydroxyethyl)thiophen-3-yl)ethyl)-1-oxa-4,9-diazaspiro[5.5]undecan-4-yl)(2-isopropylthiazol-4-yl)methanone [Example 78, step b] (0.92 g) and tert-butyl acrylate (0.38 g) in toluene (1 mL). The resultant mixture was stirred vigorously at 20° C. for 4 hours. Acetonitrile (1 mL) was added and the mixture was stirred for 18 hours and then purified without work up. The crude product was purified by flash silica chromatography, using 6% methanol in ethyl acetate with 1% triethylamine as solvent. Fractions containing the product were evaporated to dryness to afford the subtitled compound. Yield 0.84 g.

m/z 592 (M+H)⁺ (APCI).

EXAMPLE 79

N-Ethyl-N-(2-(2-(4-hydroxy-2-oxo-2,3-dihydrobenzo[d]thiazol-7-yl)ethylamino)ethyl)-3-(2-(4-(2-(4-(2-isopropylthiazole-4-carbonyl)-1-oxa-4,9-diazaspiro[5.5]undecan-9-yl)ethyl)thiophen-2-yl)ethoxy)propanamide ditrifluoroacetate

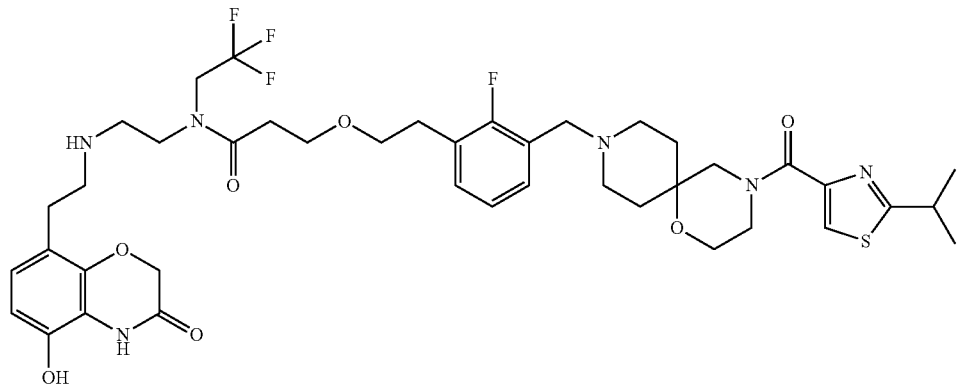

Tosic acid monohydrate (0.33 g) was added to a solution of N-(2,2-dimethoxyethyl)-3-(2-fluoro-3-((4-(2-isopropylthiazole-4-carbonyl)-1-oxa-4,9-diazaspiro[5.5]undecan-9-yl)methyl)phenethoxy)-N-(2,2,2-trifluoroethyl)propanamide (0.15 g) in DCM (3 mL) and the resulting mixture was stirred for 20 min at RT. The solution was then added to a suspension of 8-(2-aminoethyl)-5-hydroxy-2H-benzo[b][1,4]oxazin-3(4H)-one hydrochloride [WO 2008075025] (0.078 g) and sodium bicarbonate (0.17 g) in a mixture of NMP (2 mL) and water (0.2 mL), and the resulting cloudy solution was stirred vigorously for 10 min. Sodium triacetoxyborohydride (0.14 g) was then added and the resulting mixture was stirred vigorously for 4 hours. The reaction mixture was partitioned between ethyl acetate (15 mL) and saturated sodium bicarbonate solution (15 mL). The organic phase was separated, washed with 10% brine (2×15 mL), dried over sodium sulphate, filtered and evaporated. The residue was purified by preparative HPLC (Sunfire™, Gradient: 20-55% methanol in 0.1% aqueous TFA). The fractions containing the desired product were evaporated to dryness to afford impure product, which was further purified by preparative HPLC (Sunfire™, Gradient: 10-40% acetonitrile in 0.1% aqueous formic acid). The fractions containing the desired product were treated with trifluoroacetic acid (20 mg) and then evaporated to dryness to afford the titled compound. Yield 20 mg.

m/z 849 M+ (MultiMode+).

$^{1}$H NMR (400 MHz, D$_{6}$-DMSO, 90° C.) δ 9.39 (s, 1H), 7.94 (s, 1H), 7.45-7.37 (m, 2H), 7.21-7.15 (m, 1H), 6.66 (d, J=8.2 Hz, 1H), 6.49 (d, J=8.2 Hz, 1H), 4.52 (s, 2H), 4.31-4.15 (m, 4H), 3.75-3.61 (m, 12H), 3.35-3.25 (m, 1H), 3.20-3.01 (m, 8H), 2.91-2.79 (m, 4H), 2.69-2.62 (m, 2H), 2.07-1.96 (m, 2H), 1.84-1.69 (m, 2H), 1.35 (d, J=6.9 Hz, 6H). Four exchangeable protons not observed.

The N-(2,2-dimethoxyethyl)-3-(2-fluoro-3-((4-(2-isopropylthiazole-4-carbonyl)-1-oxa-4,9-diazaspiro[5.5]undecan-9-yl)methyl)phenethoxy)-N-(2,2,2-trifluoroethyl)propanamide used as a starting material was prepared as follows:

a) N-(2,2-Dimethoxyethyl)-3-(2-fluoro-3-((4-(2-isopropylthiazole-4-carbonyl)-1-oxa-4,9-diazaspiro[5.5]undecan-9-yl)methyl)phenethoxy)-N-(2,2,2-trifluoroethyl)propanamide

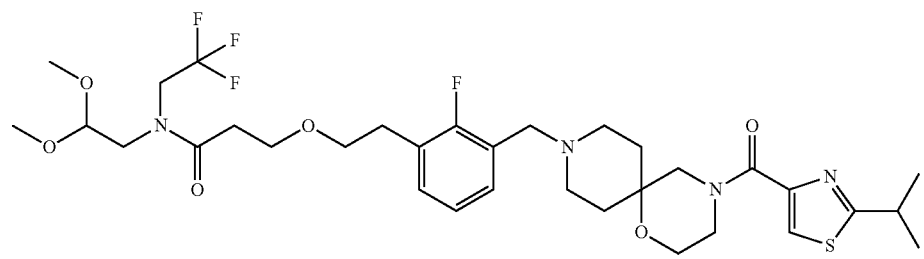

HATU (0.30 g) was added in one portion to a cooled solution (ice bath) of 3-(2-fluoro-3-((4-(2-isopropylthiazole-4-carbonyl)-1-oxa-4,9-diazaspiro[5.5]undecan-9-yl)methyl)phenethoxy)propanoic acid [Example 7, step d] (0.32 g) and N-(2,2-dimethoxyethyl)-2,2,2-trifluoroethanamine [Amine 14] (0.17 g) and triethylamine (0.25 mL) in DMF (7 mL). The mixture was stirred at 20° C. for 3 days, then partitioned between ethyl acetate and brine. The organic phase was washed with brine (×2), dried, filtered and the solvent evaporated under reduced pressure. The crude product was purified by flash silica chromatography, using 5% methanol in ethyl acetate with 1% triethylamine as solvent. Fractions containing the product were evaporated to dryness to afford the subtitled compound. Yield 0.15 g.

m/z 703 (M+H)+ (APCI).

EXAMPLE 80

N-Ethyl-N-(2-(2-(4-hydroxy-2-oxo-2,3-dihydrobenzo[d]thiazol-7-yl)ethylamino)ethyl)-3-(2-(4-(2-(4-(2-isopropylthiazole-4-carbonyl)-1-oxa-4,9-diazaspiro[5.5]undecan-9-yl)ethyl)thiophen-2-yl)ethoxy)propanamide ditrifluoroacetate

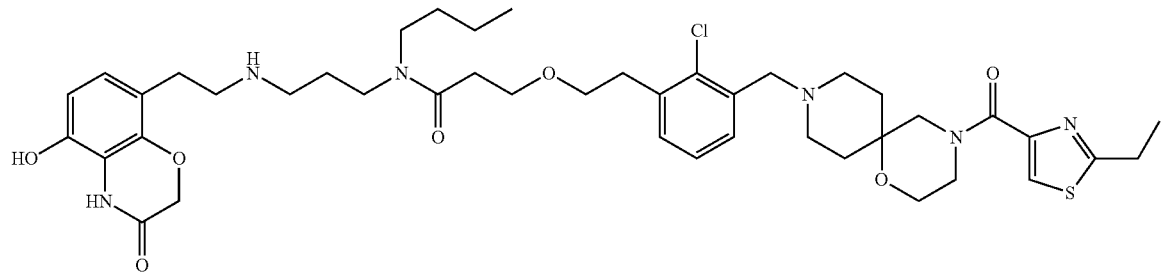

A solution of pyridine sulfur trioxide (0.20 g) dissolved in DMSO (5 mL) was added dropwise over a period of 3 minutes to a stirred solution of N-butyl-3-(2-chloro-3-((4-(2-ethylthiazole-4-carbonyl)-1-oxa-4,9-diazaspiro[5.5]undecan-9-yl)methyl)phenethoxy)-N-(3-hydroxypropyl)propanamide (0.28 g) and triethylamine (0.18 mL) in DMSO (5 mL) and DCM (10 mL) at 0° C. The resulting solution was stirred at RT for 1 h. The reaction mixture was partitioned between ethyl acetate (25 mL) and brine (25 mL), the organic layer was washed with brine (2×25 mL), dried, filtered and evaporated. The residue was dissolved in methanol (5 mL), 8-(2-aminoethyl)-5-hydroxy-2H-benzo[b][1,4]oxazin-3(4H)-one hydrochloride [WO 2008075025] (0.11 g) was added, followed by acetic acid (0.025 mL), and the mixture was stirred for 15 min. Sodium cyanoborohydride (0.04 g) was then added and the mixture was stirred overnight. The reaction mixture was partitioned between ethyl acetate (25 mL) and saturated sodium bicarbonate solution (25 mL). The organic phase was separated, washed with 10% brine (2×25 mL), dried over sodium sulphate, filtered and evaporated. The residue was purified by flash silica chromatography, elution gradient 97.25:2.5:0.25 to 92.3:7:0.7 DCM:methanol:'880' aqueous ammonia. Fractions containing the product were combined and evaporated. The resulting gum was purified further by preparative HPLC (Sunfire™, Gradient: 40-60% methanol in 0.2% aqueous TFA). The fractions containing the product were combined, evaporated, azeotroped with acetonitrile and triturated with ether to give the titled compound as a white solid. Yield 0.10 g.

m/z 839 M+ (MultiMode+).

$^1$H NMR (500 MHz, D$_6$-DMSO, 90° C.) δ 9.35 (s, 1H), 8.71-8.45 (m, 2H), 7.92 (s, 1H), 7.59-7.52 (m, 1H), 7.49-7.41 (m, 1H), 7.37-7.30 (m, 1H), 6.71-6.64 (m, 1H), 6.53-6.45 (m, 1H), 4.49 (s, 2H), 4.42 (s, 2H), 3.78-3.61 (m, 10H), 3.39-2.80 (m, 18H), 2.58-2.53 (m, 2H), 2.11-1.98 (m, 2H), 1.92-1.77 (m, 4H), 1.55-1.43 (m, 2H), 1.38-1.23 (m, 5H), 0.97-0.84 (m, 3H). Two exchangeable protons not observed.

The N-butyl-3-(2-chloro-3-((4-(2-ethylthiazole-4-carbonyl)-1-oxa-4,9-diazaspiro[5.5]undecan-9-yl)methyl)phenethoxy)-N-(3-hydroxypropyl)propanamide used as a starting material was prepared as follows:

a) N-Butyl-N-(3-(tert-butyldimethylsilyloxy)propyl)-3-(2-chloro-3-((4-(2-ethylthiazole-4-carbonyl)-1-oxa-4,9-diazaspiro[5.5]undecan-9-yl)methyl)phenethoxy)propanamide

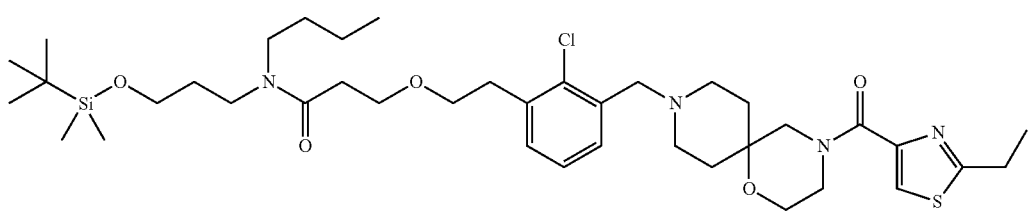

Prepared by the method of Example 26, step f using N-(3-(tert-butyldimethylsilyloxy)propyl)butan-1-amine [Amine 15] (0.17 g) in place of N-ethyl-2,2-dimethoxyethanamine. Yield 0.47 g.

m/z 763 M+ (APCI).

b) N-Butyl-3-(2-chloro-3-((4-(2-ethylthiazole-4-carbonyl)-1-oxa-4,9-diazaspiro[5.5]undecan-9-yl)methyl)phenethoxy)-N-(3-hydroxypropyl)propanamide

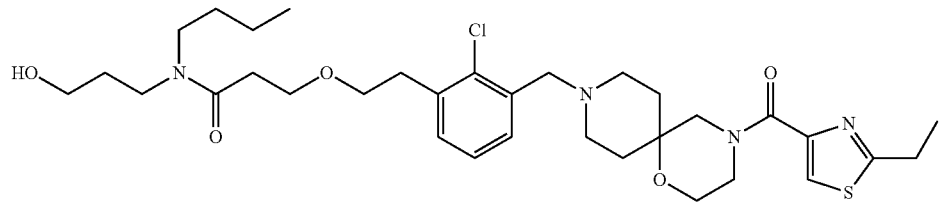

TBAF (1M in THF, 0.62 mL) was added to a solution of N-butyl-N-(3-(tert-butyldimethylsilyloxy)propyl)-3-(2-chloro-3-((4-(2-ethylthiazole-4-carbonyl)-1-oxa-4,9-diazaspiro[5.5]undecan-9-yl)methyl)phenethoxy)propanamide [Example 80, step a] (0.47 g) in THF (10 mL) and the mixture stirred overnight. The solvent was evaporated and the residue purified by flash silica chromatography, elution gradient 1:1:0.05 ethyl acetate:isohexane:triethylamine to 95:5 ethyl acetate:triethylamine, to give the subtitled compound as a clear oil. Yield 0.40 g.

m/z 649 M$^+$ (APCI).

$^1$H NMR (400 MHz, CDCl$_3$) δ 7.53-7.44 (m, 3H), 7.37 (t, J=7.7 Hz, 1H), 3.67 (t, J=6.3 Hz, 2H), 3.66 (t, J=6.5 Hz, 2H), 2.89 (t, J=6.5 Hz, 2H), 2.46 (t, J=6.4 Hz, 2H), 1.43 (s, 9H).

b) 3-(3-Cyanophenethoxy)propanoic acid

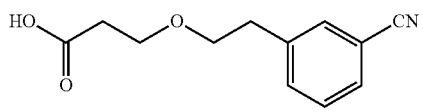

EXAMPLES 81-175

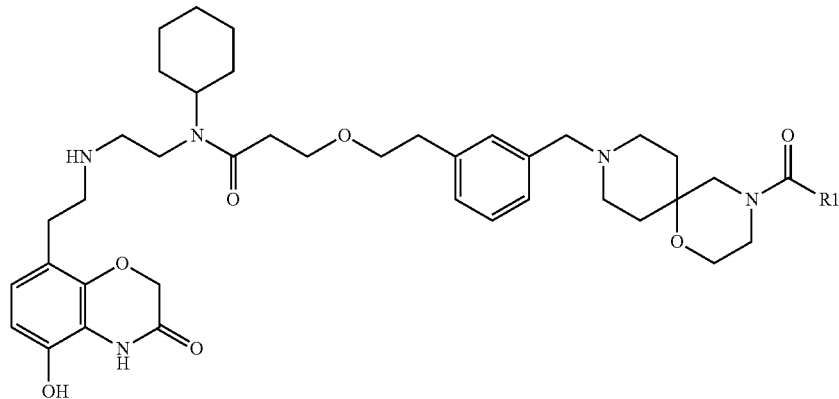

a) tert-Butyl 3-(3-cyanophenethoxy)propanoate

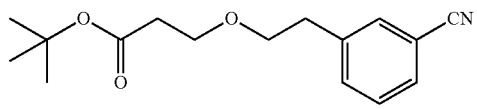

Prepared by the method of Example 1, step d using 3-(2-hydroxyethyl)benzonitrile [WO 2007069986] (4.3 g) in place of (9-(4-(2-hydroxyethyl)phenethyl)-1-oxa-4,9-diazaspiro[5.5]undecan-4-yl)(2-isopropylthiazol-4-yl)methanone. Purification was by flash silica chromatography using 15% ethyl acetate in isohexane as solvent. Yield 7.0 g.

Prepared by the method of Example 1, step e using tert-butyl 3-(3-cyanophenethoxy)propanoate [Examples 81-175, step a] (7.0 g) in place of tert-butyl 3-(4-(2-(4-(2-isopropylthiazole-4-carbonyl)-1-oxa-4,9-diazaspiro[5.5]undecan-9-yl)ethyl)phenethoxy)propanoate. After concentration in-vacuo, the residue was azeotroped with toluene (×2) to afford the subtitled compound. Yield 2.8 g.

m/z 218 (M−H)$^-$ (APCI).

c) 3-(3-Cyanophenethoxy)-N-cyclohexyl-N-(2,2-dimethoxyethyl)propanamide

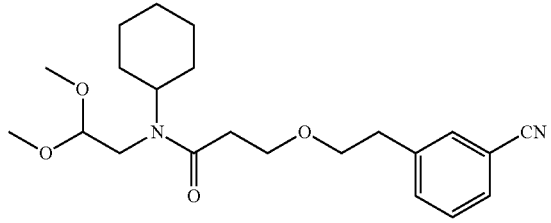

A colourless solution of 3-(3-cyanophenethoxy)propanoic acid [Examples 81-175, step b] (5.55 g) in dichloromethane (110 mL) and N,N-dimethylformamide (0.22 mL) was treated with oxalyl chloride (2.7 mL) and stirred at room temperature for 1.75 hours, then concentrated in-vacuo. The resulting oil was dissolved in more dichloromethane (50 mL) and added dropwise over 1 hour to an ice-cold solution of N-(2,2-dimethoxyethyl)cyclohexanamine [WO 2008075025] (5.68 g) and Hunig's base (8.85 mL) in dichloromethane (100 mL). The resulting solution was removed from the cooling bath and stirred at room temperature for 2.5 hours, then washed three times with water and once with brine. The organic phase was dried (MgSO$_4$), filtered and concentrated onto flash silica (50 mL) in-vacuo. The resulting powder was purified by flash chromatography on silica eluted with 75% ethyl acetate in isohexane to afford the subtitled compound. Yield 8.8 g.

m/z 389 (M+H)$^+$ (APCI).

d) 3-(3-Cyanophenethoxy)-N-cyclohexyl-N-(2-oxoethyl)propanamide

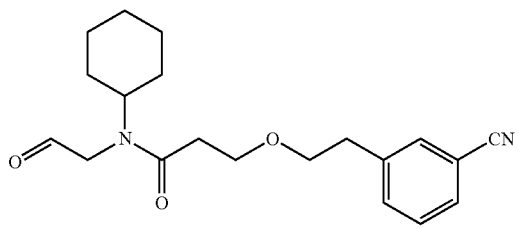

Prepared by the method of Example 42, step d using 3-(3-cyanophenethoxy)-N-cyclohexyl-N-(2,2-dimethoxyethyl)propanamide [Examples 81-175, step c] (8.8 g) in place of N-cyclohexyl-N-(2,2-dimethoxyethyl)-3-(3-((4-(2-methylthiazole-4-carbonyl)-1-oxa-4,9-diazaspiro[5.5]undecan-9-yl)methyl)phenethoxy)propanamide. Yield 8.0 g.

m/z 343 (M+H)$^+$ (APCI).

e) tert-Butyl 2-(3-(3-cyanophenethoxy)-N-cyclohexylpropanamido)ethyl(2-(5-hydroxy-3-oxo-3,4-dihydro-2H-benzo[b][1,4]oxazin-8-yl)ethyl)carbamate

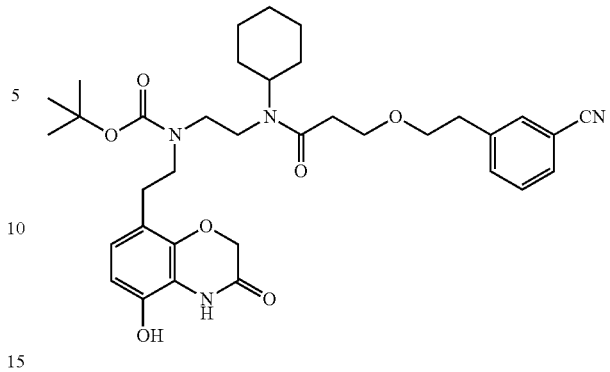

To a solution of 3-(3-cyanophenethoxy)-N-cyclohexyl-N-(2-oxoethyl)propanamide [Examples 81-175, step d] (7.8 g) in NMP (450 mL) and water (23 mL) was added 8-(2-aminoethyl)-5-hydroxy-2H-benzo[b][1,4]oxazin-3(4H)-one hydrochloride [WO 2008075025] (6.1 g) and sodium bicarbonate (2.1 g). The mixture was stirred for 5 minutes, before the addition of sodium triacetoxyborohydride (7.3 g). The mixture was stirred overnight, then diluted with ethyl acetate (900 mL) and water (900 mL). Sodium bicarbonate (9.6 g) was added, together with di-tert-butyl dicarbonate (5.0 g), and the two-phase mixture was stirred at room temperature over a weekend. The mixture was then separated, and the aqueous phase extracted once more with ethyl acetate. The combined organic phases were washed three times with water and once with brine, then dried (MgSO$_4$) and concentrated onto flash silica (50 mL) in-vacuo. The residue was purified by flash chromatography on silica eluted with 75% ethyl acetate in isohexane, followed by 100% ethyl acetate to afford the subtitled compound as a white foam. Yield 7.3 g.

m/z 633 (M−H)$^-$ (APCI).

f) tert-Butyl 2-(N-cyclohexyl-3-(3-formylphenethoxy)propanamido)ethyl(2-(5-hydroxy-3-oxo-3,4-dihydro-2H-benzo[b][1,4]oxazin-8-yl)ethyl)carbamate

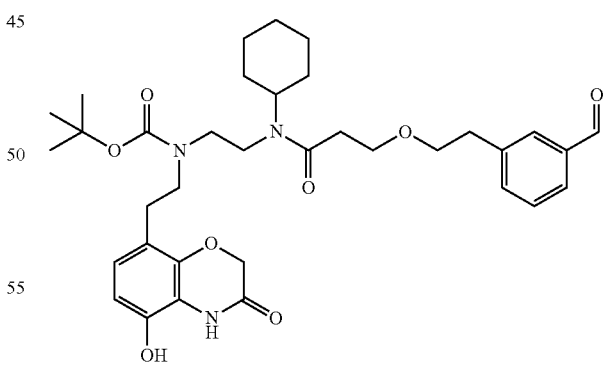

To a stirred solution of tert-butyl 2-(3-(3-cyanophenethoxy)-N-cyclohexylpropanamido)ethyl(2-(5-hydroxy-3-oxo-3,4-dihydro-2H-benzo[b][1,4]oxazin-8-yl)ethyl)carbamate [Examples 81-175, step e] (7.3 g) in pyridine (115 mL), acetic acid (58 mL) and water (58 mL), pre-cooled in ice-water under nitrogen, was added sodium hypophosphite monohydrate (14.6 g) followed by Raney® nickel (50% in water, 3.0 g). The reaction mixture was stirred at 45° C. for 8 hours, then allowed to cool and stand over a weekend. Celite was added and the suspension was filtered through a pad of Celite, washing the residue well with acetic acid and ethyl acetate. The filtrate was washed three times with water, once with brine, then dried (MgSO$_4$), filtered and concentrated in-vacuo. The residue was azeotroped twice with toluene to afford the subtitled compound as a pale yellow foam. Yield 6.6 g.

m/z 636 (M–H)⁻ (APCI).

g) tert-Butyl 2-(N-cyclohexyl-3-(3-((4-(2,2,2-trifluoroacetyl)-1-oxa-4,9-diazaspiro[5.5]undecan-9-yl)methyl)phenethoxy)propanamido)ethyl(2-(5-hydroxy-3-oxo-3,4-dihydro-2H-benzo[b][1,4]oxazin-8-yl)ethyl)carbamate

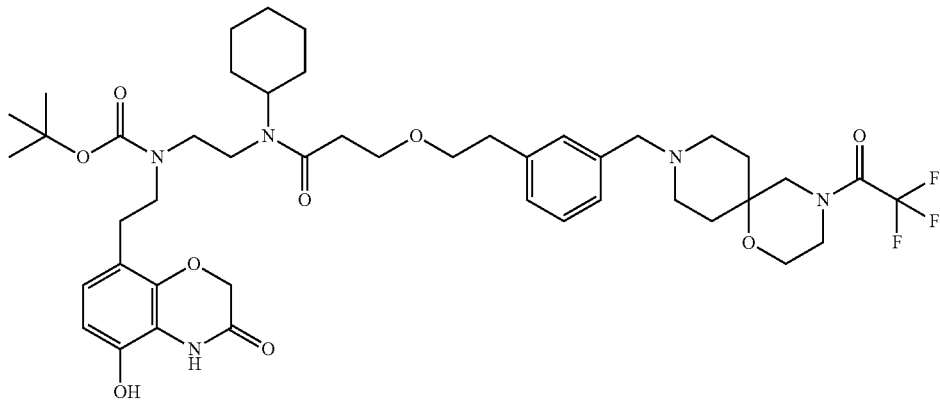

A solution of 2,2,2-trifluoro-1-(1-oxa-4,9-diazaspiro[5.5]undecan-4-yl)ethanone trifluoroacetate [Example 9, step a] (4.5 g) in NMP (30 mL) was treated with acetic acid (0.6 mL), stirred for 5 minutes, and then added in one portion to tert-butyl 2-(N-cyclohexyl-3-(3-formylphenethoxy)propanamido)ethyl(2-(5-hydroxy-3-oxo-3,4-dihydro-2H-benzo[b][1,4]oxazin-8-yl)ethyl)carbamate [Examples 81-175, step f] (6.6 g), completing the transfer with more NMP (30 mL). The resulting solution was stirred at room temperature for 4 hours and then cooled in an ice-water bath and treated with sodium triacetoxyborohydride (3.3 g) in one portion. The resulting suspension was stirred at room temperature overnight, then more sodium borohydride (2.2 g) was added and the mixture was stirred for a further 5 hours. The mixture was cautiously poured into saturated sodium bicarbonate solution and extracted twice with ethyl acetate. The combined organic phases were washed three times with water, once with brine, then dried (MgSO$_4$), filtered and concentrated onto flash silica (100 mL) in-vacuo. The resulting powder was purified by flash chromatography on silica eluted with acetic acid:methanol:dichloromethane (1:5:94) to elute off the benzyl alcohol corresponding to reduced starting material, 100% dichloromethane to wash the column free from acetic acid, then triethylamine:methanol:dichloromethane (1:5:94) to elute off the product. Fractions containing the desired product were combined and concentrated in-vacuo to afford the subtitled compound as an off-white foam. Yield 4.6 g.

m/z 873 (M–H)⁻ (APCI).

h) tert-Butyl 2-(3-(3-(1-oxa-4,9-diazaspiro[5.5]undecan-9-ylmethyl)phenethoxy)-N-cyclohexylpropanamido)ethyl(2-(5-hydroxy-3-oxo-3,4-dihydro-2H-benzo[b][1,4]oxazin-8-yl)ethyl)carbamate

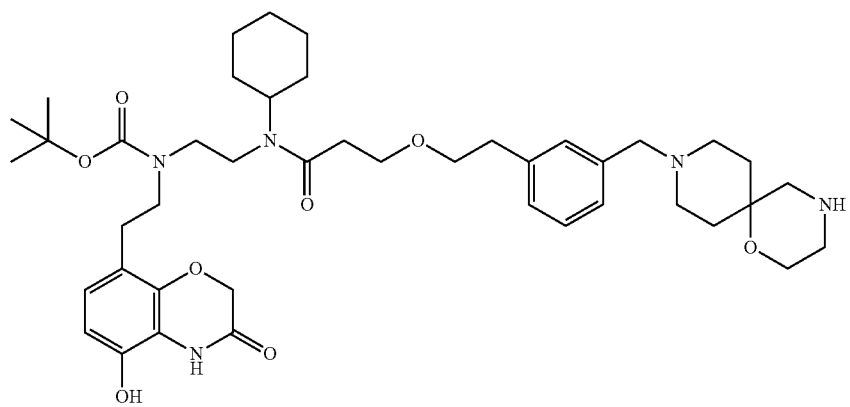

A solution of tert-butyl 2-(N-cyclohexyl-3-(3-((4-(2,2,2-trifluoroacetyl)-1-oxa-4,9-diazaspiro[5.5]undecan-9-yl)methyl)phenethoxy)propanamido)ethyl(2-(5-hydroxy-3-oxo-3,4-dihydro-2H-benzo[b][1,4]oxazin-8-yl)ethyl)carbamate [Examples 81-175, step g] (1.1 g) in methanol (10 mL) was treated with 35% aqueous ammonia (2.5 mL) and stirred at room temperature for 4.25 hours, then concentrated in-vacuo to afford the subtitled compound as a pale yellow foam. Yield 0.97 g.

m/z 778 M+ (APCI).

i) tert-Butyl 2-(3-(3-(1-oxa-4,9-diazaspiro[5.5]undecan-9-ylmethyl)phenethoxy)-N-cyclohexylpropanamido)ethyl(2-(5-(tert-butyldimethylsilyloxy)-3-oxo-3,4-dihydro-2H-benzo[b][1,4]oxazin-8-yl)ethyl)carbamate

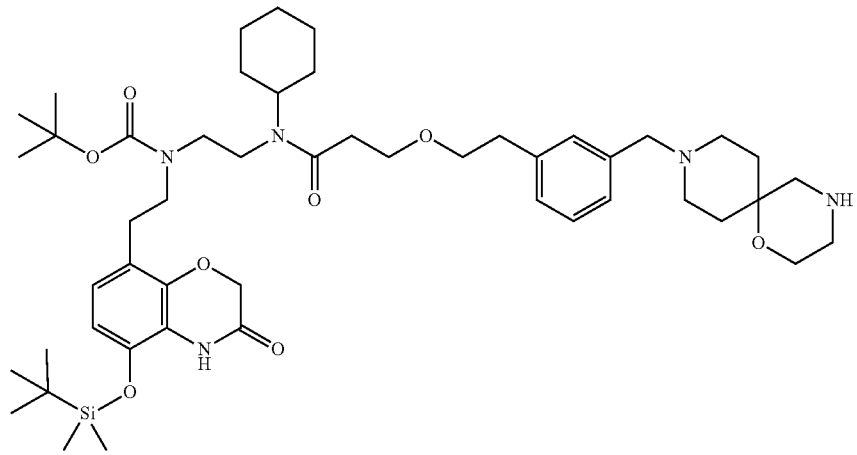

tert-Butyl 2-(3-(3-(1-oxa-4,9-diazaspiro[5.5]undecan-9-ylmethyl)phenethoxy)-N-cyclohexylpropanamido)ethyl(2-(5-hydroxy-3-oxo-3,4-dihydro-2H-benzo[b][1,4]oxazin-8-yl)ethyl)carbamate [Examples 81-175, step h] (0.97 g) was dissolved in NMP (10 mL) and treated with Hunig's base (1.0 mL) followed by tert-butyldimethylsilyl chloride (0.45 g). The resulting mixture was stirred at room temperature for 3 hours. The solution was poured into saturated sodium bicarbonate solution and extracted three times with ethyl acetate. The combined extracts were washed three times with water, once with brine, then dried (MgSO$_4$) and concentrated onto flash silica (20 mL) in-vacuo. The resulting powder was purified by flash chromatography on silica eluted with triethylamine:methanol:dichloromethane (1:5:94) to afford the subtitled compound as a white foam. Yield 0.81 g.

m/z 892 M+ (APCI).

j) Parallel Synthesis

Preparation of Examples 81-175

A solution of tert-butyl 2-(3-(3-(1-oxa-4,9-diazaspiro[5.5]undecan-9-ylmethyl)phenethoxy)-N-cyclohexylpropanamido)ethyl(2-(5-(tert-butyldimethylsilyloxy)-3-oxo-3,4-dihydro-2H-benzo[b][1,4]oxazin-8-yl)ethyl)carbamate [Examples 81-175, step i] (1.04 g) and triethylamine (0.5 mL) in NMP (2.5 mL) was dispensed as aliquots of 30 μL total volume into solutions or suspensions of the appropriate carboxylic acids (0.01 mmol) in NMP (80 μL). To each reaction mixture was then added a solution of HATU (4.9 mg) in NMP (30 μL). The reaction mixtures were agitated to mix and allowed to stand at room temperature overnight. Acetonitrile (800 μL) was added and the mixtures were passed through Tosic-65 resin (350 mg). The resin was washed with acetonitrile (800 μL) and the combined washings collected and passed again through the Tosic-65 resin. The combined washings were collected and passed twice through a second batch of Tosic-65 resin (350 mg). The two batches of resin were then separately washed with acetonitrile (3 mL). A solution of ammonia in methanol (3.5 M, 2.4 mL) was separately passed through the two batches of resin and the two sets of washings collected and evaporated under a stream of nitrogen gas. The two resulting sets of residues were combined in methanol and evaporated under a stream of nitrogen gas. The residues were dissolved in formic acid (300 μL), agitated to mix, and allowed to stand at room temperature overnight. Acetonitrile (800 μL) was added and the solutions were passed through Tosic-65 resin (350 mg). The resin was washed with acetonitrile (800 μL) and the combined washings collected and passed through the Tosic-65 resin twice more. The resin was then washed with acetonitrile (3 mL). A solution of ammonia in methanol (3.5M, 2.4 mL) was passed through the resin and the resulting washings collected and evaporated under a stream of nitrogen gas. DMSO (360 μL) was added to the residues and the resulting solutions were purified by preparative HPLC using a Waters Sunfire™ Prep C18 (19×50 mm, 5 μm) column eluted with a gradient of acetonitrile in 0.1% aqueous TFA. The fractions containing the product were evaporated to give the titled compounds as their trifluoroacetic acid salts.

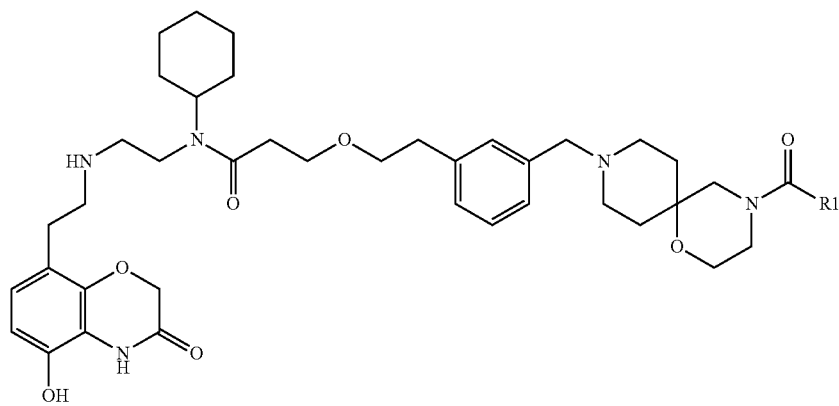

| Example Number | C(O)R1 Group | Name | Molecular Mass | Found Mass* | Retention Time** (min) |
|---|---|---|---|---|---|
| 81 | | 3-(3-((4-(Benzo[b]thiophene-2-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 838.08 | 837.41 | 1.50 |
| 82 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-phenylthiazole-4-carbonyl)-1-oxa-4,9-diazaspiro[5.5]undecan-9-yl)methyl)phenethoxy)propanamide | 865.11 | 864.42 | 1.51 |
| 83 | | N-Cyclohexyl-3-(3-((4-(5-ethylthiophene-2-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 816.07 | 815.43 | 1.47 |
| 84 | | 3-(3-((4-(Benzofuran-5-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 822.02 | 821.44 | 1.42 |

-continued

| Example Number | C(O)R1 Group | Name | Molecular Mass | Found Mass* | Retention Time** (min) |
|---|---|---|---|---|---|
| 85 | 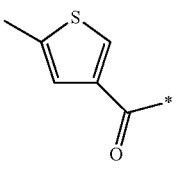 | N-Cyclohexyl-N-(2-(2-(5-hydroxy-3-oxo-3,4-dihydro-2H-benzo[b][1,4]oxazin-8-yl)ethylamino)ethyl)-3-(3-((4-(5-methylthiophene-3-carbonyl)-1-oxa-4,9-diazaspiro[5.5]undecan-9-yl)methyl)phenethoxy)propanamide | 802.05 | 801.41 | 1.39 |
| 86 | 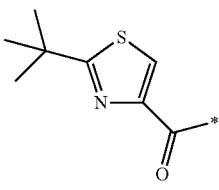 | 3-(3-((4-(2-tert-Butylthiazole-4-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 845.12 | 844.46 | 1.44 |
| 87 | 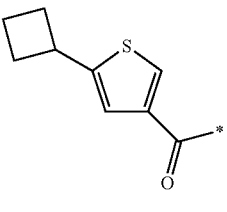 | 3-(3-((4-(2-Cyclobutylthiazole-4-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 843.10 | 842.44 | 1.45 |
| 88 | 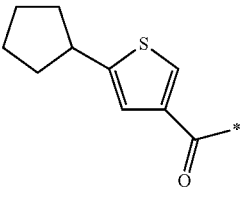 | N-Cyclohexyl-3-(3-((4-(2-cyclopentylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 857.13 | 856.46 | 1.49 |
| 89 | 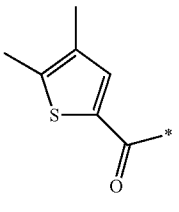 | N-Cyclohexyl-3-(3-((4-(4,5-dimethylthiophene-2-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 816.07 | 815.43 | 1.44 |
| 90 | 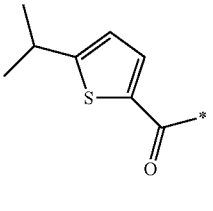 | N-Cyclohexyl-N-(2-(2-(5-hydroxy-3-oxo-3,4-dihydro-2H-benzo[b][1,4]oxazin-8-yl)ethylamino)ethyl)-3-(3-((4-(5-isopropylthiophene-2-carbonyl)-1-oxa-4,9-diazaspiro[5.5]undecan-9-yl)methyl)phenethoxy)propanamide | 830.10 | 829.44 | 1.51 |

| Example Number | C(O)R1 Group | Name | Molecular Mass | Found Mass* | Retention Time** (min) |
|---|---|---|---|---|---|
| 91 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(5-isopropylthiophene-3-carbonyl)-1-oxa-4,9-diazaspiro[5.5]undecan-9-yl)methyl)phenethoxy)propanamide | 830.10 | 829.44 | 1.52 |
| 92 | | 3-(3-((4-(Benzo[b]thiophene-5-carobonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 838.08 | 837.41 | 1.46 |
| 93 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(5-propylthiophene-3-carbonyl)-1-oxa-4,9-diazaspiro[5.5]undecan-9-yl)methyl)phenethoxy)propanamide | 830.10 | 829.44 | 1.53 |
| 94 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-isobutylthiazole-4-carbonyl)-1-oxa-4,9-diazaspiro[5.5]undecan-9-yl)methyl)phenethoxy)propanamide | 845.12 | 844.46 | 1.49 |
| 95 | | N-Cyclohexyl-3-(3-((4-(2-ethylthiazole-4-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 817.06 | 816.42 | 1.37 |
| 96 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-(pentan-3-yl)thiazole-4-carbonyl)-1-oxa-4,9-diazaspiro[5.5]undecan-9-yl)methyl)phenethoxy)propanamide | 859.14 | 858.47 | 1.51 |

-continued

| Example Number | C(O)R1 Group | Name | Molecular Mass | Found Mass* | Retention Time** (min) |
|---|---|---|---|---|---|
| 97 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(6-isopropylpicolinoyl)-1-oxa-4,9-diazaspiro[5.5]undecan-9-yl)methyl)phenethoxy)propanamide | 825.06 | 824.48 | 1.43 |
| 98 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(4-isopropylthiophene-2-carbonyl)-1-oxa-4,9-diazaspiro[5.5]undecan-9-yl)methyl)phenethoxy)propanamide | 830.10 | 829.44 | 1.48 |
| 99 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(quinoline-3-carbonyl)-1-oxa-4,9-diazaspiro[5.5]undecan-9-yl)methyl)phenethoxy)propanamide | 833.04 | 832.45 | 1.35 |
| 100 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(quinoline-8-carbonyl)-1-oxa-4,9-diazaspiro[5.5]undecan-9-yl)methyl)phenethoxy)propanamide | 833.04 | 832.45 | 1.35 |
| 101 | | N-Cyclohexyl-3-(3-((4-(2-ethoxynicotinoyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 827.04 | 826.46 | 1.38 |
| 102 | | 3-(3-((4-(5-Bromonicotinoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 861.88 | 860.35 | 1.35 |

| Example Number | C(O)R1 Group | Name | Molecular Mass | Found Mass* | Retention Time** (min) |
|---|---|---|---|---|---|
| 103 | | 3-(3-((4-(3-(1H-Benzo[d]imidazol-2-yl)propanoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 850.07 | 849.48 | 1.23 |
| 104 | | N-Cyclohexyl-3-(3-((4-(3-hydroxy-2-phenylpropanoyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 826.05 | 825.47 | 1.33 |
| 105 | | 3-(3-((4-(Cyclohex-3-enecarbonyl)-1-oxa-4,9-diazaspiro[5.5]undecan-9-yl)methyl)phenethoxy)-N-cylcohexyl-N-(2-(2-(5-hydroxy-3-oxo-3,4-dihydro-2H-benzo[b][1,4]oxazin-8-yl)ethylamino)ethyl)propanamide | 786.03 | 785.47 | 1.38 |
| 106 | | 3-(3-((4-(5-Chlorothiophene-2-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 822.47 | 821.36 | 1.39 |
| 107 | | N-Cyclohexyl-3-(3-((4-(5-fluoro-1H-indole-2-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 839.02 | 838.44 | 1.41 |
| 108 | | N-Cyclohexyl-3-(3-((4-(2,7-dimethylpyrazolo[1,5-a]pyrimidine-6-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 851.06 | 850.47 | 1.36 |

-continued

| Example Number | C(O)R1 Group | Name | Molecular Mass | Found Mass* | Retention Time** (min) |
|---|---|---|---|---|---|
| 109 | 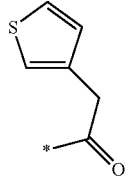 | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-(thiophen-3-yl)acetyl)-1-oxa-4,9-diazaspiro[5.5]undecan-9-yl)methyl)phenethoxy)propanamide | 802.05 | 801.41 | 1.41 |
| 110 | 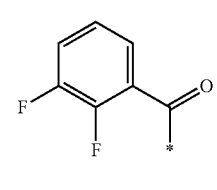 | N-Cyclohexyl-3-(3-((4-(2,3-difluorobenzoyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 817.97 | 817.42 | 1.40 |
| 111 | 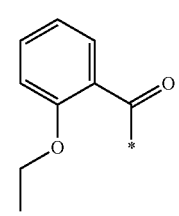 | N-Cyclohexyl-3-(3-((4-(2-ethoxybenzoyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 826.05 | 825.47 | 1.44 |
| 112 | 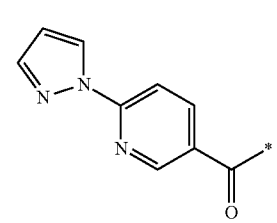 | 3-(3-((4-(6-(1H-Pyrazol-1-yl)nicotinoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 849.05 | 848.46 | 1.37 |
| 113 | 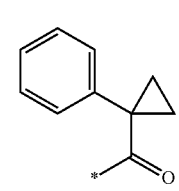 | N-Cyclohexyl-N-(2-(2-(5-hydroxy-3-oxo-3,4-dihydro-2H-benzo[b][1,4]oxazin-8-yl)ethylamino)ethyl)-3-(3-((4-(1-phenylcyclopropanecarbonyl)-1-oxa-4,9-diazaspiro[5.5]undecan-9-yl)methyl)phenethoxy)propanamide | 822.06 | 821.47 | 1.43 |
| 114 | 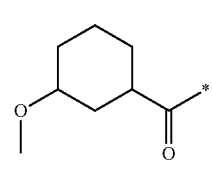 | N-Cyclohexyl-N-(2-(2-(5-hydroxy-3-oxo-3,4-dihydro-2H-benzo[b][1,4]oxazin-8-yl)ethylamino)ethyl)-3-(3-((4-(3-methoxycyclohexanecarbonyl)-1-oxa-4,9-diazaspiro[5.5]undecan-9-yl)methyl)phenethoxy)propanamide | 818.07 | 817.50 | 1.36 |

| Example Number | C(O)R1 Group | Name | Molecular Mass | Found Mass* | Retention Time** (min) |
|---|---|---|---|---|---|
| 115 | | N-Cyclohexyl-3-(3-((4-(2,3-dihydrobenzo[b][1,4]dioxine-2-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethyalmino)ethyl)propanamide | 840.03 | 839.45 | 1.42 |
| 116 | | N-Cyclohexyl-3-[2-[3-[[10-[2-(3-hydroxy-1-adamantyl)acetyl]-7-oxa-3,10-diazaspiro[5.5]undecan-3-yl]methyl]phenyl]ethoxy]-N-[2-[2-(5-hydroxy-3-oxo-4H-1,4-benzoxazin-8-yl)ethylamino]ethyl]propanamide | 870.14 | 869.53 | 1.32 |
| 117 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-methyl-1H-benzo[d]imidazole-5-carbonyl)-1-oxa-4,9-diazaspiro[5.5]undecan-9-yl)methyl)phenethoxy)propanamide | 836.05 | 835.46 | 1.14 |
| 118 | | 3-(3-((4-(5-Bromo-2-methylnicotinoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 875.91 | 874.36 | 1.23 |
| 119 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(quinoxazoline-2-carbonyl)-1-oxa-4,9-diazaspiro[5.5]undecan-9-yl)methyl)phenethoxy)propanamide | 834.03 | 833.45 | 1.42 |
| 120 | | 3-(3-((4-(1H-Indazole-3-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 822.02 | 821.45 | 1.40 |

| Example Number | C(O)R1 Group | Name | Molecular Mass | Found Mass* | Retention Time** (min) |
|---|---|---|---|---|---|
| 121 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(4-(trifluoromethyl)nicotinoyl)-1-oxa-4,9-diazaspiro[5.5]undecan-9-yl)methyl)phenethoxy)propanamide | 850.98 | 850.42 | 1.38 |
| 122 | | 3-(3-((4-(4-(1H-Pyrazol-1-yl)benzoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethyalmino)ethyl)propanamide | 848.06 | 847.46 | 1.39 |
| 123 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(4,5,6,7-tetrahydro-2H-indazole-3-carbonyl)-1-oxa-4,9-diazaspiro[5.5]undecan-9-yl)methyl)phenethoxy)propanamide | 826.05 | 825.48 | 1.36 |
| 124 | | 3-(3-((4-(2-(Benzo[d]isoxazol-3-yl)acetyl)-1-oxa-4,9-diazaspiro[5.5]undecan-9-yl)methyl)phenethoxy)-N-cylcohexyl-N-(2-(2-(5-hydroxy-3-oxo-3,4-dihydro-2H-benzo[b][1,4]oxazin-8-yl)ethylamino)ethyl)propanamide | 837.03 | 836.45 | 1.39 |
| 125 | | 3-(3-((4-(2-(1H-Benzo[d]imidazol-1-yl)acetyl)-1-oxa-4,9-diazaspiro[5.5]undecan-9-yl)methyl)phenethoxy)-N-cylcohexyl-N-(2-(2-(5-hydroxy-3-oxo-3,4-dihydro-2H-benzo[b][1,4]oxazin-8-yl)ethylamino)ethyl)propanamide | 836.05 | 835.46 | 1.19 |
| 126 | | 3-(3-((4-(2-(Benzo[d]thiazol-2-ylmethoxy)acetyl)-1-oxa-4,9-diazaspiro[5.5]undecan-9-yl)methyl)phenethoxy)-N-cylcohexyl-N-(2-(2-(5-hydroxy-3-oxo-3,4-dihydro-2H-benzo[b][1,4]oxazin-8-yl)ethylamino)ethyl)propanamide | 883.12 | 882.43 | 1.37 |

| Example Number | C(O)R1 Group | Name | Molecular Mass | Found Mass* | Retention Time** (min) |
|---|---|---|---|---|---|
| 127 | 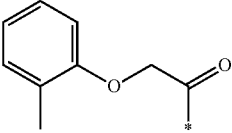 | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-(o-tolyloxy)acetyl)-1-oxa-4,9-diazaspiro[5.5]undecan-9-yl)methyl)phenethoxy)propanamide | 826.05 | 825.47 | 1.33 |
| 128 | 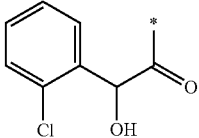 | 3-(3-((4-(2-(2-Chlorophenyl)-2-hydroxyacetyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 846.47 | 845.41 | 1.42 |
| 129 | 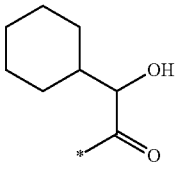 | (S)-N-Cyclohexyl-3-(3-((4-(2-cyclohexyl-2-hydroxyacetyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 818.07 | 817.50 | 1.40 |
| 130 | 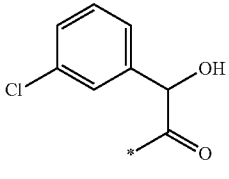 | (R)-3-(3-((4-(2-(3-Chlorophenyl)-2-hydroxyacetyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 846.47 | 845.41 | 1.43 |
| 131 | 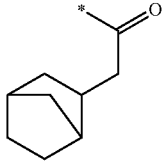 | 3-(3-((4-(2-((1S,4R)-Bicyclo[2.2.1]heptan-2-yl)acetyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 814.08 | 813.50 | 1.51 |
| 132 | 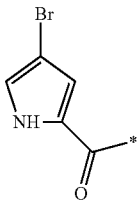 | 3-(3-((4-(4-Bromo-1H-pyrrole-2-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 849.87 | 848.35 | 1.42 |

-continued

| Example Number | C(O)R1 Group | Name | Molecular Mass | Found Mass* | Retention Time** (min) |
|---|---|---|---|---|---|
| 133 | | 3-(3-((4-(4-Chloro-1H-pyrazole-3-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 806.40 | 805.39 | 1.28 |
| 134 | | (S)-N-Cyclohexyl-N-(2-(2-(5-hydroxy-3-oxo-3,4-dihydro-2H-benzo[b][1,4]oxazin-8-yl)ethylamino)ethyl)-3-(3-((4-(2-hydroxy-3-phenylpropanoyl)-1-oxa-4,9-diazaspiro[5.5]undecan-9-yl)methyl)phenthoxy)propanamide | 826.05 | 825.47 | 1.35 |
| 135 | | 3-(3-((4-(4-(1H-Imidazol-1-yl)benzoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 848.06 | 847.46 | 1.17 |
| 136 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(5-methyl-1H-indole-2-carbonyl)-1-oxa-4,9-diazaspiro[5.5]undecan-9-yl)methyl)phenethoxy)propanamide | 835.06 | 834.47 | 1.44 |
| 137 | | (S)-N-Cyclohexyl-N-(2-(2-(5-hydroxy-3-oxo-3,4-dihydro-2H-benzo[b][1,4]oxazin-8-yl)ethylamino)ethyl)-3-(3-((4-(2-hydroxy-4-methylpentanoyl)-1-oxa-4,9-diazaspiro[5,5]undecan-9-yl)methyl)phenethoxy)propanamide | 792.03 | 791.48 | 1.32 |
| 138 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(4-methylthiophene-2-carbonyl)-1-oxa-4,9-diazaspiro[5.5]undecan-9-yl)methyl)phenethoxy)propanamide | 802.05 | 801.41 | 1.27 |

| Example Number | C(O)R1 Group | Name | Molecular Mass | Found Mass* | Retention Time** (min) |
|---|---|---|---|---|---|
| 139 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-o-tolylacetyl)-1-oxa-4,9-diazaspiro[5.5]undecan-9-yl)methyl)phenethoxy)propanamide | 810.05 | 809.47 | 1.48 |
| 140 | | 3-(3-((4-(2-(Benzo[d][1,3]dioxol-5-yl)acetyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 840.03 | 839.45 | 1.40 |
| 141 | | 3-(3-((4-(2-(1H-Indol-3-yl)acetyl)-1-oxa-4,9-diazaspiro[5.5]undecan-9-yl)methyl)phenethoxy)-N-cyclohexy-N-(2-(2-(5-hydroxy-3-oxo-3,4-dihydro-2H-benzo[b][1,4]oxazin-8-yl)ethylamino)ethyl)propanamide | 835.06 | 834.47 | 1.42 |
| 142 | | N-Cyclohexyl-3-(3-((4-(5,7-dimethylpyrazolo[1,5-a]pyrimidine-2-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 851.06 | 850.47 | 1.33 |
| 143 | | N-Cyclohexyl-3-[2-[3-[[10-(3,5-difluoroadamantane-1-carbonyl)-7-oxa-3,10-diazaspiro[5.5]undecan-3-yl]methyl]phenyl]ethoxy]-N-[2-[2-(5-hydroxy-3-oxo-4H-1,4-benzoxazin-8-yl)ethylamino]ethyl]propanamide | 876.10 | 875.50 | 1.41 |
| 144 | | N-Cyclohexyl-3-(3-((4-(5-ethylthiophene-3-carbonyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 816.07 | 815.43 | 1.23 |

-continued

| Example Number | C(O)R1 Group | Name | Molecular Mass | Found Mass* | Retention Time** (min) |
|---|---|---|---|---|---|
| 145 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-phenyl-1H-imidazole-5-carbonyl)-1-oxa-4,9-diazaspiro[5.5]undecan-9-yl)methyl)phenethoxy)propanamide | 848.06 | 847.46 | 1.30 |
| 146 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(pyrazolo[1,5-a]pyridine-2-carbonyl)-1-oxa-4,9-diazaspiro[5.5]undecan-9-yl)methyl)phenethoxy)propanamide | 822.02 | 821.45 | 1.36 |
| 147 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(5-isopropylisoxazole-3-carbonyl)-1-oxa-4,9-diazaspiro[5.5]undecan-9-yl)methyl)phenethoxy)propanamide | 815.02 | 814.46 | 1.45 |
| 148 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-(1-hydroxycycloheptyl)acetyl)-1-oxa-4,9-diazaspiro[5,5]undecan-9-yl)methyl)phenethoxy)propanamide | 832.10 | 831.51 | 1.42 |
| 149 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(5-(trifluoromethyl)picolinoyl)-1-oxa-4,9-diazaspiro[5.5]undecan-9-yl)methyl)phenethoxy)propanamide | 850.98 | 850.42 | 1.40 |
| 150 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(7-methylimidazo[1,4-a]pyridine-2-carbonyl)-1-oxa-4,9-diazaspiro[5.5]undecan-9-yl)methyl)phenethoxy)propanamide | 836.05 | 835.46 | 1.19 |

| Example Number | C(O)R1 Group | Name | Molecular Mass | Found Mass* | Retention Time** (min) |
|---|---|---|---|---|---|
| 151 | 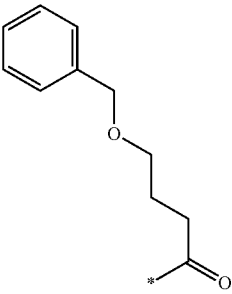 | 3-(3-((4-(4-(Benzyloxy)butanoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 854.10 | 853.50 | 1.43 |
| 152 | 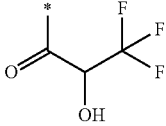 | N-Cyclohexyl-N-(2-(2-(5-hydroxy-3-oxo-3,4-dihydro-2H-benzo[b][1,4]oxazin-8-yl)ethylamino)ethyl)-3-(3-((4-(3,3,3-trifluoro-2-hydroxypropanoyl)-1-oxa-4,9-diazaspiro[5.5]undecan-9-yl)methyl)phenethoxy)propanamide | 803.92 | 803.41 | 1.20 |
| 153 | 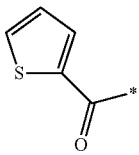 | N-Cyclohexyl-N-(2-(2-(5-hydroxy-3-oxo-3,4-dihydro-2H-benzo[b][1,4]oxazin-8-yl)ethylamino)ethyl)-3-(3-((4-(thiophene-2-carbonyl)-1-oxa-4,9-diazaspiro[5.5]undecan-9-yl)methyl)phenethoxy)propanamide | 788.02 | 787.40 | 1.37 |
| 154 | 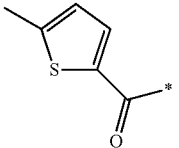 | N-Cyclohexyl-N-(2-(2-(5-hydroxy-3-oxo-3,4-dihydro-2H-benzo[b][1,4]oxazin-8-yl)ethylamino)ethyl)-3-(3-((4-(5-methylthiophene-2-carbonyl)-1-oxa-4,9-diazaspiro[5.5]undecan-9-yl)methyl)phenethoxy)propanamide | 802.05 | 801.41 | 1.40 |
| 155 | 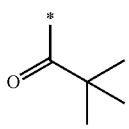 | N-Cyclohexyl-N-(2-(2-(5-hydroxy-3-oxo-3,4-dihydro-2H-benzo[b][1,4]oxazin-8-yl)ethylamino)ethyl)-3-(3-((4-pivaloyl-1-oxa-4,9-diazaspiro[5.5]undecan-9-yl)methyl)phenethoxy)propanamide | 762.00 | 761.47 | 1.37 |
| 156 | 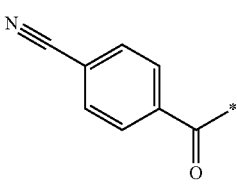 | 3-(3-((4-(4-Cyanobenzoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 807.00 | 806.44 | 1.36 |

| Example Number | C(O)R1 Group | Name | Molecular Mass | Found Mass* | Retention Time** (min) |
|---|---|---|---|---|---|
| 157 | | 3-(3-((4-(Benzo[d][1,3]dioxole-5-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 826.00 | 825.43 | 1.36 |
| 158 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-methylbenzoyl)-1-oxa-4,9-diazaspiro[5.5]undecan-9-yl)methyl)phenethoxy)propanamide | 796.02 | 795.46 | 1.37 |
| 159 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(3-methylfuran-2-carbonyl)-1-oxa-4,9-diazaspiro[5.5]undecan-9-yl)methyl)phenethoxy)propanamide | 785.98 | 785.44 | 1.33 |
| 160 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-methylpentanoyl)-1-oxa-4,9-diazaspiro[5.5]undecan-9-yl)methyl)phenethoxy)propanamide | 776.03 | 775.49 | 1.36 |
| 161 | | 3-(3-((4-(1,8-Naphthyridine-2-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 834.03 | 833.45 | 1.23 |
| 162 | | N-Cyclohexyl-3-(3-((4-(2,4-difluorobenzoyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 817.97 | 817.42 | 1.34 |

-continued

| Example Number | C(O)R1 Group | Name | Molecular Mass | Found Mass* | Retention Time** (min) |
|---|---|---|---|---|---|
| 163 | (2,6-difluorobenzoyl) | N-Cyclohexyl-3-(3-((4-(2,6-difluorobenzoyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 817.97 | 817.42 | 1.25 |
| 164 | (3-chlorobenzoyl) | 3-(3-((4-(3-Chlorobenzoyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 816.44 | 815.40 | 1.45 |
| 165 | (3-phenoxypropanoyl) | N-Cylcohexyl-N-(2-(2-(5-hydroxy-3-oxo-3,4-dihydro-2H-benzo[b][1,4]oxazin-8-yl)ethylamino)ethyl)-3-(3-((4-(3-phenoxypropanoyl)-1-oxa-4,9-diazaspiro[5.5]undecan-9-yl)methyl)phenethoxy)propanamide | 826.05 | 825.47 | 1.45 |
| 166 | (2-hydroxy-2-phenylacetyl) | (R)-N-Cyclohexyl-3-(3-((4-(2-hydroxy-2-phenylacetyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 812.02 | 811.45 | 1.36 |
| 167 | (2-phenylcyclopropanecarbonyl) | N-Cyclohexyl-N-(2-(2-(5-hydroxy-3-oxo-3,4-dihydro-2H-benzo[b][1,4]oxazin-8-yl)ethylamino)ethyl)-3-(3-((4-((1R,2R)-2-phenylcyclopropanecarbonyl)-1-oxa-4,9-diazaspiro[5.5]undecan-9-yl)methyl)phenethoxy)propanamide | 822.06 | 821.47 | 1.47 |
| 168 | (1H-indole-4-carbonyl) | 3-(3-((4-(1H-Indole-4-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 821.03 | 820.45 | 1.35 |

-continued

| Example Number | C(O)R1 Group | Name | Molecular Mass | Found Mass* | Retention Time** (min) |
|---|---|---|---|---|---|
| 169 | | N-Cyclohexyl-3-(3-((4-(2-(2-fluorophenyl)acetyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 814.01 | 813.45 | 1.38 |
| 170 | | N-Cyclohexyl-3-(3-((4-(2-(2-ethoxyphenyl)acetyl)-1-oxa-4,9-diazaspiro[5.5]undecan-9-yl)methyl)phenethoxy)-N-(2-(2-(5-hydroxy-3-oxo-3,4-dihydro-2H-benzo[b][1,4]oxazin-8-yl)ethylamino)ethyl)propanamide | 840.07 | 839.48 | 1.42 |
| 171 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-methoxy-2-phenylacetyl)-1-oxa-4,9-diazaspiro[5.5]undecan-9-yl)methyl)phenethoxy)propanamide | 826.05 | 825.47 | 1.34 |
| 172 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(6-methylimidazo[1,2-a]pyridine-2-carbonyl)-1-oxa-4,9-diazaspiro[5.5]undecan-9-yl)methyl)phenethoxy)propanamide | 836.05 | 835.46 | 1.19 |
| 173 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(4-(2-methoxyethoxy)benzoyl)-1-oxa-4,9-diazaspiro[5.5]undecan-9-yl)methyl)phenethoxy)propanamide | 856.07 | 855.48 | 1.32 |
| 174 | | N-Cyclohexyl-N-(2-(2-(5-hydroxy-3-oxo-3,4-dihydro-2H-benzo[b][1,4]oxazin-8-yl)ethylamino)ethyl)-3-(3-((4-(2-(2,2,2-trifluoroethyl)thiazole-4-carbonyl)-1-oxa-4,9-diazaspiro[5.5]undecan-9-yl)methyl)phenethoxy)propanamide | 871.03 | 870.40 | 1.36 |

-continued

| Example Number | C(O)R1 Group | Name | Molecular Mass | Found Mass* | Retention Time** (min) |
|---|---|---|---|---|---|
| 175 | 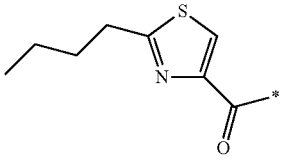 | 3-(3-((4-(2-Butylthiazole-4-carbonyl)-1-oxa-4,9-diazaspiro[5.5]undecan-9-yl)methyl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide | 845.12 | 844.46 | 1.35 |

*The found molecular mass corresponds to a (M - 2 + H)⁺ fragment and varies with instrument calibration.
**Analytical HPLC conditions: Waters Sunfire™ C18 (4.6 × 30 nnm, 2.5 μm) column, elution gradient 5-95% acetonitrile in 0.1% aqueous TFA buffer according to the timetable shown below:

| Time (min) | % Aqueous buffer | % Acetonitrile | Flow (ml/min) |
|---|---|---|---|
| 0.3 | 95 | 5 | 2.5 |
| 2.7 | 5 | 95 | 2.5 |
| 2.8 | 5 | 95 | 2.5 |
| 2.9 | 95 | 5 | 2.5 |

EXAMPLE 176

N-Cyclohexyl-N-(2-(2-(5-hydroxy-3-oxo-3,4-dihydro-2H-benzo[b][1,4]oxazin-8-yl)ethylamino)ethyl)-3-(3-(2-(8-(2-isopropylthiazole-4-carbonyl)-5-oxa-2,8-diazaspiro[3.5]nonan-2-yl)ethyl)phenethoxy) propanamide, trifluoroacetate salt

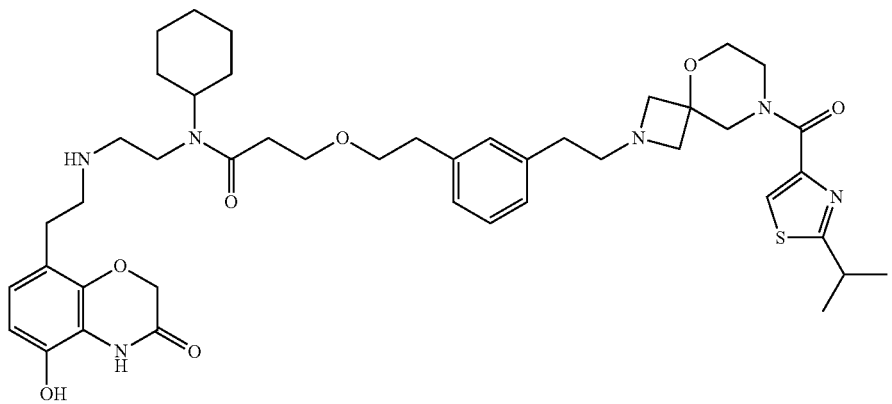

Tosic Acid monohydrate (0.383 g) was added to a solution of N-cyclohexyl-N-(2,2-dimethoxyethyl)-3-(3-(2-(8-(2-isopropylthiazole-4-carbonyl)-5-oxa-2,8-diazaspiro[3.5]nonan-2-yl)ethyl)phenethoxy)propanamide (0.27 g) (example 176 step i) in THF (8 ml) and the resulting mixture stirred for 1 hour at RT. NMP (1 mL) was added and the solution was then added to a suspension of 8-(2-aminoethyl)-5-hydroxy-2H-benzo[b][1,4]oxazin-3(4H)-one HCl (0.148 g) and sodium bicarbonate (0.270 g) in a mixture of NMP (4 mL) and water (0.4 mL) which had been stirring for 45 min. The aldehyde flask was rinsed with NMP (1 mL) and the washings added to the suspension and the resulting cloudy solution was stirred for 20 min. Sodium triacetoxyborohydride (0.256 g) was then added and the resulting mixture stirred for 1 hr. The reaction mixture was partitioned between ethyl acetate and saturated sodium bicarbonate solution. The mixture was shaken for 10 min (until gas evolution had ceased). The ethyl acetate solution was washed with sodium bicarbonate (×2), separated, dried over sodium sulphate, filtered and evaporated. The residue was purified by flash silica chromatography eluting with methanol:dichloromethane: 880 ammonia, 8:91:1. The crude product was purified by preparative HPLC on a Sunfire column using a 12-47% gradient of aqueous 0.1% trifluoroacetic acid in acetonitrile as eluent. The fractions containing the desired compound were evaporated to dryness to afford the titled compound. Yield 0.091 g.

m/z 817.2 (multimode+)

¹H NMR (400 MHz, DMSO, 90° C.) δ 9.46 (s, 1H), 8.38 (s, 1H), 7.99 (s, 1H), 7.23 (t, J=7.6 Hz, 1H), 7.10 (t, J=9.9 Hz, 3H), 6.66 (d, J=8.3 Hz, 1H), 6.48 (d, J=8.3 Hz, 1H), 4.53 (s, 2H), 4.14 (s, 2H), 4.04 (s, 2H), 3.91 (s, 2H), 3.79-3.20 (m, 14H), 3.10 (t, 2H), 2.99 (t, 2H), 2.85-2.75 (m, 6H), 2.60 (t, 2H), 1.83-1.70 (m, 2H), 1.66-1.55 (m, 3H), 1.46-1.27 (m, 10H), 1.16-1.02 (m, 1H). plus 3 exchangeables not observed a) 2-Benzhydryl-5-oxa-2,8-diazaspiro[3.5]nonane

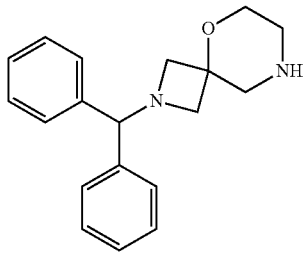

Borane-methyl sulfide complex in THF (13.38 mL) was added in one portion to 2-benzhydryl-5-oxa-2,8-diazaspiro[3.5]nonan-7-one (2.5 g) (WO2009098448, example 33, step e) in THF (50 mL) at room temperature under argon. The resulting solution was stirred at reflux for 90 minutes. The reaction was cooled to room temperature then the reaction mixture was quenched with methanol (50.0 mL). N,N'-Dimethylethylenediamine (5.18 mL) was added and the reaction mixture allowed to stir at room temperature for 1 week. The reaction mixture was evaporated to dryness and re-dissolved in ethyl acetate (250 mL), and washed with water (250 mL). The organic layer was dried over MgSO4, filtered and evaporated to afford crude product. The crude product was dissolved in iso-hexane (10 mL) and was purified by flash silica chromatography, eluting with 10% methanolic ammonia in DCM. Pure fractions were evaporated to dryness to afford 2-benzhydryl-5-oxa-2,8-diazaspiro[3.5]nonane. Yield 1.647 g.

The product (1.647 g) was dissolved in 1,4-dioxane (20 mL) and treated with Hydrogen chloride (2.95 mL of 4M in 1,4-dioxane) at room temperature. The mixture was concentrated in vacuo then triturated with diethylether (20 mL) to afford the subtitled compound Yield 2.403 g.

m/z 295.5 (M+H)+ b) tert-Butyl 2-benzhydryl-5-oxa-2,8-diazaspiro[3.5]nonane-8-carboxylate

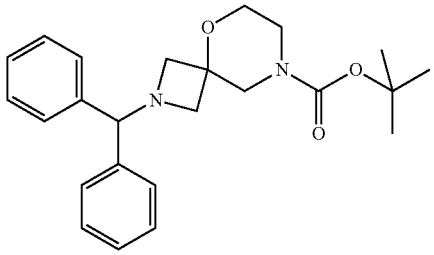

A mixture of 2-benzhydryl-5-oxa-2,8-diazaspiro[3.5]nonane 2HCl (1.52 g) (example 176 step a) and triethylamine (1.730 mL) in DCM (30 mL) was treated with BOC-anhydride (0.961 mL) and the reaction mixture stirred at RT for 18 hours. The mixture was washed with water and the organic layer was dried, filtered and the solvent evaporated under reduced pressure. The crude product was purified by flash silica chromatography, 1% methanol in dichloromethane containing 1% triethylamine. Pure fractions were evaporated to dryness to afford the subtitled compound. Yield 0.880 g.

m/z 395.1 (M+H)+ c) tert-Butyl 5-oxa-2,8-diazaspiro[3.5]nonane-8-carboxylate

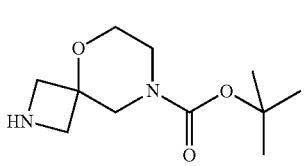

A mixture of tert-butyl 2-benzhydryl-5-oxa-2,8-diazaspiro[3.5]nonane-8-carboxylate (0.85 g) (example 176 step b), ammonium formate (0.883 g) and palladium on carbon JM type 87 L (0.459 g) in ethanol (50 mL) was refluxed for 30 minutes. The mixture was cooled to RT and filtered through celite, the solvent was evaporated under reduced pressure. The celite pad was washed with 10 mL of DMF) and then with 50 mL of acetonitrile. These washings were used to dissolve the residue obtained from evaporation of the initial mixture. This solution was passed through a 10 g SCX cartridge, followed by washing with acetonitrile. The cartridge was the eluted with a 10% solution of 880 ammonia in acetonitrile (80 mL) to bring off product. The solvents were evaporated under reduced pressure and the residue diluted with acetonitrile and evaporated under reduced pressure to afford the subtitled compound. Yield 0.490 g.

m/z 229.3 (M+H)+ d) tert-Butyl 2-(3-(2-hydroxyethyl)phenethyl)-5-oxa-2,8-diazaspiro[3.5]nonane-8-carboxylate

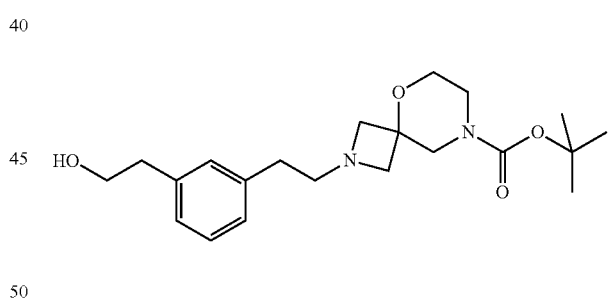

A mixture of tert-butyl 5-oxa-2,8-diazaspiro[3.5]nonane-8-carboxylate (0.49 g) (example 176 step c), 2-(3-(2-bromoethyl)phenyl)ethanol (0.738 g) [Organometallics 2002, 21(20), 4217] and potassium carbonate (1.187 g) in acetonitrile (30 mL) and water (0.5 mL) was heated at 60° C. for 24 hours. The mixture was cooled to RT and filtered. The solvent was passed through a 10 g SCX cartridge and further acetonitrile then eluted through. The cartridge was then eluted with a 10% solution of 880 ammonia in acetonitrile (80 mL) to bring off product. The solvents were evaporated under reduced pressure and the residue was diluted with acetonitrile and then evaporated to dryness to afford the subtitled compound. Yield 0.610 g.

m/z 377.3 (M+H)+ e) 2-(3-(2-(5-Oxa-2,8-diazaspiro[3.5]nonan-2-yl)ethyl)phenyl)ethanol, 2HCl

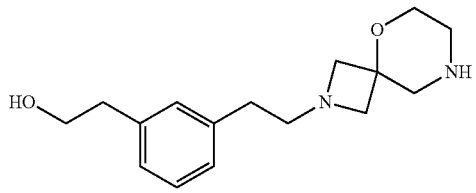

A solution of 4M HCl in dioxane (3 mL) was added to a solution of tert-butyl 24342-hydroxyethyl)phenethyl)-5-oxa-2,8-diazaspiro[3.5]nonane-8-carboxylate (0.61 g) (example 176 step d) in methanol (10 mL) and the reaction mixture was allowed to stand at RT for 8 hours. The solvent was evaporated under reduced pressure and the residue azeotroped with acetonitrile to afford the subtitled compound. Yield 0.560 g. (M+H)⁺ is 277 f) (2-(3-(2-Hydroxyethyl)phenethyl)-5-oxa-2,8-diazaspiro[3.5]nonan-8-yl)(2-isopropylthiazol-4-yl)methanone

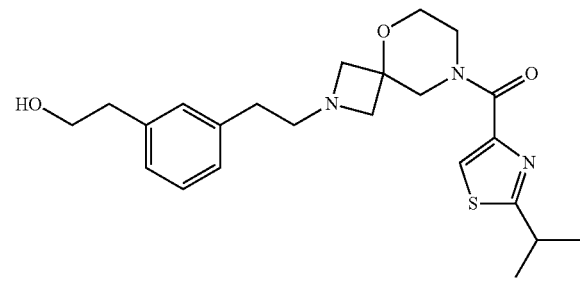

HATU (0.792 g) was added in one portion to a stirred solution at 0° C. of 2-(3-(2-(5-oxa-2,8-diazaspiro[3.5]nonan-2-yl)ethyl)phenyl)ethanol 2HCl (0.56 g) (example 176 step e), 2-isopropylthiazole-4-carboxylic acid (0.275 g) and triethylamine (1.117 ml) in DMF (7 mL). The mixture was stirred at 20° C. for 3 hours and then partitioned between ethyl acetate and brine, the organic layer was washed with brine (×2), dried, filtered and the solvent evaporated under reduced pressure. The crude product was purified by flash silica chromatography, 5% methanol in ethyl acetate with 1% triethylamine. Pure fractions were evaporated to dryness to afford the subtitled compound. Yield 0.475 g m/z 430.1 (M+H)⁺ g) tert-Butyl 3-(3-(2-(8-(2-isopropylthiazole-4-carbonyl)-5-oxa-2,8-diazaspiro[3.5]nonan-2-yl)ethyl)phenethoxy)propanoate

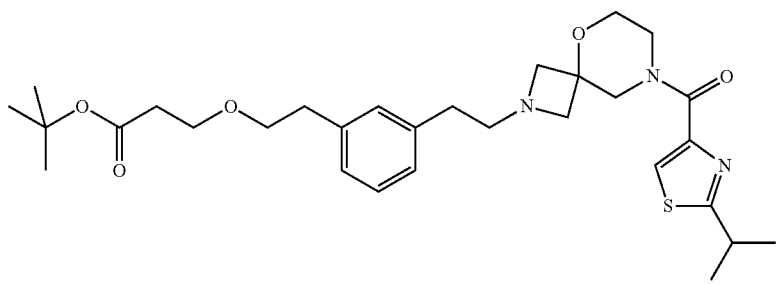

(2-(3-(2-hydroxyethyl)phenethyl)-5-oxa-2,8-diazaspiro[3.5]nonan-8-yl)(2-isopropylthiazol-4-yl)methanone (475 mg) (example 176 step f) was dissolved in acetonitrile (2 mL) and tert-butyl acrylate (312 mg) was added followed by benzyltrimethylammonium hydroxide (0.15 mL of 40 Wt % aqueous solution). The mixture was stirred at ambient temperature for 3 hours. The volatiles were removed under reduced pressure and the residue purified (silica) eluting with 5% methanol and 1% triethylamine in ethyl acetate to afford the subtitled compound. Yield 460 mg.

m/z 558.3 (M+H)⁺ h) 3-(3-(2-(8-(2-Isopropylthiazole-4-carbonyl)-5-oxa-2,8-diazaspiro[3.5]nonan-2-yl)ethyl)phenethoxy)propanoic acid, trifluoroacetate salt

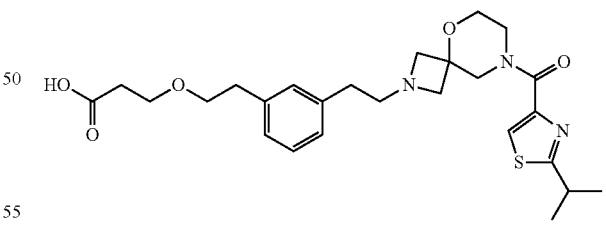

A solution of tert-butyl 3-(3-(2-(8-(2-isopropylthiazole-4-carbonyl)-5-oxa-2,8-diazaspiro[3.5]nonan-2-yl)ethyl)phenethoxy)propanoate (460 mg) (example 176 step g) in DCM (6 mL) was treated with TFA (2 mL) and the solution allowed to stand at RT for 1 hour. Toluene (10 mL) was added and the solvents were evaporated under reduced pressure and the residue dissolved in acetonitrile and the solution evaporated under reduced pressure to afford the subtitled compound. Yield 500 mg.

m/z 502.3 (M+H)⁺ i) N-Cyclohexyl-N-(2,2-dimethoxyethyl)-3-(3-(2-(8-(2-isopropylthiazole-4-carbonyl)-5-oxa-2,8-diazaspiro[3.5]nonan-2-yl)ethyl)phenethoxy)propanamide

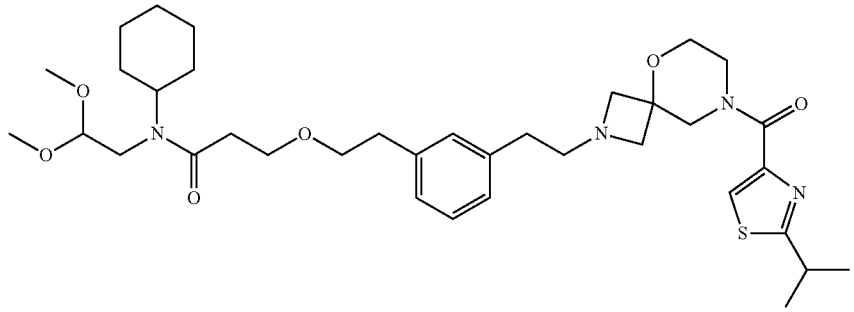

HATU (0.201 g) was added in one portion to a stirred solution at 0° C. of 3-(3-(2-(8-(2-isopropylthiazole-4-carbonyl)-5-oxa-2,8-diazaspiro[3.5]nonan-2-yl)ethyl)phenethoxy)propanoic acid trifluoroacetate salt (0.25 g) (example 176 step h), N-(2,2-dimethoxyethyl)cyclohexanamine (0.076 g) (WO2008075025) and triethylamine (0.283 ml) in DMF (4 mL) at 0° C. The mixture was stirred at 20° C. for 3 hours and then partitioned between ethyl acetate and brine, the organic layer was washed with brine (×2), dried over sodium sulphate, filtered and the solvent evaporated under reduced pressure to afford the subtitled compound. Yield 0.270 g.

m/z 671.3 (M+H)$^+$

EXAMPLE 177

N-ethyl-N-(2-(2-(5-hydroxy-3-oxo-3,4-dihydro-2H-benzo[b][1,4]oxazin-8-yl)ethylamino)ethyl)-3-(3-(2-(8-(2-isopropylthiazole-4-carbonyl)-5-oxa-2,8-diazaspiro[3.5]nonan-2-yl)ethyl)phenethoxy)propanamide, trifluoroacetate salt Tosic Acid monohydrate (0.385 g) was added to a solution of N-(2,2-dimethoxyethyl)-N-ethyl-3-(3-(2-(8-(2-isopropylthiazole-4-carbonyl)-5-oxa-2,8-diazaspiro[3.5]nonan-2-yl)ethyl)phenethoxy)propanamide (0.25 g) (example 177 step a) in THF (8 mL) and the resulting mixture stirred for 1 hour at RT. NMP (1 mL) was added and the solution was then added to a suspension of 8-(2-aminoethyl)-5-hydroxy-2H-benzo[b][1,4]oxazin-3(4H)-one HCl (0.149 g) and sodium bicarbonate (0.272 g) in a mixture of NMP (4 mL) and water (0.4 mL) which had been stirring for 45 min. The aldehyde flask was rinsed with NMP (1 mL) and the washings added to the suspension and the resulting cloudy solution was stirred for 20 min. Sodium triacetoxyborohydride (0.258 g) was then added and the resulting mixture stirred for 1 hr. The reaction mixture was partioned between ethyl acetate and saturated sodium bicarbonate solution. The mixture was shaken for 10 min (until gas evolution had ceased). The organic was washed with sodium bicarbonate solution (×2), separated, dried over sodium sulphate, filtered and evaporated. The residue was purified by flash silica chromatography, 8:91:1 methanol:dichloromethane:880 ammonia. Pure fractions were evaporated to dryness to afford crude product. The product was further purified on a SunFire Prep C8 10 um 30×100 OBD column eluting on a 18 to 53 gradient of MeOH in water (0.1% TFA) to afford the titled compound. Yield 0.096 g.

m/z 763.3 (M+H)$^+$

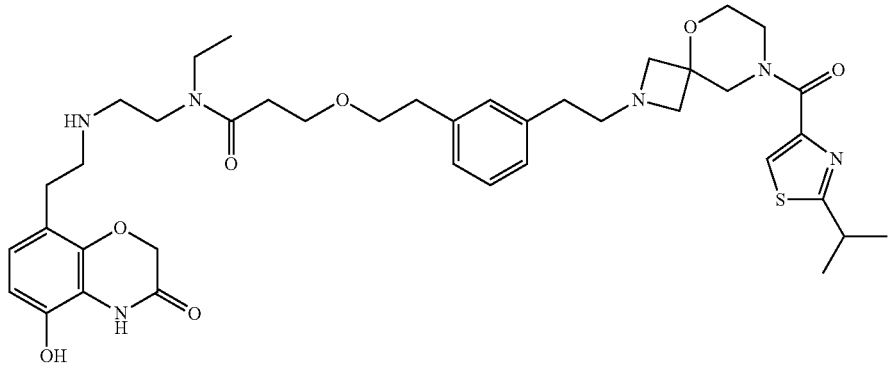

¹H NMR (400 MHz, DMSO, 90° C.) δ 9.46 (s, 1H), 8.37 (s, 1H), 7.99 (s, 1H), 7.23 (t, J=7.6 Hz, 1H), 7.15-7.04 (m, 3H), 6.66 (d, J=8.3 Hz, 1H), 6.48 (d, J=8.2 Hz, 1H), 4.53 (s, 2H), 4.15 (s, 2H), 4.05 (s, 2H), 3.91 (s, 2H), 3.78-3.27 (m, 15H), 3.14-3.02 (m, 4H), 2.88-2.74 (m, 6H), 2.56 (t, J=6.6 Hz, 2H), 1.34 (d, J=6.8 Hz, 6H), 1.09 (s, 3H). Assigned Hs: 53. plus 3 exchangeables not observed.

a) N-(2,2-dimethoxyethyl)-N-ethyl-3-(3-(2-(8-(2-isopropylthiazole-4-carbonyl)-5-oxa-2,8-diazaspiro[3.5]nonan-2-yl)ethyl)phenethoxy)propanamide

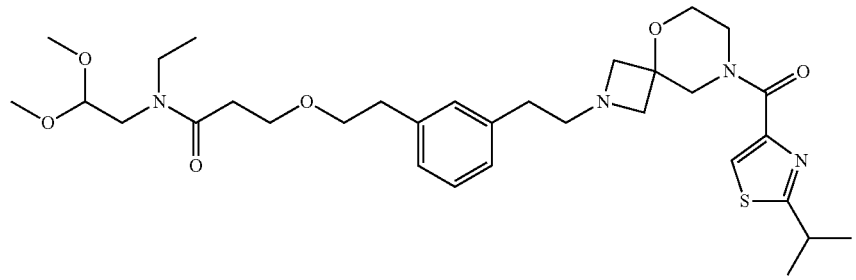

HATU (0.201 g) was added in one portion to a stirred solution at 0° C. of 3-(3-(2-(8-(2-isopropylthiazole-4-carbonyl)-5-oxa-2,8-diazaspiro[3.5]nonan-2-yl)ethyl)phenethoxy)propanoic acid trifluoroacetate salt (0.25 g) (example 176 step b), N-ethyl-2,2-dimethoxyethanamine (0.059 g) (U.S. Pat. No. 2,707,186) and triethylamine (0.283 ml) in DMF (4 mL). The mixture was stirred at 20° C. for 3 hours and then partitioned between ethyl acetate and aq brine, the organic layer was washed with brine (×2), dried, filtered and the solvent evaporated under reduced pressure to afford the subtitled compound. Yield 0.250 g.

m/z 617.4 (M+H)⁺

EXAMPLE 178

N-butyl-N-(2-(2-(5-hydroxy-3-oxo-3,4-dihydro-2H-benzo[b][1,4]oxazin-8-yl)ethylamino)ethyl)-3-(2-(2-(4-(2-isopropylthiazole-4-carbonyl)-1-oxa-4,9-diazaspiro[5.5]undecan-9-yl)ethoxy)phenethoxy)propanamide trifluoroacetate salt

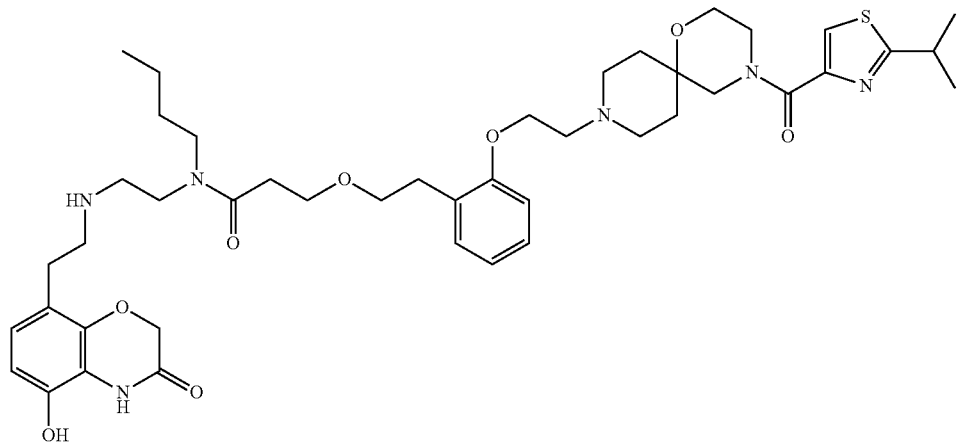

Ts-OH (0.179 g) was added to a stirred solution of N-butyl-N-(2,2-dimethoxyethyl)-3-(2-(2-(4-(2-isopropylthiazole-4-carbonyl)-1-oxa-4,9-diazaspiro[5.5]undecan-9-yl)ethoxy)phenethoxy)propanamide (0.130 g) (example 178 step e) in THF (1 mL). After 1.5 h, the solution was added to 5-hydroxy-8-(2-hydroxyethyl)-2H-benzo[b][1,4]oxazin-3(4H)-one (0.070 g)(HCl salt) and sodium bicarbonate (0.127 g) in NMP (0.5 mL) and water (0.05 mL) which had been stirring for 1 h. The aldehyde flask was washed with NMP (0.3 ml) and added to the reaction mixture. After 20 min, sodium triacetoxyborohydride (0.120 g) was added. After 3 h, the reaction mixture was partitioned between methylTHF (6 ml) and sat. sodium bicarbonate (5 ml) and the mixture shaken vigourously for 5 min. Water (4 ml) was added followed by methylTHF (4 ml) to aid separation. The methylTHF layer was dried (sodium sulphate), filtered and evaporated. Purification was by preparative HPLC (SunFire Prep C8 10 um 30×100 OBD column eluting on a 18 to 53 gradient of MeOH in water (0.1% TFA)) to afford the titled compound. Yield 0.05 g m/z 836 (M+H)$^+$ $^1$H NMR (400 MHz, DMSO, 90° C.) δ 7.97 (s, 1H), 7.20-7.18 (m, 2H), 6.99 (d, J=8.4 Hz, 1H), 6.91 (t, J=8.0 Hz, 1H), 6.65 (d, J=6.4 Hz, 1H), 6.48 (d, J=6.4 Hz, 1H), 4.53 (s, 2H), 4.35-4.33 (m, 2H), 3.80-3.00 (m, 25H), 2.81 (t, J=6.8 Hz, 4H), 2.55-2.48 (m, 2H), 2.15-2.00 (m, 2H), 1.90-1.70 (m, 2H), 1.50-1.40 (m, 2H), 1.35 (d, J=6.8 Hz, 6H), 1.35-1.20 (m, 2H), 0.99 (t, J=7.2 Hz, 3H), exchangeable Hs missing a) 2-(2-(2,2-diethoxyethoxy)phenyl)ethanol

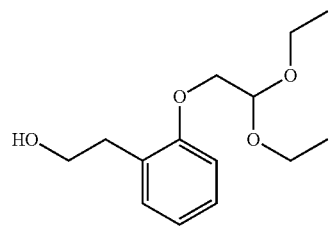

2-bromo-1,1-diethoxyethane (5.13 g) was added to a stirred mixture of cesium carbonate (8.49 g) and 2-(2-hydroxyethyl)phenol (3.00 g) in DMF (20 mL). After 5 minutes the reaction mixture was heated at 80° C. 16 h, the reaction mixture was allowed to cool and partitioned between ethyl acetate and water. The ethyl acetate layer was washed with water (×3) then evaporated. Purification by silica gel chromatography eluting with ethyl acetate:iso-hexanes, 1:3 gave the subtitle compound as a green oil. Yield 3.6 g.

1H NMR (400 MHz, CDCl₃) δ 7.23-7.10 (m, 2H), 7.95-7.80 (m, 2H), 4.78 (t, J=7.2 Hz, 1H), 4.01 (d, J=7.2 Hz, 2H), 3.90-3.70 (m, 6H), 2.92 (t, J=8 Hz, 2H), 1.98 (t, J=8.0 Hz, 1H), 1.25 (t, J=9.2 Hz, 6H).

b) (9-(2-(2-(2-hydroxyethyl)phenoxy)ethyl)-1-oxa-4,9-diazaspiro[5.5]undecan-4-yl)(2-isopropylthiazol-4-yl)methanone

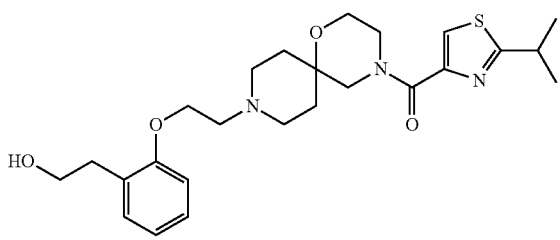

conc hydrochloric acid (3 mL) was added to a stirred solution of 2-(2-(2,2-diethoxyethoxy)phenyl)ethanol (2.70 g) (example 178 step a) in 1,4-dioxane (10 mL). After 0.5 h, the solution was poured into water and extracted with ethyl acetate. The ethyl acetate solutions were combined, washed with water, dried over sodium sulphate, filtered and evaporated in vacuo. The resulting gum was dissolved in DCM (30 mL) and (2-isopropylthiazol-4-yl)(1-oxa-4,9-diazaspiro[5.5]undecan-4-yl)methanone (1.0 g) and sodium triacetoxyborohydride (2.0 g) added. After 2 h, sodium bicarbonate soln was added and the mixture extracted with DCM (×2). The combined DCM extracts were evaporated and applied to a silica gel column eluting with 10% triethylamine in ethyl acetate to give 1 g of crude product. The Product was re-purified by silica gel chromatography eluting with 10% methanol in DCM to give the subtitled compound. Yield 0.6 g.
m/z 474 (M+H)⁺ c) tert-butyl 3-(2-(2-(4-(2-isopropylthiazole-4-carbonyl)-1-oxa-4,9-diazaspiro[5.5]undecan-9-yl)ethoxy)phenethoxy)propanoate

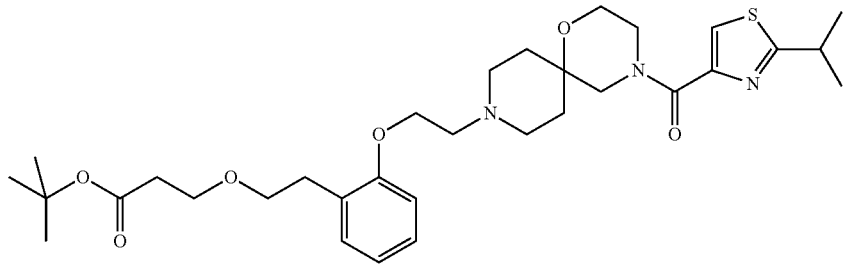

benzyltrimethylammonium hydroxide (0.2 mL) was added to (9-(2-(2-(2-hydroxyethyl)phenoxy)ethyl)-1-oxa-4,9-diazaspiro[5.5]undecan-4-yl)(2-isopropylthiazol-4-yl)methanone (0.60 g) (example 178 step b) and tert-butyl acrylate (0.244 g) in toluene (1 mL) and the reaction mixture stirred vigorously. After 16 h, more benzyltrimethylammonium hydroxide (0.2 mL) and tert-butyl acrylate (0.244 g) was added. After a further 48 h the reaction mixture was evaporated in vacuo and applied to a silica gel column eluting with 5% methanol in DCM. Yield as a gum 0.52 g.

1H NMR (400 MHz, DMSO) δ 8.00 (s, 1H), 7.13 (d, J=7.6 Hz, 2H), 7.96-7.89 (m, 1H), 6.83 (t, J=7.6 Hz, 1H), 4.10-4.00 (m, 2H), 3.80-3.50 (m, 10H), 3.30 (m, 1H), 2.80-2.65 (m, 4H), 2.39 (m, 2H), 1.75-1.60 (m, 2H), 1.60-1.40 (m, 2H), 1.37 (s, 9H), 1.33 (d, J=6.8 Hz, 6H), Hs under DMSO peak d) 3-(2-(2-(4-(2-isopropylthiazole-4-carbonyl)-1-oxa-4,9-diazaspiro[5.5]undecan-9-yl)ethoxy)phenethoxy)propanoic acid

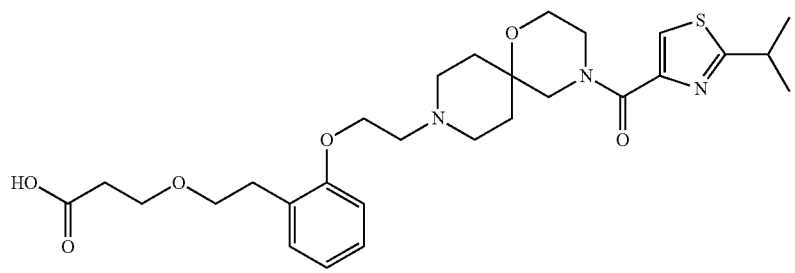

trifluoroacetic acid (2 mL) was added to a stirred solution of tert-butyl 3-(2-(2-(4-(2-isopropylthiazole-4-carbonyl)-1-oxa-4,9-diazaspiro[5.5]undecan-9-yl)ethoxy)phenethoxy)propanoate (0.320 g) (example 178 step c) in DCM (5 mL). After 16 h, the solution was evaporated to a gum. The gum was dissolved in acetonitrile (5 mL) and evaporated in vacuo (repeated 3 times). Yield 0.4 g.

m/z 546 (M+H)$^+$ e) N-butyl-N-(2,2-dimethoxyethyl)-3-(2-(2-(4-(2-isopropylthiazole-4-carbonyl)-1-oxa-4,9-diazaspiro [5.5]undecan-9-yl)ethoxy)phenethoxy)propanamide

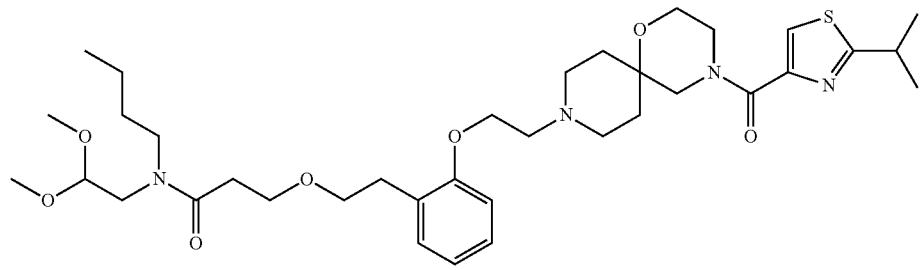

HATU (0.337 g) was added to a stirred solution of N-(2,2-dimethoxyethyl)butan-1-amine (0.105 g), 3-(2-(2-(4-(2-isopropylthiazole-4-carbonyl)-1-oxa-4,9-diazaspiro[5.5]undecan-9-yl)ethoxy)phenethoxy)propanoic acid (0.390 g) (example 178 step d) and Hunig's Base (0.516 mL) in N,N-dimethylformamide (3 mL). After 1 h, the solution was partitioned between ethyl acetate and brine. The ethyl acetate layer was washed with brine (×3) and evaporated in vacuo. Purification was silica gel chromatography eluting with 10% triethylamine in ethyl acetate. Yield 0.4 g.

m/z 689 (M+H)$^+$

The compounds of the invention may be tested for pharmaceutical activity using assays know in the art, such as for example:

Assay for Adrenergic β2 Mediated Camp Production
Cell Preparation

H292 cells are grown in 225 cm2 flasks incubator at 37° C., 5% $CO_2$ in RPMI medium containing 10% (v/v) FBS (foetal bovine serum) and 2 mM L-glutamine.

Experimental Method

Adherent H292 cells re removed from tissue culture flasks by treatment with Accutase™ cell detachment solution for 15 minutes. Flasks are incubated for 15 minutes in a humidified incubator at 37° C., 5% $CO_2$. Detached cells are re-suspended in RPMI media (containing 10% (v/v) FBS and 2 mM L-glutamine) at 0.1×10$^6$ cells per mL. 10000 cells in 100 μL are added to each well of a tissue-culture-treated 96-well plate and the cells incubated overnight in a humidified incubator at 37° C., 5% $CO_2$. The culture media is removed and cells are washed twice with 100 μL assay buffer and replaced with 50 μL assay buffer (HBSS solution containing 10 mM HEPES pH7.4 and 5 mM glucose). Cells are rested at room temperature for 20 minutes after which time 25 μL of rolipram (1.2 mM made up in assay buffer containing 2.4% (v/v) dimethylsulphoxide) is added. Cells are incubated with rolipram for 10 minutes after which time test compounds are added and the cells are incubated for 60 minutes at room temperature. The final rolipram concentration in the assay is 300 μM and final vehicle concentration is 1% (v/v) dimethylsulphoxide. The reaction is stopped by removing supernatants, washing once with 100 μL assay buffer and replacing with 50 μL lysis buffer. The cell monolayer is frozen at −80° C. for 30 minutes (or overnight).

AlphaScreen™ cAMP Detection

The concentration of cAMP (cyclic adenosine monophosphate) in the cell lysate is determined using AlphaScreen™ methodology. The frozen cell plate is thawed for 20 minutes on a plate shaker then 10 μL of the cell lysate is transferred to a 96-well white plate. 40 μL of mixed AlphaScreen™ detection beads pre-incubated with biotinylated cAMP, is added to each well and the plate incubated at room temperature for 3 hours in the dark. The AlphaScreen™ signal is measured using an EnVision spectrophotometer (Perkin-Elmer Inc.) with the recommended manufacturer's settings. cAMP concentrations are determined by reference to a calibration curve determined in the same experiment using standard cAMP concentrations. Concentration response curves for agonists are constructed and data is fitted to a four parameter logistic equation to determine both the $pEC_{50}$ and Intrinsic Activity. Intrinsic Activity is expressed as a fraction relative to the maximum activity determined for formoterol in each experiment.

Muscarinic 3 Receptor Binding Assay

The affinity ($pIC_{50}$) of compounds binding to the $M_3$ receptor is determined by competition binding of [$^3$H]N-methyl scopolamine (NMS) to CHO-K1 (Chinese Hamster Ovary) cell membranes expressing the human muscarinic acetylcholine $M_3$ receptor ($M_3$-ACh) in a scintillation proximity assay (SPA) format.

SPA beads are precoated with membranes and then incubated at 2 mg of beads per well with serial dilutions of compounds of the invention, [$^3$H]NMS at 0.1 nM, quarter Kd (experimentally determined dissociation constant) and assay buffer (20 mM HEPES pH 7.4 containing 5 mM $MgCl_2$ and 0.1% (w/v) bovine serum albumin). The assay is conducted in a final volume of 200 μL, in the presence of 1% (v/v) dimethyl sulphoxide (DMSO). Total binding of [$^3$H]NMS is determined in the absence of competing compound and non-specific binding of [$^3$H]NMS is determined in the presence of 1 μM atropine. The plates are incubated for 16 hours at room temperature and then read on Wallac Microbeta™ using a normalised $^3$H protocol. The $pIC_{50}$, defined as the negative logarithm of the molar concentration of compound required for 50% reduction in specific [$^3$H]-NMS binding, is determined.

Compounds of the invention were tested in the above assays and the following results obtained:

| Example No. | β2 pEC$_{50}$ | β2 Intrinsic Activity | M$_3$ Binding pIC$_{50}$ |
|---|---|---|---|
| 1 | 7.5 | 0.7 | 8.7 |
| 2 | 7.5 | 0.9 | 9.0 |
| 3 | 6.7 | 1.0 | 9.0 |
| 4 | 7.6 | 0.8 | 9.1 |
| 5 | 7.7 | 0.9 | 9.7 |
| 6 | 7.5 | 1.0 | 10 |
| 7 | 7.4 | 1.0 | 9.2 |
| 8 | 7.4 | 1.1 | 9.6 |
| 9 | 7.5 | 0.8 | 9.3 |
| 10 | 7.5 | 0.8 | 9.2 |
| 11 | 7.1 | 1.1 | 9.5 |
| 12 | 7.4 | 1.0 | 9.3 |
| 13 | 7.6 | 0.8 | 9.2 |
| 14 | 7.3 | 1.0 | 9.4 |
| 15 | 7.5 | 0.7 | 9.4 |
| 16 | 6.7 | 0.8 | 9.6 |
| 17 | 7.3 | 1.0 | 9.5 |
| 18 | 7.7 | 1.0 | 9.4 |
| 19 | 7.3 | 0.9 | 9.2 |
| 20 | 7.1 | 1.1 | 9.7 |
| 21 | 7.2 | 1.1 | 9.5 |
| 22 | 7.1 | 1.2 | 9.6 |
| 23 | 7.1 | 1.2 | 9.5 |
| 24 | 7.1 | 0.9 | 9.0 |
| 25 | 7.4 | 0.8 | 9.8 |
| 26 | 8.1 | 0.8 | 9.2 |
| 27 | 7.7 | 0.9 | 8.7 |
| 28 | 7.9 | 0.8 | 8.7 |
| 29 | 7.4 | 0.9 | 8.9 |
| 30 | 8.1 | 0.8 | 9.5 |
| 31 | 7.7 | 1.0 | 9.4 |
| 32 | 7.8 | 0.9 | 9.4 |
| 33 | 7.8 | 1.0 | 9.4 |
| 33a | 7.8 | 1.0 | 9.3 |
| 34 | 8 | 1.0 | 9.0 |
| 34a | 7.8 | 1.0 | 9.2 |
| 35 | 8.5 | 1.0 | 8.4 |
| 36 | 7.9 | 1.0 | 8.6 |
| 37 | 8 | 0.9 | 9.1 |
| 38 | 7.8 | 1.0 | 9.4 |
| 39 | 8 | 1.0 | 9 |
| 40 | 7.7 | 1.0 | 8.9 |
| 41 | 7.7 | 0.9 | 9.1 |
| 42 | 6.4 | 1.0 | >10.5 |
| 43 | 6.4 | 0.9 | 9 |
| 44 | 6.3 | 1.1 | 9.3 |
| 45 | 7.4 | 0.9 | 8.2 |
| 46 | 6.4 | 0.9 | 9.5 |
| 47 | 7.2 | 0.9 | 9.4 |
| 48 | 6.7 | 0.9 | 9.7 |
| 49 | 6.8 | 0.9 | 8.5 |
| 50 | 6.9 | 0.9 | 6.1 |
| 51 | 7.2 | 1.1 | 8.4 |
| 52 | 7.9 | 0.9 | 8.8 |
| 53 | 7.7 | 1.0 | 8.1 |
| 54 | 7 | 0.9 | 10.0 |
| 55 | 7 | 0.6 | 9.9 |
| 56 | 6.7 | 1.2 | 10.2 |
| 57 | 6.5 | 0.9 | >10.3 |
| 58 | 7 | 0.9 | 10.2 |
| 59 | 6.2 | 0.9 | 9.6 |
| 60 | 7.3 | 0.7 | 9.7 |
| 61 | 7.7 | 0.7 | 8.7 |
| 62 | 7 | 0.7 | 9.1 |
| 63 | 6.8 | 1.1 | 8.7 |
| 64 | 7.7 | 1.0 | 8.6 |
| 65 | 7.2 | 1.0 | 9.3 |
| 66 | 6.6 | 0.5 | 9.3 |
| 67 | 7.5 | 0.8 | 9.6 |
| 68 | 8 | 0.6 | 8.0 |
| 69 | 7.5 | 0.8 | 9.6 |
| 70 | 7.3 | 1.0 | 9.9 |
| 71 | 7.3 | 1.0 | 9.6 |
| 72 | 7.5 | 0.9 | 9.9 |
| 73 | 7.6 | 1.1 | 10 |
| 74 | 7 | 0.7 | 9.7 |
| 75 | 7.3 | 0.9 | 9.3 |
| 76 | 7.3 | 1.0 | 9.2 |
| 77 | 7.9 | 0.8 | 8.4 |
| 78 | 7.9 | 1.0 | 8.6 |
| 79 | 6.9 | 1.0 | 9.9 |
| 80 | 7.2 | 0.5 | 9.2 |
| 81 | 6.6 | 0.9 | 8.4 |
| 82 | 6.3 | 1.0 | 8.9 |
| 83 | 6.6 | 1.1 | 9.5 |
| 84 | 6.7 | 1.0 | 9.7 |
| 85 | 6.9 | 0.9 | 9.9 |
| 86 | 6.8 | 1.0 | 8.8 |
| 87 | 6.8 | 1.0 | 9.7 |
| 88 | 6.7 | 1.0 | 9.7 |
| 89 | 6.7 | 1.0 | 8.3 |
| 90 | 6.6 | 1.0 | 9.3 |
| 91 | 6.6 | 1.2 | 9.7 |
| 92 | 6.6 | 1.1 | 8.9 |
| 93 | 6.6 | 1.1 | 9.7 |
| 94 | 6.9 | 1.0 | 9.6 |
| 95 | 7 | 1.0 | 9.9 |
| 96 | 6.8 | 1.0 | 9.6 |
| 97 | 6.8 | 1.0 | 8.9 |
| 98 | 6.7 | 1.1 | 9.1 |

The following experimental procedure was used to measure the beta-2% effect at 1 μM for the compounds of Examples 99-175.

Adrenergic β2 Mediated cAMP Production cell preparation

H292 cells are grown in 225 cm2 flasks incubator at 37° C., 5% CO$_2$ in RPMI medium containing 10% (v/v) FBS (foetal bovine serum) and 2 mM L-glutamine.

Experimental Method

Compounds are prepared by an initial first dilution into DMSO to give 1 mM stock concentration. This is followed by a 1 in 10 dilution of the stock concentration (10 μl stock compound+90 μl DMSO) to give 0.1 mM compound. A compound addition plate is prepared by making a further 1 in 25 dilution in assay buffer (HBSS solution containing 10 mM HEPES pH7.4 and 5 mM glucose) containing 4% dimethylsulfoxide. The final compound concentration in assay is 1 μM.

Adherent H292 cells are removed from tissue culture flasks by treatment with Accutase™ cell detachment solution for 15 minutes. Flasks are incubated for 15 minutes in a humidified incubator at 37° C., 5% CO$_2$. Detached cells are re-suspended in RPMI media (containing 10% (v/v) FBS and 2 mM L-glutamine) at 0.1×10$^6$ cells per mL. 10000 cells in 100 μL are added to each well of a tissue-culture-treated 96-well plate and the cells incubated overnight in a humidified incubator at 37° C., 5% CO$_2$. The culture media is removed and cells are washed twice with 100 μL assay buffer and replaced with 50 μL assay buffer (HBSS solution containing 10 mM HEPES pH7.4 and 5 mM glucose). Cells are rested at room temperature for 20 minutes after which time 25 μL of rolipram (1.2 mM made up in assay buffer) is added. Cells are incubated with rolipram for 10 minutes after which time 25 μl test compounds are added and the cells are incubated for 60 minutes at room temperature. The final rolipram concentration in the assay is 300 μM and final vehicle concentration is 1% (v/v) dimethylsulphoxide. The reaction is stopped by removing supernatants, washing once with 100 μL assay buffer and replacing with 50 μA lysis buffer. The cell monolayer is frozen at −80° C. for 30 minutes (or overnight).

AlphaScreen™ cAMP Detection

The concentration of cAMP (cyclic adenosine monophosphate) in the cell lysate is determined using AlphaScreen™ methodology. The frozen cell plate is thawed for 20 minutes on a plate shaker then 10 μL of the cell lysate is transferred to a 96-well white plate. 40 μL of mixed AlphaScreen™ detection beads (containing equal volumes of donor beads (pre-incubated with biotinylated cAMP in the dark for 30 minutes) and acceptor beads is added to each well and the plate incubated at room temperature for 3 hours in the dark. The AlphaScreen™ signal is measured using an EnVision spectrophotometer (Perkin-Elmer Inc.) with the recommended manufacturer's settings. Concentration of cAMP produced per well were calculated with reference to the cAMP standard curve determined in the same experiment and expressed as a percentage of the maximum response generated by 1E-07M formoterol.

The following experimental procedure was used to determine the M3% inhibition at 104 of the compounds of Examples 99-175

Muscarinic 3 Receptor Binding Assay

The activity (% inhibition specific binding) of compounds on the $M_3$ receptor is determined by competition binding of [$^3$H]N-methyl scopolamine (NMS) to CHO-K1 (Chinese Hamster Ovary) cell membranes expressing the human muscarinic acetylcholine $M_3$ receptor ($M_3$-ACh) in a scintillation proximity assay (SPA) format. SPA beads are precoated with membranes and then incubated at 2 mg of beads per well with 1 μM compound of the invention, [$^3$H]NMS at 0.1 nM, quarter Kd (experimentally determined dissociation constant) and assay buffer (20 mM HEPES pH 7.4 containing 5 mM $MgCl_2$ and 0.1% (w/v) bovine serum albumin). The assay is conducted in a final volume of 200 μL, in the presence of 1% (v/v) dimethyl sulphoxide (DMSO). Total binding of [$^3$H]NMS is determined in the absence of competing compound and nonspecific binding of [$^3$H]NMS is determined in the presence of 1 μM atropine. The plates are incubated for 16 hours at room temperature and then read on Wallac Microbeta™ using a normalised $^3$H protocol. The compound activity at 1 μM, defined as % inhibition specific [$^3$H]-NMS binding, is determined.

| Example No. | $\beta_2$ $pEC_{50}$ | $\beta_2$ intrinsic activity | $M_3$ Binding $pIC_{50}$ | $M_3$ % inhibition @1 uM | $\beta_2$ % effect @1 uM |
|---|---|---|---|---|---|
| 99 | | | | 99 | 112 |
| 100 | | | | 96 | 95 |
| 101 | | | | 95 | 105 |
| 102 | | | | 99 | 108 |
| 103 | | | | 90 | 109 |
| 104 | | | | 101 | 100 |
| 105 | | | | 99 | 109 |
| 106 | 7.3 | 1.0 | 9.2 | 100 | 102 |
| 107 | | | | 100 | 101 |
| 108 | | | | 80 | 98 |
| 109 | | | | 99 | 98 |
| 110 | | | | 100 | 99 |
| 111 | | | | 96 | 107 |
| 112 | | | | 98 | 105 |
| 113 | | | | 100 | 112 |
| 114 | | | | 100 | 106 |
| 115 | 6.9 | 0.6 | 9.8 | 100 | 93 |
| 116 | | | | 94 | 80 |
| 117 | | | | 99 | 90 |
| 118 | | | | 96 | 97 |
| 119 | 6.8 | >0.9 | 8.7 | 100 | 84 |
| 120 | | | | 101 | 97 |
| 121 | | | | 88 | 84 |
| 122 | | | | 84 | 87 |
| 123 | | | | 99 | 97 |
| 124 | | | | 100 | 101 |
| 125 | | | | 93 | 114 |
| 126 | | | | 101 | 103 |
| 127 | | | | 97 | 110 |
| 128 | | | 9.0 | 99 | 125 |
| 129 | | | | 99 | 110 |
| 130 | | | | 99 | 114 |
| 131 | | | | 99 | 97 |
| 132 | | | | 101 | 96 |
| 133 | | | | 101 | 83 |
| 134 | | | | 97 | 89 |
| 135 | | | | 66 | 86 |
| 136 | | | | 99 | 92 |
| 137 | | | | 100 | 88 |
| 138 | 6.9 | 0.9 | 9.7 | 100 | 92 |
| 139 | | | | 100 | 94 |
| 140 | 6.7 | 1.0 | 9.0 | 100 | 100 |
| 141 | | | | 96 | 108 |
| 142 | | | | 100 | 83 |
| 143 | | | | 101 | 105 |
| 144 | 7.4 | 1.0 | 9.8 | 100 | 100 |
| 145 | | | | 90 | 117 |
| 146 | 7.1 | 0.9 | 9.4 | 100 | 96 |
| 147 | 6.8 | 1.0 | 8.8 | 99 | 107 |
| 148 | | | | 95 | 108 |
| 149 | 6.9 | 1.0 | 9.3 | 99 | 90 |
| 150 | 7.1 | 0.5 | 8.5 | 99 | 104 |
| 151 | | | | 97 | 113 |
| 152 | | | | 100 | 112 |
| 153 | | | | 101 | 98 |
| 154 | 7.0 | 1.0 | 9.5 | 101 | 101 |
| 155 | | | | 99 | 93 |
| 156 | | | | 93 | 86 |
| 157 | 7.2 | 0.8 | 8.8 | 101 | 97 |
| 158 | | | | 98 | 94 |
| 159 | 7.1 | 0.9 | 8.9 | 100 | 87 |
| 160 | | | | 99 | 79 |
| 161 | 7.4 | 1.0 | 9.3 | 100 | 97 |
| 162 | | | | 100 | 95 |
| 163 | | | | 98 | 97 |
| 164 | 7.1 | 0.8 | 8.6 | 99 | 96 |
| 165 | 7.1 | 1.1 | 9.0 | 100 | 99 |
| 166 | | | | 100 | 96 |
| 167 | 7.0 | 0.4 | 9.5 | 101 | 105 |
| 168 | | | | 92 | 103 |
| 169 | | | | 101 | 102 |
| 170 | | | | 98 | 112 |
| 171 | | | | 96 | 94 |
| 172 | | | | 91 | 94 |
| 173 | | | | 95 | 82 |
| 174 | 7.3 | 1.0 | 9.6 | 100 | 88 |
| 175 | 7.2 | 1.0 | 9.5 | 100 | 86 |

| Example No. | $\beta_2$ $pEC_{50}$ | $\beta_2$ Intrinsic Activity | $M_3$ Binding $pIC_{50}$ |
|---|---|---|---|
| 176 | 7.8 | 1.2 | 8.6 |
| 177 | 8.0 | 1.1 | 8.9 |
| 178 | 6.3 | 1.2 | 7.9 |

XRD Data

Instrument Details:

X-Ray Powder Diffraction (XRPD)—PANalytical X'Pert machine in 2∅-∅ configuration or a PANalytical Cubix machine in ∅-∅ configuration over the scan range 2° to 40° 2∅ with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

Differential Scanning calorimetry (DSC) thermograms were measured using a TA Q1000 Differential Scanning Calorimeter, with aluminium pans. The sample is weights varied between 0.5 to 5 mg. The procedure was carried out under a flow of nitrogen gas (50 ml/min) and the temperature studied from 25 to 300° C. at a constant rate of temperature increase of 10° C. per minute.

Thermogravimetric Vapour Sorption (TGA) thermograms were measured using a TA Q500 Thermogravimetric Analyser, with platinum pans. The sample weights varied between 1 and 5 mg. The procedure was carried out under a flow of nitrogen gas (60 ml/min) and the temperature studied from Room Temperature to 300° C. at a constant rate of temperature increase of 10° C. per minute.

Gravimetric Vapour Sorption (GVS) profiles were measured using a Surface Measurements Systems Dynamic Vapour Sorption DVS-1 or a DVS Advantage instrument. The solid sample ca. 1-5 mg was placed into a glass or metal vessel and the weight of the sample was recorded during a dual cycle step method (40 to 90 to 0 to 90 to 0% relative humidity (RH), in steps of 10% RH).

EXAMPLE 33a

Sulphate Salt (XRD Spectrum is Shown in FIG. 1)

| XRPD data Example 33a Sulphate salt | | |
| --- | --- | --- |
| 2Ø | Rel Int % | d spacing |
| 4.4 | 4.51 | 20.30048 |
| 6.1 | 100 | 14.50763 |
| 6.9 | 11.28 | 12.73003 |
| 7.8 | 14.82 | 11.26734 |
| 9.1 | 8.3 | 9.72695 |
| 9.5 | 3.59 | 9.29727 |
| 9.9 | 9.72 | 8.89847 |
| 11.8 | 35.65 | 7.48101 |
| 12.2 | 26.49 | 7.24933 |
| 13.1 | 10.86 | 6.77877 |
| 13.5 | 2.98 | 6.54974 |
| 14.0 | 11.03 | 6.34316 |
| 14.8 | 20.25 | 5.98558 |
| 15.4 | 8.96 | 5.76719 |
| 15.7 | 88.25 | 5.64579 |
| 16.4 | 10.06 | 5.4091 |
| 16.7 | 11.03 | 5.30622 |
| 17.3 | 6.3 | 5.12687 |
| 17.5 | 11.35 | 5.0547 |
| 18.0 | 16.65 | 4.91905 |
| 18.3 | 12.72 | 4.85584 |
| 19.0 | 7.3 | 4.7 |
| 19.7 | 49.7 | 4.5 |
| 20.2 | 17.4 | 4.4 |
| 20.8 | 9.5 | 4.3 |
| 21.4 | 61.6 | 4.2 |
| 21.9 | 8.1 | 4.1 |
| 22.1 | 9.1 | 4.0 |
| 22.4 | 19.4 | 4.0 |
| 22.7 | 18.3 | 3.9 |
| 23.6 | 23.0 | 3.8 |
| 24.2 | 9.7 | 3.7 |
| 24.5 | 47.9 | 3.6 |
| 25.0 | 10.3 | 3.6 |
| 25.6 | 2.5 | 3.5 |
| 26.1 | 8.4 | 3.4 |
| 26.9 | 10.2 | 3.3 |
| 27.2 | 8.5 | 3.3 |
| 27.5 | 9.8 | 3.2 |
| 29.7 | 2.2 | 3.0 |
| 30.8 | 21.6 | 2.9 |

EXAMPLE 34a

Sulphate Form a (XRD Spectrum is Shown in FIG. 2)

| XRPD Example 34 sulphate form A | | |
| --- | --- | --- |
| 2Ø | Rel Int % | d spacing |
| 4.8 | 100.0 | 18.6 |
| 8.0 | 6.0 | 11.1 |
| 9.5 | 15.6 | 9.3 |
| 11.3 | 2.8 | 7.8 |
| 14.1 | 15.3 | 6.3 |
| 15.7 | 8.5 | 5.6 |
| 16.2 | 7.1 | 5.5 |
| 17.9 | 13.6 | 5.0 |
| 18.6 | 8.4 | 4.8 |
| 21.4 | 20.2 | 4.1 |
| 23.0 | 8.0 | 3.9 |
| 24.7 | 4.4 | 3.6 |
| 28.7 | 2.8 | 3.1 |
| 31.9 | 1.0 | 2.8 |
| 34.2 | 0.9 | 2.6 |

Accuracy—+/−0.1

EXAMPLE 34c

Sulphate Form B (XRD Spectrum is Shown in FIG. 3)

| XRPD Example 34 sulphate form B | | |
| --- | --- | --- |
| 2Ø | Rel Int % | d spacing |
| 4.6 | 67.8 | 19.1 |
| 7.9 | 20.7 | 11.1 |
| 9.3 | 84.0 | 9.6 |
| 10.0 | 10.7 | 8.9 |
| 11.2 | 7.0 | 7.9 |
| 12.1 | 4.2 | 7.3 |
| 13.9 | 100.0 | 6.4 |
| 15.3 | 29.3 | 5.8 |
| 16.2 | 15.7 | 5.5 |
| 18.0 | 14.1 | 4.9 |
| 18.5 | 22.2 | 4.8 |
| 20.1 | 24.0 | 4.4 |
| 21.2 | 19.4 | 4.2 |
| 22.2 | 15.0 | 4.0 |
| 23.2 | 10.7 | 3.8 |
| 24.7 | 15.7 | 3.6 |
| 25.7 | 15.1 | 3.5 |
| 26.6 | 8.0 | 3.4 |
| 27.9 | 27.8 | 3.2 |
| 30.1 | 4.3 | 3.0 |
| 34.4 | 3.2 | 2.6 |

Accuracy—+/−0.1

EXAMPLE 34d

Sulphate Form C (XRD Spectrum is Shown in FIG. 4)

| XRPD Example 34 Sulphate form C | | |
|---|---|---|
| 2Ø | Rel Int % | d spacing |
| 4.4 | 100 | 20.3 |
| 5.8 | 5.34 | 15.2 |
| 7.8 | 7.62 | 11.4 |
| 8.7 | 5.48 | 10.2 |
| 9.5 | 16.14 | 9.3 |
| 12.0 | 7.09 | 7.4 |
| 13.0 | 6.81 | 6.8 |
| 14.2 | 7.97 | 6.2 |
| 15.6 | 6.32 | 5.7 |
| 16.6 | 15.22 | 5.3 |
| 17.4 | 27.82 | 5.1 |
| 17.8 | 30.16 | 5.0 |
| 18.4 | 19.39 | 4.8 |
| 20.7 | 21.31 | 4.3 |
| 21.8 | 23.55 | 4.1 |
| 23.4 | 10.81 | 3.8 |
| 24.7 | 9.78 | 3.6 |
| 26.0 | 7.53 | 3.4 |
| 26.8 | 6.45 | 3.3 |
| 28.4 | 3.69 | 3.1 |
| 31.4 | 2.19 | 2.8 |
| 33.7 | 2.26 | 2.7 |
| 37.0 | 1.65 | 2.4 |

Accuracy—+/−0.1

EXAMPLE 34e

Sulphate Form D (XRD Spectrum is Shown in FIG. 5)

| XRPD Example 34 sulphate form D | | |
|---|---|---|
| 2Ø | Rel Int % | d spacing |
| 4.3 | 100.0 | 20.3 |
| 4.7 | 69.7 | 18.8 |
| 5.8 | 9.7 | 15.2 |
| 7.7 | 9.5 | 11.4 |
| 8.7 | 4.1 | 10.2 |
| 9.5 | 24.3 | 9.3 |
| 11.6 | 5.4 | 7.6 |
| 12.0 | 8.6 | 7.4 |
| 13.0 | 3.4 | 6.8 |
| 13.5 | 6.5 | 6.6 |
| 14.2 | 13.3 | 6.3 |
| 14.8 | 6.1 | 6.0 |
| 15.1 | 4.4 | 5.9 |
| 15.8 | 8.9 | 5.6 |
| 16.5 | 14.5 | 5.4 |
| 17.3 | 10.1 | 5.1 |
| 17.9 | 23.9 | 4.9 |
| 18.4 | 14.8 | 4.8 |
| 19.0 | 5.6 | 4.7 |
| 19.9 | 3.9 | 4.5 |
| 20.6 | 15.8 | 4.3 |
| 21.3 | 14.9 | 4.2 |
| 21.8 | 14.8 | 4.1 |
| 22.5 | 9.7 | 4.0 |
| 23.4 | 7.0 | 3.8 |
| 24.7 | 8.4 | 3.6 |
| 26.8 | 4.2 | 3.3 |
| 28.6 | 4.1 | 3.1 |
| 29.5 | 6.4 | 3.0 |
| 31.9 | 1.7 | 2.8 |
| 33.9 | 1.5 | 2.6 |

Accuracy—+/−0.1

EXAMPLE 34f

Sulphate Form E (XRD Spectrum is Shown in FIG. 6)

| XRPD Example 34 sulphate form E | | |
|---|---|---|
| 2Ø | Rel Int % | d spacing |
| 4.3 | 93.2 | 20.5 |
| 5.8 | 11.8 | 15.2 |
| 7.8 | 15.0 | 11.4 |
| 8.6 | 11.1 | 10.2 |
| 9.5 | 55.5 | 9.3 |
| 11.6 | 22.5 | 7.6 |
| 12.1 | 18.0 | 7.3 |
| 13.0 | 35.6 | 6.8 |
| 13.6 | 6.4 | 6.5 |
| 14.3 | 28.3 | 6.2 |
| 14.9 | 32.6 | 5.9 |
| 15.1 | 60.5 | 5.9 |
| 15.5 | 18.1 | 5.7 |
| 16.5 | 23.8 | 5.4 |
| 17.3 | 100.0 | 5.1 |
| 17.7 | 59.3 | 5.0 |
| 18.0 | 29.0 | 4.9 |
| 18.4 | 15.8 | 4.8 |
| 19.0 | 26.9 | 4.7 |
| 19.7 | 26.7 | 4.5 |
| 20.5 | 72.7 | 4.3 |
| 20.8 | 18.2 | 4.3 |
| 21.3 | 20.0 | 4.2 |
| 21.7 | 60.4 | 4.1 |
| 22.0 | 44.7 | 4.0 |
| 22.6 | 74.2 | 3.9 |
| 23.4 | 60.8 | 3.8 |
| 24.1 | 22.4 | 3.7 |
| 24.6 | 43.0 | 3.6 |
| 25.7 | 14.8 | 3.5 |
| 26.7 | 53.0 | 3.3 |
| 27.2 | 15.6 | 3.3 |
| 28.1 | 17.6 | 3.2 |
| 29.2 | 12.9 | 3.1 |
| 30.4 | 16.3 | 2.9 |
| 31.3 | 10.3 | 2.9 |
| 32.7 | 5.1 | 2.7 |
| 33.3 | 7.4 | 2.7 |
| 34.4 | 8.6 | 2.6 |
| 36.3 | 8.4 | 2.5 |
| 37.0 | 9.9 | 2.4 |

Accuracy—+/−0.1

EXAMPLE 34g

Sulphate Form F (XRD Spectrum is Shown in FIG. 7)

| XRPD data Example 34 sulphate form F | | |
|---|---|---|
| 2Ø | Rel Int % | d spacing |
| 4.7 | 100.0 | 18.8 |
| 7.9 | 18.7 | 11.3 |
| 9.4 | 10.2 | 9.4 |
| 9.7 | 19.6 | 9.1 |
| 11.3 | 14.5 | 7.8 |
| 13.6 | 12.3 | 6.5 |
| 14.2 | 15.5 | 6.3 |
| 15.3 | 12.6 | 5.8 |
| 15.8 | 23.4 | 5.6 |
| 17.1 | 13.8 | 5.2 |
| 17.9 | 51.2 | 5.0 |
| 18.6 | 20.0 | 4.8 |
| 19.8 | 38.6 | 4.5 |
| 20.3 | 9.7 | 4.4 |
| 21.4 | 37.8 | 4.1 |
| 22.9 | 14.5 | 3.9 |
| 24.8 | 14.3 | 3.6 |
| 26.3 | 9.7 | 3.4 |
| 28.1 | 8.2 | 3.2 |

Accuracy—+/−0.1

EXAMPLE 34h

Sulphate Form G (XRD Spectrum is Shown in FIG. 8)

| XRPD data Example 34 sulphate form G | | |
|---|---|---|
| 2Ø | Rel Int % | d spacing |
| 6.0 | 7.8 | 14.6 |
| 6.3 | 7.6 | 14.1 |
| 7.5 | 4.6 | 11.7 |
| 8.0 | 9.7 | 11.1 |
| 9.3 | 45.8 | 9.5 |
| 10.9 | 84.6 | 8.1 |
| 12.5 | 16.5 | 7.1 |
| 13.3 | 36.9 | 6.7 |
| 13.9 | 41.2 | 6.4 |
| 14.2 | 9.9 | 6.2 |
| 15.0 | 41.7 | 5.9 |
| 16.0 | 47.0 | 5.5 |
| 16.2 | 100.0 | 5.5 |
| 17.0 | 15.9 | 5.2 |
| 17.6 | 15.2 | 5.0 |
| 18.3 | 79.7 | 4.8 |
| 18.7 | 68.4 | 4.8 |
| 18.9 | 67.4 | 4.7 |
| 19.2 | 21.4 | 4.6 |
| 19.5 | 19.3 | 4.6 |
| 19.8 | 16.9 | 4.5 |
| 20.7 | 13.8 | 4.3 |
| 21.1 | 40.1 | 4.2 |
| 21.3 | 28.0 | 4.2 |
| 21.7 | 16.4 | 4.1 |
| 22.4 | 46.7 | 4.0 |
| 22.7 | 18.4 | 3.9 |
| 23.5 | 6.2 | 3.8 |
| 24.4 | 27.8 | 3.7 |
| 25.0 | 20.6 | 3.6 |
| 25.2 | 75.5 | 3.5 |
| 25.8 | 13.9 | 3.5 |
| 27.5 | 20.5 | 3.2 |
| 28.5 | 23.6 | 3.1 |
| 31.2 | 4.7 | 2.9 |
| 32.8 | 10.6 | 2.7 |
| 34.0 | 4.2 | 2.6 |

Accuracy—+/−0.1

EXAMPLE 34i

Napadisylate Form B (XRD Spectrum is Shown in FIG. 9)

| XRPD data Example 34 napadisylate form B | | |
|---|---|---|
| 2Ø | Rel Int % | d spacing |
| 4.6 | 1.8 | 19.2 |
| 6.3 | 28.1 | 14.0 |
| 7.7 | 5.5 | 11.5 |
| 8.6 | 15.7 | 10.3 |
| 9.5 | 9.1 | 9.3 |
| 10.5 | 27.8 | 8.4 |
| 10.7 | 8.1 | 8.2 |
| 11.2 | 27.1 | 7.9 |
| 11.8 | 20.1 | 7.5 |
| 12.7 | 13.8 | 7.0 |
| 14.1 | 4.8 | 6.3 |
| 14.7 | 14.0 | 6.0 |
| 15.0 | 8.8 | 5.9 |
| 15.4 | 43.3 | 5.8 |
| 15.6 | 51.1 | 5.7 |
| 16.0 | 100.0 | 5.5 |
| 17.2 | 16.0 | 5.1 |
| 17.7 | 10.2 | 5.0 |
| 18.3 | 9.7 | 4.8 |
| 18.8 | 31.8 | 4.7 |
| 19.2 | 75.6 | 4.6 |
| 19.8 | 19.3 | 4.5 |
| 20.2 | 10.2 | 4.4 |
| 21.0 | 46.2 | 4.2 |
| 21.2 | 38.4 | 4.2 |
| 21.6 | 26.1 | 4.1 |
| 22.2 | 53.7 | 4.0 |
| 22.5 | 16.4 | 3.9 |
| 23.6 | 25.8 | 3.8 |
| 24.3 | 11.7 | 3.7 |
| 25.4 | 53.8 | 3.5 |
| 25.9 | 8.6 | 3.4 |
| 26.8 | 2.8 | 3.3 |
| 27.3 | 12.3 | 3.3 |
| 27.5 | 8.5 | 3.2 |
| 28.0 | 6.1 | 3.2 |
| 28.4 | 5.1 | 3.1 |
| 29.3 | 9.1 | 3.1 |
| 29.6 | 10.6 | 3.0 |
| 30.5 | 7.0 | 2.9 |
| 31.9 | 2.0 | 2.8 |
| 32.9 | 1.9 | 2.7 |
| 33.5 | 3.7 | 2.7 |
| 35.9 | 1.4 | 2.5 |
| 37.6 | 3.9 | 2.4 |

Accuracy—+/−0.1

EXAMPLE 39a

Napadisylate Form A (XRD Spectrum is Shown in FIG. 10)

| XRPD data Example 39 napadisylate form A | | |
|---|---|---|
| 2Ø | Rel Int % | d spacing |
| 6.3 | 36.8 | 14.0 |
| 7.6 | 11.8 | 11.7 |
| 8.5 | 26.7 | 10.4 |
| 9.4 | 7.6 | 9.4 |
| 10.4 | 31.6 | 8.5 |
| 10.8 | 19.8 | 8.2 |
| 11.3 | 46.1 | 7.8 |
| 11.9 | 4.5 | 7.4 |
| 12.3 | 12.6 | 7.2 |
| 12.6 | 10.5 | 7.0 |
| 12.9 | 3.9 | 6.9 |
| 13.9 | 8.2 | 6.4 |
| 15.1 | 63.8 | 5.9 |
| 15.5 | 78.0 | 5.7 |
| 15.9 | 85.3 | 5.6 |
| 16.6 | 4.7 | 5.3 |
| 17.1 | 19.3 | 5.2 |
| 17.4 | 24.8 | 5.1 |
| 17.9 | 14.2 | 5.0 |
| 18.2 | 7.8 | 4.9 |
| 18.5 | 5.3 | 4.8 |
| 19.1 | 18.8 | 4.6 |
| 19.5 | 100.0 | 4.6 |
| 20.0 | 45.9 | 4.4 |
| 20.2 | 26.6 | 4.4 |
| 20.9 | 41.6 | 4.3 |
| 21.2 | 31.1 | 4.2 |
| 21.5 | 11.2 | 4.1 |
| 21.9 | 31.5 | 4.1 |
| 22.1 | 51.2 | 4.0 |
| 22.8 | 32.4 | 3.9 |
| 23.3 | 29.5 | 3.8 |
| 23.7 | 10.6 | 3.8 |
| 23.9 | 11.0 | 3.7 |
| 24.2 | 11.0 | 3.7 |
| 24.7 | 22.5 | 3.6 |
| 25.3 | 52.6 | 3.5 |
| 25.6 | 12.7 | 3.5 |
| 26.2 | 6.0 | 3.4 |
| 26.6 | 4.1 | 3.4 |
| 27.4 | 5.2 | 3.3 |
| 27.9 | 5.4 | 3.2 |
| 28.5 | 5.4 | 3.1 |
| 29.7 | 14.9 | 3.0 |
| 30.4 | 6.7 | 2.9 |
| 31.7 | 3.9 | 2.8 |
| 32.2 | 7.8 | 2.8 |
| 34.9 | 1.7 | 2.6 |
| 36.3 | 1.8 | 2.5 |

Accuracy—+/−0.1

FIG. 1 shows the XRD spectrum for the sulphate salt of Example 33a;

FIG. 2 shows the XRD spectrum for the sulphate Form A of Example 34a;

Figure 1:
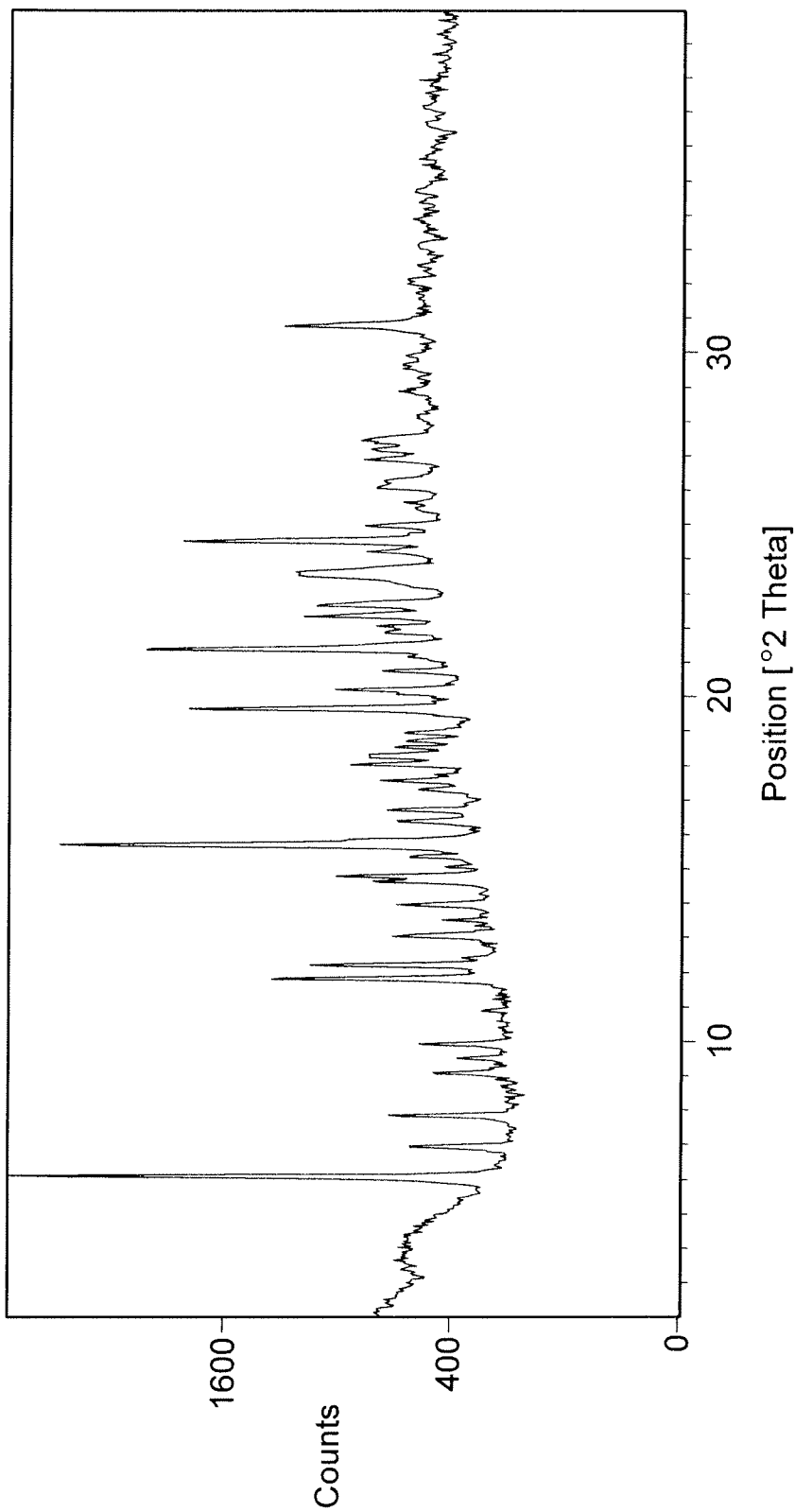
Figure 2:
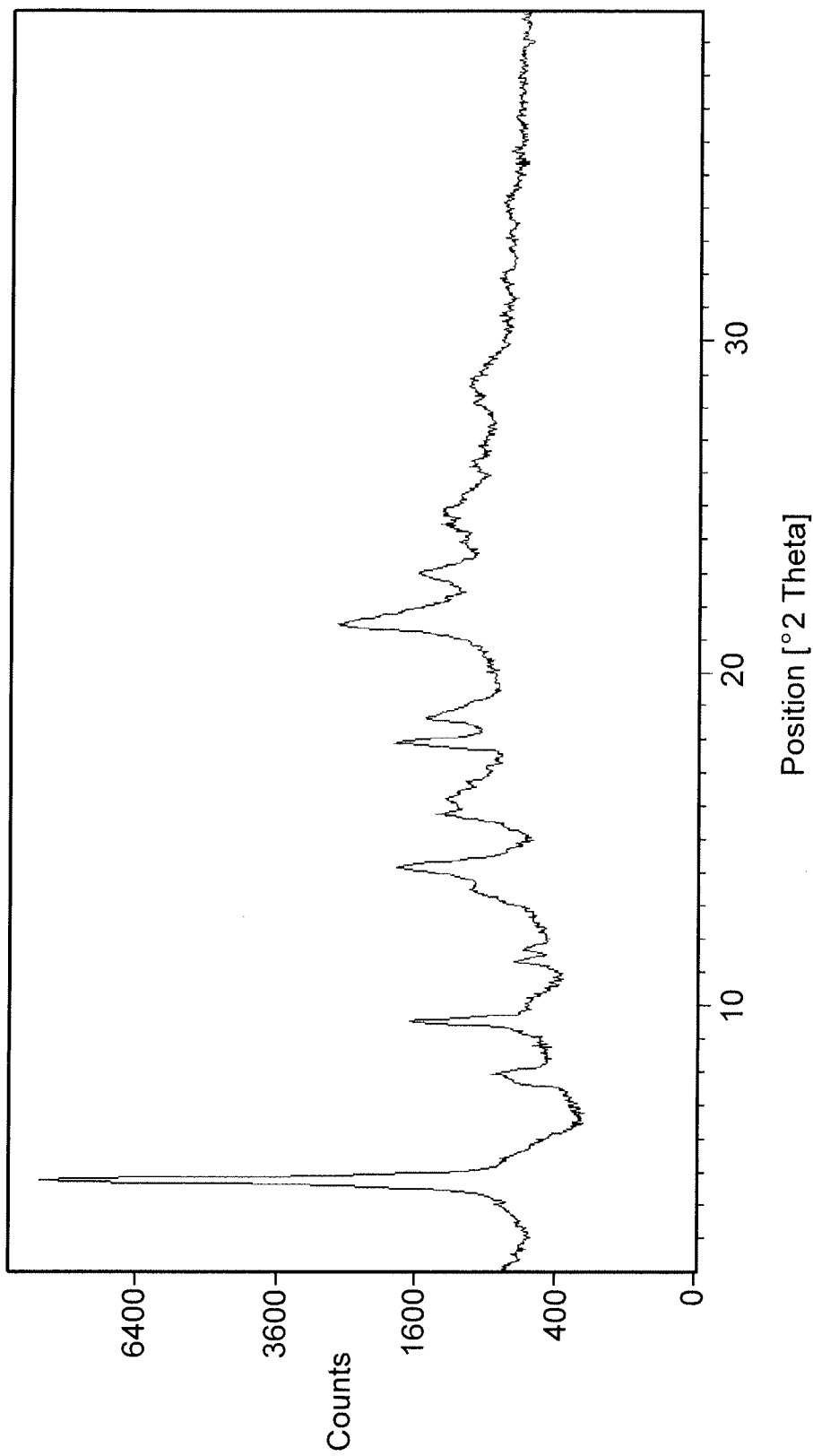
Figure 3:
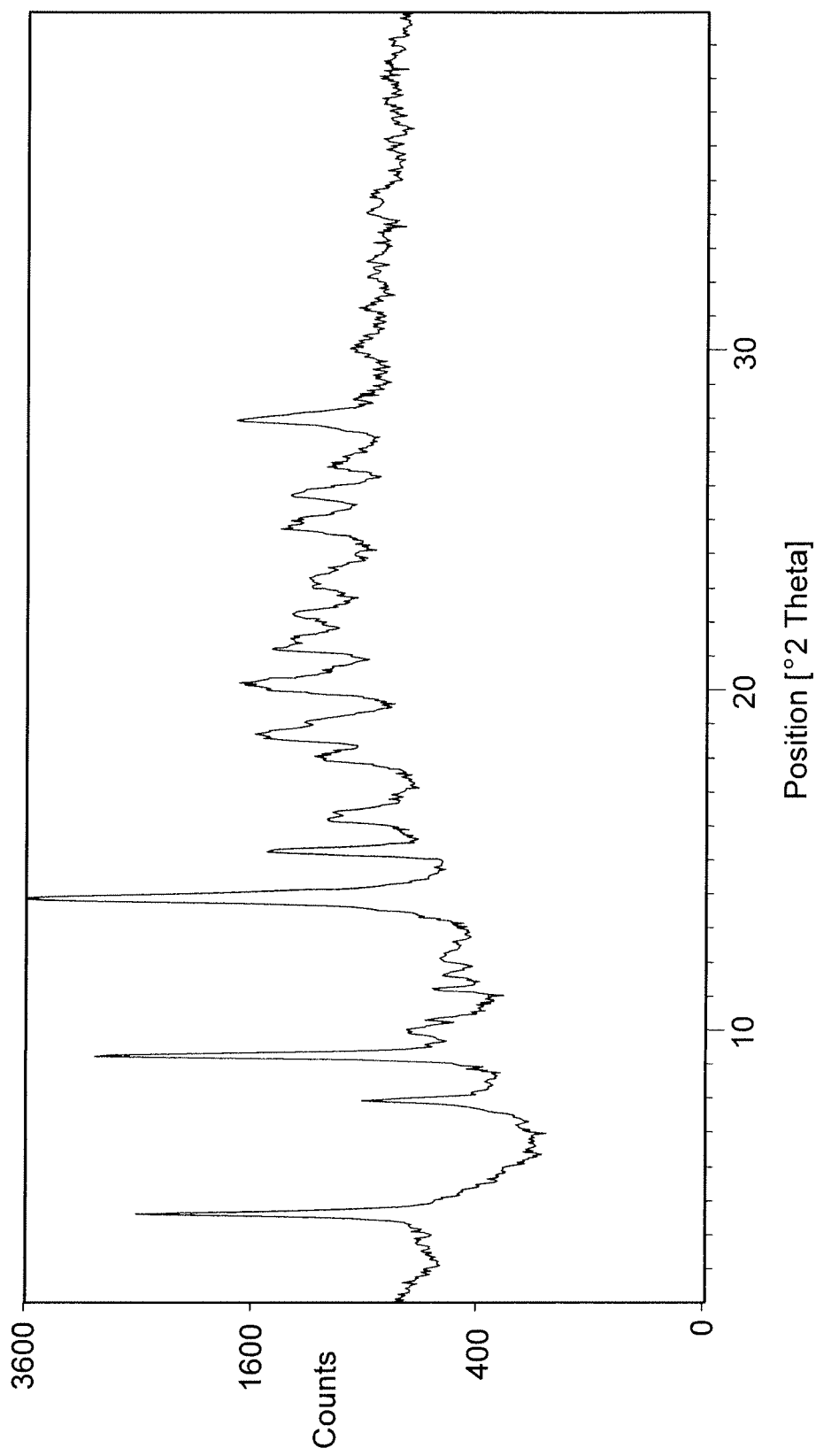
FIG. 3 shows the XRD spectrum for the sulphate Form B of Example 34c.
Figure 4:
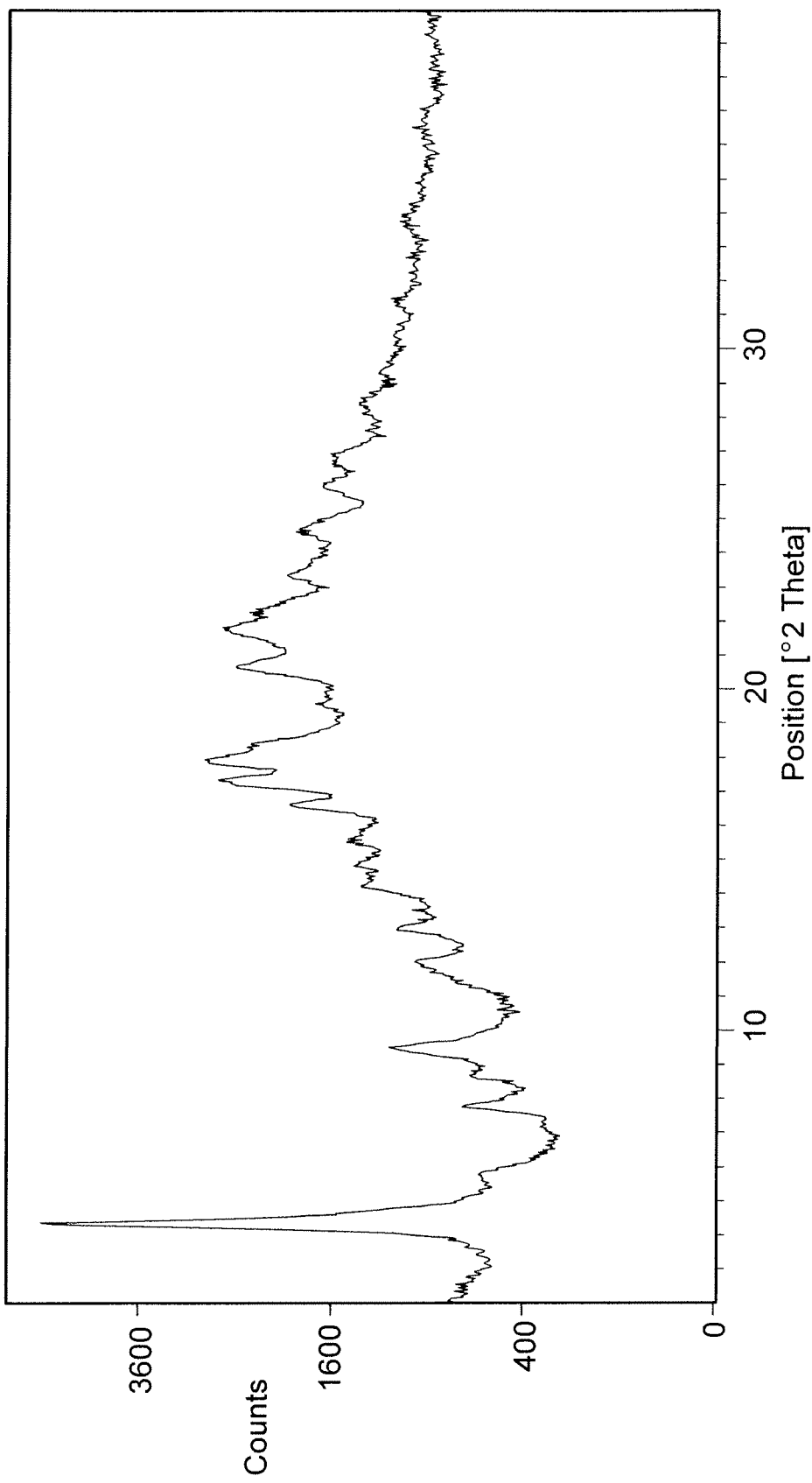
FIG. 4 shows the XRD spectrum for the sulphate Form C of Example 34d.
Figure 5:
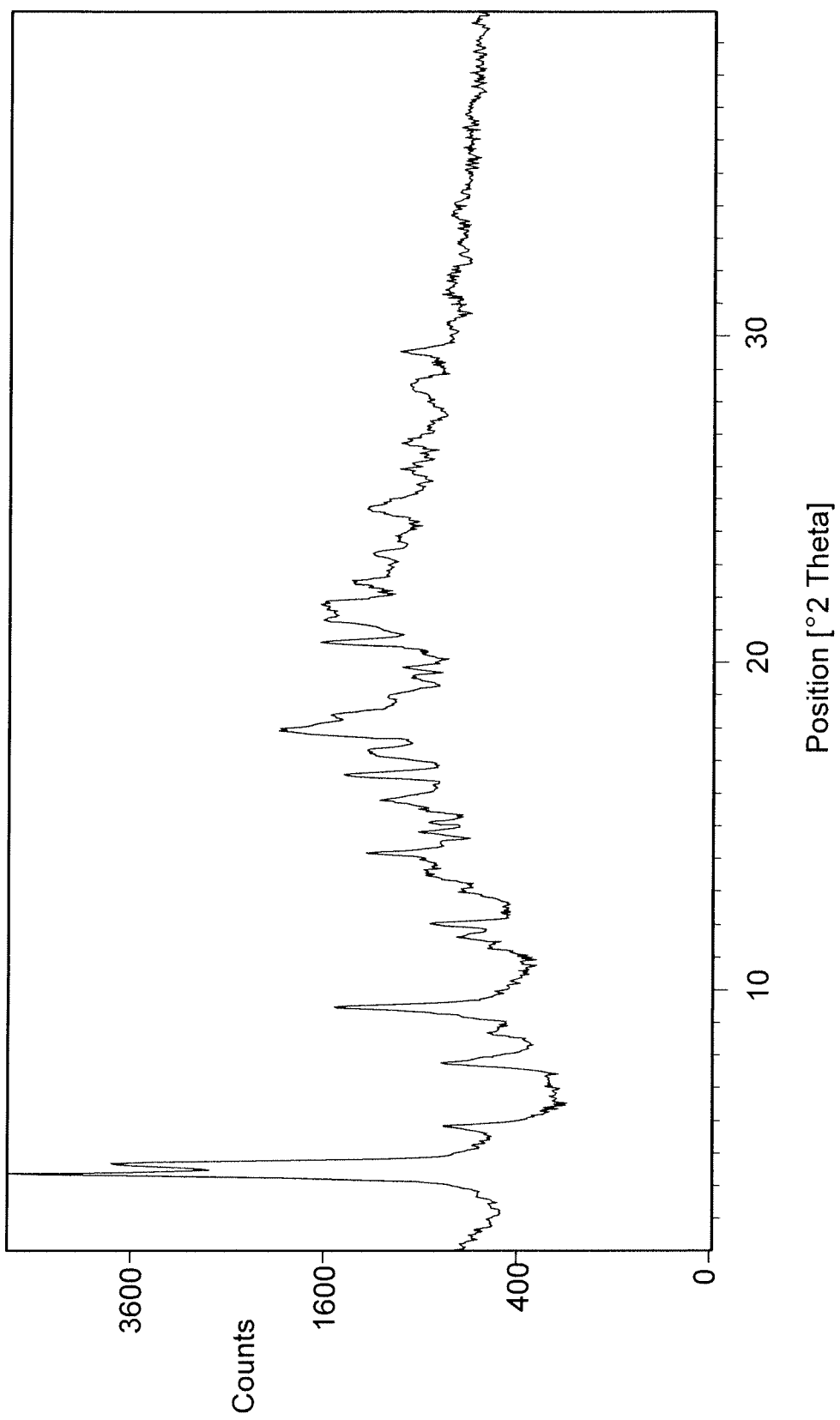
FIG. 5 shows the XRD spectrum for the sulphate Form D of Example 34e.
Figure 6:
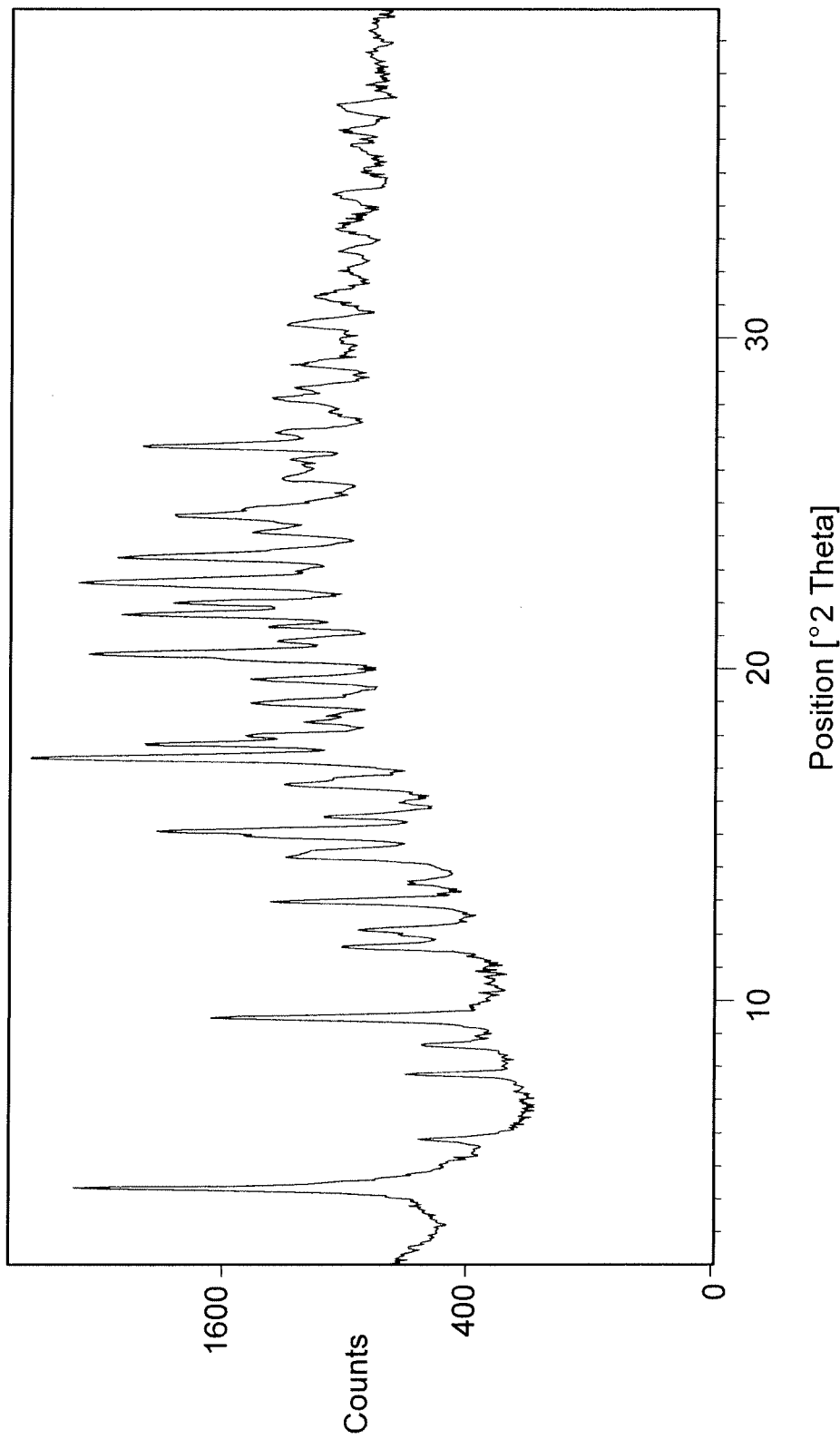
FIG. 6 shows the XRD spectrum for the sulphate Form E of Example 34f.
Figure 7:
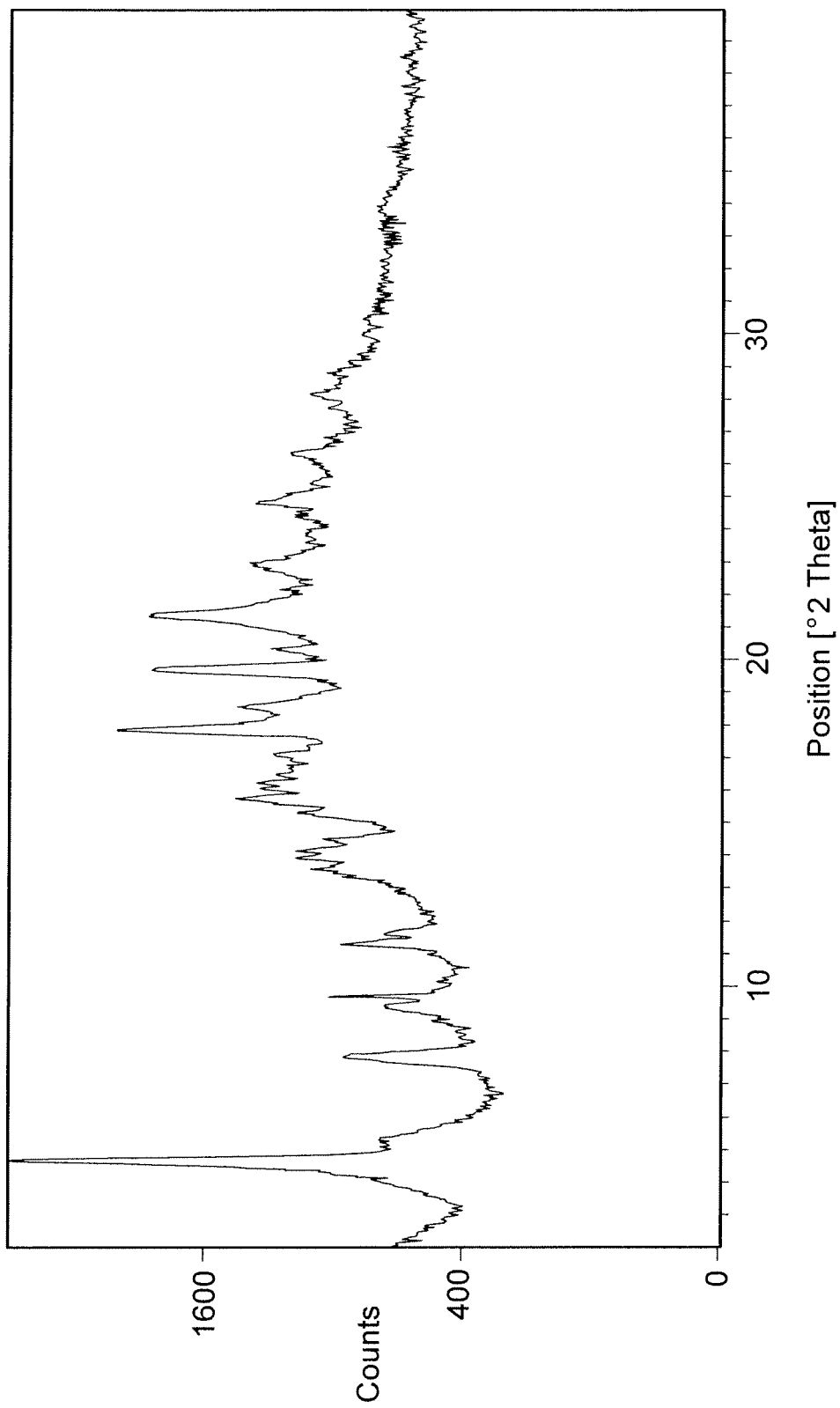
FIG. 7 shows the XRD spectrum for the sulphate Form F of Example 34 g.
Figure 8:
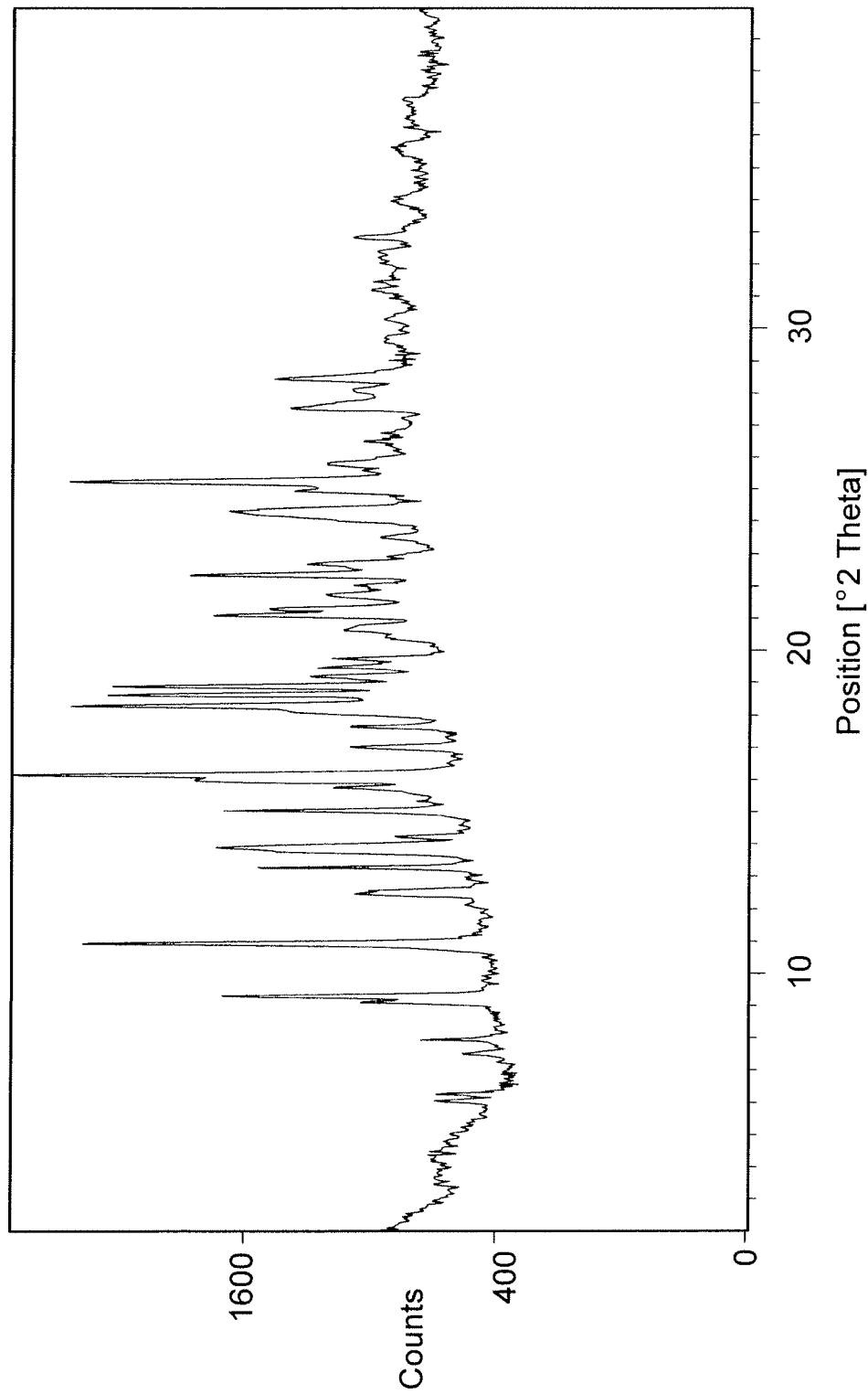
FIG. 8 shows the XRD spectrum for the sulphate Form G of Example 34h.
Figure 9:
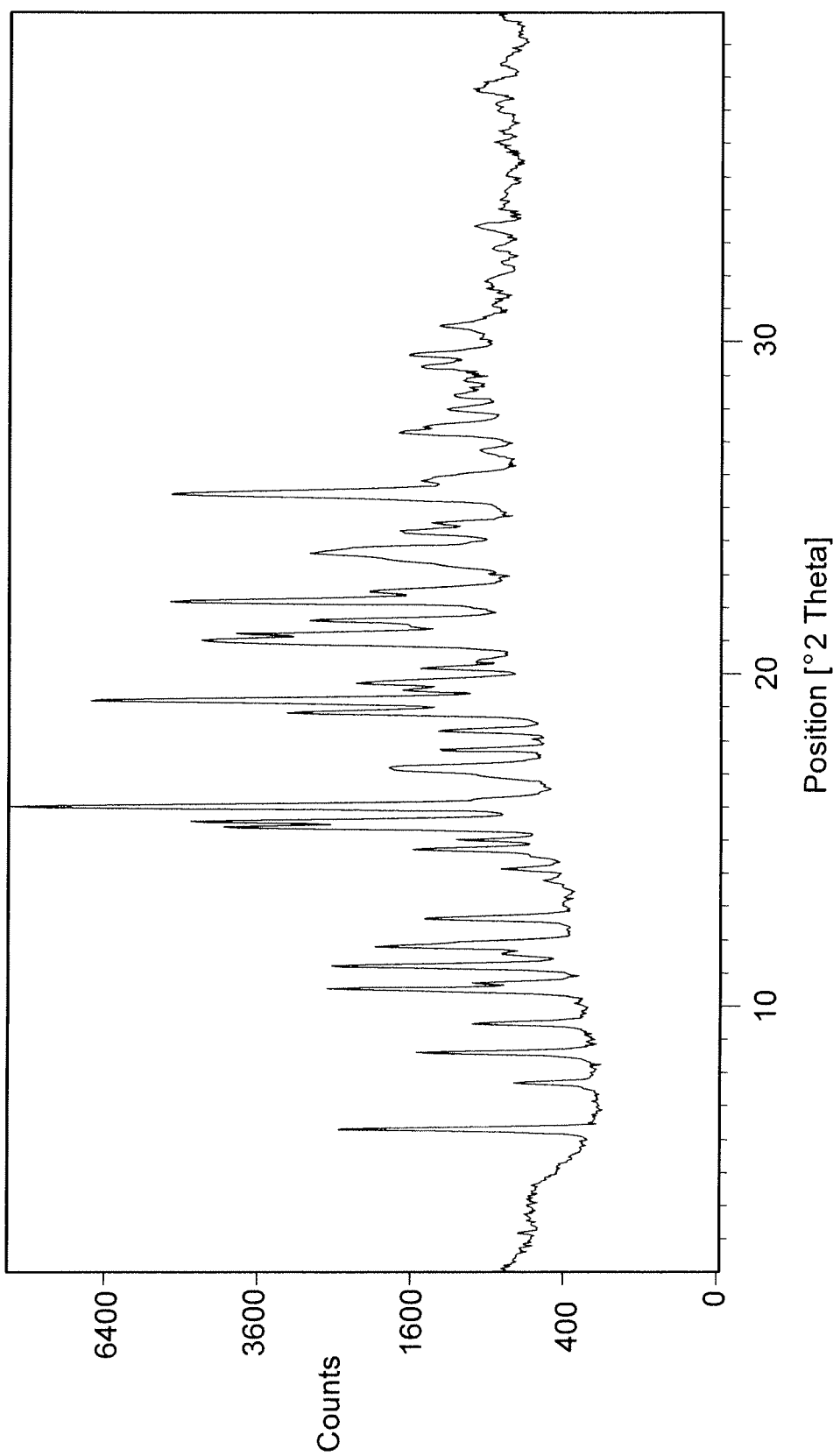
FIG. 9 shows the XRD spectrum for the napadisylate Form B of Example 34i.
Figure 10:
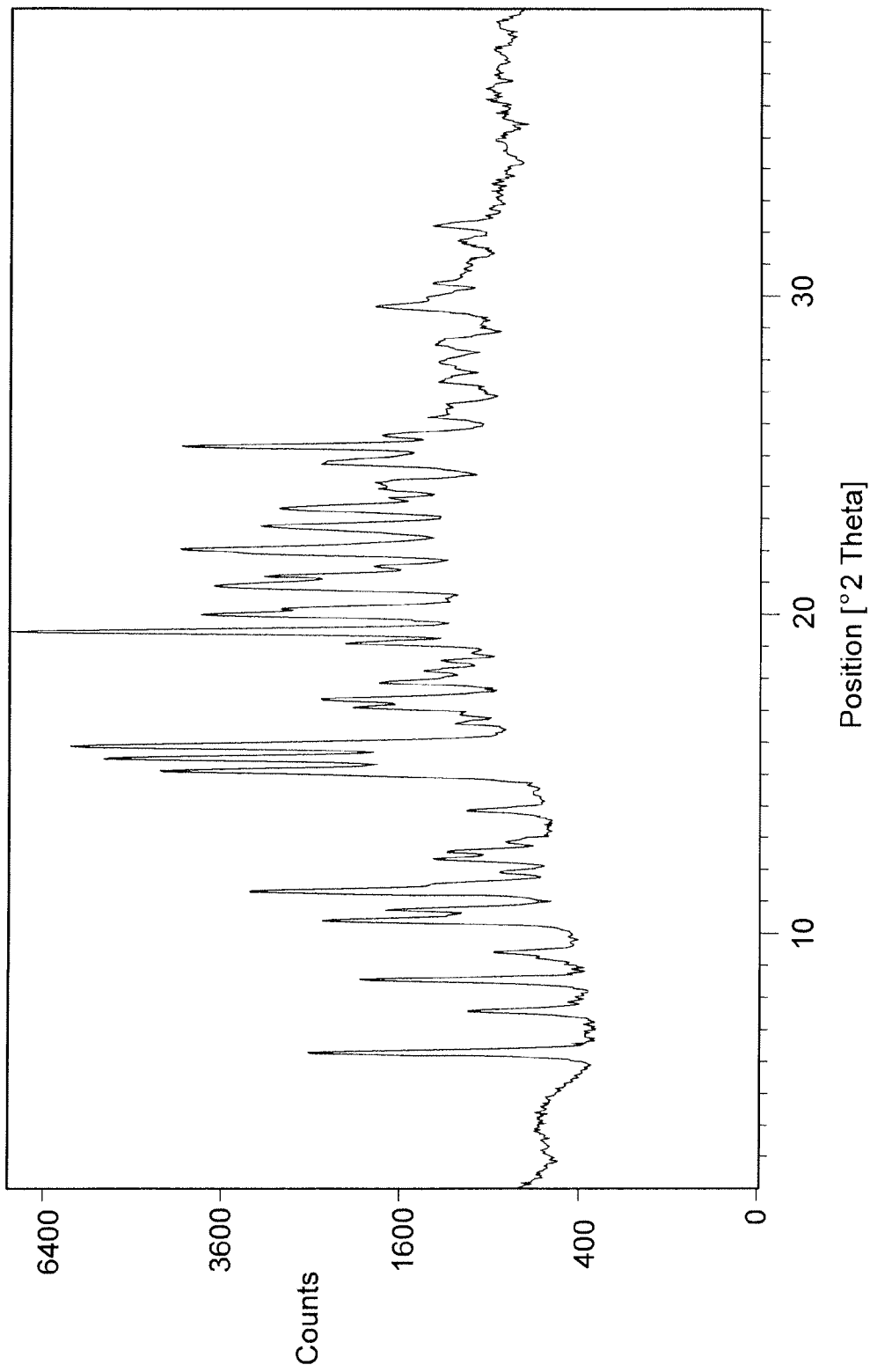
FIG. 10 shows the XRD spectrum for the napadisylate Form A of Example 39.

The invention claimed is:

1. A compound having the formula:

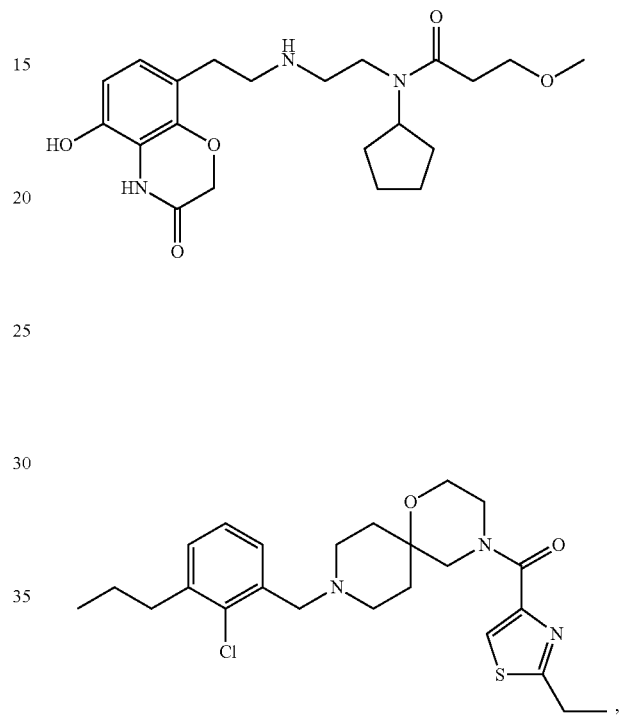

or a pharmaceutically acceptable salt thereof.

2. The compound or pharmaceutically acceptable salt thereof, as claimed in claim 1, wherein the pharmaceutically acceptable salt thereof is selected from a hydrochloride salt, a dihydrochloride salt, a hydrobromide salt, a dihydrobromide salt, a trifluoroacetate salt, a di-trifluoroacetate salt, a sulphate salt, a phosphate salt, an acetate salt, a fumarate salt, a maleate salt, a tartrate salt, a lactate salt, a citrate salt, a pyruvate salt, a succinate salt, an oxalate salt, a methanesulphonate salt, and a p-toluenesulphonate salt.

3. The compound or pharmaceutically acceptable salt thereof, as claimed in claim 1, wherein the pharmaceutically acceptable salt thereof is selected from a dihydrochloride salt, a dihydrobromide salt, a di-trifluoroacetate salt, a sulphate salt, a phosphate salt, an acetate salt, a fumarate salt, a maleate salt, a tartrate salt, a lactate salt, a citrate salt, a pyruvate salt, a succinate salt, an oxalate salt, a methanesulphonate salt, and a p-toluenesulphonate salt.

4. The compound or pharmaceutically acceptable salt thereof, as claimed in claim 1, wherein the pharmaceutically acceptable salt thereof is a di-trifluoroacetate salt.

5. The compound or pharmaceutically acceptable salt thereof, as claimed in claim 1, wherein the pharmaceutically acceptable salt thereof is a sulphate salt.

6. A compound having the formula:

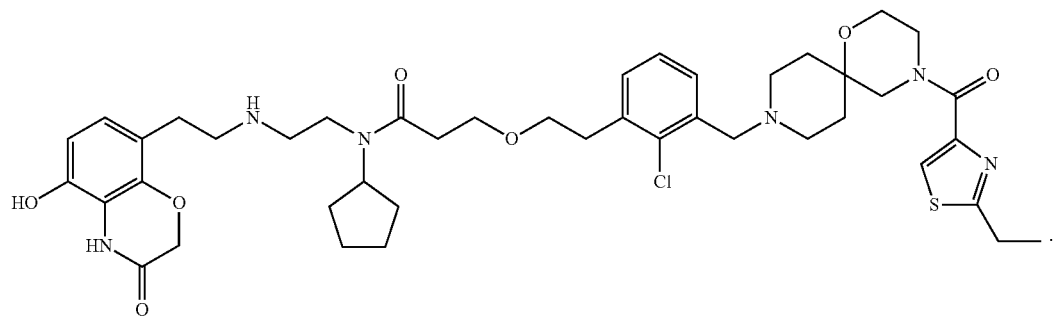

7. A compound having the formula:

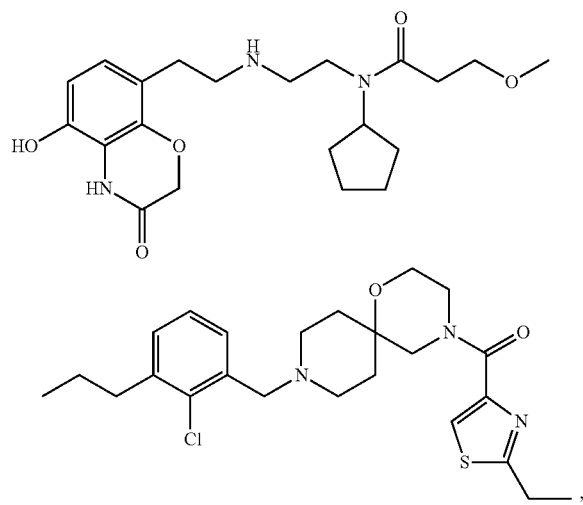

in the form of a pharmaceutically acceptable salt.

8. The pharmaceutically acceptable salt as claimed in claim 7, wherein the compound is in the form of a pharmaceutically acceptable salt selected from a hydrochloride salt, a dihydrochloride salt, a hydrobromide salt, a dihydrobromide salt, a trifluoroacetate salt, a di-trifluoroacetate salt, a sulphate salt, a phosphate salt, an acetate salt, a fumarate salt, a maleate salt, a tartrate salt, a lactate salt, a citrate salt, a pyruvate salt, a succinate salt, an oxalate salt, a methanesulphonate salt, and a p-toluenesulphonate salt.

9. The pharmaceutically acceptable salt as claimed in claim 7, wherein the compound is in the form of a pharmaceutically acceptable salt selected from a dihydrochloride salt, a dihydrobromide salt, a di-trifluoroacetate salt, a sulphate salt, a phosphate salt, an acetate salt, a fumarate salt, a maleate salt, a tartrate salt, a lactate salt, a citrate salt, a pyruvate salt, a succinate salt, an oxalate salt, a methanesulphonate salt, and a p-toluenesulphonate salt.

10. The pharmaceutically acceptable salt as claimed in claim 7, wherein the compound is in the form of a di-trifluoroacetate salt.

11. The pharmaceutically acceptable salt as claimed in claim 7, wherein the compound is in the form of a sulphate salt.

12. The pharmaceutically acceptable salt as claimed in claim 7, wherein the compound is in the form of a sulfuric acid monohydrate salt.

13. A pharmaceutical composition comprising a compound or pharmaceutically acceptable salt thereof, as claimed in claim 1, in association with a pharmaceutically acceptable adjuvant, diluent or carrier.

14. A pharmaceutical composition comprising a compound as claimed in claim 6, in association with a pharmaceutically acceptable adjuvant, diluent or carrier.

15. A pharmaceutical composition comprising a pharmaceutically acceptable salt, as claimed in any one of claims 7-12, in association with a pharmaceutically acceptable adjuvant, diluent or carrier.

* * * * *

UNITED STATES PATENT AND TRADEMARK OFFICE
CERTIFICATE OF CORRECTION

PATENT NO. : 8,455,483 B2
APPLICATION NO. : 12/847000
DATED : June 4, 2013
INVENTOR(S) : Alcaraz et al.

Page 1 of 1

It is certified that error appears in the above-identified patent and that said Letters Patent is hereby corrected as shown below:

In the Specification

In column 1, line 4, "09113342.2" should read -- 0913342.2 --

Signed and Sealed this
Twenty-ninth Day of October, 2013

Teresa Stanek Rea
*Deputy Director of the United States Patent and Trademark Office*